US009970036B2

(12) United States Patent
Jarrell et al.

(10) Patent No.: US 9,970,036 B2
(45) Date of Patent: May 15, 2018

(54) GENERATION OF ACYL AMINO ACIDS

(71) Applicant: Modular Genetics, Inc., Woburn, MA (US)

(72) Inventors: Kevin A. Jarrell, Lincoln, MA (US); Gabriel O. Reznik, Waltham, MA (US); Prashanth Vishwanath, Arlington, MA (US); Michelle Pynn, Andover, MA (US)

(73) Assignee: MODULAR GENETICS, INC., Woburn, MA (US)

( * ) Notice: Subject to any disclaimer, the term of this patent is extended or adjusted under 35 U.S.C. 154(b) by 0 days. days.

(21) Appl. No.: 14/776,805

(22) PCT Filed: Mar. 14, 2014

(86) PCT No.: PCT/US2014/029150
§ 371 (c)(1),
(2) Date: Sep. 15, 2015

(87) PCT Pub. No.: WO2014/144649
PCT Pub. Date: Sep. 18, 2014

(65) Prior Publication Data
US 2016/0076065 A1  Mar. 17, 2016

Related U.S. Application Data

(60) Provisional application No. 61/788,346, filed on Mar. 15, 2013.

(51) Int. Cl.
*C12N 1/20* (2006.01)
*C12P 13/02* (2006.01)
*C12N 9/00* (2006.01)
*A01N 37/36* (2006.01)
*C07C 235/06* (2006.01)

(52) U.S. Cl.
CPC .............. *C12P 13/02* (2013.01); *A01N 37/36* (2013.01); *C07C 235/06* (2013.01); *C12N 9/93* (2013.01); *C12Y 603/02* (2013.01)

(58) Field of Classification Search
CPC ................................... C07K 7/06; C12N 9/93
USPC ............................................ 435/183, 252.31
See application file for complete search history.

(56) References Cited

U.S. PATENT DOCUMENTS

| 5,652,116 | A | 7/1997 | Grandi et al. |
|---|---|---|---|
| 5,795,738 | A | 8/1998 | Grandi et al. |
| 7,981,685 | B2 | 7/2011 | Jarrell et al. |
| 8,318,950 | B2 | 11/2012 | Nebolsin et al. |
| 2011/0030102 | A1 | 2/2011 | Jarrell et al. |
| 2011/0030103 | A1* | 2/2011 | Reznik ............... C07K 7/06 800/298 |
| 2012/0128603 | A1 | 5/2012 | Tanaka | |

FOREIGN PATENT DOCUMENTS

| WO | WO-2008/131002 A2 | 10/2008 |
|---|---|---|
| WO | WO-2008/131014 A1 | 10/2008 |
| WO | WO-2014/144649 A1 | 9/2014 |

OTHER PUBLICATIONS

Aguilar et al., A Bacillus subtilis gene induced by cold shock encodes a membrane phospholipid desaturase, Journal of Bacteriology., 180(8): 2194-2200 (1998).
Beasley et al., Mutation of L-2, 3-diaminopropionic acid synthase genes blocks staphyloferrin B synthesis in *Staphyloccus aureus*., BMC Microbilogy., 11:199 (2011).
Choi et al., β-ketoacyl-acyl carrier protein synthase III (FabH) is a determining factor in branched-cahin fatty acid biosynthesis., Journal of Bacteriology., 182(2): 365-370 (2000).
Coque et al., The cephamycin biosynthetic genes pcbAB, encoding a large multidomain peptide synthetase, and pcbC of Nocardia lactamdurans are clustered together in an organization different from the same genes in Acremonium chrysogenum and Penicillium chrysogenum, Mol. Microbiol. 5(5):1125-1133 (1991).
Cosmina et al., Sequence and analysis of the genetic locus responisble for surfactin synthesis in Bacillus subtilis, Mol. Microbiol. 8(5): 821-831 (1993).
Diez et al., The Cluster of Penicillin Biosynthetic Genes, J. Biol. Chem 265(27): 16358-16365 (1990).
Duitman et al., The Mycosubtilin synthetase of Bacillus subtilis ATCC6633: A multifunctional hybrid between a peptide synthetase, an amino transferase, and a fatty acid synthase. PNAS, 96(23): 13294-13299 (1999).
Felnagle et al., Identification of the biosynthetic gene cluster and an additional gene for resistance to the antituberculosis drug capreomycin., Applied and Environmental Microbiology., 73(13): 4162-4170 (2007).
Hojati et al., Structure, biosynthetic origin, and engineered Biosynthesis of calcium-Dependent Antibiotics from Streptomyces coelicolor., Chemistry & biology, 9: 1175-1187 (2002).
International Search Report for PCT/US2014/029150, 5 pages. (dated Aug. 7, 2014).
Kaneda, Iso- and anteiso-fatty acids in bacteria: biosynthesis, function, and taxonomic significance., Microbiological Reviews., 55(2): 288-302 (1991).
Kaneda., Fatty Acids of the Genus *Bacillus*: an example of branched-chain preference, Bacteriological Review., 41(2): 391-418 (1977).
Khandekar et al., Identification, substrate specificity, and inhibition of the *Streptococcus pneumonia* β-ketoacyl-acyl carrier protein synthase III (FabH)., Journal of Biological Chemistry , 276(32): 30024-30030 (2001).
Kleinkauf et al., A nonribosomal system of peptide biosynthesis., Eur J. Biochem., 236: 335-351 (1996).
Komiyama et al., A new antibiotic, cypemycin taxonomy, fermentation, isolation and biological characteristics., The Journal of Antibiotics., 46(11): 1666-1671 (1993).
Kratzschmar et al., Geramicidin S biosynthesis operon containing the structural genes grsA and grsB has an open reading frame encoding a protein homologous to fatty acid thioesterases, J. Bacteriol. 171(10): 5422-5429 (1989).

(Continued)

*Primary Examiner* — Tekchand Saidha
(74) *Attorney, Agent, or Firm* — Choate, Hall & Stewart, LLP

(57) ABSTRACT

Engineered polypeptides useful in synthesizing acyl amino acids are provided. Also provided are methods of making acyl amino acids using engineered polypeptides.

14 Claims, 6 Drawing Sheets

(56) References Cited

OTHER PUBLICATIONS

Li et al., Alteration of the fatty acid profile of Streptomyces coelicolor by replacement of the initiation enzyme 3-ketoacyl acyl carrier protein synthase III (FabH). Journal of Bacteriology, 187(11): 3795-3799 (2005).

Li et al., Identification and functional expression of a 9-fatty acid desaturase from Psychorobacter urativorans in *Escherichia coli.*, Lipids., 43(3): 207-213 (2008).

Maccabe et al., -(L-α-Aminoadipyl)-L-cysteinyl-D-valine Synthetase from Aspergillus nidulans, J. Biol. Chem. 266(19): 12646-12654 (1991).

Martin et al., A lipA (yutB) mutant, encoding lipoic acid synthase, provides insight into the interplay between branched-chain and unsaturated fatty acid biosynthesis in Bacillus subtilis., Journal of Bacteriology., 191(24): 7447-7455 (2009).

Miao et al., Daptomycin biosynthesis in Streptomyces roseosporus: cloning and analysis of the gene cluster and revision of peptide stereochemisty., Microbiology., 151: 1507-1523 (2005).

Rausch et al., Phylogenetic analysis of condensation domains in NRPOS sheds light on their functional evolution., BMC Evolutionary Biology., 7(78): 1-15 (2007).

Richardt et al., Ebony, A novel nonribosomal peptide synthetase for beta-Alanine conjugation with biogenic amines in *Drosophila.*, J. Biol. Chem 278(42): 41160-41166 (2003).

Roongsawang et al., Phylogenetic analysis of condesation domains in nonribosomal peptide synthetases, FEMS Microbiology Letters., 252: 143-151 (2005).

Sakuradani et al., Δ9-fatty acid desaturase from arachidonic acid-producting fungus unique gene sequence and its heterologous expression in a fungus, Aspergillus., Biochem., 260: 208-219 (1999).

Segolene et al., NORINE: a database of nonribosomal peptides, Nucleic Acid Research., 36: D327-D331 (2008).

Smith et al., β-Lactam antibiotic biosynthetic genes have been conservedin clusters in prokaryotes and ukaryotes, EMBO J. 9(3): 741-747 (1990).

Smith et al., The multifunctional peptide synthetase performing the first step of penicillin biosyntehsis in Penicillium chrysogenum is a 421 073 dalton protein similar to Bacillus brevis peptide antibiotic synthetases, EMBO J. 9(9):2743-2750 (1990).

Stellar et al., Initiation of Surfactin Biosynthesis and the Role of the SrfD-Thioesterase Protein., Biochemistry, 43: 11331-11343 (2004).

Symmank, H. et al., Analysis of engineered multifunctional peptide synthetases. Enzymatic characterization of surfactin synthetase domains in hybrid bimodular systems, Journal of Biological Chemistry, 274(31): 21581-21588 (1999).

Tsay, J-T. et al., Isolation and characterization of the -ketoacyl-acyl carrier protein synthatse III gene (fabH) from *Escherichia coli* K-12., JBC., 267(10): 6807-6814 (1992).

Van Wagoner, R.M. and Clardy, J., FeeM, an N-acyl amino acid synthase from an uncultured soil microbe: structure, mechanism, and acyl carrier protein binding, Structure, 14(9):1425-1435 (2006).

Wang et al., The primary structure of branched-chain a-oxo acid dehydrogenase from Bacillus subtilis and its similarity to other a-oxo acid dehydrogenases., Eur. J. Biochem., 213: 1091-1099 (1993).

Weckermann et al., Complete nucleotide sequence of the tycA gene coding the tyrocidine synthetase 1 from Bacillus brevis, Nucl. Acid. Res. 16(24): 11841-11843 (1988).

Welch., Applications of cellular fatty acid analysis., Clinical Microbiology Reviews, 4(4):422-438 (1991).

Willecke et al., Fatty acid-requiring mutant of bacillus subtilis defective in branched chain α-keto acid dehydrogenase., The Journal of Biological Chemistry., 246(17): 5264-5272 (1971).

Wittmann et al., Role of DptE and DptF in the lipidation reaction of daptomycin., FEBS Journal., 275: 5343-5353 (2008).

Written Opinion for PCT/US2014/029150, 5 pages (dated Aug. 7, 2014).

Yuan et al., Fatty Acid Biosynthsis in Pseudomonas aeruginosa Is Initiated by the FabY Class of β-Ketoacyl Acyl Carrier Protein Synthases, Journal of Bacteriology, 194(19): 5174-5184 (2012).

Zhang et al., Catalytic promiscuity of a bacterial α-N-methyltransferase., FEBS Letters., 586(19): 3391-3397 (2012).

GenBank Accession No. AAX31555.1, acyl-CoA ligase [Streptomyces roseosporus NRRL 11379], 2 pages (Jul. 26, 2016). [Retrieved Apr. 21, 2017].

GenBank Accession No. AAX31556.1, probable acyl carrier protein [Streptomyces roseosporus NRRL 11379], 1 page (Jul. 26, 2016). [Retrieved Apr. 21, 2017].

Aron et al., FenF: Servicing the Mycosubtilin Synthetase Assembly Line in trans, ChemBioChem, 8: 613-616 (2007).

Hansen et al., The Loading Module of Mycosubtilin: An adenylation Domain with fatty Acid Selectivity., J Am Chem Soc., 129(20): 6366-6367 (2007).

Kaneda and Smith., Relationship of primer specificity of fatty acid de novo synthetase to fatty acid composition in 10 species of bacteria and yeasts., Can. J. Microbiol, 26(8): 893-898 (1980).

Kleinkauf, H. and Von Dohren, H. Biosynthesis of Peptide Antibiotics, Annu. Rev. Microbiology., 41: 259-289 (1987).

Krass et al., Functional Dissection of Surfactin Synthetase Initiation Module Reveals Insights into the Mechanism of Lipoinitiation., Chemistry & Biology, 17: 872-880 (2010).

Lee et al., Clothing of srfA operon from Bacillus subtillis C9 and its expression *E.coli.*, Appl Microbiol Biotechnol., 75(3): 567-572 (2007).

Quadri et al., Characterization of Sfp, A Bacillus subtilis phosphopantetheinyl transferase for peptididyl carrier domains in peptide synthetases, Biochemistry., 37(6): 1585-1595 (1998).

Reznik et al., Use of sustainable chemistry to produce an acyl amino acid surfactant., Appl Microbiol. Biotechnol., Online (2010).

Simon and Shokat., A method to site-specifically incorporate methyl-lysine analogues into recombinant proteins., Methods in Enzymology., 512: Nucleosomes: Histones & Chromatin, Part A (2012).

\* cited by examiner

Anionic Surfactants cocoyl glycinate $$CH_3 - (CH_2)_{8-12} - CO - NH - \begin{matrix} CH_2 \\ | \\ COO^- \end{matrix}$$

(one carboxyl group)

+ a 10-14 carbon fatty acid component

FIGURE 4

GENERATION OF ACYL AMINO ACIDS

CROSS-REFERENCE TO RELATED APPLICATIONS

This application is a U.S. national stage application under 35 U.S.C. § 371 of International patent application no. PCT/US2014/029150, filed Mar. 14, 2014, which claims the benefit of U.S. Provisional Application No. 61/788,346, filed Mar. 15, 2013, the contents of each of which are hereby incorporated herein in their entirety.

SEQUENCE LISTING

The present specification makes reference to a Sequence Listing (submitted electronically as a .txt file named "Sequence_Listing.txt" on Sep. 15, 2015). The .txt file was generated on May 30, 2014 and is 19.9 kilobytes in size. The entire contents of the Sequence listing are hereby incorporated by reference.

BACKGROUND

Acyl amino acids are commercially important compounds. Many have advantageous characteristics and are sold as surfactants, antibiotics, anti-insect agents and as a variety of other important agents.

Traditionally, acyl amino acids have been manufactured chemically. Such chemical manufacturing methods are hampered by a variety of shortcomings including the ease of obtaining and storing the starting materials, the necessity of using harsh and sometimes dangerous chemical reagents in the manufacturing process, the difficulty and efficiency of the synthesis itself, the fiscal and environmental cost of disposing of chemical by-products, etc. Thus, new compositions and methods for the efficient and cost-effective synthesis of acyl amino acids and manufacture on a commercial scale would be beneficial.

Recently, important technologies have been developed that permit production of acyl amino acids by engineered peptide synthetase polypeptides (See U.S. Pat. No. 7,981,685, issued Jul. 19, 2011 and incorporated herein by reference in its entirety). Improvements and/or supplements to such technologies would be desirable and beneficial.

SUMMARY OF THE INVENTION

In certain embodiments, the present invention comprises compositions and methods useful in the generation of acyl amino acids. In certain embodiments, the present invention provides an engineered polypeptide comprising a peptide synthetase domain; in some such embodiments, the engineered polypeptide comprises only a single peptide synthetase domain. In some embodiments, the present invention provides an engineered peptide synthetase that is substantially free of a thioesterase domain, and/or a reductase domain.

In certain embodiments, the present invention provides an acyl amino acid composition comprising a plurality of different forms of an acyl amino acid. In some such compositions, substantially all of the acyl amino acids within the composition contain the same amino acid moiety and differ with respect to acyl moiety. We also described populations where the fatty acid si for example 95% one length (C14, myristic)

In some embodiments, the present invention provides a method of making an acyl amino acid composition by contacting an engineered peptide synthetase with an amino acid substrate and an acyl entity substrate for the engineered peptide synthetase, under conditions and for a time sufficient for an acyl amino acid composition to be made. In some embodiments, the method comprises providing a cell engineered to express the engineered peptide synthetase. In some embodiments, the engineered peptide synthetase does not include a thioesterase domain; in some embodiments, the engineered peptide synthestase does not include a reductase domain; in some embodiments, the engineered peptide synthetase includes neither a thioesterase domain not a reductase domain.

In some embodiments, an amino acid substrate is or comprises an amino acid as set forth herein.

In some embodiments, an acyl entity substrate is or comprises a fatty acid moiety. In some embodiments, an acyl entity substrate is or comprises a fatty acid.

The present invention provides cells engineered to express at least one engineered peptide synthetase that synthesizes an acyl amino acid.

In some embodiments, the present invention comprises an acyl amino acid composition produced by an engineered peptide synthetase.

The present invention provides methods of preparing a product comprising: providing or obtaining an acyl amino acid composition prepared in an engineered host (e.g., microbial) cell; optionally enriching the acyl amino acid composition for a particular acyl amino acid; and, in some embodiments, combining the enriched acyl amino acid composition with at least one other component to produce a product.

In some embodiments, the invention provides a method comprising steps of: contacting an engineered peptide synthetase polypeptide that comprises a single peptide synthetase domain and lacks either of a thioesterase domain, and/or a reductase domain with (i) an amino acid substrate of the peptide synthetase polypeptide; and (ii) an acyl moiety substrate of the peptide synthetase polypeptide, the contacting being performed under conditions and for a time sufficient that the engineered peptide synthetase polypeptide covalently links the acyl moiety from the acyl moiety substrate to the amino acid so that an acyl amino acid is generated.

BRIEF DESCRIPTION OF THE DRAWING

FIG. 4 depicts cocoyl glycinate.

DESCRIPTION OF CERTAIN EMBODIMENTS

Definitions

Figure 1:
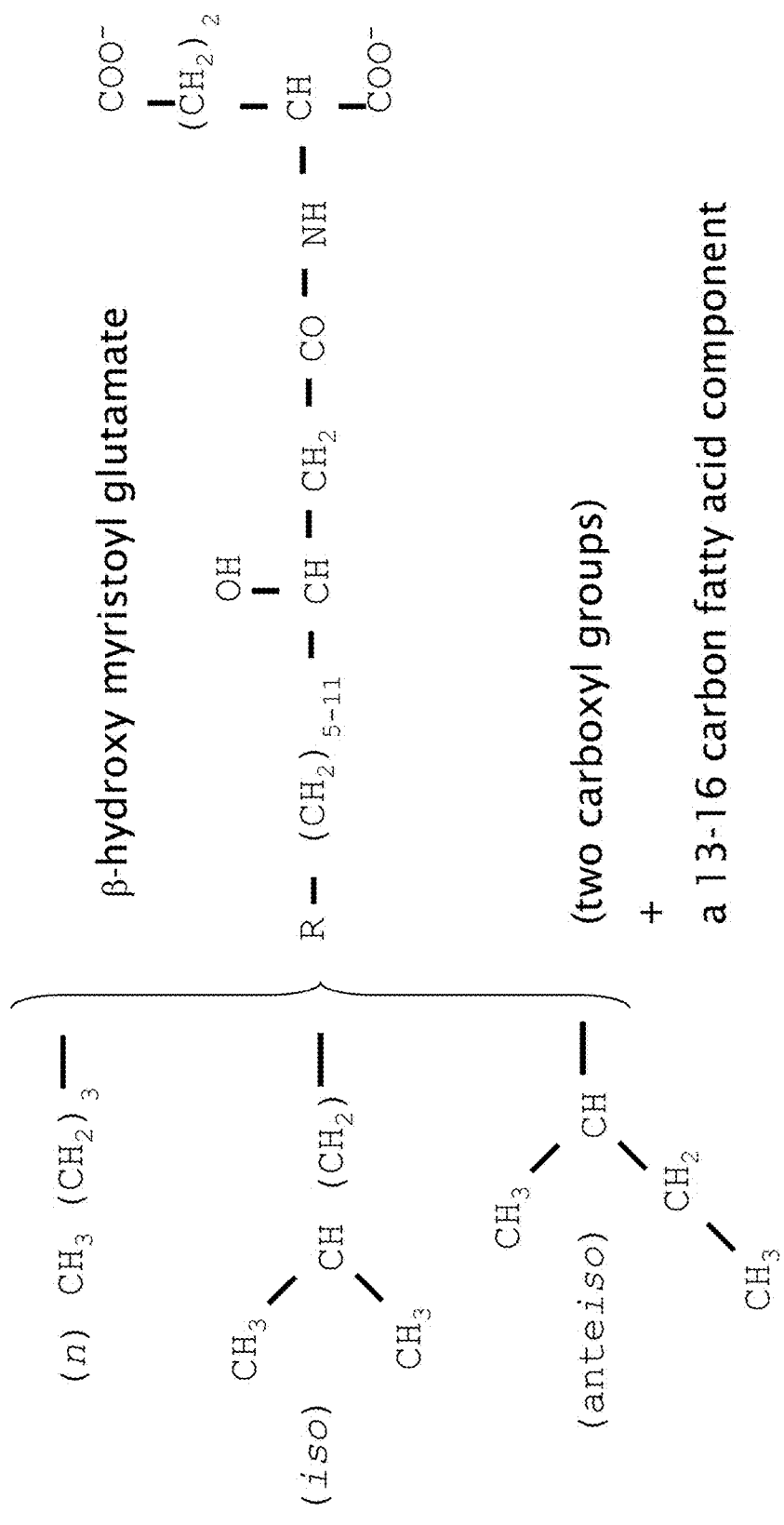
FIG. 1 depicts β-hydroxy myristoyl glutamate.
Figure 2:
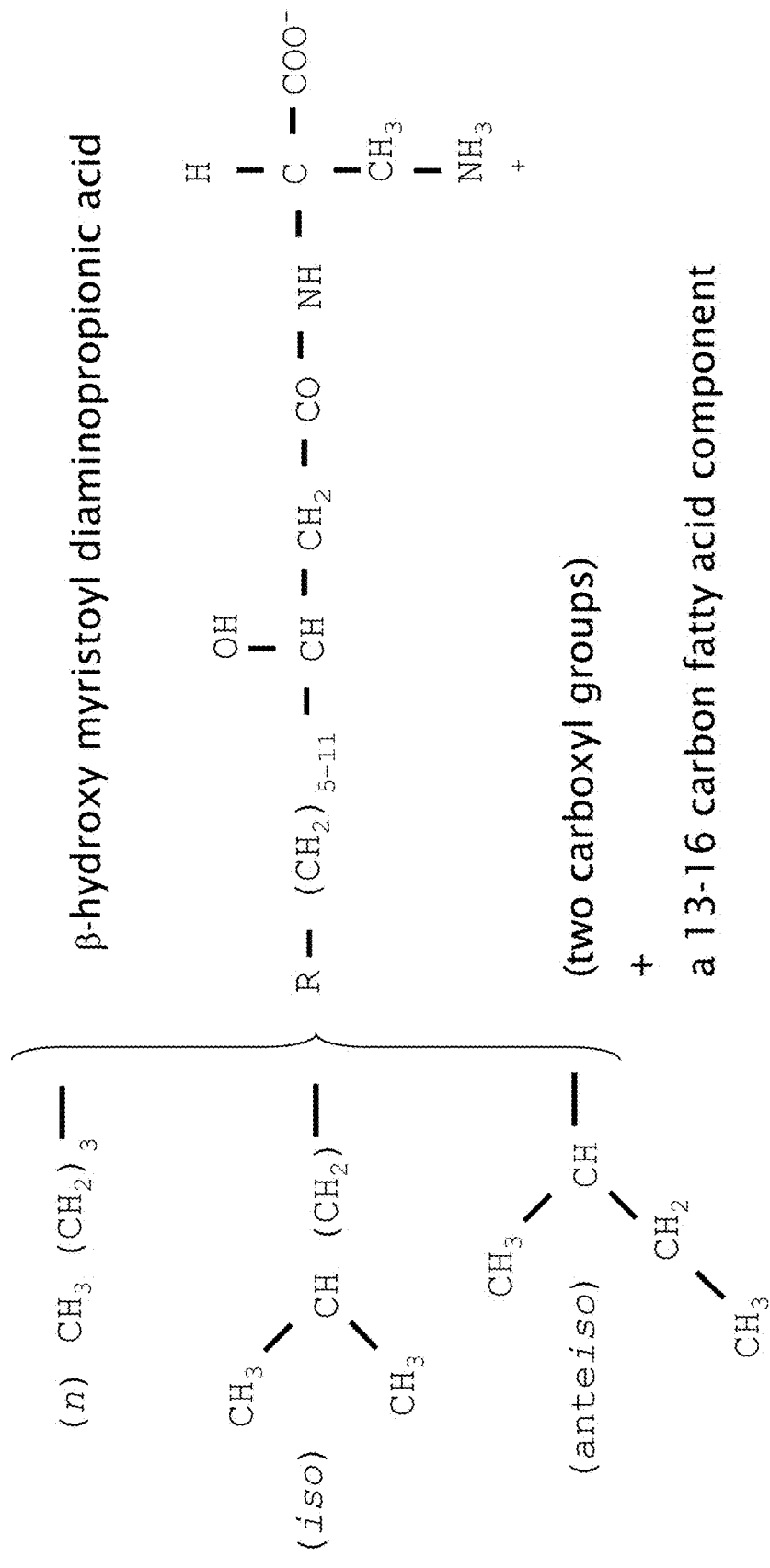
FIG. 2 depicts β-hydroxy myristoyl diaminopropionic acid, as further described in Example 6.
Figure 3:
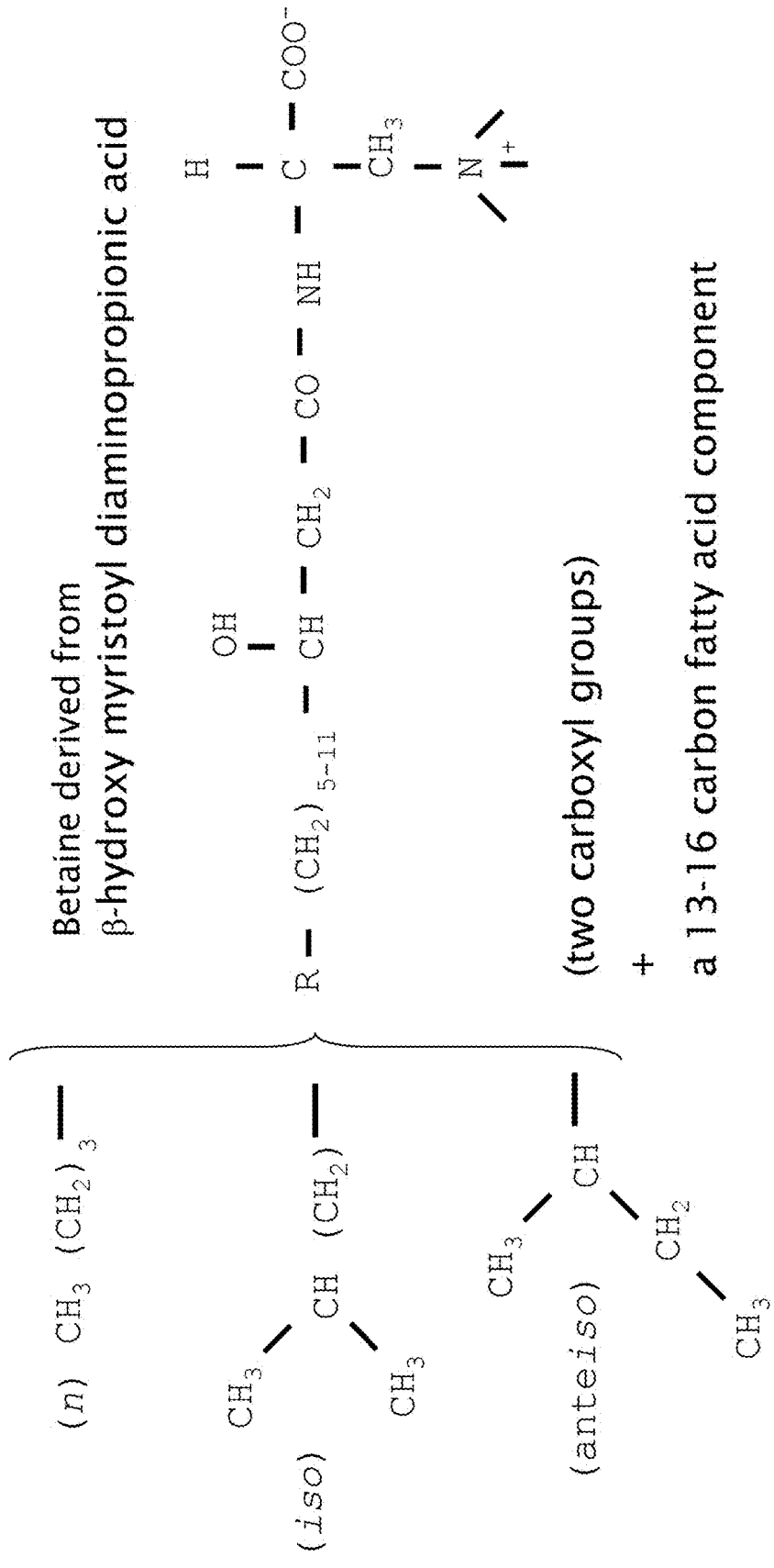
FIG. 3 depicts a betaine derived from β-hydroxy myristoyl diaminopropionic acid.

Acyl amino acid: The term "acyl amino acid" as used herein refers to an amino acid that is covalently linked to a fatty acid moiety. In some embodiments, the amino acid and fatty acid are covalently linked via an amide bond formed between a carboxylic acid group of a fatty acid and an amino group of an amino acid. In some embodiments, a fatty acid moiety or entity utilized or included in an acyl amino acid includes a β-hydroxyl group; in some embodiments, a fatty acid moiety or entity utilized or included in an acyl amino acid does not include a β-hydroxyl group. In some embodiments, a fatty acid moiety utilized or included in an acyl amino acid includes a β-amino group; in some embodiments, a fatty acid moiety or entity utilized or included in an acyl amino acid does not include a β-amino group. In some embodiments, a fatty acid moiety utilized or included in an acyl amino acid is unmodified at the β-position.

Amino acid: As used herein, the term "amino acid," in its broadest sense, refers to any compound and/or substance that can be utilized in peptide synthesis (e.g., ribosomal or non-ribosomal synthesis). In some embodiments, an amino acid is any compound and/or substance that can be incorporated into a polypeptide chain, e.g., through formation of one or more peptide bonds. In some embodiments, an amino acid is any compound and/or substance that is a substrate for a peptide synthetase; in some such embodiments, an amino acid is any compound and/or substance onto which a peptide synthetase can link an acyl entity, for example through formation of an amide bond. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide. In some embodiments, a "naturally occurring" amino acid is one of the standard group of twenty amino acids that are the building blocks of polypeptides of most organisms, including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In certain embodiments a "naturally occurring" amino acid may be one of those amino acids that are used less' frequently and are typically not included in this standard group of twenty but are nevertheless still used by one or more organisms and incorporated into certain polypeptides. For example, the codons UAG and UGA normally encode stop codons in most organisms. However, in some organisms the codons UAG and UGA encode the amino acids selenocysteine and pyrrolysine. Thus, in certain embodiments, selenocysteine and pyrrolysine are naturally occurring amino acids.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Beta-hydroxy fatty acid linkage domain: The term "beta-hydroxy fatty acid linkage domain" as used herein refers to a polypeptide domain that covalently links a beta-hydroxy fatty acid to an amino acid to form an acyl amino acid. A variety of beta-hydroxy fatty acid linkage domains are known to those skilled in the art. However, different beta-hydroxy fatty acid linkage domains often exhibit specificity for one or more beta-hydroxy fatty acids. As one non-limiting example, the beta-hydroxy fatty acid linkage domain from surfactin synthetase is specific for the beta-hydroxy myristic acid, which contains 13 to 15 carbons in the fatty acid chain. Thus, the beta-hydroxy fatty acid linkage domain from surfactin synthetase can be used in accordance with the present invention to construct an engineered polypeptide useful in the generation of an acyl amino acid that comprises the fatty acid beta-hydroxy myristic acid.

Beta-hydroxy fatty acid: The term "beta-hydroxy fatty acid" as used herein refers to a fatty acid chain comprising a hydroxy group at the beta position of the fatty acid chain. As is understood by those skilled in the art, the beta position corresponds to the third carbon of the fatty acid chain, the first carbon being the carbon of the carboxylate group. Thus, when used in reference to an acyl amino acid of the present invention, where the carboxylate moiety of the fatty acid has been covalently attached to the nitrogen of the amino acid, the beta position corresponds to the carbon two carbons removed from the carbon having the ester group. A beta-hydroxy fatty acid to be used in accordance with the present invention may contain any number of carbon atoms in the fatty acid chain. As non-limiting examples, a beta-hydroxy fatty acid may contain 3, 4, 5, 6, 7, 8, 9, 10, 11, 12, 3, 14, 15, 15, 16, 17, 18, 19, 20 or more carbon atoms. Beta-hydroxy fatty acids to be used in accordance with the present invention may contain linear carbon chains, in which each carbon of the chain, with the exception of the terminal carbon atom and the carbon attached to the nitrogen of the amino acid, is directly covalently linked to two other carbon atoms. Additionally or alternatively, beta-hydroxy fatty acids to be used in accordance with the present invention may contain branched carbon chains, in which at least one carbon of the chain is directly covalently linked to three or more other carbon atoms. Beta-hydroxy fatty acids to be used in accordance with the present invention may contain one or more double bonds between adjacent carbon atoms. Alternatively, beta-hydroxy fatty acids to be used in accordance with the present invention may contain only single-bonds between adjacent carbon atoms. A non-limiting exemplary beta-hydroxy fatty acid that may be used in accordance with the present invention is or comprises a beta-hydroxy, acid which contains 13 to 15 carbons in the fatty acid chain; in some embodiments, an exemplary beta-hydroxy fatty acid that may be used in accordance with the present invention is or comprises myristic acid myrisitc is usually used to mean 14 carbons Those of ordinary skill in the art will be aware of various beta-hydroxy fatty acids that can be used in accordance with the present invention. Different beta-hydroxy fatty acid linkage domains that exhibit specificity for other beta-hydroxy fatty acids (e.g., naturally or non-naturally occurring beta-hydroxy fatty acids) may be used in accordance with the present invention to generate any acyl amino acid of the practitioner's choosing.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Combination therapy: As used herein, the term "combination therapy" refers to those situations in which a subject is simultaneously exposed to two or more therapeutic agents. In some embodiments, such agents are administered simultaneously; in some embodiments, such agents are administered sequentially; in some embodiments, such agents are administered in overlapping regimens.

Comparable: The term "comparable", as used herein, refers to two or more agents, entities, situations, sets of conditions, etc that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc to be considered comparable.

Corresponding to: As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Domain, Polypeptide domain: The terms "domain" and "polypeptide domain" as used herein generally refer to polypeptide moieties that display a particular activity, even when isolated (e.g., cleaved) from other polypeptides or polypeptide domains. In some embodiments, a polypeptide domain folds into a particular discrete structure in three-dimensional space. In some embodiments, a polypeptide domain within a longer polypeptide is separated from one or more other polypeptide domains within the longer polypeptide by virtue of a linker element, for example, that may comprise a substantially unstructured stretch of amino acids. In some embodiments, the terms refer to domains that naturally occur in longer polypeptides; in some embodiments, the term refers to engineered polypeptide moieties that correspond and/or show significant homology and/or identity to such naturally occurring polypeptide moieties, or to other reference polypeptide moieties (e.g., historical engineered moieties). In some embodiments, an engineered domain that corresponds and/or shows significant homology and/or identity to a naturally occurring or other reference moiety shares a characteristic structure (e.g., primary structure such as the amino acid sequence of the domain, and/or secondary, tertiary, quaternary, etc. structures); alternatively or additionally, such an engineered domain may exhibit one or more distinct functions that it shares with its reference polypeptide moieties. As will be understood by those skilled in the art, in many cases polypeptides are modular and are comprised of one or more polypeptide domains; in some such embodiments, each domain exhibits one or more distinct functions that contribute to the overall function of the polypeptide. In some embodiments, the structure and/or function of many such domains are known to those skilled in the art.

Engineered: The term "engineered" as used herein refers to a non-naturally occurring moiety that has been created by the hand of man. For example, in reference to a polypeptide, an "engineered polypeptide" refers to a polypeptide that has been designed and/or produced by the hand of man. In some embodiments, an engineered polypeptide has an amino acid sequence that includes one or more sequence elements that do(es) not occur in nature. In some embodiments, an engineered polypeptide has an amino acid sequence that includes one or more sequence elements that does occur in nature, but that is present in the engineered polypeptide in a different sequence context (e.g., separated from at least one sequence to which it is linked in nature and/or linked with at least one sequence element to which it is not linked in nature) from that in which it occurs in nature. In some embodiments, an engineered polypeptide is one in which naturally-occurring sequence element(s) is/are separated from at least one sequence with which they/it is associated (e.g., linked) in nature and/or is otherwise manipulated to comprise a polypeptide that does not exist in nature. In various embodiments, an engineered polypeptide comprises two or more covalently linked polypeptide domains. Typically such domains will be linked via peptide bonds, although the present invention is not limited to engineered polypeptides comprising polypeptide domains linked via peptide bonds, and encompasses other covalent linkages known to those skilled in the art. One or more covalently linked polypeptide domains of engineered polypeptides may be naturally occurring. Thus, in certain embodiments, engineered polypeptides of the present invention comprise two or more covalently linked domains, at least one of which is naturally occurring. In certain embodiments, two or more naturally occurring polypeptide domains are covalently linked to generate an engineered polypeptide. For example, naturally occurring polypeptide domains from two or more different polypeptides may be covalently linked to generate an engineered polypeptide. In certain embodiments, naturally occurring polypeptide domains of an engineered polypeptide are covalently linked in nature, but are covalently linked in the engineered polypeptide in a way that is different from the way the domains are linked nature. For example, two polypeptide domains that naturally occur in the same polypeptide but which are separated by one or more intervening amino acid residues may be directly covalently linked (e.g., by removing the intervening amino acid residues) to generate an engineered polypeptide of the present invention. Additionally or alternatively, two polypeptide domains that naturally occur in the same polypeptide which are directly covalently linked together (e.g., not separated by one or more intervening amino acid residues) may be indirectly covalently linked (e.g., by inserting one or more intervening amino acid residues) to generate an engineered polypeptide of the present invention. In certain embodiments, one or more covalently linked polypeptide domains of an engineered polypeptide may not exist naturally. For example, such polypeptide domains may be engineered themselves.

Fatty acid linkage domain: The term "fatty acid linkage domain" as used herein refers to a polypeptide domain that covalently links a fatty acid to an amino acid to form an acyl amino acid. In some embodiments, a fatty acid linkage domain is a condensation domain; in some embodiments such a fatty acid linkage domain is part of a single polypeptide or a polypeptide complex with at least or only an adenylkation domain, a thiolation domain, or both. A variety of fatty acid linkage domains are known in the art, such as for example, fatty acid linkage domains present in various peptide synthetase complexes that produce lipopeptides. In certain embodiments, a fatty acid linkage domain links a beta-hydroxy fatty acid to an amino acid; in some embodiments, a fatty acid linkage domain links a beta-amino fatty acid to an amino acid; in some embodiments, a fatty acid linkage domain links a fatty acid that is unmodified at the beta position to an amino acid. In some embodiments, a fatty acid linkage domain catalyzes condensation of a fatty acid and an amino acid so that an amide both is formed, for example between a carboxylic acid moiety on a fatty acid and an amino moiety on an amino acid.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

Naturally occurring: The term "naturally occurring", as used herein, refers to an agent or entity that is known to exist in nature.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Peptide synthetase complex: The term "peptide synthetase complex" as used herein refers to an enzyme that catalyzes the non-ribosomal production of peptides. As will be appreciated by those of ordinary skill in the art, peptide synthetase complexes are modular, and are comprised of individual peptide synthetase modules that perform different steps in the synthesis of the ultimate peptide; typically, each module performs one step (e.g., adds a single amino acid). A peptide synthetase complex may comprise a single enzymatic subunit (e.g., a single polypeptide), or may comprise two or more enzymatic subunits (e.g., two or more polypeptides). A peptide synthetase complex typically comprises at least one peptide synthetase domain, and may further comprise one or more additional domains such as for example, a fatty acid linkage domain, a thioesterase domain, a reductase domain, etc. Peptide synthetase domains of a peptide synthetase complex may comprise two or more enzymatic subunits, with two or more peptide synthetase domains present in a given enzymatic subunit. For example the surfactin peptide synthetase complex (also referred to herein simply as "surfactin synthetase complex") comprises three distinct polypeptide enzymatic subunits: the first two subunits comprise three peptide synthetase domains, while the third subunit comprises a single peptide synthetase domain.

Peptide synthetase domain: The term "peptide synthetase domain" as used herein refers to a polypeptide domain that minimally comprises three domains: an adenylation (A) domain, responsible for selectively recognizing and activating a specific amino acid, a thiolation (T) domain, which tethers the activated amino acid to a cofactor via thioester linkage, and a condensation (C) domain, which links amino acids joined to successive units of the peptide synthetase by the formation of amide bonds. A peptide synthetase domain typically recognizes and activates a single, specific amino acid, and in the situation where the peptide synthetase domain is not the first domain in the pathway, links the specific amino acid to the growing peptide chain.

Polypeptide: The term "polypeptide" as used herein refers to a series of amino acids joined together in peptide linkages. In some embodiments, a "polypeptide" has a structure as achieve through synthesis by ribosomal machinery in naturally occurring organisms. In some embodiments a "polpeptide" has a structure as achieved through chemical synthesis (e.g., in vitro). In some embodiments, a "polypeptide" has a structure as achieved through joining of a series of amino acids joined together by non-ribosomal machinery, such as by way of non-limiting example, polypeptides synthesized by peptide synthetases. Such non-ribosomally produced polypeptides exhibit a greater diversity in covalent linkages than polypeptides synthesized by ribosomes (although those skilled in the art will understand that the amino acids of ribosomally-produced polypeptides may also be linked by covalent bonds that are not peptide bonds, such as the linkage of cystines via di-sulfide bonds). In some embodiments, the term is used to refer to specific functional classes of polypeptides, such as, for example, autoantigen polypeptides, nicotinic acetylcholine receptor polypeptides, alloantigen polypeptides, etc. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. Polypeptides can be two or more amino acids in length, although most polypeptides produced by ribosomes and peptide synthetases are longer than two amino acids. For example, in some embodiments, polypeptides may be 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, 1000, 2000, 3000, 4000, 5000, 6000, 7000, 8000, 9000, 10,000 or more amino acids in length.

Reductase Domain: The term "reductase domain" as used herein refers to a polypeptide domain that catalyzes release of an acyl amino acid produced by a peptide synthetase complex from the peptide synthetase complex. In certain embodiments, a reductase domain is covalently linked to a peptide synthetase domain and a fatty acid linkage domain such as a beta-hydroxy fatty acid linkage domain to generate an engineered polypeptide useful in the synthesis of an acyl amino acid. A variety of reductase domains are found in nature in nonribosomal peptide synthetase complexes from a variety of species. A non-limiting example of a reductase domain that may be used in accordance with the present invention includes the reductase domain from linear gramicidin (ATCC8185). However, any reductase domain that releases an acyl amino acid produced by a peptide synthetase complex from the peptide synthetase complex may be used in accordance with the present invention. In some embodiments, reductase domains are characterized by the presence of the consensus sequence: [LIVSPADNK]-x(9)-{P}-x(2)-Y-[PSTAGNCV]-[STAGNQCIVM]-[STAGC]-K-{PC}-[SAGFYR]-[LIVMSTAGD]-x-{K}-[LIVMFY-WHD]-x-{YR}-[LIVMFYWGAPTHQ]-[GSACQRHM] (SEQ ID NO: 1), where square brackets ("[ ]") indicate amino acids that are typically present at that position, squiggly brackets ("{ }") indicate amino acids that amino acids that are typically not present at that position, and "x" denotes any amino acid or a gap. X(9) for example denotes any amino acids or gaps for nine consecutive positions. Those skilled in the art will be aware of methods to determine whether a give polypeptide domain is a reductase domain.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Surfactin: Surfactin is cyclic lipopeptide that is naturally produced by certain bacteria, including the Gram-positive endospore-forming bacteria *Bacillus subtilis*. Surfactin is an amphiphilic molecule (having both hydrophobic and hydrophilic properties) and is thus soluble in both organic solvents and water. Surfactin exhibits exceptional surfactant properties, making it a commercially valuable molecule. Due to its surfactant properties, surfactin also functions as an antibiotic. For example, surfactin is known to be effective as an anti-bacterial, anti-viral, anti-fungal, anti-*mycoplasma* and hemolytic compound. Surfactin is capable of penetrating the cell membranes of all types of bacteria, including both Gram-negative and Gram-positive bacteria, which differ in the composition of their membrane. Gram-positive bacteria have a thick peptidoglycan layer on the outside of their phospholipid bilayer. In contrast, Gram-negative bacteria have a thinner peptidoglycan layer on the outside of their phospholipid bilayer, and further contain an additional outer lipopolysaccharide membrane. Surfactin's surfactant activity permits it to create a permeable environment for the lipid bilayer and causes disruption that solubilizes the membrane of both types of bacteria. In order for surfactin to carry out minimal antibacterial effects, the minimum inhibitory concentration (MIC) is in the range of 12-50 µg/ml. In addition to its antibacterial properties, surfactin also exhibits antiviral properties, and its known to disrupt enveloped viruses such as HIV and HSV. Surfactin not only disrupts the lipid envelope of viruses, but also their capsids through ion channel formations. Surfactin isoforms containing fatty acid chains with 14 or 15 carbon atoms exhibited improved viral inactivation, thought to be due to improved disruption of the viral envelope. Surfactin consists of a seven amino acid peptide loop, and a hydrophobic fatty acid chain (beta-hydroxy myristic acid) that is thirteen to fifteen carbons long. The fatty acid chain allows permits surfactin to penetrate cellular membranes. The peptide loop comprises the amino acids L-asparagine, L-leucine, glycine, L-leucine, L-valine and two D-leucines. Glycine and asparagine residues at positions 1 and 6 respectively, constitute a minor polar domain. On the opposite side, valine residue at position 4 extends down facing the fatty acid chain, making up a major hydrophobic domain. Surfactin is synthesized by the surfactin synthetase complex, which comprises the three surfactin synthetase polypeptide subunits SrfA-A, SrfA-B, and SrfA-C. The surfactin synthetase polypeptide subunits SrfA-A and SrfA-B each comprise three peptide synthetase domains, each of which adds a single amino acid to the growing surfactin peptide, while the monomodular surfactin synthetase polypeptide subunit SrfA-C comprises a single peptide synthetase domain and adds the last amino acid residue to the heptapeptide. Additionally the SrfA-C subunit comprises a thioesterase domain, which catalyzes the release of the product via a nucleophilic attack of the beta-hydroxy of the fatty acid on the carbonyl of the C-terminal Leu of the peptide, cyclizing the molecule via formation of an ester. The spectrum of the beta-hydroxy fatty acids was elucidated as iso, anteiso C13, iso, normal C14 and iso, anteiso C15, and a recent study has indicated that surfactin retains an R configuration at C-beta (Nagai et al., Study on surfactin, a cyclic depsipeptide. 2. Synthesis of surfactin B2 produced by *Bacillus* natto KMD 2311. Chem Pharm Bull (Tokyo) 44: 5-10, 1996).

Surfactin is a lipopeptide synthesized by the surfactin synthetase complex. Surfactin comprises seven amino acids, which are initially joined by peptide bonds, as well as a beta-hydroxy fatty acid covalently linked to the first amino acid, glutamate. However, upon addition the final amino acid (leucine), the polypeptide is released and the thioesterase domain of the SRFC protein catalyzes the release of the product via a nucleophilic attack of the beta-hydroxy of the fatty acid on the carbonyl of the C-terminal Leu of the peptide, cyclizing the molecule via formation of an ester, resulting in the C-terminus carboxyl group of leucine attached via a lactone bond to the b-hydroxyl group of the fatty acid.

Thioesterase domain: The term "thioesterase domain" as used herein refers to a polypeptide domain that catalyzes release of an acyl amino acid produced by a peptide synthetase complex from the peptide synthetase complex. A variety of thioesterase domains are found in nature in nonribosomal peptide synthetase complexes from a variety of species. A non-limiting example of a thioesterase domain that may be used in accordance with the present invention includes the thioesterase domain from the *Bacillus subtilis* surfactin synthetase complex, present in Srf-C subunit. However, any thioesterase domain that releases an acyl amino acid produced by a peptide synthetase complex from the peptide synthetase complex may be used in accordance with the present invention. In some embodiments, thioesterase domains are characterized by the presence of the consensus sequence: [LIV]-{KG}-[LIVFY]-[LIVMST]-G-[HYWV]-S-{YAG}-G-[GSTAC] (SEQ ID NO: 2), where square brackets ("[ ]") indicate amino acids that are typically present at that position, and squiggly brackets ("{ }") indicate amino acids that amino acids that are typically not present at that position. Those skilled in the art will be aware of methods to determine whether a give polypeptide domain is a thioesterase domain.

Engineered Polypeptides Useful in the Generation of Acyl Amino Acids

The present invention provides compositions and methods for the generation of acyl amino acids. In certain embodiments, compositions of the present invention comprise engineered polypeptides that are useful in the production of acyl amino acids. In certain embodiments, engineered polypeptides of the present invention comprise a peptide synthetase domain.

In one aspect, the present invention encompasses the recognition that a single peptide synthetase domain, not associated (e.g., not associated covalently and/or not otherwise associated) with, for example, another domain typically found in a peptide synthetase complex (e.g., a fatty acid linkage domain, a thioesterase domain, a reductase domain, etc. and/or a combination thereof), can be sufficient to produce an acyl amino acid as described herein.

In accordance with many embodiments of the present invention, peptide synthetase domains useful for the production of acyl amino acids as described herein, correspond and/or show significant homology and/or identity to a first peptide synthetase domain found in a naturally-occurring peptide synthetase complex. That is, as is known in the art, some peptide synthetase domains (i.e., some polypeptides comprising adenylation (A), thiolation (T), and condensation (C) domains) catalyze condensation of a fatty acid with an amino acid, and some catalyze condensation of two amino acids with one another. In accordance with the some embodiments of the present invention, peptide synthetase domains useful for the production of acyl amino acids as described herein are those that catalyze condensation of an amino acid with a fatty acid; such peptide synthetase domains are typically utilized herein in a form (e.g., as part of a polypeptide) that is separated from and/or does not include another peptide synthetase domain. Many naturally-occurring peptide synthetase domains are found in nature within peptide synthetase complexes that synthesize lipopeptides. Such peptide synthetase complexes are multienzymatic complexes found in both prokaryotes and eukaryotes, and comprising one or more enzymatic subunits that catalyze the non-ribosomal production of a variety of peptides (see, for example, Kleinkauf et al., Annu. Rev. Microbiol. 41:259-289, 1987; see also U.S. Pat. No. 5,652,116 and U.S. Pat. No. 5,795,738). Non-ribosomal synthesis is also known as thiotemplate synthesis (see e.g., Kleinkauf et al.). Peptide synthetase complexes typically include one or more peptide synthetase domains that recognize specific amino acids and are responsible for catalyzing addition of the amino acid to the polypeptide chain.

The catalytic steps in the addition of amino acids typically include: recognition of an amino acid by the peptide synthetase domain, activation of the amino acid (formation of an amino-acyladenylate), binding of the activated amino acid to the enzyme via a thioester bond between the carboxylic group of the amino acid and an SH group of an enzymatic co-factor, which cofactor is itself bound to the enzyme inside each peptide synthetase domain, and formation of the peptide bonds among the amino acids.

A peptide synthetase domain comprises subdomains that carry out specific roles in these steps to form the peptide product. One subdomain, the adenylation (A) domain, is responsible for selectively recognizing and activating the amino acid that is to be incorporated by a particular unit of the peptide synthetase. The activated amino acid is joined to the peptide synthetase through the enzymatic action of another subdomain, the thiolation (T) domain, that is generally located adjacent to the A domain. Amino acids joined to successive units of the peptide synthetase are subsequently linked together by the formation of amide bonds catalyzed by another subdomain, the condensation (C) domain.

Peptide synthetase domains that catalyze the addition of D-amino acids often also have the ability to catalyze the recemization of L-amino acids to D-amino acids. Peptide synthetase complexes also typically include a conserved thioesterase domain that terminates the growing amino acid chain and releases the product.

The genes that encode peptide synthetase complexes have a modular structure that parallels the functional domain structure of the complexes (see, for example, Cosmina et al., Mol. Microbiol. 8:821, 1993; Kratzxchmar et al., J. Bacteriol. 171:5422, 1989; Weckermann et al., Nuc. Acids res. 16:11841, 1988; Smith et al., EMBO J. 9:741, 1990; Smith et al., EMBO J. 9:2743, 1990; MacCabe et al., J. Biol. Chem. 266:12646, 1991; Coque et al., Mol. Microbiol. 5:1125, 1991; Diez et al., J. Biol. Chem. 265:16358, 1990).

Hundreds of peptides are known to be produced by peptide synthetase complexes. Such nonribosomally-produced peptides often have non-linear structures, including cyclic structures exemplified by the peptides surfactin, cyclosporin, tyrocidin, and mycobacillin, or branched cyclic structures exemplified by the peptides polymyxin and bacitracin. Moreover, such nonribosomally-produced peptides may contain amino acids not usually present in ribosomally-produced polypeptides such as for example norleucine, beta-alanine and/or ornithine, as well as D-amino acids. Additionally or alternatively, such nonribosomally-produced peptides may comprise one or more non-peptide moieties that are covalently linked to the peptide. As one non-limiting example, surfactin is a cyclic lipopeptide that comprises a beta-hydroxy fatty acid covalently linked to the first glutamate of the lipopeptide. Other non-peptide moieties that are covalently linked to peptides produced by peptide synthetase complexes are known to those skilled in the art, including for example sugars, chlorine or other halogen groups, N-methyl and N-formyl groups, glycosyl groups, acetyl groups, etc.

Typically, each amino acid of the non ribosomally-produced peptide is specified by a distinct peptide synthetase domain. For example, the surfactin synthetase complex which catalyzes the polymerization of the lipopeptide surfactin consists of three enzymatic subunits. The first two subunits each comprise three peptide synthetase domains, whereas the third has only one. These seven peptide synthetase domains are responsible for the recognition, activation, binding and polymerization of L-Glu, L-Leu, D-Leu, L-Val, L-Asp, D-Leu and L-Leu, the amino acids present in surfactin.

A similar organization in discrete, repeated peptide synthetase domains occurs in various peptide synthetase genes in a variety of species, including bacteria and fungi, for example srfA (Cosmina et al., Mol. Microbiol. 8, 821-831, 1993), grsA and grsB (Kratzxchmar et al., J. Bacterial. 171, 5422-5429, 1989) tycA and tycB (Weckermann et al., Nucl. Acid. Res. 16, 11841-11843, 1988) and ACV from various fungal species (Smith et al., EMBO J. 9, 741-747, 1990; Smith et al., EMBO J. 9, 2743-2750, 1990; MacCabe et al., J. Biol. Chem. 266, 12646-12654, 1991; Coque et al., Mol. Microbiol. 5, 1125-1133, 1991; Diez et al., J. Biol. Chem. 265, 16358-16365, 1990). The peptide synthetase domains of even distant species contain sequence regions with high homology, some of which are conserved and specific for all the peptide synthetases. Additionally, certain sequence regions within peptide synthetase domains are even more highly conserved among peptide synthetase domains which recognize the same amino acid (Cosmina et al., Mol. Microbiol. 8, 821-831, 1992).

Exemplary lipopeptides synthesized by peptide synthetase complexes in nature are listed below in Table 1 (See also the NORINE database, which provides access to information on peptides and lipopeptides that are known to be, or in some cases believed to be, produced by peptide synthetase enzymes; still further, see Segolene et al. (Ref 4)).

TABLE 1

Exemplary Lipopeptides Synthesized by Peptide Synthetases

| Lipopeptide Name | Fatty Acid Component | Fatty Acid Component name |
|---|---|---|
| [Ala4]surfactin aC15 | aC15:0-OH(3) | 3-hydroxy-12-methyl-tetradecanoic acid |
| [Ala4]surfactin iC14 | iC14:0-OH(3) | 3-hydroxy-12-methyl-tridecanoic acid |
| [Ala4]surfactin iC15 | iC15:0-OH(3) | 3-hydroxy-13-methyl-tetradecanoic acid |
| [Ala4]surfactin nC14 | C14:0-OH(3) | 3-hydroxy-tetradecanoic acid |
| [Ala4]surfactin nC15 | C15:0-OH(3) | 3-hydroxy-pentadecanoic acid |
| [Gln1]surfactin | C15:0-OH(3) | 3-hydroxy-pentadecanoic acid |
| [Gln1]surfactin aC15 | aC15:0-OH(3) | 3-hydroxy-12-methyl-tetradecanoic acid |
| [Gln1]surfactin iC15 | iC15:0-OH(3) | 3-hydroxy-13-methyl-tetradecanoic acid |
| [Ile2.4.7]surfactin | aC15:0-OH(3) | 3-hydroxy-12-methyl-tetradecanoic acid |
| [Ile4.7]surfactin | aC15:0-OH(3) | 3-hydroxy-12-methyl-tetradecanoic acid |
| [Ile4]surfactin | aC15:0-OH(3) | 3-hydroxy-12-methyl-tetradecanoic acid |
| [Ile7]surfactin | aC15:0-OH(3) | 3-hydroxy-12-methyl-tetradecanoic acid |
| [Leu4]surfactin | aC15:0-OH(3) | 3-hydroxy-12-methyl-tetradecanoic acid |
| [Phe25]syringopeptin 25A | C10:0-OH(3) | 3-hydroxy-decanoic acid |
| [Val7]surfactin | aC15:0-OH(3) | 3-hydroxy-12-methyl-tetradecanoic acid |
| A21978C1 | aC11:0 | 8-methyldecanoic acid |
| A21978C2 | iC12:0 | 10-methylundecanoic acid |
| A21978C3 | aC13:0 | 10-methyldodecanoic acid |
| A54145 A | iC10:0 | decanoic acid |
| A54145 A1 | C10:0 | decanoic acid |
| A54145 B | C10:0 | decanoic acid |
| A54145 B1 | iC10:0 | decanoic acid |
| A54145 C | aC11:0 | 8-methyldecanoic acid |
| A54145 D | aC11:0 | 8-methyldecanoic acid |
| A54145 E | aC11:0 | 8-methyldecanoic acid |
| A54145 F | iC10:0 | decanoic acid |
| amphibactin B | C14:0-OH(3) | 3-hydroxy-tetradecanoic acid |
| amphibactin C | C16:1(9)-OH(3) | 3-hydroxy-9-hexadecenoic acid |
| amphibactin D | C14:0 | tetradecanoic acid |
| amphibactin E | C16:1(9) | 9-hexadecenoic acid |
| amphibactin F | C16:0-OH(3) | 3-hydroxy-hexadecanoic acid |
| amphibactin G | C18:1(9)-OH(3) | 3-hydroxy-9-octadecenoic acid |
| amphibactin H | C16:0 | hexadecanoic acid |
| amphibactin I | C18:1(9) | 9-octadecenoic acid |
| amphisin | C10:0-OH(3) | 3-hydroxy-decanoic acid |
| amphomycin A1437 A | iC13:1(3) | 11-methyl-3-dodecenoic acid |
| amphomycin A1437 B | iC14:1(3) | 12-methyl-3-tridecenoic acid |
| amphomycin A1437 D | aC15:1(3) | 12-methyl-3-tetradecenoic acid |
| amphomycin A1437 E | aC13:1(3) | 10-methyl-3-dodecenoic acid |
| apramide A | C8:0:1(7)-Me(2) | 2-methylact-7-ynoic acid |
| apramide B | C8:0:1(7) | oct-7-ynoic acid |
| apramide C | C9:1(8)-Me(2) | 2-methyl-8-noneic acid |
| apramide D | C8:0:1(7)-Me(2) | 2-methylact-7-ynoic acid |
| apramide E | C8:0:1(7) | oct-7-ynoic acid |
| apramide F | C9:1(8)-Me(2) | 2-methyl-8-noneic acid |
| apramide G | C8:0:1(7)-Me(2) | 2-methylact-7-ynoic acid |
| aquachelin A | C12:1(5) | 2-methyl-5-dodecenoic acid |
| aquachelin B | C12:0 | dodecanoic acid |
| aquachelin C | C14:1(7) | 7-tetradecenoic acid |
| aquachelin D | C14:0 | tetradecanoic acid |
| arthrofactin | C10:0-OH(3) | 3-hydroxy-decanoic acid |
| arylomycin A1 | iC11:0 | 9-methyldecanoic acid |
| arylomycin A2 | iC12:0 | 10-methylundecanoic acid |
| arylomycin A3 | C12:0 | dodecanoic acid |
| arylomycin A4 | aC13:0 | 10-methyldodecanoic acid |
| arylomycin A5 | iC14:0 | 12-methyl-tridecanoic acid |
| arylomycin B1 | iC11:0 | 9-methyldecanoic acid |
| arylomycin B2 | iC12:0 | 10-methylundecanoic acid |
| arylomycin B3 | C12:0 | dodecanoic acid |
| arylomycin B4 | aC13:0 | 10-methyldodecanoic acid |
| arylomycin B5 | iC13:0 | 11-methyldodecanoic acid |
| arylomycin B6 | iC14:0 | 12-methyl-tridecanoic acid |
| arylomycin B7 | aC15:0 | 12-methyltetradecanoic acid |
| bacillomycin D-1 | C14:0-NH2(3) | 3-amino-tetradecanoic acid |
| bacillomycin D-2 | iC15:0-NH2(3) | 3-amino-13-methyl-tetradecanoic acid |

TABLE 1-continued

Exemplary Lipopeptides Synthesized by Peptide Synthetases

| Lipopeptide Name | Fatty Acid Component | Fatty Acid Component name |
| --- | --- | --- |
| bacillomycin D-3 | aC15:0-NH2(3) | 3-amino-12-methyl-tetradecanoic acid |
| bacillomycin D-4 | C16:0-NH2(3) | 3-amino-hexadecanoic acid |
| bacillomycin D-5 | iC16:0-NH2(3) | 3-amino-14-methyl-pentadecanoic acid |
| bacillomycin F-1 | iC15:0-NH2(3) | 3-amino-13-methyl-tetradecanoic acid |
| bacillomycin F-2 | aC15:0-NH2(3) | 3-amino-12-methyl-tetradecanoic acid |
| bacillomycin F-3 | iC16:0-NH2(3) | 3-amino-14-methyl-pentadecanoic acid |
| bacillomycin F-4 | C16:0-NH2(3) | 3-amino-hexadecanoic acid |
| bacillomycin F-5 | iC17:0-NH2(3) | 3-amino-15-methyl-hexadecanoic acid |
| bacillomycin F-6 | aC17:0-NH2(3) | 3-amino-14-methyl-hexadecanoic acid |
| bacillomycin L-1 | C14:0-NH2(3) | 3-amino-tetradecanoic acid |
| bacillomycin L-2 | iC15:0-NH2(3) | 3-amino-13-methyl-tetradecanoic acid |
| bacillomycin L-3 | aC15:0-NH2(3) | 3-amino-12-methyl-tetradecanoic acid |
| bacillomycin L-4 | C16:0-NH2(3) | 3-amino-hexadecanoic acid |
| bacillomycin L-5 | iC16:0-NH2(3) | 3-amino-14-methyl-pentadecanoic acid |
| beauverolide A | C10:0-Me(4)—OH(3) | 3-hydroxy-4-methyl-decanoic acid |
| beauverolide B | C10:0-Me(4)—OH(3) | 3-hydroxy-4-methyl-decanoic acid |
| beauverolide Ba | C10:0-Me(4)—OH(3) | 3-hydroxy-4-methyl-decanoic acid |
| beauverolide C | C10:0-Me(4)—OH(3) | 3-hydroxy-4-methyl-decanoic acid |
| beauverolide Ca | C10:0-Me(4)—OH(3) | 3-hydroxy-4-methyl-decanoic acid |
| beauverolide D | C8:0-Me(4)—OH(3) | 4-methyl-3-hydroxy-octanoic acid |
| beauverolide E | C8:0-Me(4)—OH(3) | 4-methyl-3-hydroxy-octanoic acid |
| beauverolide Ea | C8:0-Me(4)—OH(3) | 4-methyl-3-hydroxy-octanoic acid |
| beauverolide F | C8:0-Me(4)—OH(3) | 4-methyl-3-hydroxy-octanoic acid |
| beauverolide Fa | C8:0-Me(4)—OH(3) | 4-methyl-3-hydroxy-octanoic acid |
| beauverolide H | C9:0-OH(3) | 3-hydroxy-nonanoic acid |
| beauverolide I | C8:0-Me(4)—OH(3) | 4-methyl-3-hydroxy-octanoic acid |
| beauverolide II | C10:0-Me(4)—OH(3) | 3-hydroxy-4-methyl-decanoic acid |
| beauverolide III | C8:0-Me(4)—OH(3) | 4-methyl-3-hydroxy-octanoic acid |
| beauverolide IV | C8:0-Me(4)—OH(3) | 4-methyl-3-hydroxy-octanoic acid |
| beauverolide Ja | C8:0-Me(4)—OH(3) | 4-methyl-3-hydroxy-octanoic acid |
| beauverolide Ka | C10:0-Me(4)—OH(3) | 3-hydroxy-4-methyl-decanoic acid |
| beauverolide L | C10:0-Me(4)—OH(3) | 3-hydroxy-4-methyl-decanoic acid |
| beauverolide La | C10:0-Me(4)—OH(3) | 3-hydroxy-4-methyl-decanoic acid |
| beauverolide M | C8:0-Me(4)—OH(3) | 4-methyl-3-hydroxy-octanoic acid |
| beauverolide N | C8:0-Me(4)—OH(3) | 4-methyl-3-hydroxy-octanoic acid |
| beauverolide V | C8:0-Me(4)—OH(3) | 4-methyl-3-hydroxy-octanoic acid |
| beauverolide VI | C8:0-Me(4)—OH(3) | 4-methyl-3-hydroxy-octanoic acid |
| beauverolide VII | C8:0-Me(4)—OH(3) | 4-methyl-3-hydroxy-octanoic acid |
| beauverolide VIII | C10:0-Me(4)—OH(3) | 3-hydroxy-4-methyl-decanoic acid |
| callipeltin A | iC8:0-Me(2.4)—OH(3) | 2,4,6-trimethyl-3-hydroxy-heptanoic acid |
| callipeltin C | iC8:0-Me(2.4)—OH(3) | 2,4,6-trimethyl-3-hydroxy-heptanoic acid |
| callipeltin D | iC8:0-Me(2.4)—OH(3) | 2,4,6-trimethyl-3-hydroxy-heptanoic acid |
| callipeltin F | iC8:0-Me(2.4)—OH(3) | 2,4,6-trimethyl-3-hydroxy-heptanoic acid |
| callipeltin G | iC8:0-Me(2.4)—OH(3) | 2,4,6-trimethyl-3-hydroxy-heptanoic acid |
| callipeltin H | iC8:0-Me(2.4)—OH(3) | 2,4,6-trimethyl-3-hydroxy-heptanoic acid |
| callipeltin I | iC8:0-Me(2.4)—OH(3) | 2,4,6-trimethyl-3-hydroxy-heptanoic acid |
| callipeltin J | iC8:0-Me(2.4)—OH(3) | 2,4,6-trimethyl-3-hydroxy-heptanoic acid |
| callipeltin K | iC8:0-Me(2.4)—OH(3) | 2,4,6-trimethyl-3-hydroxy-heptanoic acid |
| callipeltin L | iC8:0-Me(2.4)—OH(3) | 2,4,6-trimethyl-3-hydroxy-heptanoic acid |
| carmabin A | C10:0:1(9)-Me(2.4) | 2,4-dimethyl-dec-9-ynoic acid |
| carmabin B | C10:0-Me(2.4)-oxo(9) | 9-oxo-2,4-dimethyldecanoic acid |
| CDA1b | C6:0-Ep(2) | 2-epoxy-hexanoic acid |
| CDA2a | C6:0-Ep(2) | 2-epoxy-hexanoic acid |
| CDA2b | C6:0-Ep(2) | 2-epoxy-hexanoic acid |
| CDA2d | C6:0-Ep(2) | 2-epoxy-hexanoic acid |
| CDA2fa | C6:0-Ep(2) | 2-epoxy-hexanoic acid |

TABLE 1-continued

Exemplary Lipopeptides Synthesized by Peptide Synthetases

| Lipopeptide Name | Fatty Acid Component | Fatty Acid Component name |
| --- | --- | --- |
| CDA2fb | C6:0-Ep(2) | 2-epoxy-hexanoic acid |
| CDA3a | C6:0-Ep(2) | 2-epoxy-hexanoic acid |
| CDA3b | C6:0-Ep(2) | 2-epoxy-hexanoic acid |
| CDA4a | C6:0-Ep(2) | 2-epoxy-hexanoic acid |
| CDA4b | C6:0-Ep(2) | 2-epoxy-hexanoic acid |
| cormycin A | C16:0-OH(3.4) | 3,4-dihydroxy-hexadecanoic acid |
| corpeptin A | C10:0-OH(3) | 3-hydroxy-decanoic acid |
| corpeptin B | C12:1(5)-OH(3) | 3-hydroxy-5-dodecenoic acid |
| corrugatin | C8:0 | octanoic acid |
| daptomycin | C10:0 | decanoic acid |
| enduracidin A | iC12:2(2.t4) | 10-methyl-2,trans4-undecanoic acid |
| enduracidin B | aC13:2(2.t4) | 10-methyl-2,trans4-dodecenoic acid |
| fengycin A | C16:0-OH(3) | 3-hydroxy-hexadecanoic acid |
| fengycin B | C16:0-OH(3) | 3-hydroxy-hexadecanoic acid |
| friulimicin A | iC13:1(3) | 11-methyl-3-dodecenoic acid |
| friulimicin B | iC14:1(3) | 12-methyl-3-tridecenoic acid |
| friulimicin C | aC13:1(3) | 10-methyl-3-dodecenoic acid |
| friulimicin D | aC15:1(3) | 12-methyl-3-tetradecenoic acid |
| fuscopeptin A | C8:0-OH(3) | 3-hydroxy-octanoic acid |
| fuscopeptin B | C10:0-OH(3) | 3-hydroxy-decanoic acid |
| Ile-polymyxin B1 | aC9:0 | 6-methyloctanoic acid |
| Ile-polymyxin E1 | aC9:0 | 6-methyloctanoic acid |
| Ile-polymyxin E2 | iC8:0 | 6-methylheptanoic acid |
| Ile-polymyxin E8 | aC10:0 | 8-methyldecanoic acid |
| iturin A-1 | C13:0-NH2(3) | 3-amino-tridecanoic acid |
| iturin A-2 | C14:0-NH2(3) | 3-amino-tetradecanoic acid |
| iturin A-3 | aC15:0-NH2(3) | 3-amino-12-methyl-tetradecanoic acid |
| iturin A-4 | iC15:0-NH2(3) | 3-amino-13-methyl-tetradecanoic acid |
| iturin A-5 | C15:0-NH2(3) | 3-amino-pentadecanoic acid |
| iturin A-6 | iC16:0-NH2(3) | 3-amino-14-methyl-pentadecanoic acid |
| iturin A-7 | C16:0-NH2(3) | 3-amino-hexadecanoic acid |
| iturin A-8 | aC17:0-NH2(3) | 3-amino-14-methyl-hexadecanoic acid |
| iturin C-1 | iC14:0-NH2(3) | 3-amino-12-methyl-tridecanoic acid |
| iturin C-2 | aC15:0-NH2(3) | 3-amino-12-methyl-tetradecanoic acid |
| iturin C-3 | iC16:0-NH2(3) | 3-amino-14-methyl-pentadecanoic acid |
| iturin C-4 | aC17:0-NH2(3) | 3-amino-14-methyl-hexadecanoic acid |
| kulomo opunalide 1 | C8:0:1(7)-Me(2)—OH(3) | 2-methyl-3-hydroxy-7-octynoic acid |
| kulomo opunalide 2 | C8:0:1(7)-Me(2)—OH(3) | 2-methyl-3-hydroxy-7-octynoic acid |
| lichenysin A aC13 | aC13:0-OH(3) | 3-hydroxy-10-methyl-dodecanoic acid |
| lichenysin A aC15 | aC15:0-OH(3) | 3-hydroxy-12-methyl-tetradecanoic acid |
| lichenysin A aC17 | aC17:0-OH(3) | 3-hydroxy-14-methyl-hexadecanoic acid |
| lichenysin A iC12 | iC12:0-OH(3) | 3-hydroxy-10-methyl-undecanoic acid |
| lichenysin A iC13 | iC13:0-OH(3) | 3-hydroxy-11-methyl-dodecanoic acid |
| lichenysin A iC14 | iC14:0-OH(3) | 3-hydroxy-12-methyl-tridecanoic acid |
| lichenysin A iC15 | iC15:0-OH(3) | 3-hydroxy-13-methyl-tetradecanoic acid |
| lichenysin A iC16 | iC16:0-OH(3) | 3-hydroxy-14-methyl-pentadecanoic acid |
| lichenysin A iC17 | iC17:0-OH(3) | 3-hydroxy-15-methyl-hexadecanoic acid |
| lichenysin A nC12 | C12:0-OH(3) | 3-hydroxy-dodecanoic acid |
| lichenysin A nC13 | C13:0-OH(3) | 3-hydroxy-tridecanoic acid |
| lichenysin A nC14 | C14:0-OH(3) | 3-hydroxy-tetradecanoic acid |
| lichenysin A nC15 | C15:0-OH(3) | 3-hydroxy-pentadecanoic acid |
| lichenysin A nC16 | C16:0-OH(3) | 3-hydroxy-hexadecanoic acid |
| lokisin | C10:0-OH(3) | 3-hydroxy-decanoic acid |
| marinobactin A | C12:0 | dodecanoic acid |
| marinobactin B | C14:1(7) | 7-tetradecenoic acid |
| marinobactin C | C14:0 | tetradecanoic acid |
| marinobactin D1 | C16:1(9) | 9-hexadecenoic acid |
| marinobactin D2 | C16:1(7) | 7-hexadecenoic acid |
| marinobactin E | C16:0 | hexadecanoic acid |
| massetolide A | C10:0-OH(3) | 3-hydroxy-decanoic acid |
| massetolide B | C11:0-OH(3) | 3-hydroxy-undecanoic acid |

TABLE 1-continued

Exemplary Lipopeptides Synthesized by Peptide Synthetases

| Lipopeptide Name | Fatty Acid Component | Fatty Acid Component name |
| --- | --- | --- |
| massetolide C | C12:0-OH(3) | 3-hydroxy-dodecanoic acid |
| massetolide D | C10:0-OH(3) | 3-hydroxy-decanoic acid |
| massetolide E | C10:0-OH(3) | 3-hydroxy-decanoic acid |
| massetolide F | C10:0-OH(3) | 3-hydroxy-decanoic acid |
| massetolide G | C11:0-OH(3) | 3-hydroxy-undecanoic acid |
| massetolide H | C12:0-OH(3) | 3-hydroxy-dodecanoic acid |
| massetolide L | C10:0-OH(3) | 3-hydroxy-decanoic acid |
| mycosubtilin 1 | C16:0-NH2(3) | 3-amino-hexadecanoic acid |
| mycosubtilin 2 | iC16:0-NH2(3) | 3-amino-14-methyl-pentadecanoic acid |
| mycosubtilin 3 | iC17:0-NH2(3) | 3-amino-15-methyl-hexadecanoic acid |
| mycosubtilin 4 | aC17:0-NH2(3) | 3-amino-14-methyl-hexadecanoic acid |
| neamphamide A | iC8:0-Me(2.4)—OH(3) | 2,4,6-trimethyl-3-hydroxy-heptanoic acid |
| Nva-polymyxin E1 | aC9:0 | 6-methyloctanoic acid |
| papuamide A | aC11:2(4.6)-Me(2.6)—OH(2.3) | 2,3-dihydroxy-2,6,8-trimethyldeca-(4Z,6E)-dienoic acid |
| papuamide B | aC11:2(4.6)-Me(2.6)—OH(2.3) | 2,3-dihydroxy-2,6,8-trimethyldeca-(4Z,6E)-dienoic acid |
| papuamide C | aC11:2(4.6)-Me(2.6)—OH(2.3) | 2,3-dihydroxy-2,6,8-trimethyldeca-(4Z,6E)-dienoic acid |
| papuamide D | aC11:2(4.6)-Me(2.6)—OH(2.3) | 2,3-dihydroxy-2,6,8-trimethyldeca-(4Z,6E)-dienoic acid |
| pholipeptin | C10:0-OH(3) | 3-hydroxy-decanoic acid |
| plusbacin A1 | C14:0-OH(3) | 3-hydroxy-tetradecanoic acid |
| plusbacin A2 | iC15:0-OH(3) | 3-hydroxy-13-methyl-tetradecanoic acid |
| plusbacin A3 | iC16:0-OH(3) | 3-hydroxy-14-methyl-pentadecanoic acid |
| plusbacin A4 | C16:0-OH(3) | 3-hydroxy-hexadecanoic acid |
| plusbacin B1 | C14:0-OH(3) | 3-hydroxy-tetradecanoic acid |
| plusbacin B2 | iC15:0-OH(3) | 3-hydroxy-13-methyl-tetradecanoic acid |
| plusbacin B3 | iC16:0-OH(3) | 3-hydroxy-14-methyl-pentadecanoic acid |
| plusbacin B4 | C16:0-OH(3) | 3-hydroxy-hexadecanoic acid |
| polymyxin B1 | aC9:0 | 6-methyloctanoic acid |
| polymyxin B2 | iC8:0 | 6-methylheptanoic acid |
| polymyxin B3 | C8:0 | octanoic acid |
| polymyxin B4 | C7:0 | heptanoic acid |
| polymyxin B5 | C9:0 | nonanoic acid |
| polymyxin B6 | aC9:0-OH(3) | 3-hydroxy-6-methyloctanoic acid |
| polymyxin E1 | aC9:0 | 6-methyloctanoic acid |
| polymyxin E2 | iC8:0 | 6-methylheptanoic acid |
| polymyxin E3 | C8:0 | octanoic acid |
| polymyxin E4 | C7:0 | heptanoic acid |
| polymyxin E7 | iC9:0 | 7-methyloctanoic acid |
| polymyxin M | aC9:0 | 6-methyloctanoic acid |
| pseudomycin A | C14:0-OH(3.4) | 3,4-dihydroxy-tetradecanoic acid |
| pseudomycin B | C14:0-OH(3) | 3-hydroxy-tetradecanoic acid |
| pseudomycin C | C16:0-OH(3.4) | 3,4-dihydroxy-hexadecanoic acid |
| pseudomycin C2 | C16:0-OH(3) | 3-hydroxy-hexadecanoic acid |
| pseudophomin A | C10:0-OH(3) | 3-hydroxy-decanoic acid |
| pseudophomin B | C12:0-OH(3) | 3-hydroxy-dodecanoic acid |
| putisolvin I | C6:0 | hexanoic acid |
| putisolvin II | C6:0 | hexanoic acid |
| putisolvin III | C6:0 | hexanoic acid |
| ramoplanin A1 | C8:2(2.t4) | 2,trans4-octenoic acid |
| ramoplanin A2 | iC9:2(2.t4) | 2,trans4-7-methyl-octenoic acid |
| ramoplanin A3 | iC10:2(2.t4) | 2,trans4-8-methyl-noneoic acid |
| serrawettin W1 | C10:0-OH(3) | 3-hydroxy-decanoic acid |
| serrawettin W2 | C10:0-OH(3) | 3-hydroxy-decanoic acid |
| surfactin aC13 | aC13:0-OH(3) | 3-hydroxy-10-methyl-dodecanoic acid |
| surfactin aC15 | aC15:0-OH(3) | 3-hydroxy-12-methyl-tetradecanoic acid |
| surfactin iC12 | iC12:0-OH(3) | 3-hydroxy-10-methyl-undecanoic acid |
| surfactin iC14 | iC14:0-OH(3) | 3-hydroxy-12-methyl-tridecanoic acid |
| surfactin iC15 | iC15:0-OH(3) | 3-hydroxy-13-methyl-tetradecanoic acid |
| surfactin iC16 | iC16:0-OH(3) | 3-hydroxy-14-methyl-pentadecanoic acid |
| surfactin nC13 | C13:0-OH(3) | 3-hydroxy-tridecanoic acid |

TABLE 1-continued

Exemplary Lipopeptides Synthesized by Peptide Synthetases

| Lipopeptide Name | Fatty Acid Component | Fatty Acid Component name |
|---|---|---|
| surfactin nC14 | C14:0-OH(3) | 3-hydroxy-tetradecanoic acid |
| surfactin nC15 | C15:0-OH(3) | 3-hydroxy-pentadecanoic acid |
| syringafactin A | C10:0-OH(3) | 3-hydroxy-decanoic acid |
| syringafactin B | C10:0-OH(3) | 3-hydroxy-decanoic acid |
| syringafactin C | C10:0-OH(3) | 3-hydroxy-decanoic acid |
| syringafactin D | C12:0-OH(3) | 3-hydroxy-dodecanoic acid |
| syringafactin E | C12:0-OH(3) | 3-hydroxy-dodecanoic acid |
| syringafactin F | C12:0-OH(3) | 3-hydroxy-dodecanoic acid |
| syringomycin A1 | C10:0-OH(3) | 3-hydroxy-decanoic acid |
| syringomycin E | C12:0-OH(3) | 3-hydroxy-dodecanoic acid |
| syringomycin G | C14:0-OH(3) | 3-hydroxy-tetradecanoic acid |
| syringopeptin 22 PhvA | C10:0-OH(3) | 3-hydroxy-decanoic acid |
| syringopeptin 22 PhvB | C12:0-OH(3) | 3-hydroxy-dodecanoic acid |
| syringopeptin 22A | C10:0-OH(3) | 3-hydroxy-decanoic acid |
| syringopeptin 22B | C12:0-OH(3) | 3-hydroxy-dodecanoic acid |
| syringopeptin 25A | C10:0-OH(3) | 3-hydroxy-decanoic acid |
| syringopeptin 25B | C12:0-OH(3) | 3-hydroxy-dodecanoic acid |
| syringopeptin 508A | C12:0-OH(3) | 3-hydroxy-dodecanoic acid |
| syringopeptin 508B | C14:0-OH(3) | 3-hydroxy-tetradecanoic acid |
| syringopeptin SC 1 | C10:0-OH(3) | 3-hydroxy-decanoic acid |
| syringopeptin SC 2 | C12:0-OH(3) | 3-hydroxy-dodecanoic acid |
| syringostatin A | C14:0-OH(3) | 3-hydroxy-tetradecanoic acid |
| syringostatin B | C14:0-OH(3,4) | 3,4-dihydroxy-tetradecanoic acid |
| syringotoxin B | C14:0-OH(3) | 3-hydroxy-tetradecanoic acid |
| tensin | C10:0-OH(3) | 3-hydroxy-decanoic acid |
| tolaasin A | Pda | pentanedioic acid |
| tolaasin B | C8:0-OH(3) | 3-hydroxy-octanoic acid |
| tolaasin C | C8:0-OH(3) | 3-hydroxy-octanoic acid |
| tolaasin D | C8:0-OH(3) | 3-hydroxy-octanoic acid |
| tolaasin E | C8:0-OH(3) | 3-hydroxy-octanoic acid |
| tolaasin I | C8:0-OH(3) | 3-hydroxy-octanoic acid |
| tolaasin II | C8:0-OH(3) | 3-hydroxy-octanoic acid |
| tripropeptin A | iC13:0-OH(3) | 3-hydroxy-11-methyl-dodecanoic acid |
| tripropeptin B | iC14:0-OH(3) | 3-hydroxy-12-methyl-tridecanoic acid |
| tripropeptin C | iC15:0-OH(3) | 3-hydroxy-13-methyl-tetradecanoic acid |
| tripropeptin D | iC16:0-OH(3) | 3-hydroxy-14-methyl-pentadecanoic acid |
| tripropeptin E | iC17:0-OH(3) | 3-hydroxy-15-methyl-hexadecanoic acid |
| tripropeptin Z | iC12:0-OH(3) | 3-hydroxy-10-methyl-undecanoic acid |
| Val-polymyxin E1 | aC9:0 | 6-methyloctanoic acid |
| Val-polymyxin E2 | iC8:0 | 6-methylheptanoic acid |
| viscosin | C10:0-OH(3) | 3-hydroxy-decanoic acid |
| viscosinamide | C10:0-OH(3) | 3-hydroxy-decanoic acid |
| White Line Inducing Principle | C10:0-OH(3) | 3-hydroxy-decanoic acid |

The present invention appreciates that, typically, in peptide synthetase complexes that synthesize lipopeptides, the first active peptide synthetase domain is the one that links a fatty acid to an amino acid; subsequent peptide synthetase domains typically add additional amino acids. In accordance with certain embodiments of the present invention, an acyl amino acid is prepared through use of an engineered peptide synthetase that comprises a first peptide synthetase domain found in a peptide synthetase complex that synthesizes a lipopeptide, and is engineered in that it is separated from at least some other domains found in the peptide synthetase complex.

Fatty acids utilized by naturally-occurring peptide synthetases can be β-hydroxy fatty acids (e.g., as found in surfactin and other β-hydroxy lipo-peptides described in Table 1). In other cases, utilized fatty acids are a β-amino fatty acid (for example, Iturin; see Table 1). In certain instances, utilized fatty acids are unmodified at the β-position (e.g., as in daptomycin and certain other lipo-peptides described in Table 1).

As described herein, the present invention encompasses the appreciation that, for all three types of fatty acids utilized by peptide synthetases that synthesize lipopeptides, the first protein domain of the first module of the relevant peptide synthetase complex typically plays a critical role in lipo-initiation. However, the precise mechanism of lipo-initiation differs for each of the three types of fatty acid. In general terms, the first modules of a peptide synthetase enzyme, which naturally creates a lipo-peptide, has a particular organization. Each module begins with a condensation domain that is required for the lipo-initiation reaction. The condensation domain is followed by an adenylation domain, which is followed by a thiolation domain (also known as a peptidyl carrier protein (PCP) domain). The adenylation domain selects the 1st amino acid that will be incorporated into the lipo-peptide and creates an amino acid adenylate. Subsequent to adenylation, the amino acid becomes tethered to the enzyme via linkage to a phosphopantethione moiety, which is attached to the thiolation domain. The chemical reaction that results in tethering of the amino acid releases AMP as a byproduct.

For synthetases that attach a β-hydroxy fatty acid to the bound amino acid, the condensation domain of the first module utilizes β-hydroxy fatty acid CoA as a substrate, and transfers the fatty acid to the N-terminus of the amino acid substrate, which is tethered to the thiolation domain. No enzyme activity, other than the activity of the C-domain itself, is required for this particular reaction, although it has been reported that the srfD protein stimulates the lipo-initiation reaction (see Steller et al., which was cited in U.S. Pat. No. 7,981,685) (Ref 5).

Figure 6:
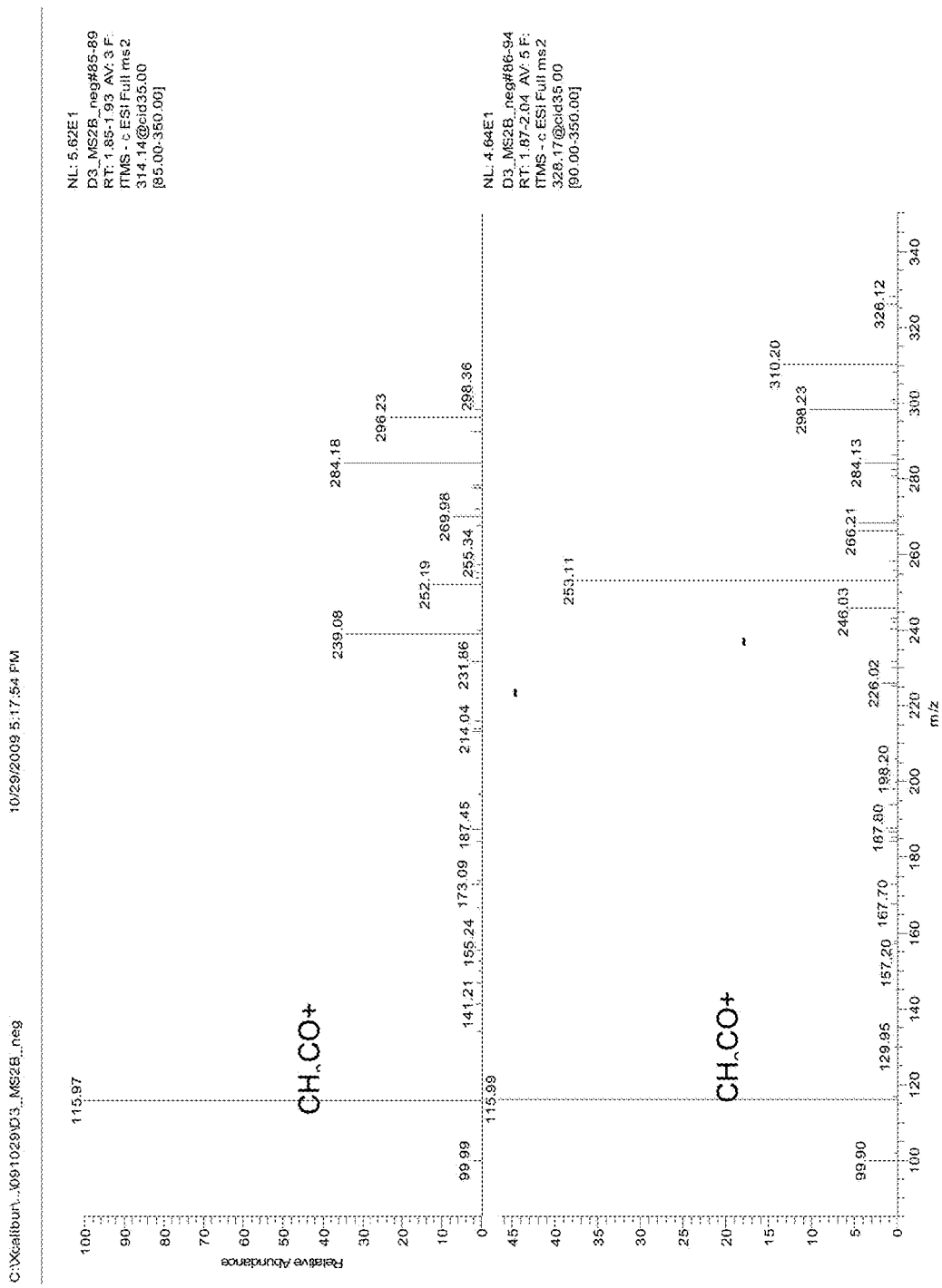
FIG. 6 depicts MS/MS analysis of the 314 Dalton and 328 Dalton species: The 314 species fragments into one species that has Gly+CH3CO and a second species that is the expected size of the remainder of the fatty acid (labeled "-Gly"). The 328 species fragments into one species that has Gly+CH3CO and a second species that is the expected size of the remainder of the fatty acid (labeled "-Gly").

For synthetases that attach a β-amino group to the fatty acid, the condensation domain has several sub-domains, each of which has a particular function (see FIG. 6 of Duitman et al.) (Ref 6). Considering the iturin synthetase as a specific examples (also known as the mycosubtilin synthetase), the mechanism of lipo-initiation is the following (see Hansen et al., (Ref 7) and Aron et al., (Ref 8) for details): the acyl ligase domain adenylates a long-chain fatty acid (in this case myristic) and the fatty acid is then transferred to an enzyme-linked 4-phosphopantetheine and AMP is released, in a separate reaction, the fenF gene product catalyzes the transfer of malonate (from manonyl-CoA) to a second acyl carrier domain (located within module 1). The β-ketoacyl synthetase domain catalyzes the condensation of the malonyl and acyl thioesters, creating a β-keto thioester, the B-keto thioester is converted into a β-amino fatty acid by a transaminase domain homologous to amino acid transferases, the β amino fatty acid is transferred to a thiolation domain and is then joined to the substrate amino acid (in this case asparagine), which was previously linked to the enzyme via the action of the module 1 adenylation domain. This series of reactions results in the joining of a beta-amino fatty acid to an amino acid.

For synthetases that attach fatty acids that are unmodified at the β-position, the condensation domain of the 1st module catalyzes the transfer of the fatty acid to the N-terminus of the amino acid substrate, which is tethered to the thiolation domain. Considering the daptomycin synthetase as an example, two additional proteins are involved: an acyl-CoA ligase (DptE) (sequence listing GenBank: AAX31555.1) and an acyl carrier protein (DptF) (sequence listing GenBank: AAX31556.1). DptE activates the fatty acid substrate by linking it to CoA, and the activated fatty acid is then transferred to DptF, and subsequently transferred to the enzyme-bound amino acid substrate (see Wittmann et al.) (Ref 9). Note that studies conducted in vitro have confirmed that DptE transfers the fatty acid to DptF, but experiments aimed at demonstrating the involvement of the condensation domain in subsequent transfer of the fatty acid from DptF to the amino acid substrate appears not to have been reported in the literature.

Phylogenetic analysis of peptide synthetase condensation domains is described in Roongsawang et al. (Ref 2), and in Rausch et al. (Ref 3). Those of ordinary skill in the art, guided by the present disclosure, and optionally in consultation with such references, can readily identify, select, and/or engineer appropriate peptide synthetase condensation domains for use in designing, constructing, producing, and/or otherwise providing engineered peptide synthetases for production of acyl amino acids in accordance with the present invention.

Non-limiting examples of peptide synthetase complexes that may contain peptide synthetase domains useful in the identification, selection, design, and/or production of engineered peptide synthetases as described herein include, for example, surfactin synthetase, fengycin synthetase, arthrofactin synthetase, lichenysin synthetase, syringomycin synthetase, syringopeptin synthetase, saframycin synthetase, gramicidin synthetase, cyclosporin synthetase, tyrocidin synthetase, mycobacillin synthetase, polymyxin synthetase, bacitracin synthetase, and combinations thereof.

Thus, the present invention provides engineered peptide synthetases, which in some embodiments comprise or consist of isolated peptide synthetase domains from reference peptide synthetase complexes that synthesize lipopeptides. In some embodiments, such reference peptide synthetase complexes are known peptide synthetase complexes. In some embodiments, such reference peptide synthetase complexes are naturally occurring peptide synthetase complexes. In some embodiments, provided engineered peptide synthetases comprise or consist of a single peptide synthetase domain. In some embodiments, provided engineered peptide synthetases comprises or consist of a first peptide synthetase domain from a peptide synthetase complex that synthesizes a lipopeptide.

In some embodiments, an engineered peptide synthetase, peptide synthetase domain, or component thereof (e.g., adenylation (A) domain, thiolation (T) domain, and/or condensation (C) domain) may contain one or more sequence modifications as compared with a reference peptide synthetase, domain, or component. Typically, however, an engineered peptide synthetase, peptide synthetase domain, or component thereof shows a high overall degree of sequence identity and/or homology with its reference peptide synthetase, domain, or component.

In some embodiments, an engineered peptide synthetase, peptide synthetase domain, or component thereof contains insertions, deletions, substitutions or inversions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or more amino acids as compared to its relevant reference.

In certain embodiments, such amino acid substitutions result in an engineered polypeptide that comprises an amino acid whose side chain contains a structurally similar side chain as compared to the corresponding amino acid in the relevant reference. For example, amino acids with aliphatic side chains, including glycine, alanine, valine, leucine, and isoleucine, may be substituted for each other; amino acids having aliphatic-hydroxyl side chains, including serine and threonine, may be substituted for each other; amino acids having amide-containing side chains, including asparagine and glutamine, may be substituted for each other; amino acids having aromatic side chains, including phenylalanine, tyrosine, and tryptophan, may be substituted for each other; amino acids having basic side chains, including lysine, arginine, and histidine, may be substituted for each other; and amino acids having sulfur-containing side chains, including cysteine and methionine, may be substituted for each other.

In certain embodiments, amino acid substitutions result in an engineered polypeptide that comprises an amino acid whose side chain exhibits similar chemical properties to a corresponding amino acid present in a relevant reference. For example, in certain embodiments, amino acids that comprise hydrophobic side chains may be substituted for each other. In some embodiments, amino acids may be substituted for each other if their side chains are of similar molecular weight or bulk. For example, an amino acid in an engineered domain may be substituted for an amino acid present in the relevant reference if its side chains exhibits a minimum/maximum molecular weight or takes up a minimum/maximum amount of space.

In certain embodiments, an engineered polypeptide shows at least about 50, 55, 60, 65, 70, 75, 80, 85, 90, 91, 92, 93, 94, 95, 96, 97, 98, or 99% homology or identity with a relevant reference (e.g., over a portion that spans at least 5, 6, 7, 8, 9, 10, 15, 20, 25, 30, 35, 40, 45, 50, 60, 70, 80, 90, 100, 200, 300, 400, 500, 600, 700, 800, 900, 1000 or more amino acids).

In certain embodiments, engineered polypeptides of the present invention comprise two or more polypeptide domains that occur in one or more naturally occurring or other known reference polypeptides, but that are i) separated from one or more sequence elements with which they are associated in the reference polypeptide; ii) associated with one or more sequence elements with which they are not associated in the reference polypeptide(s); and/or iii) associated in a different way (e.g., in a different order or via a different linkage) with one or more sequence elements with which they are associated in the reference polypeptide. As a non-limiting example, two naturally occurring polypeptide domains that are directly covalently linked in nature may be separated in an engineered polypeptide by one or more intervening amino acid residues. Additionally or alternatively, two naturally occurring polypeptide domains that are indirectly covalently linked in nature may be directly covalently linked in an engineered polypeptide, e.g. by removing one or more intervening amino acid residues.

In certain embodiments, two naturally occurring peptide domains that are from different peptide synthetases are covalently joined to generate an engineered polypeptide of the present invention.

In some embodiments, engineered peptide synthetases provided by and/or for use in accordance with the present invention do not include thioesterase and/or reductase domains. Such domains are known to function in the release of peptides and lipopeptides from the nonribosomal peptide synthetase complexes that produce them. In one aspect, the present invention provides the surprising finding that, notwithstanding their central role in release of lipopeptides from peptide synthetase complexes, such domains are often not required for release of acyl amino acids from engineered peptide synthetases as described herein. This thioesterase and/or reductase domains may optionally be included in some embodiments of the present invention, but are specifically excluded in some embodiments.

In certain embodiments, compositions and methods of the present invention are useful in large-scale production of acyl amino acids. In certain embodiments, acyl amino acids are produced in commercially viable quantities using compositions and methods of the present invention. For example, engineered polypeptides of the present invention may be used to produce acyl amino acids to a level of at least 5, 6, 7, 8, 9, 10, 11, 12, 13, 14, 15, 16, 17, 18, 19, 20, 30, 40, 50, 60, 70, 80, 90, 100, 110, 120, 130, 140, 150, 150, 200, 250, 300, 400, 500, 600, 700, 800, 900, 1000 mg/L or higher. As will be appreciated by those skilled in the art, biological production of acyl amino acids using engineered polypeptides of the present invention achieves certain advantages over other methods of producing acyl amino acids. For example, as compared to chemical production methods, production of acyl amino acids using compositions and methods of the present invention utilizes more readily available and starting materials that are easier to store, reduces the necessity of using harsh and sometimes dangerous chemical reagents in the manufacturing process, reduces the difficulty and efficiency of the synthesis itself by utilizing host cells as bioreactors, and reduces the fiscal and environmental cost of disposing of chemical by-products. Other advantages will be clear to practitioners who utilize compositions and methods of the present invention.

Acyl Amino Acids and Compositions

The present invention provides compositions comprising acyl amino acids produced by engineered peptide synthetases as described herein. In some embodiments, such compositions comprise a collection of individual acyl amino acid molecules, that are related to one another in that they are each synthesized by the same engineered peptide synthetase and together represent a distribution of chemical entities, varied in precise chemical structure (e.g., due to varying length and/or composition of acyl chains, linkages within such acyl chains and/or between an acyl chain and the amino acid, etc), that are synthesized by the relevant engineered peptide synthetase, under the conditions of synthesis (e.g., in vivo or in vitro). In some embodiments, a provided composition includes straight-chain acyl moieties, branched acyl moieties, and/or combinations thereof.

That is, it will be appreciated by those skilled in the art that, in some embodiments, one feature of engineered production of acyl amino acids is that engineered peptide synthetases may not generate pure populations of single chemical entities, particularly when acting in vivo. Thus, as noted above, the present invention provides acyl amino acid compositions comprising distributions of chemical entities. In some embodiments, the present invention provides acyl amino acid compositions in which substantially all acyl amino acids comprise the same amino acid moiety, but the composition includes a distribution of acyl moieties.

As described herein, the present invention provides a wide variety of acyl amino acids and compositions. In some embodiments, the present invention provides acyl amino acids and compositions in which the amino acid moiety is or comprises one found in an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and/or valine. Alternatively or additionally, in some embodiments, the present invention provides acyl amino acids and compositions in which the amino acid moiety is or comprises one found in an amino acid selected from the group consisting of selenocysteine and/or pyrrolysine. In some embodiments, the present invention provides acyl amino acids and compositions in which the amino acid moiety is or comprises one found in an amino acid selected from the group consisting of norleucine, beta-alanine and/or ornithine. In some embodiments, the present invention provides acyl amino acids and compositions in which the amino acid moiety is or comprises one found in an amino acid selected from the group consisting of L-amino acids. In some embodiments, the present invention provides acyl amino acids and compositions in which the amino acid moiety is or comprises one found in an amino acid selected from the group consisting of D-amino acids. In some embodiments, the present invention provides acyl amino acids and compositions in which the amino acid moiety is or comprises or comprises one found in an amino acid D-glu or D-diaminopropionic acid. Those skilled in the art will be aware of appropriate amino acid substrates, usable by peptide synthetases as described herein (and particularly by engineered peptide synthetases as described herein) to generate acyl amino acids containing such amino acid moieties. In some embodiments, the amino acid substrate is or comprises the recited amino acid. In some embodiments, the present invention provides acyl amino acids and compositions in which the acyl group is found in a saturated fatty acid such as butryic acid, caproic acid, caprylic acid, capric acid, lauric acid, myristic acid, palmitic acid, stearic arachidic acid, behenic acid, and/or lignoceric acid. the present invention provides acyl amino acids and compositions in which the acyl group is found in an unsaturated fatty acids such as, without limitation, myristoleic acid, palmitoleic acid, oliec acid, linoleic acid, alpha-linolenic acid, arachidonic acid, eicosapentaenoic acid, erucic acid, and/or docosahexaenoic acid. Other saturated and unsaturated fatty acids whose acyl moieties may be used in accordance with the present invention will be known to those of ordinary skill in the art. In certain embodiments, acyl amino acids and compositions provided by present invention comprise beta-hydroxy fatty acids as the fatty acid moiety. As is understood by those of ordinary skill in the art, beta-hydroxy fatty acids comprise a hydroxy group attached to the third carbon of the fatty acid chain, the first carbon being the carbon of the carboxylate group.

In some embodiments, the present invention provides acyl amino acids and compositions in which the acyl group comprises or consists of fatty acid chains with a length within a range bounded by a shorter length selected from the group consisting of C2, C3, C4, C5, C6, C7, C8, C9, C10, C11, C12, C13, C14, C15, C16, C17, C18, C19, C20, C21, C22, C23, C24, C25, C26, C27, C28, C29, C30, and an upper length selected from the group consisting of C30, C29, C28, C27, C26, C25, C24, C23, C22, C21, C20, C19, C18, C17, C16, C15, C14, C13, C12, C11, C10, C9, C8, C7, C6, C5, C4, C3, C2, and C1, wherein the upper length is the same as or larger than the lower length. In some particular embodiments, the present invention provides acyl amino acids and compositions in which the acyl group comprises or consists of C10-C14 fatty acid chains, C13-16 fatty acid chains, C13-15 fatty acid chains, C16-24 fatty acid chains, C18-22 fatty acid chains, C18-24 fatty acid chains, C8-C16 fatty acid chains. In some embodiments, the present invention provides acyl amino acids and compositions in which the acyl group comprises, consists predominantly of, or consists of C5, C6, C7, C8, C9, C10, C11, C12, C13, C14, C15, C16, C17, C18, C19, and/or C20 fatty acid chains. In some embodiments, the present invention provides acyl amino acids and compositions in which the acyl group comprises, consists predominantly of, or consists of comprises, consists predominantly of, or consists of C8, C9, C10, C11, C12, C13, C14, C15, and/or C16 fatty acid chains. In some embodiments, the present invention provides acyl amino acids and compositions in which the acyl group comprises, consists predominantly of, or consists of comprises, consists predominantly of, or consists of C12, C13, C14, C15, and/or C16 fatty acid chains.

In some embodiments, the present invention provides acyl amino acid compositions in which all acyl amino acids comprise the same amino acid moiety (or comprise an amino acid moiety from the same amino acid.

In some embodiments, the present invention provides acyl amino acid compositions in which different acyl amino acids within the composition have different acyl moieties (e.g., acyl moieties that differ, in composition, structure, branching, and/or length (of one or more chains). In some embodiments, such compositions predominantly include acyl moieties of a length (or within a range of lengths) as set forth above. In some such embodiments, such predominant acyl moieties are present in the composition at a level of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%<98%, or 99%. The Figures and Examples herein depict and/or describe certain particular acyl amino acids and/or acyl amino acid compositions that are provided by and can be prepared in accordance with certain embodiments of the present invention. To give but a few particular examples, the present invention specifically exemplifies and/or otherwise provides certain acyl amino acids and/or acyl amino acid compositions comprising, consisting predominantly of, or consisting of 2,4 diaminobutyric acid, (2S)-2,3-diaminobutyric acid, 2, 3-diaminoproprionic acid, β-hydroxy myristoyl glutamate, β-hydroxy myristoyl diaminopropionic acid, betaines, cocyl glycinate, gycine laureate, glutamine laureate, etc. For example, in some particular embodiments, the present invention provides acyl amino acid compositions in which the amino acid moiety within acyl amino acids in the composition is from glycine or glutamate, and the fatty acid moiety is predominantly a C12 fatty acid (i.e.g, is from lauric acid); in some such embodiments, all acyl amino acids in the composition have the same amino acid moiety.

Host Cells

Engineered polypeptides of the present invention may be introduced in any of a variety of host cells for the production of acyl amino acids. As will be understood by those skilled in the art, engineered polypeptides will typically be introduced into a host cell in an expression vector. So long as a host cell is capable of receiving and propagating such an expression vector, and is capable of expressing the engineered polypeptide, such a host cell is encompassed by the present invention. An engineered polypeptide of the present invention may be transiently or stably introduced into a host cell of interest. For example, an engineered polypeptide of the present invention may be stably introduced by integrating the engineered polypeptide into the chromosome of the host cell. Additionally or alternatively, an engineered polypeptide of the present invention may be transiently introduced by introducing a vector comprising the engineered polypeptide into a host cell, which vector is not integrated into the genome of the host cell, but is nevertheless propagated by the host cell.

In certain embodiments, a host cell is a bacterium. Non-limiting examples of bacteria that are useful as host cells of the present invention include bacteria of the genera *Escherichia, Streptococcus, Bacillus*, and a variety of other genera known to those skilled in the art. In certain embodiments, an engineered polypeptide of the present invention is introduced into a host cell of the species *Bacillus subtilis*.

Bacterial host cells of the present invention may be wild type. Alternatively, bacterial host cells of the present invention may comprise one or more genetic changes as compared to wild type species. In certain embodiments, such genetic changes are beneficial to the production of acyl amino acids in the bacterial host. For example, such genetic changes may result in increased yield or purity of the acyl amino acid, and/or may endow the bacterial host cell with various advantages useful in the production of acyl amino acids (e.g., increased viability, ability to utilize alternative energy sources, etc.).

In certain embodiments, the host cell is a plant cell. Those skilled in the art are aware of standard techniques for introducing an engineered polypeptide of the present invention into a plant cell of interest such as, without limitation, gold bombardment and *agrobacterium* transformation. In certain embodiments, the present invention provides a transgenic plant that comprises an engineered polypeptide that produces an acyl amino acid of interest. Any of a variety of plants species may be made transgenic by introduction of an engineered polypeptide of the present invention, such that the engineered polypeptide is expressed in the plant and produces an acyl amino acid of interest. The engineered polypeptide of transgenic plants of the present invention may be expressed systemically (e.g. in each tissue at all times) or only in localized tissues and/or during certain periods of time. Those skilled in the art will be aware of various promoters, enhancers, etc. that may be employed to control when and where an engineered polypeptide is expressed.

Insects, including insects that are threats to agriculture crops, produce acyl amino acids that are likely to be important or essential for insect physiology. For example, an enzyme related to peptide synthetases produces the product of the *Drosophila* Ebony genes, which product is important for proper pigmentation of the fly, but is also important for proper function of the nervous system (see e.g., Richardt et al., Ebony, a novel nonribosomal peptide synthetase for beta-alanine conjugation with biogenic amines in *Drosophila*, J. Biol. Chem., 278(42):41160-6, 2003). Acyl amino acids are also produced by certain *Lepidoptera* species that are a threat to crops. Thus, compositions and methods of the present invention may be used to produce transgenic plants that produce an acyl amino acid of interest that kills such insects or otherwise disrupts their adverse effects on crops. For example, an engineered polypeptide that produces an acyl amino acid that is toxic to a given insect species may be introduced into a plant such that insects that infest such a plant are killed. Additionally or alternatively, an engineered polypeptide that produces an acyl amino acid that disrupts an essential activity of the insect (e.g., feeding, mating, etc.) may be introduced into a plant such that the commercially adverse effects of insect infestation are minimized or eliminated. In certain embodiments, an acyl amino acid of the present invention that mitigates an insect's adverse effects on a plant is an acyl amino acid that is naturally produced by such an insect. In certain embodiments, an acyl amino acid of the present invention that mitigates an insect's adverse effects on a plant is a structural analog of an acyl amino acid that is naturally produced by such an insect. Compositions and methods of the present invention are extremely powerful in allowing the construction of engineered polypeptides that produce any of a variety of acyl amino acids, which acyl amino acids can be used in controlling or eliminating harmful insect infestation of one or more plant species.

Producing Acyl Amino Acids and Compositions

Acyl amino acids and compositions may be produced by engineered peptide synthetases as described herein. In some embodiments, acyl amino acids are produced in vitro. In some embodiments, acyl amino acids are produced in vivo, for example in host cells engineered to express an engineered peptide synthetase or component or domain thereof. In some embodiments, acyl amino acids are produced in association with one or more components of a cell and/or with an engineered peptide synthetase. In some embodiments, acyl amino acid compositions are subjected to one or more isolation procedures, for example as is known in the art, e.g., to separate produced acyl amino acid compounds from one or more components of their production system (e.g., from an engineered peptide synthetase or component or domain thereof, and/or from one or more components of a cell such as an engineered cell.

EXEMPLIFICATION

Example 1: Engineering Peptide Synthetases to Produce Acyl Amino Acids with β-Hydroxy Amino Acids In some embodiments of the present invention, an engineered peptide synthetase that produces an acyl amino acid is designed and/or produced by isolating and/or otherwise engineering a known peptide synthetase domain (e.g., by separating a first peptide synthetase domain that is found in a peptide synthetase complex that synthesizes a lipopeptide from other elements, domains, or components of the lipopeptide-synthesizing complex) to produce the acyl amino acid.

For example, an acyl amino acid with a β-hydroxy fatty acid can be created by expressing Module 1 of a synthetase, such as the srf (surfactin) synthetase in an appropriate host organism. Since Module 1 of the srfAA (sequence listing srfAA module 1) is glutamate-specific, the expression of Module 1 in an appropriate host leads to the production of β-hydroxyl myristoyl glutamate.

The same approach can be used to link fatty acids to a variety of different amino acids since there are known (sequenced) "Module 1 DNA segments", which can be cloned from various natural systems, with adenylation domains specific for four distinct amino acids (Leu, Glu, Ser or Dhb; see Table). In addition, a variety of naturally occurring β-hydroxy lipo-peptides (which are believed to be produced by peptide synthetase enzymes) have been reported, for which the gene cluster encoding the synthetase responsible for their production has not been sequenced. A new β-hydroxy acyl amino acid can be produced by using standard molecule biology techniques to specifically identify "Module 1" of one of those synthetases (which belongs to the set "Module 1's" that have not yet been sequenced) and expressing that Module 1 in an appropriate host. This approach would lead to the generation of additional new β-hydroxy acyl amino acids, including β-hydroxy acyl: Phe, D-Ala, 2,3-dehydro-2-aminobutyric acid, NMe-Ile, Gly, Thr and D-allo-threonine. The Table below summarizes various attributes of known lipopeptides and the peptide synthetases that synthesize them in nature, including the amino acid acyl group and amino acid specificity of the relevant Module 1.

The "fatty acid adding" domain of these 18 synthetases adds β-hydroxy fatty acids to the amino acid

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| 1 | amphisin (one form is arthrofactin) | C-10 | A New Lipopeptide Biosurfactant Produced by *Arthrobacter* sp. Strain MIS38 (database 692) | arfA module1 | Cloning and Characterization of the Gene Cluster Encoding Arthrofactin Synthetase from *Pseudomonas* sp. MIS38 (database 6911 | Leu | N/A | N/A | N/A |
| 2 | beauverolide | C8 to C-10 | Extraribosomal cyclic tetradepsipeptides beauverolides: profiling and modeling the fragmentation pathways (citation from PubMed) | ND | synthetase genes have not been identified | Phe | N/A | N/A | N/A |
| 3 | callipeltin | C-8 | Isolation of callipeltins A-C and of two new open-chain derivatives of callipeltin A from the marine sponge *Latrunculia* sp. A revision of the stereostructure of callipeltins (ref from Norine database) | ND | synthetase genes have not been identified | D-Ala | N/A | N/A | N/A |
| 4 | coppeptin | C-10 to C-12 | Zampella A, Randazzo A, Borbone N, Luciani S, Trevisi L, Debitus C, D Auria MV, Tetrahedron Letters, 2002, 43 (35), pp. 6163-6166 | ND | synthetase genes have not been identified | 2,3-dehydro-2-aminobutyric acid | N/A | N/A | N/A |
| 5 | fengycin | C-14 to C-18 | Application of electrospray ionization mass spectrometry in rapid typing of fengycin | fenC1 | Functional and Transcriptional Analyses of a Fengycin Synthetase Gene, fenC, | Glu | N/A | N/A | N/A |

-continued

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| 6 | fuscopeptin | C-8 to C-10 | Structure of fuscopeptins, phytotoxic metabolites of *Pseudomonas fuscovaginae*, homologues produced by *Bacillus subtilis* | ND | synthetase genes have not been identified from *Bacillus subtilis* | 2,3-dehydro-2-aminobutyric acid | N/A | N/A | N/A |
| 7 | kulomo opunalide | 2-hydroxyiso valeric and C8:01 (7)-Me(2)-OH(3) and 2-hydroxy iso valeric | More Peptides and Other Diverse Constituents of the Marine Mollusk *Philinopsis Speciosa* | ND | synthetase genes have not been identified | NMe-Ile | N/A | N/A | N/A |
| 8 | lichenysin | C-15 | Structural and immunological Characterization of a Biosurfactant Produced by *Bacillus licheniformis* JF-2 | licA module 1 | Molecular and Biochemical Characterization of the Protein Template Controlling Biosynthesis of the Lipopeptide Lichenysin | Glu | N/A | N/A | N/A |
| 9 | papuamide | C-11 | Papuamides A-D, HIV-inhibitory and cytotoxic depsipeptides from the sponges *Theonella mirabilis* and *Theonella swinhoei* collected in Papua New Guinea. | ND | synthetase genes have not been identified | Gly | N/A | N/A | N/A |
| 10 | plusbacin | C-14 to C-16 | Structures of new peptide antibiotics, plusbacins A1-A4 and B1-B4, | ND | synthetase genes have not been identified | Thr | N/A | N/A | N/A |
| 11 | serrawettin | C-10 | A Novel Extracellular Cyclic Lipopeptide Which Promotes Flagellum-Dependent and -independent | *Serratia marcescens* gene required for surfactant serrawettin W 1 | D-Leu | N/A | N/A | N/A | N/A |

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| | | | Spreading Growth of *Serratia marcescens* | production encodes putative aminolipid synthetase belonging to nonribosomal peptide synthetase family | | | | | |
| 12 | surfactin | C13 to C15 | Separation and Characterization of Surfactin Isoforms Produced by *Bacillus subtilis* OKB 105 | srfA module 1 | Sequence and analysis of the genetic locus responsible for surfactin synthesis in *Bacillus subtilis*. I do not have a copy of this paper. It is not in the database. | Glu | N/A | N/A | N/A |
| 13 | syringafactin | C-10 to C-12 | Identification of a biosynthetic gene cluster and the six associated lipopeptides involved in swarming motility of *Pseudomonas syringae* pv. tomato DC3000. | SyfA module 1 | Identification of a biosynthetic gene cluster and the six associated lipopeptides involved in swarming motility of *Pseudomonas syringae* pv. tomato DC3000. | Leu | N/A | N/A | N/A |
| 14 | syringomycin | C12 to C14 | The structure of syringomycins A1, E and G | SyrE1 | Characterization of the Syringomycin Synthetase Gene Cluster | Ser | N/A | N/A | N/A |
| 15 | syringopeptin | C10 to C14 | Novel Cyclic Lipodepsipeptide from *Pseudomonas syringae* pv. lachrymans Strain 508 and Syringopeptin Antimicrobial | SypA-M1 | the sypa sypb sypc synthetase genes encod twenty-two modules invovied nonribosomal peptide synthesis | Dhb | N/A | N/A | N/A |

-continued

| number | lipopeptide | length of fatty acid chain | Reference for fatty acid information | Activities | name of module 1 | reference for gene 1 information | amino acid specificity of the module | gene encoding adenylate-forming enzyme | gene encoding ACP | gene encoding malonyl-CoA transacylase |
|---|---|---|---|---|---|---|---|---|---|---|
| 16 | tolaasin | C8 and glutaric (pentadecanoic) | tolaasins A-E, five new lipodepsipeptides produced by *Pseudomonas tolaasii* | | synthetase genes have not been identified | syringopeptin *pseudomonas syringae* 2,3-dehydro-2-aminobutyric acid (dhb) | N/A | N/A | N/A | |
| 17 | tripropeptin | C12 to C17 | tripropeptins, novel antimicrobial agents produced by *Lysobacter* sp | | synthetase genes have not been identified | D-allo-threonine | N/A | N/A | N/A | |
| 18 | Viscosin | C10 to C12 | Massetolides A-H, antimycobacterial cyclic depsipeptides produced by two pseudomonads isolated from marine habitats | | Massatolide A biosynthesis in *Pseudomonas fluorescens* | L-leu | N/A | N/A | N/A | |

The "fatty acid adding" domain of these 14 synthetises adds fatty acids to the amino acid (no β-hydroxy)

| number | lipopeptide | length of fatty acid chain | Reference for fatty acid information | Activities | name of module 1 | reference for gene 1 information | amino acid specificity of the module | gene encoding adenylate-forming enzyme | gene encoding ACP | gene encoding malonyl-CoA transacylase |
|---|---|---|---|---|---|---|---|---|---|---|
| 19 | A54145 | C10 to C11 | A54145, a new lipopeptide antibiotic complex: isolation and characterization | | the lipopeptide antibiotic A54145 biosynthetic gene cluster from *Streptomyces fradiae* | Trp | lptEF | not identified | N/A | |
| 20 | apramide | C8 to C9 | Apramides A-G novel lipooepetides from the marine cyanobacterium *Lyngbya majuscula* | | synthetase genes have not been identified | Nme-Ala | not identified | not identified | N/A | |
| 21 | aquachelin | C12 to C14 | Structure and membrane affinity of a suite of amphiphilic siderophores produced by a marine bacterium | | synthetase genes have not been identified | D-OH-Asp | not identified | not identified | N/A | |
| 22 | arylomycin | C11 to C15 | Arylomycins A and B, new biaryl-lipopeptide | | synthetase genes have not been identified | D-Nme-Ser | not identified | not identified | N/A | |

-continued

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| 23 | CDA1b through CDA4B | 2-epoxy-hexanoic acid | antibiotics produced by Streptomyces sp. Tu 6075.II Structure elucidation | | Structure biosynthetic origin and enggineered biosynthesis of calcium-dependent antibiotics from Streptomyces coelicolor | Ser | ACS (acyl-CoA synthetase) | SCO3249 | N/A |
| 24 | carnabin | C10 | Carnabins A and B new lipopeptides from the Caribbean cyanobacterium Lyngbya majuscula | | synthetase genes have not been identified | NMe-Phe | not identified | not identified | N/A |
| 25 | corrugatin | C8 | Corrugatin A lipopeptide siderophore from Pseudomonas corrugata | | synthetase genes have not been identified | OH-His | not identified | not identified | N/A |
| 26 | daptomycin | C10 to C13 | A21978C a complex of new acidic peptide antibiotics: isolation, chemistry, and mass spectral structure elucidation | | Daptomycin biosynthesis in streptomyces roseosporus: cloning and analysis of the gene cluster and revision of peptide stereochemistry | Trp | DptE | DptF | N/A |
| 27 | enduracidin | C12 to C13 | | | The enduracidin biosynthetic gene cluster from Streptomyces fungicidicus | Asp | Orf45 | Orf35 | N/A |
| 28 | friulimicin | C13 to C15 | Friulimicins: novel lipopeptide antibiotics with peptidoglycan synthesis | | Sequencing analysis of the biosynthetic gene cluster of the lipopeptide | Asp or Asn | LipA | LipD | N/A |

-continued

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| 29 | marinobactin | C12 to C16 | Membrane affinity of the amphiphilic marinobactin siderophores | | synthetase genes have not been identified | D-OH-Asp | not identified | not identified | N/A |
| 30 | polymyxin | C7 to C9 | CONTRIBUTION TO THE ELUCIDATION OF THE STRUCTURE OF POLYMYXIN B1 | | Identification of a Polymyxin Synthetase Gene Cluster of *Paenibacillus polymyxa* and Heterologous Expression of the Gene in *Bacillus subtilis* | 2,4 diaminobutyric acid | not identified | not identified | N/A |
| 31 | putisolvin | C6 | Characterization of two *Pseudomonas putida* lipopeptide biosurfactants, putisolvin I and II, which inhibit biofilm formation and break down existing biofilms | | Genetic and functional characterization of the gene cluster directing the biosynthesis of putisolvin I and II in *Pseudomonas putida* strain PCL1445 | Leu | not identified | not identified | N/A |
| 32 | ramoplanin | C8 to C10 | Studies on the biosynthesis of the lipodepsipeptide antibiotic Ramoplanin A2 | | Chemistry and biology of the ramoplanin family of peptide antibiotics | Asn | Ramo 26 | Ramo 11 | N/A |
| 33 | Amphibactin | C14 to C18 | Structure and membrane affinity of a suite of amphiphilic siderophores produced by a marine *bacterium* | | synthetase genes have not been identified | N-acetyl-Hydroxy Ornithine | not identified | not identified | N/A |

The "fatty acid adding" domain of this synthetase adds both β-hydroxy and "normal" (not β-hydroxy) fatty acids to the amino acid -continued

| number | lipopeptide | length of fatty acid chain | Reference for fatty acid information | name of module 1 | reference for gene information | amino acid specificity of the module | gene encoding adenylate-forming enzyme | gene encoding ACP | gene encoding malonyl-CoA transacylase |
|---|---|---|---|---|---|---|---|---|---|
| | | | The "fatty acid adding" domain of this synthetase adds β-amine fatty acids to the amino acid | | | | | | |
| 34 | Iturin | C14 to C17 | Revised structure of mycosubtilin, a peptidolipid antibiotic from Bacillus subtilis | MycA | Cloning, sequencing, and characterization of the iturin A operon | Asn | N/A | N/A | fenF |

As is specifically described in Examples herein, additional new β-hydroxy acyl amino acids can be produced by operationally linking a condensation domain, which specifies the addition of a β-hydroxy fatty acid, to an adenylation domain which specifies a particular desired amino acid. In Example XXX, a condensation domain is operationally linked to an adenylation domain that is specific for glycine and, upon expression of the chimera in an appropriate host, β-hydroxy myristyl glycine is produced. One who is skilled in the art will appreciate that this approach can be used to create any desired β-hydroxy acyl amino acid, as long as an adenylation domain is available that is specific for the desired amino acid.

Naturally occurring peptide synthetase modules are available that specify the use of each of the standard 20 amino acids, and in addition adenylation domains are available that are specific for about 300 additional amino acids, or amino acid-like molecules (Kleinkauf et al) (Ref 10). This approach can be used to link a β-hydroxy fatty acid to any of these amino acids, or amino acid-like molecules.

Example 2: Engineered Peptide Synthetases Comprising or Consisting of Mycosubtilin Module 1 (MycA)

Strategies analogous to those described above can be used to link a β-amino fatty acid to any desired amino acid. One approach is to identify a naturally occurring "Module 1" (such as MycA of the mycosubtilin synthetase, see Duitman et. al.) (Ref 6) and to express the module in an appropriate host. In this specific example, the FenF gene is desirably also be expressed in the host (sequence listing AAF08794.1).

In general, a particular β-amino fatty acid can be produced in an appropriate host by expressing a module known to specify the joining of a β-amino fatty acid to a particular amino acid, along with any gene or genes that encode critical additional functions that are not naturally found in the host organism (such as for example FenF). Additional new β-amino acyl amino acids can be produced by operationally linking a condensation domain, which specifies the addition of a β-amino fatty acid, to an adenylation domain which specifies a particular desired amino acid. Again, and genes that encode additional required factors (such as homologs of FenF) can also be expressed in the host. This approach can be used to link a β-amino fatty acid to any amino acid, as long as an adenylation domain is available that is specific for the desired amino acid.

Example 3: Engineered Peptide Synthetases Comprising or Consisting of Daptomycin Synthetase Module 1

Strategies analogous to those described above can be used to link a fatty acid (which is unmodified at the β-position) to any desired amino acid. One approach is to identify a naturally occurring "Module 1" (such as the Trp1 module of the daptomycin synthetase, see Miao et. al.) (Ref 11) and to express the module in an appropriate host (Sequence listing: dptA1 module 1 of daptomycin synthetase). In addition, in this specific example, the DptE and DptF genes should also be express in the host.

In general, a particular acyl amino acid (unmodified at the β-position) can be produced in an appropriate host by expressing a module known to specify the joining of a fatty acid to a particular amino acid, along with any gene or genes that encode critical additional functions that are not naturally found in the host organism (such as for example DptE and DptF). Additional new acyl amino acids can be produced by operationally linking a condensation domain, which specifies the addition of a fatty acid, to an adenylation domain which specifies a particular desired amino acid. For example, fatty acid that is unmodified at the beta position can be attached to glycine using a chimeric synthetase composed of the condensation domain of dptA1 module 1 linked to that adenylation and thiolation domains of dptA1 module 5 (which is specific for glycine) (sequence listing dptA1 Module 5)

Example 4: Additional Genes Useful or Necessary for Some Embodiments

For the Calcium-Dependent Antibiotic (CDA) system, it is believed that specific locus-associated fatty acid synthases produce the hexanoic acid, which is joined to the first amino acid of CDA; in particular, the ACP (SCO3249), FabH4 (SCO3246), FabF3 (SCO3248) gene products are believed to be important for production of the hexanoic acid, which is then joined to the amino acid substrate, in this case Ser (Ref 12).

Example 5: FA-Glu Compositions

In some embodiments, the distribution of fatty acids produced by a typical engineered strain that utilizes an engineered peptide synthetase to synthesize FA-Glu is composed of fatty acids that all have a β-hydroxyl but that have varying chain lengths. In some particular embodiments, the chain lengths vary in the following manner: C12, 1.6%; C13, 16.2%; C14, 55%; C15, 25.9%; C16, 1.2% and C17, 0.01%.

In some embodiments, some of the even numbered fatty acids are branched and some are straight chain.

In some embodiments, none of the odd numbered fatty acids are straight chain (i.e, they are all branched). Odd numbered chains can be either iso or anteiso; in some embodiments, the present invention provides different compositions with different relative amounts (e.g., ratios) of these forms. Branching nomenclature is well presented in FIG. 1 of Ref 16. *Fatty Acids of the Genus Bacillus: an example of branched-chain preference, Toshi Kaneda, Bacteriological Review,* 1977, *Vol* 41(2), 391-418.

In some embodiments, for an engineered strain that produces FA-Glu with an engineered peptide synthetase, the fatty acid chain distribution changes when particular keto acids are fed to the strain (see Table 1 below). Dramatic changes in fatty acid chain distribution can be generated when the enzyme that synthesizes the keto acids used to initiate fatty acid synthesis in *Bacillus* is knocked out and single keto acids are fed to the strain. In some embodiments, as the concentration of the keto acid is changed, the pattern of fatty acid species is altered.

In some embodiments, compositions are provided containing FA-Glu with 95% C14 fatty acid by feeding 20 mM isobutyric to the mutant.

In some embodiments, feeding of low levels of keto acids that can only be used to produce branched fatty acids with odd number chains, is utilized to produce a population of fatty acids with about 80% (100 uM 2-methylbutyric or 100 uM isovaleric) surfactant with C14 length fatty acid.

Significantly, since the mutant cannot synthesize its own keto acid starters for even numbered branched chain fatty acid synthesis, feeding of low concentrations of either of these ketos acids (100 uM 2-methylbutyric or 100 uM isovaleric) allows the production of a population of surfactant that is predominantly even numbered and straight chain. Thus, the present invention surprising provides methods and compositions for generating, and compositions comprising mostly straight chain (rather than branched) fatty acid, produced by *B. subtilis*. Indeed, the present invention specifically describes strategies for generating a *Bacillus* strain (and strains so generated) that exclusively produces straight chain fatty acid.

Example 6: Production of Amphoteric Surfactants

The present Example describes use of engineered peptide synthetases (in engineered host cells) to produce amphoteric surfactants with one region or regions that harbor a negative charge and another region or regions that harbor a positive charge. Examples of amino acids that can be used to produce such surfactants are shown in the Figure below. The amino acids all have two amino groups and include: 2,4-diaminobutyric acid, (2S)-2,3-diaminobutyric acid, 2,3-diaminopropionic acid, ornithine and lysine.

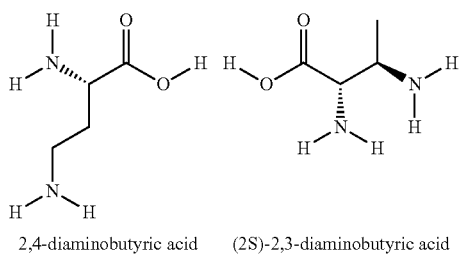

2,4-diaminobutyric acid    (2S)-2,3-diaminobutyric acid

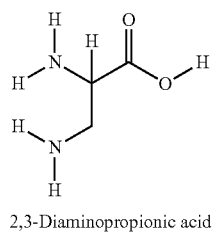

2,3-Diaminopropionic acid

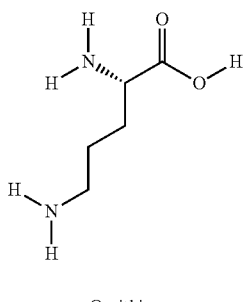

Ornithine

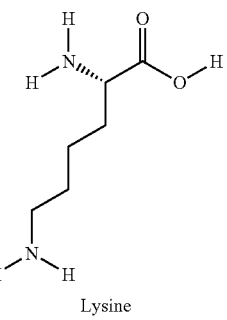

Lysine

One particular example of a surfactant of this sort is shown in the Figure below, it is β-hydroxy myristoyl diaminopropionic acid:

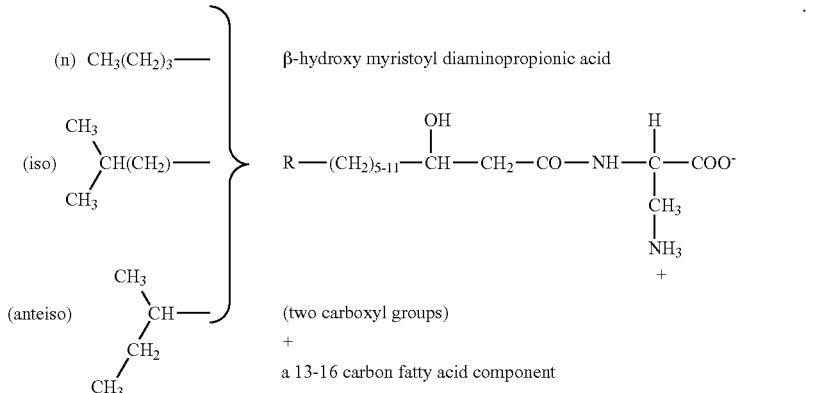

β-hydroxy myristoyl diaminopropionic acid (two carboxyl groups)
+
a 13-16 carbon fatty acid component This surfactant will be zwitterionic at physiological pH given that the pKa of the beta amine of 2,3 diaminoprionic acid is 9.57 and the pKa of an alpha carboxyl is about 2.2. To generate this surfactant, a condensation domain capable of directing the linkage of β-hydroxyl fatty acid to an amino acid (such as the condensation domain of SRFAA module 1) (sequence listing srfAA Module 1) is linked to the adenylation and thiolation domain of a module that is specific for 2,3-diaminopropionic acid (DAP). Felnagle et al., described a peptide synthetase that incorporates DAP. The synthetase is found in *Saccharothrix mutabilis* subsp. *capreolus* ATCC 23892. The DAP-specific module is the second module of CmnA (Sequence listing CmaA, A2).

*Bacillus subtilis* 168 does not synthesize DAP. Two genes need to be added to *Bacillus* in order to enable conversion of serine to DAP. The genes are described in references cited below. The genes are found in *Staphylococcus aureus* and other bacteria. The genes are called sbnA and sbnB. For example, the genes are present in *Staphylococcus aureus* strain JH9, and also in *Staphylococcus aureus* strain Mu50/ATCC 700699. The sbnA gene (sequence listing sbnA) is also known as SaurJH9 0103. The sbnB gene (sequence listing sbnB) is also known as SaurJH9 0104.

Homologues of the sbnA and sbnB genes can be used instead of, or in addition to, sbnA and sbnB. For example, *Bacillus cereus* strains that synthesize zwittermicin encode homologues of sbnA and sbnB, called ZmaU (sequence listing ZmaU) and ZmaV (sequence listing ZmaV), respectively.

The charge of the primary amine of the surfactant shown in the Figure above will depend on pH, and will be positive in the vicinity of pH 7.0. As the pH is elevated, the amine will lose a hydrogen and become neutral in charge. A surfactant with a positive charge that is independent of pH can be produced by converting the surfactant shown above into a betaine (which harbors a quaternary ammonium group) see Figure below.

Alternatively or additionally, methylation can be accomplished in vivo using a methyltransferase. One of the symbols did not translate it's shown as a boxBacterial □-N-methyltrasferases have been described by Zhang, et al. As example, genes encoding methyltrasnferases can be obtained from *Bacillus subtilis* (sequence listing *Bacillus* prmA) or *E. coli* (sequence listing *E. coli* prmA). A methyltransferase that modifies cypemycin can be used (sequencing listing cypemycin methyltrasferase); the gene is found in *Streptomyces* sp. OH-4156. A gene encoding a similar protein (76% identical) can be obtained from *Streptomyces griseus* subsp. *griseus* NBRC 13350 (sequencing listing *Streptomyces griseus* methyltransferase).

Example 7: Production of Fatty Acids and Fatty Acid Derivatives with Particular Fatty Acid Branching Patterns Naturally occurring fatty acids produced by living organisms typically have two sorts of modifications that affect the melting temperature of the fatty acids and their derivatives. These modifications are branching and desaturation (i.e., the presence of particular double bonds), and both modifications lower the melting point of the fatty acid.

Certain organisms, including particular gram positive and gram negative bacteria, as well as typical eukaryotes such as yeast, control the fluidity of membranes by desaturation of fatty acids. The ability to introduce desaturated fatty acids into membranes is important with regard to maintenance of membrane fluidity as temperature decreases. Certain bacteria, such as *Bacillus subtilis*, do not rely on desaturation to increase membrane fluidity. Instead, these bacteria control membrane fluidity via the synthesis of branched fatty acids (for a list of representative bacterial genera that synthesize branched fatty acids, see Table 3 of Ref 13.).

Given the general need of organisms to control membrane fluidity, biologically produced oils typically contain

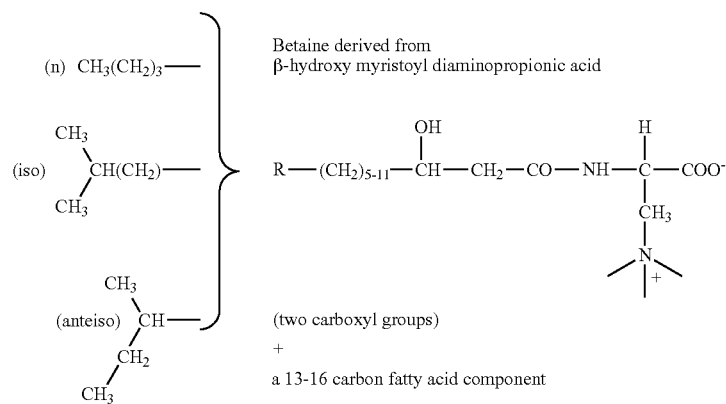

Betaine derived from β-hydroxy myristoyl diaminopropionic acid

This can be done in vitro using a method described by Simon and Shokat. (see reference in reference list). 100 mg of (2-bromoethyl) trimethylammonium bromide are added to a microfuge tube. 1 mL of a solution of the fatty Acid-DAP (FA-DAP) surfactant is added to the tube. The mixture is shaken at 50° C. until the solid dissolves. Reaction proceeds for about 5 hours. To consume the remaining alkylating agent, the reaction is quenched with 50 μl 20mer-captoethanol and incubated at room temperature for 30 minutes.

branches, double bonds, or both. From the perspective of commercial production of fatty acids and their derivatives, there is a need to control these branching and desaturation reactions in order to produce fatty acids with particular characteristics that provide specific benefits to customers. Methods for controlling branching and desaturation are described below.

As background information, we will consider *E. coli* as an example of an organism that synthesizes straight chain fatty acids (i.e., fatty acids that lack branching), fatty acid synthesis initiates when the enzyme fadH (β-ketoacyl-ACP synthase III) catalyzes condensation of acetyl-coenzyme A (acetyl CoA) with malonyl-acyl carrier protein (malonyl-ACP)(Ref 14). This condensation produces an acetoacetyl-ACP that is then elongated by the iterative action of the E. coli fatty acid synthesis machinery.

Initiation of fatty acid synthesis in Bacillus subtilis occurs by a different, but similar, mechanism. Bacillus subtilis encodes two β-ketoacyl-ACP synthase III enzymes (fadHA and fadHB). Although these enzymes will utilize acetyl-CoA as a substrate, they prefer to use branched substrates such as isobutyryl-CoA, 2-methylbutyryl-CoA and isovaleryl-CoA (REF 15). These CoA derivatives are produced from the amino acids L-valine, L-isoleucine and L-leucine, respectively (REF 16).

Initiation of fatty acid synthesis with a branched starter unit leads to the syntheses of a terminally branched fatty acid. The precise chemical composition of the branched starter impacts the length and specific branching of the synthesized fatty acid. For example, initiation with isobutyrate in Bacillus leads to production of "iso" fatty acids with even number lengths, such as 14 carbons (C14) and 16 carbons (C16). Initiation with 2-methyl butyrate leads to synthesis of odd numbered "anteiso" fatty acids (e.g., C15 and C17). Initiation with isovalerate The enzymatic activity responsible for conversion of particular amino acids (L-valine, L-isoleucine and L-leucine) to their respective keto acids is α-keto acid dehydrogenase. Mutant Bacillus cells that lack α-keto acid dehydrogenase activity require the addition of at least one keto acid for growth (isobutyrate, 2-methyl butyrate or isovalerate) (Ref 17). Feeding a specific keto acid to a strain that lacks β-keto acid dehydrogenase activity not only rescues the growth deficiency of the mutant strain but also specifically affects the fatty acid composition of the cells. For example, feeding isobutyrate to the mutant leads to the exclusive synthesis of fatty acids with even numbered chain length. These fatty acid chains include fatty acids derived from the isobutyrate starter (i14:0, 33%; i16:0, 51%) and also straight chain fatty acids produced using de novo synthesized acetate as a starter (14:0, 2%; 16:0, 13%) (see Ref 17). Furthermore, note that the odd numbered fatty acids are eliminated when a strain that lacks β-keto acid dehydrogenase activity is fed isobutyrate (but not fed 2-methyl butyrate and/or isovalerate).

Feeding of 2-methyl butyrate leads to the production of a15:0, 51% and a17:0, 39%, with some straight chain even numbered fatty acid still produced via utilization of de novo produced acetate (14:0, 2%; 16:0, 8%) (Ref 17).

Feeding of isovalerate leads to the following pattern: i15:0, 56%; a15:0, 7%; i17:0, 12%; a17:0, 2%; 14:0, 3% and 16:0, 16%). The presence of anteiso fatty acids is unexpected and suggests that the isovalerate used in the study was contaminated with a keto acid such as 2-methyl butyrate. The straight chain even numbered fatty acids are produced utilizing de novo produced acetate (these data are taken from Ref 17).

There is a commercial need to produce fatty acids and fatty acid derivatives with precise lengths and branching. In Examples herein, we describe methods for producing particular populations of fatty acids and fatty acid derivatives, such as acyl amino acid surfactants.

In addition to specifically controlling the branching of fatty acids in organisms such as Bacillus, it is advantageous in certain cases to eliminate branching in organisms such as Bacillus, for example in order to produce surfactants with straight chain rather than branched fatty acid tails. This can be accomplished by expressing a β-ketoacyl-ACP synthase III enzyme in Bacillus that prefers to use straight chain starts, such as acetyl CoA. As an example of this, Li and coworkers converted a strain of Streptomyces coelicolor (which typically predominantly synthesizes branched fatty acids) into a strain that synthesizes 86% straight chain fatty acids by replacing the endogenous β-ketoacyl-ACP synthase III enzyme with E. coli fabH (Ref 18). A general method can be followed to identify enzymes that function in a manner analogous to E. coli fadH, that is they initiate fatty acid synthesis using predominantly straight chain starter units, such as acetyl CoA, which will result in the synthesis of straight chain fatty acids.

Methods such as gas-liquid-chromatography can be used to determine whether an organism synthesizes straight chain fatty acids, or instead synthesizes a mixture of straight chain and branched fatty acids. For example, Kaneda (Ref 16) used gas-liquid-chromatography to characterize the fatty acids of sixteen species of Bacillus, and found that all sixteen species synthesized a mixture of straight chain and branched fatty acids. In contrast, a similar study reported by Kaneda and Smith (Ref 19) showed that certain bacteria and yeasts exclusively synthesize straight chain fatty acids, and indeed it is true that most organisms synthesize exclusively straight chain fatty acids. Kaneda and Smith reported that the bacteria E. coli and Pseudomonas fluorescens exclusively synthesize straight chain fatty acids. Other examples of organisms that exclusively synthesize straight chain fatty acids are reported in Ref 20 and include various Streptococcus and Enterococcus species, and other species.

Once an organism has been identified that exclusively synthesizes straight chain fatty acids, assuming the genome of the organism has been sequenced, comparative sequence analysis can be used to determine whether the organism encodes a protein similar to E. coli fabH. For example, the gene encoding the Streptococcus pneumonia fabH homologue is 39% identical to E. coli fabH. The Streptococcus fabH has been cloned and, when the enzyme was produced and studied in vitro, it was found to prefer to utilize short straight CoA primers and to synthesize straight chain fatty acids (Ref 21)(SEE SEQUENCE LISTING AF384041).

In certain instances, an organism that exclusively or predominantly synthesizes straight chain fatty acids will encode an enzyme that is functionally equivalent to E. coli fabH, but that does not have homology to fabH. As an example, the Pseudomonas aeruginosa PA5174 gene encodes a fabY enzyme that is not homologous to fadH, but serves the same function and prefers to use acetyl CoA as the starter for fatty acid synthesis (see this Ref 22 Fatty Acid Biosynthesis in Pseudomonas aeruginosa is initiated by the FabY Class of -Ketoacyl Acyl Carrier Protein Synthases). Genes homologus to PA5174, that can be used for this purpose, include the following genes and their homologues-- see Sequence listing: Pmen_0396, MDS_0454, Psefu_4068, Avin_05510, PSPA7_5914, PLES_55661 and PA14_68360.

In order to convert a strain that produces branched fatty acids (such as Bacillus subtilis) into a strain the produces predominantly or exclusively straight chain fatty acids a gene such as E. coli fabH or Pseudomonas aeruginosa PA5174 is introduced into the strain such that it is expressed at the correct time and level. In the specific case of Bacillus subtilis, to ensure that the heterologous enzyme, which prefers straight chain starters, is expressed at the correct time and at the correct level, it is advantageous to place the heterologous gene that encodes the β-ketoacyl-ACP synthase III enzyme under the control of the promoter that that usually controls the expression of Bacillus fadHA (the fadhA promoter, see sequence listing "fabhA promoter Once the heterologous β-ketoacyl-ACP synthase III enzyme is being expressed in *Bacillus*, branched fatty acid synthesis can be further reduced by reducing, altering or eliminating β-keto acid dehydrogenase activity. In addition, the level of branched fatty acid can be reduced by reducing, altering or eliminating the activity of the endogenous *Bacillus* fadHA and/or fadHB genes (also known as fadH1 or fadH2).

When engineered strains are developed with lower levels of branched fatty acids, it is advantageous to express a desaturase enzyme in *Bacillus* in order to introduce sufficient double bonds into a subset of the *Bacillus* fatty acids to enable the *Bacillus* to maintain membrane fluidity. Examples of deasturases that can be used include □9-fatty acid desaturase from *Psychrobacter urativorans* (Ref 23) (sequence listing EF617339) and the □9-fatty acid desaturase from *Mortierella* alpine (Ref 24) (sequence listing AB015611).

Alternatively or additionally, genetic changes can be made that result in the constitutive expression of the endogenous *Bacillus* desaturase, des (Ref 25) (sequence listing AF037430). For example, constitutive des expression can be enabled via deletion of desk (Seq listing DesK gen)(Ref 26). It has been demonstrated that strains with a lipA (yutB) knockout are not able to synthesize fatty acids and require both keto acids and acetate for growth Ref 26. Constitutive expression of des was achieved by knocking out desK, which leads to overexpression of the transcriptional activator DesR, resulting in constitutive expression of des. Overexpression of des led to desaturation of about 13% of the *Bacillus* fatty acids and eliminated the keto acid requirement, indicating that the growth defect caused by an inability to produce branched fatty acids can be overcome by desaturation of a certain population of *Bacillus* fatty acids.

An alternative strategy to produce acyl amino acid surfactants with straight chain fatty acids is to express the peptide synthetase enzyme that produces the acyl amino acid in a strain that does not produce branched fatty acids, such as *E. coli*. It has been reported that the srfA operon required for production of surfactin has been cloned and expressed in *E. coli* (Ref 27). However, the lipopoetide was not characterized directly, rather the authors report that the engineered strain produces a new hydrophobic compound, which was analyzed by TCL using surfactin as a control. Surfactin's Rf value was 0.63 and the new hydrophobic compound showed an Rf value of 0.52. The authors did not speculate on why the Rf values differed.

An acyl amino acid with a straight chain fatty acid can be produced by cloning a gene that encodes a peptide synthetase enzyme capable of directing the synthesis of an acyl amino acid (such as Module 1 of srfAA) into an *E. coli* plasmid under the control of a promoter such as the T7 promoter and introducing the cloned gene into *E. coli*. It is also necessary to clone and express a gene such as *Bacillus* sfp, which is a phosphpantetheinyl transferase needed to modify peptide synthetase, enzymes in order to functionally activate those enzymes (see Ref 28). The amount of surfactant produced, and the length of the fatty acid tails present on the population of surfactant molecules, can be determine using LCMS as described in Ref 29.

Once a strain is generated that produces a desired acyl amino acid, the strain can be further modified to increase the yield of the acyl amino acid. One strategy for increasing yield is to inactivate (e.g., delete) genes that limit production of the acyl amino acid. Once genes are identified that, when deleted, increase yield of an acyl amino acid, a strain harboring multiple such deletions can be generated. In addition, genes that either do not affect surfactant yield, or that negatively affect surfactant yield, can be replaced with genes that stimulate acyl amino acid production. Examples herein describe genes that, when deleted, increase yield of an acyl glutamate surfactant referred to as FA-Glu Example 8: Production of β-Hydroxy Myristoyl Glycinate by Fermentation As described in U.S. Pat. No. 7,981,685, Modular Genetics, Inc. (Modular) has shown that an engineered peptide synthetase enzyme can be used to produce an acyl amino acid (β-hydroxy myristoyl glutamate). This approach has been expanded to produce β-hydroxy myristoyl glycinate. Here is the detailed information on production of β-hydroxy myristoyl glycinate.

Engineering of a FA-GLY-TE Construct Using a Fusion Between DNA encoding the condensation domain of srfAA module 1 and DNA encoding the adenylation domain of Module 2 of Linear Gramicidin In this Example, we amplified the genomic DNA from OKB105Δ(upp)SpectRFA-GLU-TE-MG that encodes for the genes responsible for FA-GLU production, and this region was amplified using primers 35664-C4:5'-TTG-TACTGAGAGTGCACCATAtATCGACAAAAATGTCAT-GAAAGAATCG-3' (SEQ ID NO: 3) and 35664-D4:5'-ACGCCAAGCTTGCATGCCtTTATGAAACCGTTACG GTTTGTGTATT-3' (SEQ ID NO: 4). This fragment was annealed to the PCR product obtained from the template pUC19 and primers 35664-B4:5'-AGGCATGCAAGCTTG-GCGtAATCATGGTCATAGCTGTTTCCTGTG-3' (SEQ ID NO: 5) and 35664-A4:5'-ATATGGTGCACTCTCAGTA-CAaTCTGCTCTGATGCCGCATAGTT-3' (SEQ ID NO: 6). The annealed mixture was transformed into SURE cells to produce the plasmid Psrf-Glu-TE-pUC19.

Psrf-Glu-TE-pUC19 was used as a template to engineer a variant of this plasmid that contained a fusion of the condensation domain of srfAA module 1 to the adenylation domain of Module 2 of Linear Gramicidin (which adenylation domain is specific for the amino acid glycine), followed by the TE.

The DNA sequence corresponding to Module 2 of Linear Gramicidin was amplified from genomic DNA of strain *Bacillus brevis* (ATCC 8185) using primers 35664-G4:5'-GCTTGCTTGCGGAGCAGATCA-3' (SEQ ID NO: 7) and 35664-H4:5'-TCGAATCTCCGCCCAGTTCGA-3' (SEQ ID NO: 8). The resulting PCR was used as a template for primers 35664-H2:5'-CACTGATTTCTGATGCGGA-gAAACGCGATTTGTTTTTGCGG-3' (SEQ ID NO: 9) and 35664-F2:5'-CTCCGAGCGCAAAGAAATcGTCGC-GAATCCCGATCCG-3' (SEQ ID NO: 10).

This fragment was annealed to the PCR product obtained from the template Psrf-Glu-TE-pUC19 using primers 35664-C7:5'-GATTTCTTTGCGCTCGGAgGGCATTCCT-TGAAGGCCATGA-3' (SEQ ID NO: 11) and 35664-E7:5'-CTCCGCATCAGAAATCAGTgTTAATTCATCAATTG-TATGTTCTGGATGC-3' (SEQ ID NO: 12). The annealed mixture was transformed into SURE cells to produce the plasmid Psrf-Gly-lgr_m2-F3-TE-pUC19. This plasmid was used to transform 23844-d1 OKB105Δ(upp)SpectR(Δ mod (2-7))upp+KanR. The resulting strain was named OKB105Δ(upp)SpectRFA-GLY-TE.

One strain derived from this strategy, which had the correct sequence to produce FA-GLY, was named 37237-d3. Analysis of the production of FA-GLY by strain OKB105Δ(upp)SpectRFA-GLY-TE shows that the strain was able to produce detectable amounts of FA-GLY. Data was obtained using LC-MS analysis. MS-MS analysis of the material derived from OKB105Δ(upp)SpectRFA-GLY-TE revealed that the product was indeed FA-GLY. (sequence listing Psrf-Gly-lgr_m2-F3-TE-pUC19).

Figure 5:
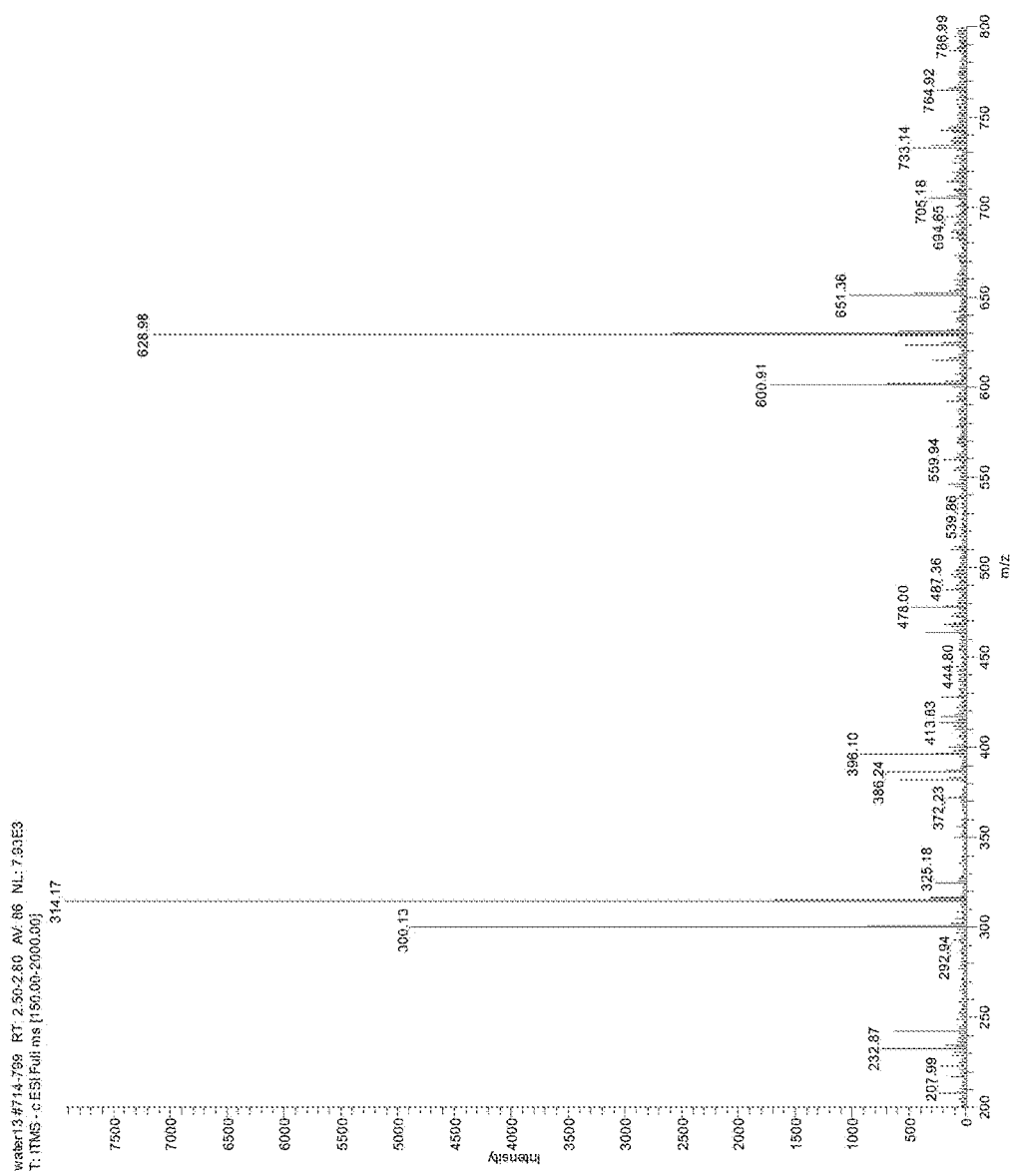
FIG. 5 LCMS analysis of FA-Gly. The 300 Dalton species is FA-Glu with a 14 carbon fatty acid tail. The 600 Dalton species is a dimer of the 300 Dalton species. The 314 Dalton species is FA-Glu with a 15 carbon fatty acid tail. The 628 Dalton species is a dimer of the 314 Dalton species.

See FIG. 5 for an LCMS analysis of FA-Gly. The 300 Dalton species is FA-Glu with a 14 carbon fatty acid tail. The 600 Dalton species is a dimer of the 300 Dalton species. The 314 Dalton species is FA-Glu with a 15 carbon fatty acid tail. The 628 Dalton species is a dimer of the 314 Dalton species.

See FIG. 6 for an MS/MS analysis of the 314 Dalton and 328 Dalton species: The 314 species fragments into one species that has Gly+CH₃CO and a second species that is the expected size of the remainder of the fatty acid (labeled "-Gly"). The 328 species fragments into one species that has Gly+CH₃CO and a second species that is the expected size of the remainder of the fatty acid (labeled "-Gly").

Example 9

The *Bacillus* α-keto acid dehydrogenase activity was knocked out by deleting the genes that encode two enzymes bkdAA and bkdAB. These genes encode the *Bacillus* E1□ and E1β components of α-keto acid dehydrogenase (also known as branched chain □-oxo acid dehydrogenase) see Ref 30. These genes were knocked out in a strain that produces an acyl amino acid surfactant called FA-Glu, which is composed of fatty acid (FA) linked to the amino acid glutamic acid (Glu).

As is shown in Table A for the control strain (which retains α-keto acid dehydrogenase activity), the surfactant is composed of a population of molecules with fatty acid tails that vary in length from C12 to C17, with C14 predominant (55%). When the mutant strain (which lacks α-keto acid dehydrogenase activity) is fed 20 mM isobutyrate the fatty acid composition of the surfactant population narrows to about 95% C14. Surfactants with a fatty acid tail length of C14 are particularly useful for certain applications, such as use in personal care products such as shampoos, body washes and other products. The population of surfactant fatty acid tail lengths can be specifically modified by feeding the mutant strain a starter keto acid that results in production of odd numbered branched fatty acids. Specifically, a population of surfactant molecules with a fatty acid tail composition of C13:0,27%; C15:0,65% was produced upon feeding the mutant 20 mM 2-methylbutyric acid. Thus, the strain produced surfactant with over 90% odd numbered branched fatty acid tails (presumably anteiso). A population of surfactant molecules with a fatty acid tail composition of C12:0,3.71%; C14:0,76.04%; C16:0,2.20% was produced upon feeding the mutant 100 μM 2-methylbutyric acid. Thus, the strain produced surfactant with over 80% even numbered fatty acid tails. Given that the mutant strain is incapable of producing branched fatty acids with even numbered chain lengths, and was fed a keto acid that can only be used to produce odd numbered branched fatty acids this population of even numbered fatty acid molecules is comprised of straight chain (unbranched) fatty acids. Feeding of 20 mM isovaleric produced surfactant with over 90% odd numbered branched fatty acid tails (presumably iso). Feeding of 100 μM isovaleric produced surfactant with over 80% even numbered (straight chain) fatty acid tails.

We have demonstrated previously that acylases can be used to specifically cleave an acyl amino acid surfactant to generate a free fatty acid and an amino acid. This approach can be used with the surfactant populations described above to produce particular purified populations of fatty acids, for example a population composed of over 90% C14 fatty acid or a population composed of over 90% anteiso C13 and C15 or over 90% iso C13 and C15, or over 80% straight chain (even numbered fatty acids).

Experimental Details:

In this example, we amplified the genomic region of *B. subtilis* strain OKB105 encoding for the bkdAA and bkdAB genes and upstream and downstream flanking genes (buk, 1pdV, bkdB, bmrR, and bmr) using primers 47014:5'-AATATCGTATTGAATAGACAGACAGG-3' (SEQ ID NO: 13) and 47015:5'-ATCTTTATTTGCATTATTCGTGGAT-3' (SEQ ID NO: 14). The resulting PCR was used as a template to amplify both upstream and downstream fragments.

The upstream fragment was amplified using primers 47020:5'-GTGTAAATCATTTAAT-GAAAAAAGGAAAAATTGACGTG-3' (SEQ ID NO: 15) and 47023:5'-ATCATTAAGCCTTCCTGGCAGTCAGC-CCTAGTGCTTGATGTCGGTTTG-3' (SEQ ID NO: 16). The downstream fragment was amplified using primers 47026:5'-AATTAAAAGCCATTGAGGCAGACG-TAAGGGAGGATACAATCATGGCAATT-3' (SEQ ID NO: 17) and 47021:5'-GGTATTCTTGCTGACAACGGTACAT-TCATATG-3' (SEQ ID NO: 18). The genes encoding for UPP/Kan were amplified from the template pUC19-UPP-KAN using primers 47024:5'-ACACGATATAGCCAG-GAAGGCGGGTTTTTTGACGATGTTCTTGAAACTC-3' (SEQ ID NO: 19) and 47025:5'-AATTAAAAGCCA-CAAAGGCCTAGGTACTAAAACAATTCATCCAGTAA-3' (SEQ ID NO: 20).

The upstream, downstream and UPP/Kan fragments were all digested to completion with restriction endonuclease BglI. All 3 fragments were subsequently ligated together with T4 DNA ligase. The ligated DNA mix was transformed into FA-Glu producing strain 43074-B2 and transformants were selected for ability to grow on LB agar supplemented with Kanamycin (30 ug/mL) and Isobutyric, Isovaleric and 2-methylbutyric acids (100 uM). One strain derived from this strategy, which had the correct sequence to replace bkdAA and bkdAB with UPP/Kan, was named 47392-A6 and was used in subsequent experiments.

47392-A6 was grown alongside 43074-B2 in S7(Phos7.5) (minimal media containing 100 mM Potassium Phosphate Buffer pH7.5, 10 mM Ammonium Sulfate, 20 mM Monosodium Glutamate, 2% Glucose and trace metals) supplemented with 0, 100 uM, 1 mM, 5 mM or 20 mM 2-methylbutyric, Isovaleric, Isobutyric acids (all neutralized to pH7.5) in 10 mM cultures for 4 days at 37 C.

TABLE A

|  |  | 344 = C12 | 358 = C13 | 372 = C14 | 386 = C15 | 400 = C16 | 414 = C17 | FA-Glu (mg/L) |
|---|---|---|---|---|---|---|---|---|
| Control | No Acid | 1.60% | 16.29% | 54.78% | 26.02% | 1.19% | 0.12% | 439.2 |
|  | 100 uM 2-methylbutyric | 1.76% | 18.27% | 52.08% | 26.68% | 1.09% | 0.12% | 397.1 |
|  | 1 mM 2-methylbutyric | 1.25% | 23.84% | 34.54% | 39.28% | 0.74% | 0.35% | 443.8 |
|  | 5 mM 2-methylbutyric | 0.99% | 26.91% | 22.05% | 49.22% | 0.38% | 0.46% | 409.6 |

TABLE A-continued

|  |  | 344 = C12 | 358 = C13 | 372 = C14 | 386 = C15 | 400 = C16 | 414 = C17 | FA-Glu (mg/L) |
|---|---|---|---|---|---|---|---|---|
|  | 20 mM 2-methylbutyric | 0.57% | 26.79% | 16.49% | 55.19% | 0.30% | 0.65% | 333.6 |
|  | 100 uM Isovaleric | 1.66% | 17.42% | 53.04% | 26.70% | 1.05% | 0.12% | 451.4 |
|  | 1 mM Isovaleric | 1.15% | 24.84% | 39.84% | 33.28% | 0.75% | 0.15% | 437.6 |
|  | 5 mM Isovaleric | 0.64% | 34.26% | 19.87% | 44.67% | 0.33% | 0.22% | 434.4 |
|  | 20 mM Isovaleric | 0.53% | 34.06% | 8.55% | 56.54% | 0.14% | 0.19% | 338.5 |
|  | 100 uM Isobutyric | 1.72% | 15.64% | 58.19% | 23.08% | 1.23% | 0.13% | 457.1 |
|  | 1 mM Isobutyric | 1.53% | 11.44% | 63.98% | 21.51% | 1.45% | 0.10% | 470.1 |
|  | 5 mM Isobutyric | 1.55% | 9.43% | 69.63% | 17.76% | 1.53% | 0.09% | 433.2 |
|  | 20 mM Isobutyric | 1.33% | 9.09% | 69.83% | 17.86% | 1.82% | 0.07% | 434.5 |
| Mutant | No Acid | no growth observed | | | | | | |
|  | 100 uM 2-methylbutyric | 3.71% | 10.41% | 76.04% | 7.56% | 2.20% | 0.07% | 401.4 |
|  | 1 mM 2-methylbutyric | 2.38% | 25.73% | 32.49% | 38.46% | 0.57% | 0.36% | 441.4 |
|  | 5 mM 2-methylbutyric | 1.00% | 31.76% | 10.00% | 56.32% | 0.21% | 0.71% | 415.2 |
|  | 20 mM 2-methylbutyric | 0.68% | 27.28% | 6.37% | 64.77% | 0.17% | 0.73% | 307.2 |
|  | 100 uM Isovaleric | 3.53% | 8.30% | 78.33% | 7.89% | 1.93% | 0.02% | 417.9 |
|  | 1 mM Isovaleric | 1.28% | 22.86% | 36.65% | 38.72% | 0.43% | 0.06% | 370.8 |
|  | 5 mM Isovaleric | 0.48% | 38.41% | 11.76% | 49.02% | 0.20% | 0.13% | 425.8 |
|  | 20 mM Isovaleric | 0.31% | 36.41% | 4.14% | 58.89% | 0.09% | 0.16% | 334.9 |
|  | 100 uM Isobutyric | 2.88% | 5.96% | 84.74% | 4.67% | 1.72% | 0.03% | 250.1 |
|  | 1 mM Isobutyric | 2.34% | 3.37% | 90.10% | 2.08% | 2.08% | 0.02% | 420.3 |
|  | 5 mM Isobutyric | 1.82% | 0.66% | 94.03% | 1.01% | 2.48% | 0.01% | 433.0 |
|  | 20 mM Isobutyric | 1.68% | 0.30% | 94.50% | 0.81% | 2.69% | 0.02% | 390.7 |

BKD up-U/K-down sequence using restriction sites (SEQ ID NO: 21):

AATATCGTATTGAATAGACAGACAGGAGTGAGTCACCAT

GGCAACTGAGTATGACGTAGTCATTCTGGGCGGCGGTACCGGCGGTTATG

TTGCGGCCATCAGAGCCGCTCAGCTCGGCTTAAAAACAGCCGTTGTGGAA

AAGGAAAAACTCGGGGGAACATGTCTGCATAAAGGCTGTATCCCGAGTAA

AGCGCTGCTTAGAAGCGCAGAGGTATACCGGACAGCTCGTGAAGCCGATC

AATTCGGAGTGGAAACGGCTGGCGTGTCCCTCAACTTTGAAAAAGTGCAG

CAGCGTAAGCAAGCCGTTGTTGATAAGCTTGCAGCGGGTGTAAATCATTT

AATGAAAAAAGGAAAAATTGACGTGTACACCGGATATGGACGTATCCTTG

GACCGTCAATCTTCTCTCCGCTGCCGGGAACAATTTCTGTTGAGCGGGGA

AATGGCGAAGAAAATGACATGCTGATCCCGAAACAAGTGATCATTGCAAC

AGGATCAAGACCGAGAATGCTTCCGGGTCTTGAAGTGGACGGTAAGTCTG

TACTGACTTCAGATGAGGCGCTCCAAATGGAGGAGCTGCCACAGTCAATC

ATCATTGTCGGCGGAGGGGTTATCGGTATCGAATGGCGTCTATGCTTCA

TGATTTTGGCGTTAAGGTAACGGTTATTGAATACGCGGATCGCATATTGC

CGACTGAAGATCTAGAGATTTCAAAAGAAATGGAAAGTCTTCTTAAGAAA

AAAGGCATCCAGTTCATAACAGGGGCAAAAGTGCTGCCTGACACAATGAC

AAAAACATCAGACGATATCAGCATACAAGCGGAAAAAGACGGAGAAACCG

TTACCTATTCTGCTGAGAAAATGCTTGTTTCCATCGGCAGACAGGCAAAT

ATCGAAGGCATCGGCCTAGAGAACACCGATATTGTTACTGAAAATGGCAT

GATTTCAGTCAATGAAAGCTGCCAAACGAAGGAATCTCATATTTATGCAA

TCGGAGACGTAATCGGTGGCCTGCAGTTAGCTCACGTTGCTTCACATGAG

GGAATTATTGCTGTTGAGCATTTTGCAGGTCTCAATCCGCATCCGCTTGA

TCCGACGCTTGTGCCGAAGTGCATTTACTCAAGCCCTGAAGCTGCCAGTG

-continued

```
TCGGCTTAACCGAAGACGAAGCAAAGGCGAACGGGCATAATGTCAAAATC

GGCAAGTTCCCATTTATGGCGATTGGAAAAGCGCTTGTATACGGTGAAAG

CGACGGTTTTGTCAAAATCGTGGCTGACCGAGATACAGATGATATTCTCG

GCGTTCATATGATTGGCCCGCATGTCACCGACATGATTTCTGAAGCGGGT

CTTGCCAAAGTGCTGGACGCAACACCGTGGGAGGTCGGGCAAACGATTCA

CCCGCATCCAACGCTTTCTGAAGCAATTGGAGAAGCTGCGCTTGCCGCAG

ATGGCAAAGCCATTCATTTTTAAAAGCATAAAGGAGGGGCTTGAATGAGT

ACAAACCGACATCAAGCACTAGGGCTGACTGCCAGGAAGGC
```

GGGTTTTTTGACG 1200

```
1201  ATGTTCTTGAAACTCAATGTCTTTTTTTGTAGAATCAATAGAAGTGTGTA  1250

1251  ATTGTTGATGGGACAATAAAAAAGGAGCTGAAACACAGTATGGGAAAGGT  1300

1301  TTATGTATTTGATCATCCTTTAATTCAGCACAAGCTGACATATATACGGA  1350

1351  ATGAAAATACAGGTACGAAGGATTTTAGAGAGTTAGTAGATGAAGTGGCT  1400

1401  ACACTCATGGCATTTGAAATTACCCGCGATCTTCCTCTGGAAGAAGTGGA  1450

1451  TATCAATACACCGGTTCAGGCTGCGAAATCGAAAGTCATCTCAGGGAAAA  1500

1501  AACTCGGAGTGGTTCCTATCCTCAGAGCAGGATTGGGAATGGTTGACGGC  1550

1551  ATTTTAAAGCTGATTCCTGCGGCAAAAGTGGGACATGTCGGCCTTTACCG  1600

1601  TGATCCAGAAACCTTAAAACCCGTGGAATACTATGTCAAGCTTCCTTCTG  1650

1651  ATGTGGAAGAGCGTGAATTCATCGTGGTTGACCCGATGCTCGCTACAGGC  1700

1701  GGTTCCGCAGTTGAAGCCATTCACAGCCTTAAAAAACGCGGTGCGAAAAA  1750

1751  TATCCGTTTCATGTGTCTTGTAGCAGCGCCGGAGGGTGTGGAAGAATTGC  1800

1801  AGAAGCATCATTCGGACGTTGATATTTACATTGCGGCGCTAGATGAAAAA  1850

1851  TTAAATGAAAAAGGATATATTGTTCCAGGTCTCGGAGATGCGGGTGACCG  1900

1901  CATGTTTGGAACAAAATAAAAAATGAAATCCCCAAAAGGGGGTTTCATTT  1950

1951  TTTTATCCAGTTTTTTGCTATTCGGTGAATCTGTATACAATTATAGGTGA  2000

2001  AAATGTGAACATTCTGGGATCCGATAAACCCAGCGAACCATTTGAGGTGA  2050

2051  TAGGTAAGATTATACCGAGGTATGAAAACGAGAATTGGACCTTTACAGAA  2100

2101  TTACTCTATGAAGCGCCATATTTAAAAAGCTACCAAGACGAAGAGGATGA  2150

2151  AGAGGATGAGGAGGCAGATTGCCTTGAATATATTGACAATACTGATAAGA  2200

2201  TAATATATCTTTTATATAGAAGATATCGCCGTATGTAAGGATTTCAGGGG  2250

2251  GCAAGGCATAGGCAGCGCGCTTATCAATATATCTATAGAATGGGCAAAGC  2300

2301  ATAAAAACTTGCATGGACTAATGCTTGAAACCCAGGACAATAACCTTATA  2350

2351  GCTTGTAAATTCTATCATAATTGTGGTTTCAAAATCGGCTCCGTCGATAC  2400

2401  TATGTTATACGCCAACTTTCAAAACAACTTTGAAAAAGCTGTTTTCTGGT  2450

2451  ATTTAAGGTTTTAGAATGCAAGGAACAGTGAATTGGAGTTCGTCTTGTTA  2500

2501  TAATTAGCTTCTTGGGGTATCTTTAAATACTGTAGAAAAGAGGAAGGAAA  2550

2551  TAATAAATGGCTAAAATGAGAATATCACCGGAATTGAAAAAACTGATCGA  2600

2601  AAAATACCGCTGCGTAAAAGATACGGAAGGAATGTCTCCTGCTAAGGTAT  2650

2651  ATAAGCTGGTGGGAGAAAATGAAAACCTATATTTAAAAATGACGGACAGC  2700

2701  CGGTATAAAGGGACCACCTATGATGTGGAACGGGAAAAGGACATGATGCT  2750

2751  ATGGCTGGAAGGAAAGCTGCCTGTTCCAAAGGTCCTGCACTTTGAACGGC  2800
```

-continued

```
2801  ATGATGGCTGGAGCAATCTGCTCATGAGTGAGGCCGATGGCGTCCTTTGC  2850
2851  TCGGAAGAGTATGAAGATGAACAAAGCCCTGAAAAGATTATCGAGCTGTA  2900
2901  TGCGGAGTGCATCAGGCTCTTTCACTCCATCGACATATCGGATTGTCCCT  2950
2951  ATACGAATAGCTTAGACAGCCGCTTAGCCGAATTGGATTACTTACTGAAT  3000
3001  AACGATCTGGCCGATGTGGATTGCGAAAACTGGGAAGAAGACACTCCATT  3050
3051  TAAAGATCCGCGCGAGCTGTATGATTTTTTAAAGACGGAAAAGCCCGAAG  3100
3101  AGGAACTTGTCTTTTCCCACGGCGACCTGGGAGACAGCAACATCTTTGTG  3150
3151  AAAGATGGCAAAGTAAGTGGCTTTATTGATCTTGGGAGAAGCGGCAGGGC  3200
3201  GGACAAGTGGTATGACATTGCCTTCTGCGTCCGGTCGATCAGGGAGGATA  3250
3251  TCGGGGAAGAACAGTATGTCGAGCTATTTTTTGACTTACTGGGGATCAAG  3300
3301  CCTGATTGGGAGAAAATAAAATATTATATTTTACTGGATGAATTGTTTTA  3350
3351  GTACCTAGGCCTTTG
```

(SEQ ID NO: 21)

AGGCAGACGTAAGGGAGGAT

ACAATCATGGCAATTGAACAAATGACGATGCCGCAGCTTGGAGAAAGCGT

AACAGAGGGGACGATCAGCAAATGGCTTGTCGCCCCCGGTGATAAAGTGA

ACAAATACGATCCGATCGCGGAAGTCATGACAGATAAGGTAAATGCAGAG

GTTCCGTCTTCTTTTACTGGTACGATAACAGAGCTTGTGGGAGAAGAAGG

CCAAACCCTGCAAGTCGGAGAAATGATTTGCAAAATTGAAACAGAAGGCG

CGAATCCGGCTGAACAAAAACAAGAACAGCCAGCAGCATCAGAAGCCGCT

GAGAACCCTGTTGCAAAAAGTGCTGGAGCAGCCGATCAGCCCAATAAAAA

GCGCTACTCGCCAGCTGTTCTCCGTTTGGCCGGAGAGCACGGCATTGACC

TCGATCAAGTGACAGGAACTGGTGCCGGCGGGCGCATCACACGAAAAGAT

ATTCAGCGCTTAATTGAAACAGGCGGCGTGCAAGAACAGAATCCTGAGGA

GCTGAAAACAGCAGCTCCTGCACCGAAGTCTGCATCAAAACCTGAGCCAA

AAGAAGAGACGTCATATCCTGCGTCTGCAGCCGGTGATAAAGAAATCCCT

GTCACAGGTGTAAGAAAAGCAATTGCTTCCAATATGAAGCGAAGCAAAAC

AGAAATTCCGCATGCTTGGACGATGATGGAAGTCGACGTCACAAATATGG

TTGCATATCGCAACAGTATAAAAGATTCTTTTAAGAAGACAGAAGGCTTT

AATTTAACGTTCTTCGCCTTTTTTGTAAAAGCGGTCGCTCAGGCGTTAAA

AGAATTCCCGCAAATGAATAGCATGTGGGCGGGGGACAAAATTATTCAGA

AAAAGGATATCAATATTTCAATTGCAGTTGCCACAGAGGATTCTTTATTT

GTTCCGGTGATTAAAAACGCTGATGAAAAAACAATTAAAGGCATTGCGAA

AGACATTACCGGCCTAGCTAAAAAAGTAAGAGACGGAAAACTCACTGCAG

ATGACATGCAGGGAGGCACGTTTACCGTCAACAACACAGGTTCGTTCGGG

TCTGTTCAGTCGATGGGCATTATCAACTACCCTCAGGCTGCGATTCTTCA

AGTAGAATCCATCGTCAAACGCCCGGTTGTCATGGACAATGGCATGATTG

CTGTCAGAGACATGGTTAATCTGTGCCTGTCATTAGATCACAGAGTGCTT

GACGGTCTCGTGTGCGGACGATTCCTCGGACGAGTGAAACAAATTTTAGA

ATCGATTGACGAGAAGACATCTGTTTACTAAATAAGCAAAAAGAGCATTT

TTTGAAGTTTTGTTTCAAAAAATGCTCTTTTTCTATGCTTTATTATTCAG

-continued

```
CGATCCGTATTTTCATTTCGACTCGATATTCTTCTTGTTTTTTCGGGGAG

TAATGAATCGGTATGATTAACTCGTATACATCACTGACAACTGTTAATTG

GCGGTCCGCGATATATTTGATAAGCTTCTGTAAGTTGAGAAAATAATGTT

CAGGCGAAAAATTATACGCGATACACGCATACCTCCCTTTAGGGATCGTT

GTGATTTCCATATCCGGCGTAATTGATGAAATCTGTTTATTCGTCAATAC

AGGTGTGAAAATATGACGGTAAGTCATTTCATCAATGCTGGTGTAGGGCT

GAAAAGAGAAAGTAGCGCCGTAGCTATTGTTCGTAAATCCATCTGCTGAC

TCGATAAATTTTTTAATTTGCTGTAGGAGGCGTTGAGCACGTTTTCAGG

CCCGATTCCTTCTGCCTCTGTCTGAATGATCCGTATTTCTTCTTCATCTA

AAACAAACACCTCACCGAGCGCGGGATATTCCATCTGCCGTTTCATCCGC

TTTTTCACCAATGAAATGGTTTGCTCCAGGGCTGATAAAAAGTCTAATTT

CTCCCTGATTTGCCTCTCCTGCTCTGTATAAAAAGCAAACAGTTCTTCCA

TCTCTAAGTCCTGTGCTTTTTTCATCTCTTCTAAAGGTGTGCCGATATAT

TTCAATGATTTGATCAAATCCAGATGAATGAGCTGAGAATCTGTATAATA

GCGGTAGCTGGTATCCGGGTCGACGTAGGCTGGTTTAAATAAATCAATTT

TATCGTAATAACGGAGCGCTTTTATCGACACGTTTGCCAGTTTTGATACT

TCCCCAATTGAGTAATACGATTCCTTCATGCCATCACTCCTTCTATCATC

AGTATAAAGAAGAAGCGCATTCTTTGCAGTACACAAAGAATGCGCTTCTT

ATCACGTGCTGGCTTTAAGATGTGCAGGCGCTTTCCAAGCAATGGTCAGT

GCAATCCCTATGGCTAAGGTGACCGTTGCAAAGTAGAAAGGATAGTTTAC

ATCTATATCGAACAGCATTCCGCCGATAATAGGCCCGAATACATTGCCGA

TACTTGTAAACATTGAATTCATACCGCCGGCAAACCCCTGTTCATTTCCC

GCAATCTTTGACAGGTAAGTCGTTACCGCAGGCCGCATGAGATCAAATCC

GACAAATACGGTGACTGTCACCAGCAGAATCGCAACATATGAATGTACCG

TTGTCAGCAAGAATACCAGACTCGTCGAGAGAATTAAGCTGTACCGAATT

AAATGAATTTCGCCAAACCATCTTGTGAAGCGGTCGAATAAGACGACTTG

CGTAATGGCGCCAACAATCGCTCCTCCTGTAATCATAATGGCAATGTCGC

TGGCCGTAAATCCGAATTTATGATCCACGAATAATGCAAATAAAGAT
```

Example 10

The following genes were deleted by replacing the coding sequence of each gene with a upp/kan cassette. The effect on FA-Glu yield is shown in Table #: Maf, Abh, RocG, degU, RapC, eps, yngF, yhaR, mmgB, spxA.

An additional copy of each of the following gene was introduced into *Bacillus* under the control of either a constitutive promoter (e.g., PgroEL or under the control of the Psrf promoter, which normally controls expression of genes in the srf operon (which genes are required for production of surfactin). The effect on FA-Glu yield is shown in Table B:

| Single Knockouts | FA-Glu Increase relative to parental strain | Ave |
|---|---|---|
| RapC | 34.1% | 25.9% |
| | 17.6% | |
| plip | 21.2% | 21.2% |
| yqxM | 19.7% | 19.7% |
| eps | 19.1% | 19.1% |
| degU | 13.3% | 18.0% |
| | 22.8% | |
| yngF | 14.5% | 14.5% |
| RocG | 12.0% | 12.0% |
| yhaR | 13.3% | 11.5% |
| | 9.6% | |
| mmgB | 11.4% | 11.4% |
| | 6.2% | 9.7% |
| abh | 16.0% | |
| | 6.9% | |
| maf | 15.6% | 8.0% |
| | 0.5% | |
| spoIIAC | 7.8% | 7.8% |
| fapR | 3.3% | 4.8% |
| | 6.3% | |
| spxA | 2.7% | 2.7% |

| Knockin | FA-Glu Increase relative to parental strain |
|---|---|
| eps->pGroEL-lcfA | 11.5% |
| amyE->Pspac-srfD | 12.7% |
| amyE->PgroEL-sfp-srfD | 44.3% |
| phe+ | 79.2% |

NOTE:
All Single knockouts are in the 43074-B2 background that contains 1) plip KO, 2) phe+, 3)amyE->PgroEL-sfp-srfD and 4) spoIIAC KO

REFERENCES

1. Krass et al., "Functional Dissection of Surfactin Synthetase Initiation Module Reveals Insights into the Mechanism of Lipoinitiation" *Chemistry & Biology*, 17:872-880, 2010.
2. Roongsawang et al., "Phylogeneticv analysis of condensation domains in nonribosomal peptide synthetases" *FEMS Microbiology Letters*, 252:143-151, 2005.
3. Rausch et al., "Phylogenetic analysis of condensation domains in NRPS sheds light on their functional evolution" *BMC Evolutionary Biology* 7(78): 1-15, 2007.
4. Segolene et al., "NORINE: a database of nonribosomal peptides." *Nucleic Acids Research*, 36: D327-D331, 2008.
5. Steller, et al., "initiation of Surfactin Biosynthesis and the Role of the SrfD-Thioesterase Protein." *Biochemistry*, 43:11331-11343, 2004.
6. Duitman et al., "The Mycosubtilin synthetase of *Bacillus subtilis* ATCC6633: A Multifunctional Hybrid Between a Peptide Synthetase, an Amino Transferase, and a fatty Acid Synthase" *PNAS*, 96(23):13294-13299, 1999.
7. Hansen et al., "The Loading Module of Mycosubtilin: An adenylation Domain with fatty Acid Selectivity" *J Am Chem Soc*, 129(20): 6366-6367, 2007.
8. Aron et al., "FenF: Servicing the Mycosubtilin Synthetase Assembly Line in trans" *ChemBioChem*, 8: 613-616, 2007.
9. Wittmann et al., "Role of DptE and DptF in the lipidation reaction of daptomycin" *FEBS Journal*, 275:5343-5353, 2008.
10. Kleinkauf et al., "A nonribosomal system of peptide biosynthesis" *Eur J Biochem*, 236: 335-351, 1996.
11. Miao et al., "Daptomycin biosynthesis in *Streptomyces roseosporus*: cloning and analysis of the gene cluster and revision of peptide stereochemistry" *Microbiology*, 151: 1507-1523, 2005.
12. Zohreh et al., "Structure, biosynthetic origin, and engineering Biosynthesis of calcium-Dependent Antibiotics from *Streptomyces coelicolor*" *Chemistry & Biology*, 9:1175-1187, 2002.
13. Kaneda, "Iso- and anteiso-fatty acids in bacteria: biosynthesis, function, and taxonomic significance," *Microbiological Reviews*, 55(2):288-302, 1991.
14. Isolation and characterization of the □□-ketoacyl-acyl carrier protein synthatse III gene (fabH) from *Escherichia coli* K-12, Tsay, et al., JBC, 267(10), 6807-6814, 1992.
15. Choi et al., "□-ketoacyl-acyl carrier protein synthase III (FabH) is a determining factor in branched-chain fatty acid biosynthesis," *Journal of Bacteriology*, 182(2):365-370, 2000.
16. Kaneda, "Fatty acids of the genus *Bacillus*: an example of branched-chain preference," *Bacteriological Reviews*, 41(2):391-418, 1977.
17. Willecke et al., "Fatty acid-requiring mutant of *bacillus subtilis* defective in branched chain α-keto acid dehydrogenase," *The Journal of Biological Chemistry*, 246(17): 5264-5272.
18. Alteration of the fatty acid profile of *Streptomyces coelicolor* by replacement of the initiation enzyme 3-ketoacyl acyl carrier protein synthase III (FabH).
19. Relationship of primer specificity of fatty acid de novo synthetase to fatty acid composition in 10 species of bacteria and yeasts. Kaneda dn Smith. Can. J. Microbiol., Vol 26, 1980.
20. Application of cellular fatty acid analysis, david welch, Clinical Microbiology Reviews, October 1991, 422-438.
21. Identification, substrate specificity, and inhibition of the *Streptococcus pneumonia* b-ketoacyl-acp carrier protein synthase III (FabH), Khandekar, et al., JBC, 276(32), 2001.
22. Fatty Acid Biosynthesis in *Pseudomonas aeruginosa* Is Initiated by the FabY Class of -Ketoacyl Acyl Carrier Protein Synthases
23. Identification and functional expression of a □9-fatty acid desaturase from *Psychrobacter urativorans* in *Escherichia coli*, Li et al., Lipids, 43, 207-213, 2008.
24. Δ9-fatty acid desaturase from arachidonic acid-producing fungus unique gene sequence and its heterologous expression in a fungus, *Aspergillus*, Sakuradani et al., Eur. J. Biochem., 260, 208-219, 1999.
25. A *Bacillus subtilis* gene induced by cold shock encodes a membrane phospholipid desaturase, Aguilar et al., Journal of bacteriology, 180(8):2194-2200, 1998.
26. Martin, et al., "a lipA (yutB) mutant, encoding lipoic acid synthase, provides insight into the interplay between branched-chain and unsaturated fatty acid biosynthesis in *Bacillus subtilis,*" *Journal of Bacteriology*, 191(24):7447-7455, 2009.
27. Lee et al., "Cloning of srfA operon from *Bacillus subtilis* C9 and its expression in *E. coli,*" *Appl Microbiol Biotechnol*, 75(3):567-572, 2007.
28. Quadri et al., "Characterization of Sfp, a *Bacillus subtilis* phosphopantetheinyl transferase for peptididyl carrier domains in peptide synthetases," *Biochemistry*, 37(6): 1585-1595, 1998.
29. Reznik et al., "Use of sustainable chemistry to produce an acyl amino acid surfactant,", *Appl Microbiol Biotechnol*, published online, 2010.
30. Wang, et al., "The primary structure of branched-chain a-oxo acid dehydrogenase from *bacillus subtilis* and its similarity to other a-oxo acid dehydrogenases," *Eur. J. Biochem.*, 213:1091-1099, 1993.
31. This reference is out of order relative to its position in the text. Felnagle, et al., "Identification of the biosynthetic gene cluster and an additional gene for resistance to the antituberculosis drug capreomycin," Applied and Environmantal Microbiology, 73(13):4162-4170, 2007.
32. This reference is out of order relative to where it is mentioned in the text. Beasley et al., "Mutation of L-2,3-diaminopropionic acid synthase genes blocks staphyloferrin B synthesis in *Staphylococcus aureus,*" BMC Microbilogy, 11:199, 2011.
33. This reference is out of order relative to its position in the text. Simon and Shokat, "A method to site-specifically incorporate methyl-lysine analogues into recombinant proteins," Methods in Enzymology, Volue 512, Nuclososomes: Histones & Chromatin, Part A, edited Carl Wu and C. David Allis, Elsevier, Inc., 2012.
34. This reference is out of order relative to its position in the text. Zhang et al., "Catalytic promiscuity of a bacterial □-N-methyltransferase," *FEBS Letters*, 586:3391-3397, 2012.
35. This reference is out of order relative to its position in the text. Komiyama, et al., "A new antibiotic, cepemycin taxonomy, fermentation, isolation and biological characteristics," *The Journal of Antibiotics*, 46(11):1666-1671, 1993.

Sequence Listing
Proteins for synthesis of 2,3-diaminopropionic acid
sbna
>sp|Q7A1Z6|SBNA_STAAW Probable siderophore biosynthesis protein SbnA
OS = *Staphylococcus aureus* (strain MW2) GN = sbna PE = 3 SV = 1
MIEKSQACHDSLLDSVGQTPMVQLHQLFPKHEVFAKLEYMNPGGSMKDRPAKYTIEHGIK

HGLITENTHLIESTSGNLGIALAMIAKIKGLKLTCVVDPKISPTNLKIIKSYGANVEMVE

EPDAHGGYLMTRIAKVQELLATIDDAYWINQYANELNWQSHYHGAGTEIVETIKQPIDYF

VAPVSTTGSIMGMSRKIKEVHPNAQIVAVDAKGSVIFGDKPINRELPGIGASRVPEILNR

SEINQVIHVDDYQSALGCRKLIDYEGTFAGGSTGSTIAAIEQLITSIEEGATIVTILPDR

GDRYLDLVYSDTWLEKMKSRQGVKSE (SEQ ID NO: 22)

sbnB
>tr|Q6X7U6|Q6X7U6_STAAU SbnB OS = *Staphylococcus aureus*
GN = snbB PE = 4 SV = 1
MNREMLYLNRSDIEQAGGNHSQVYVDALTEALTAHAHNDFVQPLKPYLRQDPENGHTADR

IIAMPSHIGGEHAISGIKWIGSKHDNPSKRNMERASGVIILNDPETNYPIAVEASLISS

MRTAAVSVIAAKHLAKKGFKDLTIIGCGLIGDKQLQSMLEQFDHIERVFVYDQFSEACAR

FVDRWQQQRPEINFIATENAKEAVSNGEVVITCTVTDQPYIEYDWLQKGAFISNISIMDV

HKEVFIKADKVVVDDWSQCNREKKTINQLVLEGKFSKEALHAELGQLVTGDIPGREDDDE

IILLNPMGMAIEDISSAYFIYQQAQQQNIGTTLNLY (SEQ ID NO: 23)

ZmaU
>gi|223047493|gb|ACM79820.1|ZmaU [*Bacillus cereus*]
MSFRYKFYLKYIRNKIYTLYSLIIFLDFNQERKQIMLKKLESLERVIGNTPMIKLEHEKINLYAKLEYYN

LMNSVKVRAAYHILKSAINRGEVNENSTIIESSSGNFAVALATLCRYIGLKFIPVIDPNINDSYENFLRA

TSYQVANVDERDETGGYLLTRLNKVKELLNTIPNAYWTNQYNNADNFEAHYQGIGGEISNDFKQLDYAFI

GVSTGGTIAGVSTRLKEKFPNIKIIAVDSQGSITFGDKPRKRYIPGIGASMIPGMVKKALIDDVMIVPEV

HTVAGCYELFNKHATFAGGSSGTSYYAIQKYFENRDVQNTPNVVFLCPDNGQAYTSTIYNVEWVEWLNTQ

KSVEDQLVSL (SEQ ID NO: 24)

ZmaV
>gi|223047494|gb|ACM79821.1|ZmaV [*Bacillus cereus*]
MMYLNTKHFNEMGVNWEETINVISKAVKSLDSEDFSQPIKPYLRFDDPANRIIAMPAYIGGEFKVSGIKW

IASFPKNIEKGIQRAHSVTILNDAMTGKPFATLNTAMVSVIRTASVTGLMIREFAKLRDLNNVKVGIIGF

GPIGQMHLKMVTALLGDKIEGVYLYDINGIKDELIPEEIYSKTQKVNAYEEAYNDADIFITCTVSAEGYI

DKKPKDGALLNVSLRDFKPDILEYTKSLVVDNWEEVCREKTDVERMHLERGLQKEDTVSIADVVIRGAL

QNFPYDKAILFNPMGMAIFDVAIAAYYYQRARENEMGVLLED (SEQ ID NO: 25)

Methyltrasferases
Bacillus prmA
>gnl|BSUB|BSU25450-MONOMER ribosomal protein Lil methyltransferase
(complement (2624760 . . . 2623825)) *Bacillus subtilis* subtilis 168
MKWSELSIHT THEAVEPISN ILHEAGASGV VIEDPLKLIK ERENVYGEIY QLDPNDYPDE

GVIVKAYLPV NSFLGETVDG IKETINNLLL YNIDLGRNHI TISEVNEEEW ATAWKKYYHP

VKISEKFTIV PTWEEYTPVH TDELIIEMDP GMAFGTGTHP TTVLCIQALE RFVQKGDKVI

DVGTGSGILS IAAAMLEAES VHAYDLDPVA VESARLNLKL NKVSDIAQVK QNNLLDGTEG

EHDVIVANIL AEVILRFTSQ AYSLLKEGGH FITSGIIGHK KQEVKEALEQ AGFTIVEILS

MEDWVSIIAK K (SEQ ID NO: 26)

*E. coli* prmA
>gnl|ECOLI|EG11497-MONOMER methyltransferase for 50S ribosomal
subunit protein
L11 3407092 . . . 3407973 *Escherichia coli* K-12 substr. MG1655
MPWIQLKLNT TGANAEDLSK ALMEAGAVSI TFQDTHDTPV FEPLPGETRL WGDTDVIGLF

DAETDMVDVV AILENHPLLG AGFAHKIEQL EDKDWEREWM DNFHPMRFGE RLWICPSWRD

```
VPDENAVNVM LDPGLAFGTF THPTTSLCLQ WLDSLDLTGK TVIDFGCGSG ILAIAALKLG

AAKAIGIDID PQAIQASRDN AERNGVSDRL ELYLPKDQPE EMKADVVVAN ILAGPLRELA

PLISVLPVSG GLLGLSGILA SQAESVCEAY ADSFALDPVV EKEEWCRITG RKN
(SEQ ID NO: 27)

cypemycin methyltrasferase
>sp|E5KIC0|CYPM_STRSQ Cypemycin methyltransferase OS = Streptomyces
sp. GN = sypM PE = 1 SV = 1
MSDPSVYDETAIEAYDLVSSMLSPGAGLVAWVSSHRPLDGRTVLDLGCGTGVSSFALAEA

GARVVAVDASRPSLDMLEKKRLDRDVEAVEGDFRDLTFDSTFDVVTMSRNTFFLAQEQEE

KIALLRGIARHLKPGGAAFLDCTDPAEFQRAGGTDARSVTYPLGRDRMVTVTQTADRAGQQ

ILSIFLVQGATTLTAFHEQATWATLAEIRLMARTAGLEVTGVDGSYAGEPYTARSREMLV

VLERQ (SEQ ID NO: 28)

Streptomyces griseus methyltransferase
>gi|182440155|ref|YP_001827874.1|methyltransferase [Streptomyces griseus
subsp. griseus NBRC 13350]
MSEPTVYDAAAIDAYDLISSMLSPGAGLAAWVSSHRPLAGRTVLDLGAGTGVSSFALADAGAQVVAVDAS

RPSLDLLESRRGERKVDTVEADFRDLRLDSAFDVVTMSKNTFFLAQSHDEKIELLRAIGRHLKPGGAVFL

DCTDPVEYLRADGAAHTVTYPLGREQMVTITQNADRATQAIMSIFMVQSASTLTSFHEMATWASLPEIRL

LARAAGLEVTAVDGSYAGDAYTARSREMLVVLEAK (SEQ ID NO: 29)

Proteins for initiation of straight chain fatty acid synthesis
fadH family members for initiation of straight chain fatty acid synthesis
M77744
>M77744_1 (M77744|pid:none) Escherichia coli beta-ketoacyl-acyl carrier
protein synthase III (fagH) gene, complete cds.
MYTKIIGTGSYLPEQVRTNADLEKMVDTSDEWIVTRTGIRERHIAAPNETVSTMGFEAAT

RAIEMAGIEKDQIGLIVVATTSATHAFPSAACQIQSMLGIKGCPAFDVAAACAGFTYALS

VADQYVKSGAVKYALVVGSDVLARTCDPTDRGTIIIFGDGAGAAVLAASEEPGIISTHLH

ADGSYGELLTLPNADRVNPENSIHLTMAGNEVFKVAVTELAHIVDETLAANNLDRSQLDW

LVPHQANLRIISATAKKLGMSMDNVVVTLDRHGNTSAASVPCALDEAVRDGRIKPGQLVL

LEAFGGGFTWGSALVRF (SEQ ID NO: 30)

AF384041
>sp|P0A3C5|FABH_STRPN 3-oxoacyl-[acyl-carrier-protein] synthase 3
OS = Streptococcus pneumoniae serotype 4 (strain ATCC BAA-334/TIGR4)
GN = fabH PE = 3 SV = 1
MAFAKISQVAHYVPEQVVTNHDLAQIMDTNDEWISSRTGIRQRHISRTESTSDLATEVAK

KLMAKAGITGEELDFIILATITPDSMMPSTAARVQANIGANKAFAFDLTAACSGFVFALS

TAEKFIASGRFQKGLVIGSETLSKAVDWSDRSTAVLFGDGAGGVLLEASEQEHFLAESLN

SDGSRSECLTYGHSGLHSPFSDQESADSFLKMDGRTVFDFAIRDVAKSIKQTIDESPIEV

TDLDYLLLHQANDRILDKMARKIGVDRAKLPANMMEYGNTSAASIPILLSECVEQGLIPL

DGSQTVLLSGFGGGLTWGTLILTI (SEQ ID NO: 31)

fadY family members for initiation of straight chain fatty acid synthesis
PA5174
>tr|Q9HU15|Q9HU15_PSEAE Probable bets-ketoacyl synthase OS = Pseudomonas
aeruginosa (strain ATCC 15692/PAO1/1C/PRS 101/LMG 12228) GN = PA5174
PE = 3 SV = 1
MSRLPVIVGFGGYNAAGRSSFHHGFRRMVIESMDPQARQETLAGLAVMMKLVKAEGGRYL

AEDGTPLSPEDIERRYAERIFASTLVRRIEPQYLDPDAVHWHKVLELSPAEGQALTFKAS

PKQLPEPLPANWSIAPAEDGEVLVSIHERCEFKVDSYRALTVKSAGQLPTGFEPGELYNS

RFHPRGLQMSVVAATDAIRSTGIDWKTIVDNVQPDEIAVFSGSIMSQLDDNGFGGLMQSR

LKGHRVSAKQLPLGFNSMPTDFINAYVLGSVGMTGSITGACATFLYNLQKGIDVITSGQA
```

RVVIVGNSEAPILPECIEGYSAMGALATEEGLRLIEGRDDVDFRRASRPFGENCGFTLAE

SSQYVVLMDDELALRLGADIHGAVTDVFINADGFKKSISAPGPGNYLTVAKAVASAVQIV

GLDTVRHASFVHAHGSSTPANRVTESEILDRVASAFGIDGWPVTAVKAYVGHSLATASAD

QLISALGTFKYGILPGIKTIDKVADDVHQQRLSISNRDMRQDKPLEVCFINSKGFGGNNA

SGVVLSPRIAEKMLRKRHGQAAFAAYVEKREQTRAAARAYDQRALQGDLEIIYNFGQDLI

DEHAIEVSAEQVTVPGFSQPLVYKKDARFSDMLD (SEQ ID NO: 32)

Pmen_0396
>pmy:Pmen_0396 pyrC; dihydroorotase (EC:3.5.2.3); K01465
dihydroorotase [EC:3.5.2.3](A)
MRTAILGARVIDPASGLDQVTDLYIDGTKLVAFGQAPAGFTADKTLNAQGLIAAPGLVDL

SVALREPGYSRKGSIATETLAAAAGGVTSLCCPPLTKPVLDTPAVAELILDRAREAGHTK

VFPIGALSKGLAGEQLAELVALRDAGCVAPGNGLDNFRSARTLRRALEYAATFDLQVIFH

SQDFSLAEGGLAHEGPTASFLGLAGIPETAETVALARDLLLVEQSGVRAHFSQITSARGA

ELIANAQARGLPVTADVALYQLILTDEALIDFSSLYHVQPPLRSRADRDGLREAVKAGVI

SAIASHHQPHERDAKLAPFAATEPGISSVQLQLPLAMSLVQDGLLDLPTLLARLSSGPAA

ALRLPAGTLSVGGAADIVLFDAQASTVAGEQWYSKGSNCPFIGHCLPGAVRYTLVDGHIS

YQS (SEQ ID NO: 33)

MDS_0454
>pmk:MDS_0454 beta-ketoacyl sythase (A)
MSRLPVIVGFGGYNAAGRSSFHHGFRRTVQESLEPQARQETLAGLAQMMKLVRVVDGYQ

DQDGQPLSLADIESRYAKQILAGTLVRRIEKQHLDPDAAHWQKSIGVTPADGTSLSFLTQ

RKQLPEPLPANWSIEELEGNEVRVTLHDSCEFKVDSYRPLAVKSAGQLPTGFEPSELYNA

RFHPRGLAMTVVGVTDALRSVGIDWQRIVQHVAPDEIAVFASCIMSQLDENGFGGMMQSR

LKGGRVTAKQLALGLNTMPADFINAYVLGSVGTTGSITGACATFLYNLQKGIEQIASGKA

RVVIVGSBEAPINQECIEGYGAMGALATEEGLRQIEGKSEVDFRRASRPFGDNCGFTLAE

ACQFVVLMDDELALELGADIHGAVPDVFINADGFKKSISAPGPGNYLTVAKAVASAVQLL

GLDAVRNRSFVHAHGSSTPANRVTESEILDRVAAAFGIEQWPVTAVKAFVGHSLATASGD

QVIGALGAFKYGIVPGIKTIDAVAGDVHQHHLSLSTEDRKVGDQALDVAFINSKGFGGNN

ASALVLAPHVTERMLRKRHGQAAFDAYLARREGTRAAAAAYDQQALQGKLDIIYNFGNDM

IDDQAISITTEEVKVPGFDQPLVFRKDARYSDMLD (SEQ ID NO: 34)

Psefu_4068
>tr|F6AJT1|F6AJT1_PSEF1 Beta-ketoacyl synthase OS =
Pseudomonas fulva (strain 12-X) GN = Psefu_4068 PE = 3 SV = 1
MKSRLPVIVGFGGYNAAGRSSFHHGFRRTVIESLDEQARQETLTGLAVMTKLVRVVDGRY

QSQDGEALSPADIERRYGAQILASTLVRRIEKQHLDPDAAHWHKSIAVGGEAGSLTFVSS

RKQLPEPLPANWTVEELGGNDVRVTLHDSCEFKVDSYRALPVKSAGQLPTGFEPGELYNS

RFHPRGLQMAVVGVTDALRATGVPWQTIVDHVAPDEIAVFAGSIMSQLDENGFGGLMQSR

LKGHRVSSKQLALGLNTMPADFINAYVLGSVGTTGSVTGACATFLYNLQKGIEQINAGKA

RVVIVGNSEAPINAECIEGYGAMGALATEDGLRLIEGKDDVDFRRASRPFGENCGFTLSE

ACQFVVLMDDELALQLGADIHGAATDVFINADGFKKSISAPGPGNYLTVAKAVAATQLV

GIDAVRRRSFVHAHGSSTPANRVTESELLDRVAAAFAIDSWPVAAVKAFVGHSLATASGD

QVISALGTFKYGIIPGIKTIDEVAADVHQQHLSINVDRHDQRMDVCFINSKGFGGNNAS

AVVLAPHVVERMLRKRHGEAAFSAYQQRREQTRANAQAYDEQATKGQLEIIYNFGNDLID

DTEIAIDDAQIKVPGFAQPLLYKQDDRYSDMLD (SEQ ID NO: 35)

Avin_05510
>avn:Avin_05510 beta-ketoacyl synthase (A)
MSRLPVIVGFGGYNSAGRSSFHHGFRRTVIESLTPQARQETLAGLAVMMKLVSVVDGQYR
DSDGSTLTPAEIERRHGERILAATLIRRIERQYFDVDATHWHKSLTLSGEDQPLHFTTSA
KQLPEPLPANWSVEPLEEHQVRVTIHGSCEFKVDSYREMPVKSAGQLPTGFEPGELYNSR
FHPRGLQLSVVAATDALRSTGIDWQTILDHVQPDEVAVFSGSIMSQLDENGYGGLLQSRL
KGHRVSSKQLPLGFNSMPTDFINAYVLGSVGSTGSITGACATFLYNLQKGIDVITSGQAR
VVVAGNAEAPITPEIVEGYAAMGALATEEGLRHIEGRDQVDFRRASRPFGANCGFTLAEA
AQYVVLMDDSLALELGADIHGAVPDVFVNADGFKKSISAPGPGNYLTVAKAVASAMQLVG
EDGVRQRSFIHAHGSSTPANRVTESELLDRVAGAFGIADWPVAAVKAYVGHSLATASGDQ
LISALGTFKYGLLPGIKTVDRFADDVHDQHLRLSMRDVRRDDLDVCFINSKGFGGNNATG
VLLSPRVTEKMLRKRHGEAAFADYRSRREATREAARRYDEQVLQGRFDILYNFGQDMIDE
HAIEVNEEGVKVPGFKQAIRFRKDERFGDMLD (SEQ ID NO: 36)

PSPA7_5914
>pap:PSPA7_5914 putative beta_ketoacyl synthase (A)
MSRLPVIVGFGGYNAAGRSSFHHGFRRMVIESMDPQARQETLAGLAVMMKLVKAEGGRYL
AEDGTPLSPEDIERRYAERIFASTLVRRIEPQYLDPDAVHWHKVLEATPAEGQALTFKAS
PKQLPEPLPGNWSVTPAADGEVLVSIHERCEFKVDSYRPLTVKSAGQLPTGFEPGELYNS
RFHPRGLQMSVVAATDAIRSTGIDWQTIVDNVQPDEIAVFSGSIMSQLDDNGFGGLMQSR
LKGHRVSAKQLPLGFNSMPTDFINAYVLGSVGMTGSITGACATFLYNLQKGIDVITSGQA
RVVIVGNSEAPILPECIEGYSAMGALATEEGLRLIEGRDEVDFRRASRPFGENCGFTLAE
SSQYVVLMDDELALRLGADIHGAVTDVFINADGFKKSISAPGPGNYLTVAKAVASAVQIV
GLDYVRHASFVHAHGSSTPANRVTESEILDRVASAFGIDGWPVTAVKAYVGHSLATASAD
QLISALGTFKYGILPGIKTIDKVADDVHQQRLSISNPDVRQDKPLEVCFINSKGPGGNNA
SGVVLSPRIAEKMLRRRHGEAAFAAYVEKREQTRGAARAYDQRALQGDLEIIYNFGQDLI
DEQAIEVSAEQVTVPGFSQPLVYKKDAPFSDMLD (SEQ ID NO: 37)

PLES_55661
>pag:PLES_55661 putative beta-ketoacyl synthase (A)
MYRLPVIVGFGGYMAAGRSSFHHGFRRMVIESMDPQARQETLAGLAVMMKLVKAEGGRYL
AEDGTPLSPEDIERRYAERIFASTLVRRIEPQYLDPDAVHWHKVLELSPAEGQALTFKAS
PKQLPEPLPANWTIAPAEDGEVLVSIHERCEFKVDSYRALTVKSAGQLPTGFEPGELYNS
RFHPRGLQMSVVAATDAIRSTGIDWKTIVDNVQPDEIAVFSGSIMSQLDDNGFGGLMQSR
LKGHRVSAKQLPLGFNSMPTDFINAYVLGSVGMTGSITGACATFLYNLQKGIDVITSGQA
RVVIVGNSEAPILPECIEGYSAMGALATEEGLRLIEGRDDVDFRRASRPFGENCGFTLAE
SSQYVVLMDDELALRLGADIHGAVTDVFINADGFKKSISAPGPGNYLTVAKAVASAVQIV
GLDTVRHASFVHAHAGSSTPANRVTESEILDRVASAFGIDGWPVTAVKAYVGHSLATASAD
QLISALGTFKYGILPGIKTIDKVADDVHQQRLSISNRDMRQDKPLEVCFINSKGFGGNNA
SGVVLSPRIAEKMLRKRHGQAAFAAYVEKREQTRAAARAYDQRALQGDLEITYNFGQDLI
DEHAIEVSAEQVTVPGFSQPLVYKKDARFSDMLD (SEQ ID NO: 38)

PA14_68360
>tr|Q02EJ1|Q02EJ1_PSEAE Putative beta-ketoacyl synthase OS = *Pseudomonas aeruginosa* (strain UCBPP-PA14) GN = PA14_68360 PE = 3 SV = 1
MSRLPVIVGFGGYNAAGRSSFHHGFRRMVIESMDPQARQETLAGLAVMMKLVKAEGGRYL

AEDGTPLSPEDIERRYAERIFASTLVRRIEPRYLDPDAVHWHKVLELSPAEGQALTFKAS

PKQLPEPLPANWSIAPAEDGEVLVSIHERCEFKVDSYRALTVKSAGQLPTGFEPGELYNS

RFHPRGLQMSVVAATDAIRSTGIDWKTIVDNVQPDEIAVFSGSIMSQLDDNGFGGLMQSR

LKGHRVSAKQLPLGFNSMPTDFINAYVLGSVGMTGSITGACATFLYNLQKGIDVITSGQA

RVVIVGNSEAPILPECIEGYSAMGALATEEGLRLIEGRDDVDFRRASRPFGENCGFTLAE

SSQYVVLMDDELALRLGADIHGAVTDVFINADGFKKSISAPGPGNYLTVAKAVASAVQIV

GLDTVRHASFVHAHGSSTPANRVTESEILDRVASAFGIDGWPVTAVKAYVGHSLATASAD

QLISALGTFKYGILPGIKTIDKVADDVHQQRLSISNRDMRQDKPLEVCFINSKGFGGNNA

SGVVLSPRIAEKMLRKRHGQAAFAAYVEKREQTRAAARAYDQRALRGDLEIIYNFGQDLI

DEHAIEVSAEQVTVPGFSQPLVYKKDARFSDMLD (SEQ ID NO: 39)

fabHA promoter
ACGCCTCCTTTCCATATACCATACTCTATGAGTAAGATGAACTGATAGTTTAGACGAATATAT

TGCCATGTGAAAAAAAATAGGATAGAATTAGTACCTGATACTAATAATTGATCACAACCTGAT

TGATCTTCTAAATTTAAGATATAAAGGAGTCTTCCCTA (SEQ ID NO: 40)

Proteins that prefer to initiation fatty acid synthesis using
short straight chain starters
fabHA
>gnl|BSUB|BSU11330-MONOMER beta-ketoacyl-acyl carrier protein
synthase III 1208222 . . . 1209160 *Bacillus subtilis* subtilis 168
MKAGILGVGR YIPEKVLTNH DLEKMVETSD EWIRTRTGIE ERRIAADDVF SSHMAVAAAK

NALEQAEVAA EDLDMILVAT VTPDQSFPTV SCMIQEQLGA KKACAMDISA ACAGFMYGVV

TGKQFIESGT YKHVLVVGVE KLSSITDWED RNTAVLFGDG AGAAVGPVS DDRGILSFEL

GADGTGGQHL YLNEKRHTIM NGREVFKFAV RQMGESCVNV IEKAGLSKED VDFLIPHQAN

IRIMEAARER LELPVEKMSK TVHKYGNTSA ASIPISLVEE LEAGKIKDGD VVVMVGFGGG

LTWGAIAIRW GR (SEQ ID NO: 41)

fabHB
>gnl|BSUB|SU10170-MONOMER beta-ketoacyl-acyl carrier protein synthase III
(complement (1093747 . . . 1092770)) *Bacillus subtilis* subtilis 168
MSKAKITAIG TYAPSRRLTN ADLEKIVDTS DEWIVQRTGM RERRIADEHQ FTSDLCIEAV

KNLKSRYKGT LDDVDMILVA TTTSDYAFPS TACRVQEYFG WESTGALDIN ATCAGLTYGL

HLANGLITSG LHQKILVIAG ETLSKVTDYT DRTTCVLFGD AAGALLVERD EETPGFLASV

QGTSGNGGDI LYRAGLRNEI NGVQLVGSGK MVQNGREVYK WAARTVPGEF ERLLHKAGLS

SDDLDWFVPH SANLRMIESI CEKTPFPIEK TLTSVEHYGN TSSVSIVLAL DLAVKAGKLK

KDQIVLLFGF GGGLTYTGLL IKWGM (SEQ ID NO: 42)

Desaturase enzymes
EF617339
>gi|148791377|gb|ABR12480.1|D9-fatty acid desaturase [*Psychrobacter urativorans*]
MIAKTAMGLPLKGLRLAIKSSDILIQTAGTQALRLKTWYEEGKANEAASEQPTATSNVNELSPANDDTSI

NTKTSASTSDNNKTLSTEKPIDIRELEFKKAPINWIPATILITTPIAAAVITPWYLFTHQVSAPVWGVFG

AFMVWTGISITAGYHRLLAHRAYKAHPIVKNFLLLGSTLAVQGSAFDWVSGHRSHHRHVDDRMDDPYSAK

RGFFFSHIGWMLKNYPSGKFDYKNIPKLTKDRTLQIQHKYYGLWVLAANVGLVAAIGWLIGDVWGTLVLA

GLLRLVLTHHFTFFINSLCHMFGSRPYTDTNTARDNFFLALFTWGEGYHNYHHFFQYDYRNGVKWWQYDP

TKWLIAGLSKVGLTTELRTIDDTTIKHAEVQMQFKKAQQQIDTVNAGGLDIPHAMKTFQDRIKFEFEAFT

QTVEEWQALKAKAIEMKKTEFADRLHEVDDKLKHEYANIEQKTHEHNDNLKVAFRSIGHNSKAA (SEQ ID NO: 43)
AB015611

>tr|O94747|O94747_MORAP Delta-9 fatty acid desaturase OS =
*Mortierella alpina* PE = 2 SV = 1
MATPLPPSFVVPATQTETRRDPLQHEELPPLFPEKITIYNIWRYLDYKHVVGLGLTPLIA

LYGLLTTEIQTKTLIWSIIYYYATGLGITAGYHRLWAHRAYNAGPAMSFVLALLGAGAVE

GSIKWWSRGHRAHHRWTDTEKDPYSAHRGLFFSHIGWMLIKRPGWKIGHADVDDLNKSKL

VQWQHKNYLPLVLIMGVVFPTLVAGLGWGDWRGGYFYAAILRLVFVHHATFCVNSLAHWL

GDGPFDDRHSPRDHFITAFVTLGEGYHNFHHQFPQDYPNAIRFYQYDPTKWVIALCAFFG

LASHLKTFPENEVRKGQLQMIEKRVLEKKTKLQWGTPIADLPILSFEDYQHACKNDNKKW

ILLEGVVYDVADFMSEHPGGEKYIKMGVGKDMTAAFNGGMYDHSNAARNLLSLMRVAVVE

YGGEVEAQKKNPSMPIYGTDHAKAE (SEQ ID NO: 44)

AF037430
>sp|O34653|DES_BACSU Fatty acid desaturase OS = *Bacillus subtilis*
(strain 168) GN = des PE = 2 SV = 1
MTEQTIAHKQKQLTKQVAAFAQPETKNSLIQLLNTFIPFFGLWFLAYLSLDVSYLLTLAL

TVIAAGFLTRIFIIFHDCCHQSFFKQKRYNHILGFLTGVLTLFPYLQWQHSHSIHHATSS

NLDKRGTGDIWMLTVNEYKAASRRTKLAYRLYRNPFIMFILGPIYVFLITNRFNKKGARR

KERVNTYLTNLAIVALAAACCLIFGWQSFLLVQGPIFLISGSIGVWLFYVQHTFEDSYFE

ADENWSYVQAAVEGSSFYKLPKLLQWLTGNIGYHHVHHLSPKVPNYKLEVAHEHHEPLKN

VPTITLKTSLQSLAFRLWDEDNKQFVSFRATKHIPVSLPPDSPEKQKLRKNA (SEQ ID NO: 45)

Regulatory factors
DesK
>gnl|BSUB|BSU19190-MONOMER DesK two-component sensory histidine kinase
2090574 . . . 2091686 *Bacillus subtilis* subtilis 168
MIKNHFTFQK LNGITYPYWT IFFILPFYFI WKSSSTFVII VGIILTLLFF SVYRFAFVSK

GWTIYLWGFL LIGISTASIT LFSYIYFAFF IAYFIGNIKE RVPFHILYYV HLISAAVAAN

FSLVLKKEFF LTQIPFVVIT LISAILLPFS IKDRKERERL EEKLEDANER IAELVKLEER

QRIARDLHDT LGQKLSLIGL KSDLARKLTY KDPEQAAREL KSVQQTARTS LNEVRKIVSS

MKGIRLKDEL INIKQILEAA DIMFIYEEEK WPENISLLNE NILSMCLKEA VTNVVKHSQA

KTCRVDIQQL WKEVVITVSD DGTFKGEENS FSKGHGLLGM RERLEFANGS LHTDTENGTK

LTMAIPNNSK (SEQ ID NO: 46)

Peptide synthetase modules
srfAA module a
(condensation domain, adenylation domain, thiolation domain, it
is glutamate specific)
MEITFYPLTDAQKRIWYTEKFYPHTSISNLAGIGKLVASADAIDYVLVEQAIQEFIRRNDA

MRLRLRLDENGEPVQYISEYRPVDIKHTDTTEDPNAIEFISQWSREETKKPLPLYDCDLF

RFSLFTIKENEVWFYANVHHVISDGISMNILGNAIMHIYLELASGSETKEGISHSFIDHV

LSEQEYAQSKRFEKDKAFWNKQFESVPELVSLKRNASAGGSLDAERFSKDVPEALHQQIL

SFCEANKVSVLSVFQSLLAAYLYRVSGQNDVVTGTFMGNRTNAKEKQMLGMFVSTVPLRT

NIDGGQAFSEFVKDRMKDLMKTLRHQKYPYNLLINDLRETKSSLTKLFTVSLEYQVMQWQ

KEEDLAFLTEPIFSGSGLNDVSIHVKDRWDTGKLTIDFDYRTDLFSREEINMICERMITM

LENALTHPEHTIDELTLISDAEKEKLLAPAGGKSVSYRKDMTIPELFQEKAELLSDHPAV

VFEDRTLSYRTLHEQSARIANVLKQKGVGPDSPVAVLIERSERMITAIMGILKAGGAYVP

IDPGFPAERIQYILEDCGADFILTESKVAAPEADAELIDLDQAIEEGAEESLNADVNARN

LAYIIYTSGTTGRPKGVMIEHRQVHHLVESLQQTIYQSGSQTLRMALLAPFHFDASVKQI

FASLLLGQTLYIVPKKTVTNGAALTAYYRKNSIEATDGTPAHLQMLAAAGDFEGLKLKHM

LIGGEGLSSVVADKLLKLFKEAGTAPRLTNVYGPTETCVDASVHPVIPENAVQSAYVPIG

KALGNNRLYILDQKGRLQPEGVAGELYIAGDGVGRGYLHLPELTEEKFLQDPFVPGDRMY

RTGDVVRWLPDGTIEYLGREDDQVKVRGYRIELGEIEAVIQQAPDVAKAVVLARPDEQGN

LEVCAYVVQKPGSEFAPAGLREHAARQLPDYMVPAYFTEVTEIPLTPSGKVDRRKLFALE

VKAVSGTAYTAPRNETEKAIAAIWQDVLNVEKAGIFDNFFETGGHSLKAMTLLTKIHKET

GIEIPLQFLFEHPTITALAEEADHRESKAFAVIEPAEKQEHYPL (SEQ ID NO: 47)

dptA1 module 1 of daptomycin synthetase
MDMQSQRLGVTAAQQSVWLAGQLADDHRLYHCAAYLSLTGSIDPRTLGTAVRRTLDETEALRTRFVPQDG

ELLQILEPGAGQLLLEADFSGDPDPERAAHDWMHAALAAPVRLDRAGTATHALLTLGPSRHLLYFGYHHI

ALDGYGALLHLRRLAHVYTALSNGDDPGPCPFGPLAGVLTEEAAYRDSDNHRRDGEFWTRSLAGADEAPG

LSEREAGALAVPLRRTVELSGERTEKLAASAAATGARWSSLLVAATAAFVRRHAAADDTVIGLPVTARLT

GPALRTPCMLANDVPLRLDARLDAPFAALLADTTRAVGTLARHQRFRGEELHRNLGGVGRTAGLARVTVN

VLAYVDNIRFGDCRAVVHELSSGPVRDFHINSYGTPGTPDGVQLVFSGNPALYTATDLADHQERFLRFLD

AVTADPDLPTGRHRLLSPGTRARLLDDSRGTERPVPRATLPELFAEQARRTPDAPAVQHDGTVLTYRDLH

RSVERAAGRLAGLGLRTEDVVALALPKSAESVAILLGIQRAGAAYVPLDPTHPAERLARVLDDTRPRYLV

TTGHIDGLSHPTPQLAAADLLREGGPEPAPGRPAPGNAAYIIQTSGSTGRPKGVVVTHEGLATLAADQIR

RYRTGPDARVLQFISPGFDVFVSELSMTLLSGGCLVIPPDGLTGRHLADFLAAEAVTTTSLTPGALATMP

ATDLPHLRTLIVGGEVCPPEIFDQWGRGRDIVNAYGPTETTVEATAWHRDGATHGPVPLGRPTLNRRGYV

LDPALEPVPDGTTGELYLAGEGLARGYVAAPGPTAERFVADPFGPPGSRMYRTGDLVRRSGGMLEFVGR

ADGQVKLRGFRIELGEVQAALTALPGVRQAGVLIREDRPGDPRLVGYIVPAPGAEPDAGELRAALARTLP

PHMVPWALVPLPALPLTSNGKLDRAALPVPAARAGGSGQRPVTPQEKTLCALFADVLGVTEVATDDVFFE

LGGHSLNGTRLLARIRTEFGTDLTLRDLFAFPTVAGLLPLLDDNGRQHTTPPLPPRPERLPLS (SEQ ID NO: 48)

dptA1 module 5
                                               IDRRPERLPLSFAQRRLWFL
SKLEGPSATYNIPVAVRLTGALDVPALRAALGDVTARHESLRTVFPDDGGEPRQLVLPHAEPPFLTHEVT

VGEVAEQAASATGYAFDITSDTPLRATLLRVSPEEHVLVVVIHHIAGDGWSMGPLVRDLVTAYRARTRGD

APEYTPLPVQYADYALWQHAVAGDEDAPDGRTARRLGYWREMLAGLPEEHTLPADRPRPVRSSHRGGRVR

FELPAGVHRSLLAVARDRRATLFMVVQAALAGLLSRLGAGDDIPIGTPVAGRGDEALDDVVGFFVNTLVL

RTNLAGDPSFADLVDRVRTADLDAFAHQDVPFERLVEALAPRRSLARHPLFQIWYTLTNADQDITGQALN

ALPGLTGDEYPLGASAAKFDLSFTFTEHRTPDGDAAGLSVLLDYSSDLYDHGTAAALGHRLTGFFAALAA

DPTAPLGTVPLLTDDERDRILGDWGSGTHTPLPPRSVAEQIVRRAALDPDAVAVITAEEELSYRELERLS

GETARLLADRGIGRESLVAVALPRTAGLVTTLLGVLRTGAAYLPLDTGYPAERLAHVLSDARPDLVLTHA

GLAGRLPAGLAPTVLVDEPQPPAAAAPAVPTSPSGDHLAYVIHTSGSTGRPKGVAIAESSLRAFLADAVR

RHDLTPHDRLLAVTTVGFDIAGLELFAPLLAGAAIVLADEDAVRDPASITSLCARHHVTVVQATPSWWRA

MLDGAPADAAARLEHVRILVGGEPLPADLARVLTATGAAVTNVYGPTEATIWATAAPLTAGDDRTPGIGT

PLDNWRVHILDAALGPVPPGVPGEIHIAGSGLARGYLRRPDLTAERFVANPFAPGERMYRTGDLGRFRPD

GTLEHLGRVDDQVKVRGFRIELGDVEAALARHPDVGRAAAAVRPDHRGQGRLVAYVVPRPGTRGPDAGEL

RETVRELLPDYMVPSAQVTLTTLPHTPNGKLDRAALPAPVFGTPAGRAPATREEKILAGLFADILGLPDV

GADSGFFDLGGDSVLSIQLVSRARREGLHITVRDVFEHGTVGALAAAALPAPADDADDTVPGTDVLPSIS

DDEFEEFELELGLEGEEEQW (SEQ ID NO: 49)

Module 2 of CmnA (Sequence listing CmaA, A2)

PSPEPVAEVSRAEQR

IWLLSRLGGHPAEYAIPVALRLAGPLDVAKLKNAVDAVVRRHEGLRHVFPEVDGSPTRAVLDPGSITVAE

EANRSVREVLAEGVAALDPATGPLARFTLVNQGPQDHVLAIVLHHLIADGWSVDVLLRDIAAHYTGAPTA

TPGRYADYLALERAEEQDGALGRALEHFVTALDGVPDEVSFPPDHPRPAQRTGRGDVVRHRIDAAPVTAL

AERLRTTPFAVLLAAVGVLLHRVGGHRDVVVGTAVARRPDAGLDGLVGLCLNTLALRWPVQPHDTLGEVV

RAVTDRLADGLQHDAASFDRVVDKLAPARDSGRTPVFQVMALYEEPYETALALPDVTTTDVTVHCGSAQA

DAAFGFVPREGGIDLTLQFSTDVFTRATASRWARRLATLLAGARADTRVADLPLLPEDESQDLERWSGTT

GEAPTTTLHALAHEIAQRHPDRPAIHFGQNSLTYGEFDARSAQLAHELRARGVRAETPVVVCLERSPEAL

IAVYGVLKAGGAYVPVETSNPDLRIAELIADSGAALVLTQRRLADRLAALGAEVVVVDEPLPRHPTTDPE

PLTGPDHLAYVIYTSGSTGRPKGVMVQHGSVLNFLDALDRRFDLTPDDRLLHKSPALFDVSVREVFWALT

RGASVVVAEPGRHADPGHLVDLVERERVTVAHFVPSSLAVFLEGLPGPGRCPTLRHVLTSGETLPVTTAR

AARDLLGARLRNMYGPTETTVEMTDHDVVDDTVDRLPIGHPFEGAVVRVLDADLRPVPPGSTGELCVGGL

PVARGYLGRPALTAERFVPDPLGPAGARLYRTGDLARLLPDGQLDFLGRNDFQVKVRGHRIEPGEVEAVL

GALPGVHGALVTAHDDRLIGYAVTDRDGEELRTALAERLPEHLVPSVVLTLDRFPLTGNGKLDRAALPTP

TGRHTGDSRPLTATEAALAAIWRDLLDVPEVRADDHFFALGGHSLLAARVAARAGAALGVALPLPTVLRF

PRLADLATAVDGTRADREPVRPRPDRRRRAPLSSAQRRLWIEENLRPGTATYTVAEAFRLRGELDEEAFA

AAVDDVLRRHDALRAHVESVEDGEPELVVAPEPRTALRVGDLPADRVRDALAAESARVFDPAGPLVATSL

HRLAPDEWLFQFTAHHLVVDGWSLDVLWRDLAACYHDRRAGRAPRPRDGLTFTDYTWWERDVRSRDLEPH

LAFWRGELAGLRPQPPADAHGPGAVLDFALGAALSDELRATAAGLGVSPFVLGLTAFALALGEDSPGAIG

VEVANRASAETADLVGLFVNHVPVRVAPRGTGRAAVAAVDEARRRVLPHEHVPFDLVVDLLGPGRAPTSV

AFSHLDVRGHSPRLDGVTATRLTPPHNGTAKFDLLLEVLDTEHGLTGAFEYRPERFTAARVAQVRNHWEA

ALLTLLADPDLPVDARRPDFA (SEQ ID NO: 50)

```
        /gene="mycA"
        /coded_by="AF184956.1:3161 . . . 15076"
        /transl_table=11

ORIGIN
    1 mytsqfqtlv dvirnrsnis drgirfiesd kietfvsyrq lfdeaggflg ylqhigiqpk
   61 qeivfqiqen ksfvvafwac liggmipvpv sigedndhkl kvwriwniln npfllasetv
  121 ldkmkkfaad hdlqdfhhql ieksdiiqdr iydhpasqye peadelafiq fssgstgdpk
  181 gvmlthhnli hntcairnal aidlkdtlls wmplthdmgl iachlvpala ginqnlmpte
  241 lfirrpilwm kkahehkasi lsspnfgyny flkflkdnks ydwdlshirv iangaepilp
  301 elcdeflltrc aafnmkrsai lnvyglaead vgatfsnige rfvpvylhrd hlnlgerave
  361 vskedqncas fvevgkpidy cqiricnean egledfgigh iqikgenvtq gyynnpestn
  421 raltpdgwvk tgdlgfirkg nlvvtgrekd iifvngknvy phdiervaie ledidlgrva
  481 acgvydgetr sreivlfavy kksadrfapl vkdikkhlyq rggwsikeil pirklpktts
  541 gkvkryelae qyesgkfale stkikegleg hstepvqtpi heietallsi fsevmdgkki
  601 hlndhyfdmg atslqlsqia erieqkfgce ltvadlftyp siadlaafly enhseikqtd
  661 takpsrsssk diaiigmsln vpgasnksdf whllengehg ireypaprvk daidylrsik
  721 sernekqfvr ggyldeidrf dysffglapk takfmdpngr lflqsawhai edagyagdti
  781 sgsqlgvyvg yskvgydyer llsanypeel hhyivgnlps vlasriayfl nlkgpavtvd
  841 tacssslvav hmackalltg dcemalaggi rtsllpmrig ldmessdgit ktfskdsdgt
  901 gsgegvaavl lkplqaaird gdhiygvikg saingdgttv gitapspaaq teviemawkd
  961 agiapetlsf ieahgtgtkl gdpvefnglc kafekvtekk qfcaigsvka nighlfeaag
 1021 ivgliksalm lnhkkipppla hfnkpnplip fhsspfyvnq evmdftpedr plrggissfg
 1081 fsgtnahvvl eeytpeseya pedgndphlf vlsahteasl yelthqyrqy isddsqsslr
 1141 sicytastgr ahldyclami vssnqelfdk ltsliqgern lpqvhfgykn ikemqpaekd
 1201 nlskqisdlm qhrpctkder itwlnriael yvqravidwr avysnevvqk tplplypfer
```

-continued

```
1261 nrcwveavye sakerkekge valdinhtkt hiesflktve snasgirade idsnahfigf
1321 gldsimltqv kkaiadefnv dipmerffdt mnniesvvdy laenvpsaas tppqesvtaq
1381 eelvisgaqp elehqehmld kiiasqnqli qqtlqaqlds fnllrnnshf vskeseisqd
1441 ktslspksvt akknsaqeak pyipfqrqtl neqvnytpqq rqylesfiek yvdktkgskq
1501 ytdetrfaha nnrnlssfrs ywkemvypii aersdgsrmw didgneyidi tmgfgvnlfg
1561 hhpsfitqtv vdsthsalpp lgpmsnvage vadriractg vervafynsg teavmvalrl
1621 araatgrtkv vvfagsyhgt fdgvlgvant kggaepanpl apgipqsfmn dliilhynhp
1681 dsldvirnlg nelaavlvep vqsrrpdlqp esflkelrai tqqsgtalim deiitgfrig
1741 lggaqewfdi qadlvtygki igggqplgiv agkaefmnti dggtwqygdd syptdeakrt
1801 fvagtfnthp ltmrmslavl rylqaegetl yerlnqktty lvdqlnsyfe qsqvpirmvq
1861 fgslfrfvss vdndlffyhl nykgvyvweg rncflstaht sddiayiiqa vqetvkdlrr
1921 ggfipegpds pndgghkepe tyelspeqkq lavvsqygnd asaalnqsim lkvkgavght
1981 llkqavrniv krhdalrtvi hvddevqqvq arinveipii dftgypneqr esivqkwlte
2041 dakrpfhfhe qkplfrvhvl tskqdehliv ltfhhiiadg wsiavfvqel estyaaivqg
2101 splpshevvs frqyldwqqa qienghyeeg irywrqylse pipqailtsm sssryphgye
2161 gdrytvtldr plskaiksls irmknsvfat ilgafhlflq gltkqaglvi giptagqlhm
2221 kqpmlvgncv nmvpvkntas sestladylg hmkenmdqym rhqdvpmtlv asqlphdqmp
2281 dmriifnldr pfrklhfgqm eaeliaypik cisydlflnv tefdqeyvld fdfntsviss
2341 eimnkwgtgf vnllkkmveg dsasldslkm fskedqhdll elyadhqlri astldhkgvr
2401 avyeepenet elqiaqiwae liglekvgrs dhflslggns lkatlmlski qqtfnqkvsi
2461 gqffshqtvk elanfirgek nvkyppmkpv eqkafyrtsp aqqrvyflhq mepnqvsqnm
2521 fgqisiigky dekaliaslq qvmqrheafr tsfhiidgei vqqiageldf nvrvhsmdre
2581 efeayadgyv kpfrleqapl vraelikvdn egaellidmh hiisdgysms iltnelfaly
2641 hgnplpeipf eykdfaewqn qlligevmeq qeeywlegfk qevpilqlpa dgsramewss
2701 eggqrvtcslq sslirslqem aqqkgttlym vllaaynvll hkytgqediv vgtpvsgrnq
2761 pniesmigif iqtmgirtkp qankrftdyl devkrqtlda fenqdypfdw lvekvnvqre
2821 ttgkslfntm fvyqniefqe ihqdgctfrv kernpgvsly dlmltiedae kqidihfdfn
2881 pnqfeqetie qiirhytsll dslvkepeks lssvpmlsdi erhqllmgcn dtetpfphnd
2941 tvcqwfetqa eqrpddeavi fgnerctygq lnervnglar tlrtkgvqad gfvaiicphr
3001 ielivgilav lkaggayvpi dpeypedriq ymlkdseaki vlaqldlhkh ltfdadvvll
3061 deessyhedr snleptcgan dlaymiytsg stgnpkgvli ehrglanyie wakevyvnde
3121 ktnfplyssi sfdltvtsif tplvtgntii vfdgedksav lstimqdpri diikltpahl
3181 hvlkemkiad gttirkmivg genlstrlaq svscqfkggl difneygpte avvgemiyry
3241 dtkrdrrefv pigapaants iyvidasmnl vpvgvpgemy iggagvargy whrpdltaek
3301 fvhnpfapgt imyktgdlak rirdgnllyl grideqvkir ghrielgeve aamhkveavq
3361 kavvlareee dglqqlcayy vsnkpitiae ireqlslelp dymvpshyiq leqlpltsng
3421 kinrkalpap evsleqiaey vppgnevesk lavlwqemlg ihrvgikhnf fdlggnsira
3481 talaarihke ldvnlsvkdi fkfptieqla nmalrmekir yvsipsaqki syypvssaqk
3541 rmyllshteg geltynmtga msvegaidle rltaafqkli erhevlrtsf elyegepaqr
3601 ihpsieftie qiqareeeve dhvldfiksf dlakpplmrv glieltpekh vllvdmhhii
3661 sdgvsmnilm kdlnqfykgi epdplpiqyk dyavwqqtea qrqnikkqea ywinrfhdei
3721 pvldmptdye rpairdyege sfeflipiel kqrlsqmeea tgttlymilm aaytillsky
3781 sgqedivvgt pvsgrshmdv esvvgmfvnt lvirnhpagr kifedylnev kenmlnaygn
3841 qdypleeliq hvhllkdssr nplfdtmfvl qnldqvelnl dslrftpykl hhtvakfdlt
3901 lsiqtdqdkh hglfeyskkl fkksrieals kdylhilsvi sqqpsigieh ielsgstaed
3961 dnlihsieln f (SEQ ID NO: 51)
```

Psrf-Gly-1gr_m2-F3-TE-pUC19

```
   1 TCGCGCGTTTCGGTGATGACGGTGAAAACCTCTGACACATGCAGCTCCCG        50
  51 GAGACGGTCACAGCTTGTCTGTAAGCGGATGCCGGGAGCAGACAAGCCCG       100
 101 TCAGGGCGCGTCAGCGGGTGTTGGCGGGTGTCGGGGCTGGCTTAACTATG       150
 151 CGGCATCAGAGCAGATTGTACTGAGAGTGCACCATATATCGACAAAAATG       200
 201 TCATGAAAGAATCGTTGTAAGACGCTCTTCGCAAGGGTGTCTTTTTTTGC       250
 251 CTTTTTTTTCGGTTTTTGCGCGGTACACATAGTCATGTAAAGATTGTAAAT      300
 301 TGCATTCAGCAATAAAAAAAGATTGAACCCAGCACTTTGGTTTAAAAATT       350
 351 TTTATTTTTCTGTAAATAATGTTTAGTGAAATGATTGCGGCATCCCGCA        400
 401 AAAAATATTGCTGTAAATAAACTGGAATCTTTCGGCATCCCGCATGAAAC       450
 451 TTTTCACCCATTTTTCGGTGATAAAAACATTTTTTTCATTTAAACTGAAC       500
 501 GGTAGAAAGATAAAAAATATTGAAAACAATGAATAAATAGCCAAAATTGG       550
 551 TTTCTTATTAGGGTGGGGTCTTGCGGTCTTTATCCGCTTATCTTAAACGC       600
 601 CGCAATGCTGACTGACGGCAGCCTGCTTTAATAGCGGCCATCTGTTTTTT       650
 651 GATTGGAAGCACTGCTTTTTAAGTGTAGTACTTTGGGCTATTTCGGCTGT       700
 701 TAGTTCATAAGAATTAAAAGCTGATATGGATAAGAAAGAGAAAATGCGTT       750
 751 GCACATGTTCACTGCTTATAAAGATTAGGGGAGGTATGACAATATGGAAA       800
 801 TAACTTTTTACCCTTTAACGGATGCACAAAAACGAATTTGGTACACAGAA       850
 851 AAATTTTATCCTCACACGAGCATTTCAAATCTTGCGGGGATTGGTAAGCT       900
 901 GGTTTCAGCTGATGCGATTGATTATGTGCTTGTTGAGCAGGCGGATTCAAG      950
 951 AGTTTATTCGCAGAAATGACGCCATGCGCCTTCGGTTGCGGCTAGATGAA      1000
1001 AACGGGGAGCCTGTTCAATATATTAGCGAGTATCGGCCTGTTGATATAAA      1050
1051 ACATACTGACACTACTGAAGATCCGAATGCGATAGAGTTTATTTCACAAT      1100
1101 GGAGCCGGGAGGAAACGAAGAAACCTTTGCCGCTATACGATTGTGATTTG      1150
1151 TTCCGTTTTTCCTTGTTCACCATAAAGGAAAATGAAGTGTGGTTTTACGC      1200
1201 AAATGTTCATCACGTGATTTCTGATGGTATGTCCATGAATATTGTCGGGA      1250
1251 ATGCGATCATGCACATTTATTTAGAATTAGCCAGCGGCTCAGAGACAAAA      1300
1301 GAAGGAATCTCGCATTCATTTATCGATCATGTTTATCTGAACAGGAATA       1350
1351 TGCTCAATCGAAGCGGTTTGAAAAGGACAAGGCGTTTTGGAACAAACAAT      1400
1401 TTGAATCGGTGCCTGAACTTGTTTCCTTGAAACGGAATGCATCCGCAGGG      1450
```

```
1451  GGAAGTTTAGATGCTGAGAGGTTCTCTAAAGATGTGCCTGAAGCGCTTCA  1500
1501  TCAGCAGATTCTGTCGTTTTGTGAGGCGAATAAAGTCAGTGTTCTTTCGG  1550
1551  TATTTCAATCGCTGCTCGCCGCCTATTTGTACAGGGTCAGCGGCCAGAAT  1600
1601  GATGTTGTGACGGGAACATTTATGGGCAACCGGCAAAATGCGAAAGAGAA  1650
1651  GCAGATGCTTGGCATGTTTGTTTCTACGGTTCCGCTTCGGACAAACATTG  1700
1701  ACGGCGGGCAGGCGTTTTCAGAATTTGTCAAAGACCGGATGAAGGATCTG  1750
1751  ATGAAGACACTTCGCCACCAAAAGTATCCGTATAATCTCCTAATCAACGA  1800
1801  TTTGCGTGAAACAAAGAGCTCTCTGACCAAGCTGTTCACGGTTTCTCTTG  1850
1851  AATATCAAGTGATGCAGTGGCAGAAAGAAGAGGATCTTGCCTTTTTGACT  1900
1901  GAGCCGATTTTCAGCGGCAGCGGATTAAATGATGTCTCAATTCATGTAAA  1950
1951  GGATCGATGGGATACTGGGAAACTCACCATAGATTTTGATTACCGCACTG  2000
2001  ATTTATTTTCACGTGAAGAAATCAACATGATTTGTGAGCGCATGATTACC  2050
2051  ATGCTGGAGAACGCGTTAACGCATCCAGAACATACAATTGATGAATTAAC  2100
2101  ACTGATTTCTGATGCGGAGAAACGCGATTTGTTTTTGCGGGTGAACGATA  2150
2151  CAGCCAAGGCGTATCCGAACAAGCTGATCATGTCGATGCTGGAGGATTGG  2200
2201  GCGGCGGCTACCCCTGACAAAACAGCGCTAGTCTTCCGCGAACAACGCGT  2250
2251  GACGTATCGCGAGCTGAACGAGCGGGTCAACCAGTTGGCACACACTTTGC  2300
2301  GCGAAAAAGGGGTGCAACCTGACGATCTCGTGATGCTGATGGCAGAGCGG  2350
2351  TCGGTCGAGATGATGGTGGCGATTTTCGCTGTGTTGAAAGCGGGCGGAGC  2400
2401  GTACTTGCCCATCGACCCGCACAGTCCGGCGGAGCGAATCGCCTACATTT  2450
2451  TCGCAGACAGCGGAGCCAAGCTGGTGCTGGCACAGTCGCCGTTTGTGGAA  2500
2501  AAGGCAAGCATGCGGAAGTGGTCCTTGATCTGAACAGTGCGAGCAGCTA  2550
2551  TGCGGCGGATACGAGCAACCCGCCACTGGTCAACCAGCCAGGCGATCTGG  2600
2601  TGTATGTCATGTACACTTCCGGCTCAACGGGAAAACCAAAAGGCGTGATG  2650
2651  ATCGAGCACGGAGCGCTGCTCAATGTGCTTCACGGAATGCAGGACGAGTA  2700
2701  CCCGCTTTTGCAGGACGATGCCTTCTTGCTCAAGACAACCTACATATTCG  2750
2751  ATATTTCAGTCGCGGAAATTTTCGGGTGGGTTCCGGGTCGTGGCAAACTG  2800
2801  GTGATTTTGGAACCGGAGGCGGAAAAGAACCCGAAGGCTATTTGGCAGGC  2850
2851  GGTAGTCGGAGCGGGAATTACCCACATCAACTTCGTGCCCTCCATGCTGA  2900
2901  TCCCGTTTGTCGAGTATTTGGAAGGGCGAACAGAAGCAAATCGCTTGCGG  2950

2951  TACATCTTGGCTTGCGGCGAAGCGATGCCGGATGAACTCGTGCCAAAAGT  3000
3001  GTACGAAGTATTGCCAGAGGTGAAGCTGGAAAACATCTACGGCCCGACAG  3050
3051  AAGCGACGATTTACGCTTCCCGTTACTCGCTCGCGAAAGGCTCGCAGGAA  3100
3101  AGTCCTGTTCCAATCGGAAAGCCGCTGCCCAACTATCGCATGTATATCAT  3150
3151  CAATCGGCATGGACAACTGCAACCAATCGGCGTACCAGGAGAGCTATGCA  3200
3201  TCGCAGGAGCAAGTCTGGCGAGAGGGTATTTGAACAATCCAGCGCTGACA  3250
3251  GAAGAAAAATTCACTCCTCATCCGCTGGAGAAAGGCGAGCGGATTTATCG  3300
3301  CACGGGTGATCTCGCCCGTTATCGCGAGGATGGCAACATCGAATACCTCG  3350
3351  GACGGATGGACCATCAGGTGAAAATTCGCGGATACCGGATCGAACTGGAC  3400
3401  GAAATCCGCAGCAAGCTGATTCAGGAGGAAACGATTCAGGACGCGGTGGT  3450
3451  CGTAGCCCGAAACGATCAAAACGGCCAAGCGTACTTGTGCGCCTACCTGC  3500
3501  TGTCCGAACAGGAGTGGACAGTCGGTCAACTGCGCGAGTTGCTTCGCCGT  3550
3551  GAACTGCCTGAATACATGATTCCGGCCCATTTCGTTTTGCTGAAACAGTT  3600
3601  CCCGCTCACAGCCAATGGCAAGCTCGATCGCAAGGCTTTGCCAGAACCGG  3650
3651  ACGGCAGTGTGAAAGCGGAAGCGGAATATGCAGCGCCGCGCACGGAACTG  3700
3701  GAAGCGACTTTGGCGCACATTTGGGGCGAAGTGCTCGGAATCGAACGGAT  3750
3751  CGGGATTCGCGACGATTTCTTTGCGCTCGGAGGGCATTCCTTGAAGGCCA  3800
3801  TGACCGCCGTCCCGCATCAACAAGAGCTCGGGATTGATCTTCCAGTGAAG  3850
3851  CTTTTGTTTGAAGCGCCGACGATCGCCGGCATTTCAGCGTATTTGAAAAA  3900
3901  CGGGGGCTCTGATGGCTTGCAGGATGTAACGATAATGAATCAGGATCAGG  3950
3951  AGCAGATCATTTTCGCATTTCCGCCGGTTCTGGGCTATGGCCTTATGTAC  4000
4001  CAAAATCTGTCCAGCCGCTTGCCGTCATACAAGCTATGCGCCTTTGATTT  4050
4051  TATTGAGGAGGAAGACCGGCTTGACCGCTATGCGGATTTGATCCAGAAGC  4100
4101  TGCAGCCGGAAGGGCCTTTAACATTGTTTGGATATTCAGCGGGATGCAGC  4150
4151  CTGGCGTTTGAAGCTGCGAAAAAGCTTGAGGAACAAGGCCGTATTGTTCA  4200
4201  GCGGATCATCATGGTGGATTCCTATAAAAAACAAGGTGTCAGTGATCTGG  4250
4251  ACGGACGCACGGTTGAAAGTGATGTCGAAGCGTTGATGAATGTCAATCGG  4300
```

```
4301  GACAATGAAGCGCTCAACAGCGAAGCCGTCAAACACGGCCTCAAGCAAAA  4350
4351  AACACATGCCTTTTACTCATACTACGTCAACCTGATCAGCACAGGCCAGG  4400
4401  TGAAAGCAGATATTGATCTGTTGACTTCCGGCGCTGATTTTGACATGCCG  4450
4451  GAATGGCTTGCATCATGGGAAGAAGCTACAACAGGTGTTTACCGTGTGAA  4500
4501  AAGAGGCTTCGGAACACACGCAGAAATGCTGCAGGGCGAAACGCTAGATA  4550
4551  GGAATGCGGAGATTTTGCTCGAATTTCTTAATACACAAACCGTAACGGTT  4600
4601  TCATAAAGGCATGCAAGCTTGGCGTAATCATGGTCATAGCTGTTTCCTGT  4650
4651  GTGAAATTGTTATCCGCTCACAATTCCACACAACATACGAGCCGGAAGCA  4700
4701  TAAAGTGTAAAGCCTGGGGTGCCTAATGAGTGAGCTAACTCACATTAATT  4750
4751  GCGTTGCGCTCACTGCCCGCTTTCCAGTCGGGAAACCTGTCGTGCCAGCT  4800
4801  GCATTAATGAATCGGCCAACGCGCGGGGAGAGGCGGTTTGCGTATTGGGC  4850
4851  GCTCTTCCGCTTCCTCGCTCACTGACTCGCTGCGCTCGGTCGTTCGGCTG  4900
4901  CGGCGAGCGGTATCAGCTCACTCAAAGGCGGTAATACGGTTATCCACAGA  4950
4951  ATCAGGGGATAACGCAGGAAAGAACATGTGAGCAAAAGGCCAGCAAAAGG  5000
5001  CCAGGAACCGTAAAAAGGCCGCGTTGCTGGCGTTTTTCCATAGGCTCCGC  5050
5051  CCCCCTGACGAGCATCACAAAAATCGACGCTCAAGTCAGAGGTGGCGAAA  5100
5101  CCCGACAGGACTATAAAGATACCAGGCGTTTCCCCCTGGAAGCTCCCTCG  5150
5151  TGCGCTCTCCTGTTCCGACCCTGCCGCTTACCGGATACCTGTCCGCCTTT  5200
5201  CTCCCTTCGGGAAGCGTGGCGCTTTCTCATAGCTCACGCTGTAGGTATCT  5250
5251  CAGTTCGGTGTAGGTCGTTCGCTCCAAGCTGGGCTGTGTGCACGAACCCC  5300
5301  CCGTTCAGCCCGACCGCTGCGCCTTATCCGGTAACTATCGTCTTGAGTCC  5350
5351  AACCCGGTAAGACACGACTTATCGCCACTGGCAGCAGCCACTGGTAACAG  5400
5401  GATTAGCAGAGCGAGGTATGTAGGCGGTGCTACAGAGTTCTTGAAGTGGT  5450
5451  GGCCTAACTACGGCTACACTAGAAGAACAGTATTTGGTATCTGCGCTCTG  5500
5501  CTGAAGCCAGTTACCTTCGGAAAAAGAGTTGGTAGCTCTTGATCCGGCAA  5550
5551  ACAAACCACCGCTGGTAGCGGTGGTTTTTTTGTTTGCAAGCAGCAGATTA  5600
5601  CGCGCAGAAAAAAAGGATCTCAAGAAGATCCTTTGATCTTTTCTACGGGG  5650
5651  TCTGACGCTCAGTGGAACGAAAACTCACGTTAAGGGATTTTGGTCATGAG  5700
5701  ATTATCAAAAAGGATCTTCACCTAGATCCTTTTAAATTAAAAATGAAGTT  5750
5751  TTAAATCAATCTAAAGTATATATGAGTAAACTTGGTCTGACAGTTACCAA  5800

5801  TGCTTAATCAGTGAGGCACCTATCTCAGCGATCTGTCTATTTCGTTCATC  5850
5851  CATAGTTGCCTGACTCCCCGTCGTGTAGATAACTACGATACGGGAGGGCT  5900
5901  TACCATCTGGCCCCAGTGCTGCAATGATACCGCGAGACCCACGCTCACCG  5950
5951  GCTCCAGATTTATCAGCAATAAACCAGCCAGCCGGAAGGGCCGAGCGCAG  6000
6001  AAGTGGTCCTGCAACTTTATCCGCCTCCATCCAGTCTATTAATTGTTGCC  6050
6051  GGGAAGCTAGAGTAAGTAGTTCGCCAGTTAATAGTTTGCGCAACGTTGTT  6100
6101  GCCATTGCTACAGGCATCGTGGTGTCACGCTCGTCGTTTGGTATGGCTTC  6150
6151  ATTCAGCTCCGGTTCCCAACGATCAAGGCGAGTTACATGATCCCCCATGT  6200
6201  TGTGCAAAAAAGCGGTTAGCTCCTTCGGTCCTCCGATCGTTGTCAGAAGT  6250
6251  AAGTTGGCCGCAGTGTTATCACTCATGGTTATGGCAGCACTGCATAATTC  6300
6301  TCTTACTGTCATGCCATCCGTAAGATGCTTTTCTGTGACTGGTGAGTACT  6350
6351  CAACCAAGTCATTCTGAGAATAGTGTATGCGGCGACCGAGTTGCTCTTGC  6400
6401  CCGGCGTCAATACGGGATAATACCGCGCCACATAGCAGAACTTTAAAAGT  6450
6451  GCTCATCATTGGAAAACGTTCTTCGGGGCGAAAACTCTCAAGGATCTTAC  6500
6501  CGCTGTTGAGATCCAGTTCGATGTAACCCACTCGTGCACCCAACTGATCT  6550
6551  TCAGCATCTTTTACTTTCACCAGCGTTTCTGGGTGAGCAAAAACAGGAAG  6600
6601  GCAAAATGCCGCAAAAAAGGGAATAAGGGCGACACGGAAATGTTGAATAC  6650
6651  TCATACTCTTCCTTTTTCAATATTATTGAAGCATTTATCAGGGTTATTGT  6700
6701  CTCATGAGCGGATACATATTTGAATGTATTTAGAAAAATAAACAAATAGG  6750
6751  GGTTCCGCGCACATTTCCCCGAAAAGTGCCACCTGACGTCTAAGAAACCA  6800
6801  TTATTATCATGACATTAACCTATAAAAATAGGCGTATCACGAGGCCCTTT  6850
6851  CGTC  6854   (SEQ ID NO: 52)
```

CoA Ligases
GenBank: AAX31555.1
acyl-CoA ligase [*Streptomyces roseosporus* NRRL 11379]
GenPept Graphics
>gi|60650930|gb|AAX31555.1|acyl-CoA ligase [*Streptomyces roseosporus* NRRL 11379]
MSESRCAGQGLVGALRTWARTRARETAVVLVRDTGTTDDTASVDYGQLDEWARSIAVTLRQQLAPGGRAL

LLLPSGPEFTAAYLGCLYAGLAAVPAPLPGGRHFERRRVAAIAADSGAGVVLTVAGETASVHDWLTETTA

PATRVVAVDDRAALGDPAQWDDPGVAPDDVALIQYTSGSTGNPKGVVVTHANLLANARNLAEACELTAAT

PMGGWLPMYHDMGLLGTLTPALYLGTTCVLMSSTAFIKRPHLWLRTIDRFGLVWSSAPDFAYDMCLKRVT

DEQIAGLDLSRWRWAGNGAEPIRAATVRAFGERFARYGLRPEALTAGYGLAEATLFVSRSQGLHTARVAT

AALERHEFRLAVPGEAAREIVSCGPVGHFRARIVEPGGHRVLPPGQVGELVLQGAAVCAGYWQAKEETEQ

TFGLTLDGEDGHWLRTGDLAALHEGNLHITGRCKEALVIRGRNLYPQDIEHELRLQHPELESVGAAFTVP

AAPGTPGLMVVHEVRTPVPADDHPALVSALRGTINREFGLDAQGIALVSRGTVLRTTSGKVRRGAMRDLC

LRGELNIVHADKGWHAIAGTAGEDIAPTDHAPHPHPA (SEQ ID NO: 53)

Acyl Carrier proteins
GenBank: AAX31556.1
probable acyl carrier protein [*Streptomyces roseosporus* NRRL 11379]
GenPept Graphics
<gi|6050931|gb|AAX31556.1|probable acyl carrier protien
[*Streptomyces roseosporus* NRRL 11379]
MNPPEAVSTPSEVTAWITGQIAEFVNETPDRIAGDAPLTDHGLDSVSGVALCAQVEDRYGIE

VDPELLWS

VPTLNEFVQALMPQLADRT (SEQ ID NO: 54)

malonyl-CoA transacylase
/protein_id = "AAF08794.1"
/gen = "fenF"
/note = "malonyl-CoA transacylase"
/codon_start = 1
/transl_table = 11
/product = "FenF"
/db_xref = "GI:6449054"
/translation = "MNNLAFLFPGQGSQFVGMGKSFWNDFVLAKRLFEEASDAISMDV

KKLCFDGMTELTRTMNAQPAILTVSVIAYQVYMQEIGIKPHFLAGHSLGEYSALVCA

GVLSFQEAVKLIRQRGILMQNADPEQLGTMAAITQVYIQPLQDLCTEISTEDFPVGVA

CMNSDQQHVISGHRQAVEFVIKKAERMGANHTYLNVSAPFHSSMMRSASEQFQTALNQ

YSFRDAEWPIISNVTAIPYNNGHSVREHLQTHMTMPVRWAESMHYLLLHGVTEVIEMG

PKNVLVGLLKKITNHIAAYPLGQTSDLHLLSDSAERNENIVNLRKKQLNKMMIQSIIA

RNYNKDAKTYSNLTTPLFPQIQLLKERVERKEVELSAEELEHSIHLCQLICEAKQLPT

WEQLRILK" (SEQ ID NO: 55)

We claim:

1. A *Bacillus subtilis* cell engineered to express at least one engineered peptide synthetase lacking a thioesterase domain and lacking a reductase domain, which peptide synthetase synthesizes an acyl amino acid.

2. The *Bacillus subtilis* cell of claim 1, wherein the engineered peptide synthetase includes an adenylation (A) domain, a thiolation (T) domain, and a condensation (C) domain.

3. The *Bacillus subtilis* cell of claim 1, wherein the engineered peptide synthetase contains only a single peptide synthetase domain.

4. The *Bacillus subtilis* cell of claim 1, wherein the engineered peptide synthetase is or comprises a peptide synthetase domain found in a peptide synthetase complex as a first domain in a peptide synthetase that synthesizes a lipopeptide.

5. The *Bacillus subtilis* cell of claim 1, wherein acyl amino acid composition includes, as a prominent component, an acyl amino acid whose amino acid moiety is from an amino acid selected from the group consisting of glycine or glutamate and whose acyl moiety is from a fatty acid selected from the group consisting of myristic acid and lauric acid.

6. The *Bacillus subtilis* cell of claim 4, wherein the peptide synthetase domain is or comprises Module 1 of a surfactin (srf) synthetase.

7. The *Bacillus subtilis* cell of claim 6, wherein the srf synthetase is srfAA.

8. The *Bacillus subtilis* cell of claim 4, wherein the peptide synthetase domain is or comprises Module 1 of a mycosubtilisin synthetase.

9. The *Bacillus subtilis* cell of claim 8, wherein the mycosubtilisin synthetase is or comprises MycA.

10. The *Bacillus subtilis* cell of claim 4, wherein the peptide synthetase domain is or comprises Module 1 of a daptomycin synthetase.

11. The *Bacillus subtilis* cell of claim 10, wherein the daptomycin synthetase is or comprises dptA1.

12. The *Bacillus subtilis* cell engineered of claim 1, wherein the engineered peptide synthetase acylates an amino acid selected from the group consisting of 2,4-diaminobutyric acid, (2S)-2,3-diaminobutyric acid, 2,3-diaminopropionic acid, ornithine and lysine.

13. A method of making an acyl amino acid composition by culturing the engineered cell of claim 1 under conditions and for a time sufficient for an acyl amino acid composition to be made.

14. A method of claim 13, further comprising steps of:
    enriching the acyl amino acid composition for a particular acyl amino acid; and
    combining the enriched acyl amino acid composition with at least one other component to produce a product.

* * * * *

SEQUENCE LISTING

<160> NUMBER OF SEQ ID NOS: 55

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ile, Val, Ser, Pro, Ala, Asp, Asn or Lys
<220> FEATURE:
<221> NAME/KEY: MOD_RES
<222> LOCATION: (2)..(10)
<223> OTHER INFORMATION: Any amino acid or absent
<220> FEATURE:
<221> NAME/KEY: MOD_RES
<222> LOCATION: (11)..(11)
<223> OTHER INFORMATION: Any amino acid except Pro
<220> FEATURE:
<221> NAME/KEY: MOD_RES
<222> LOCATION: (12)..(13)
<223> OTHER INFORMATION: Any amino acid or absent
<220> FEATURE:
<221> NAME/KEY: MOD_RES
<222> LOCATION: (15)..(15)
<223> OTHER INFORMATION: Pro, Ser, Thr, Ala, Gly, Asn, Cys or Val
<220> FEATURE:
<221> NAME/KEY: MOD_RES
<222> LOCATION: (16)..(16)
<223> OTHER INFORMATION: Ser, Thr, Ala, Gly, Asn, Gln, Cys, Ile, Val or
      Met
<220> FEATURE:
<221> NAME/KEY: MOD_RES

```
<222> LOCATION: (17)..(17)
<223> OTHER INFORMATION: Ser, Thr, Ala, Gly or Cys
<220> FEATURE:
<221> NAME/KEY: MOD_RES
<222> LOCATION: (19)..(19)
<223> OTHER INFORMATION: Any amino acid except Pro or Cys
<220> FEATURE:
<221> NAME/KEY: MOD_RES
<222> LOCATION: (20)..(20)
<223> OTHER INFORMATION: Ser, Ala, Gly, Phe, Tyr or Arg
<220> FEATURE:
<221> NAME/KEY: MOD_RES
<222> LOCATION: (21)..(21)
<223> OTHER INFORMATION: Leu, Ile, Val, Met, Ser, Thr, Ala, Gly or Asp
<220> FEATURE:
<221> NAME/KEY: MOD_RES
<222> LOCATION: (22)..(22)
<223> OTHER INFORMATION: Any amino acid or absent
<220> FEATURE:
<221> NAME/KEY: MOD_RES
<222> LOCATION: (23)..(23)
<223> OTHER INFORMATION: Any amino acid except Lys
<220> FEATURE:
<221> NAME/KEY: MOD_RES
<222> LOCATION: (24)..(24)
<223> OTHER INFORMATION: Leu, Ile, Val, Met, Phe, Tyr or Trp
<220> FEATURE:
<221> NAME/KEY: MOD_RES
<222> LOCATION: (25)..(25)
<223> OTHER INFORMATION: Any amino acid except Asp
<220> FEATURE:
<221> NAME/KEY: MOD_RES
<222> LOCATION: (26)..(26)
<223> OTHER INFORMATION: Any amino acid or absent
<220> FEATURE:
<221> NAME/KEY: MOD_RES
<222> LOCATION: (27)..(27)
<223> OTHER INFORMATION: Any amino acid except Tyr or Arg
<220> FEATURE:
<221> NAME/KEY: MOD_RES
<222> LOCATION: (28)..(28)
<223> OTHER INFORMATION: Leu, Ile, Val, Met, Phe, Tyr, Trp, Gly, Ala,
      Pro, Thr, His or Gln
<220> FEATURE:
<221> NAME/KEY: MOD_RES
<222> LOCATION: (29)..(29)
<223> OTHER INFORMATION: Gly, Ser, Ala, Cys, Gln, Arg, His or Met

<400> SEQUENCE: 1

Xaa Xaa Xaa Xaa Xaa Xaa Xaa Xaa Xaa Xaa Xaa Xaa Xaa Tyr Xaa Xaa
1               5                   10                  15

Xaa Lys Xaa Xaa Xaa Xaa Xaa Xaa Xaa Xaa Xaa Xaa Xaa
            20                  25

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<221> NAME/KEY: MOD_RES
<222> LOCATION: (1)..(1)
<223> OTHER INFORMATION: Leu, Ile or Val
<220> FEATURE:
<221> NAME/KEY: MOD_RES
<222> LOCATION: (2)..(2)
<223> OTHER INFORMATION: Any amino acid except Lys or Gly
<220> FEATURE:
<221> NAME/KEY: MOD_RES
<222> LOCATION: (3)..(3)
<223> OTHER INFORMATION: Leu, Ile, Val, Phe or Tyr
<220> FEATURE:
<221> NAME/KEY: MOD_RES
<222> LOCATION: (4)..(4)
```

```
<223> OTHER INFORMATION: Leu, Ile, Val, Met, Ser or Thr
<220> FEATURE:
<221> NAME/KEY: MOD_RES
<222> LOCATION: (6)..(6)
<223> OTHER INFORMATION: His, Tyr, Trp or Val
<220> FEATURE:
<221> NAME/KEY: MOD_RES
<222> LOCATION: (8)..(8)
<223> OTHER INFORMATION: Any amino acid except Tyr, Ala or Gly
<220> FEATURE:
<221> NAME/KEY: MOD_RES
<222> LOCATION: (10)..(10)
<223> OTHER INFORMATION: Gly, Ser, Thr, Ala or Cys

<400> SEQUENCE: 2

Xaa Xaa Xaa Xaa Gly Xaa Ser Xaa Gly Xaa
1               5                   10

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgtactgag agtgcaccat atatcgacaa aaatgtcatg aaagaatcg            49

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgccaagct tgcatgcctt tatgaaaccg ttacggtttg tgtatt               46

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggcatgcaa gcttggcgta atcatggtca tagctgtttc ctgtg                45

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atatggtgca ctctcagtac aatctgctct gatgccgcat agtt                 44

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 7
gcttgcttgc ggagcagatc a          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcgaatctcc gcccagttcg a          21

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cactgatttc tgatgcggag aaacgcgatt tgttttgcg g          41

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctccgagcgc aaagaaatcg tcgcgaatcc cgatccg          37

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatttctttg cgctcggagg gcattccttg aaggccatga          40

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctccgcatca gaaatcagtg ttaattcatc aattgtatgt tctggatgc          49

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatatcgtat tgaatagaca gacagg                                        26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atctttattt gcattattcg tggat                                         25

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgtaaatca tttaatgaaa aaaggaaaaa ttgacgtg                            38

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcattaagc cttcctggca gtcagccctta gtgcttgatg tcggtttg               48

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aattaaaagc cattgaggca gacgtaaggg aggatacaat catggcaatt              50

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtattcttg ctgacaacgg tacattcata tg                                 32

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
acacgatata gccaggaagg cgggttttt gacgatgttc ttgaaactc          49
```

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 20

```
aattaaaagc cacaaaggcc taggtactaa aacaattcat ccagtaa            47
```

<210> SEQ ID NO 21
<211> LENGTH: 6475
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 21

```
aatatcgtat tgaatagaca gacaggagtg agtcaccatg gcaactgagt atgacgtagt    60
cattctgggc ggcggtaccg gcggttatgt tgcggccatc agagccgctc agctcggctt   120
aaaaacagcc gttgtggaaa aggaaaaact cggggaaca tgtctgcata aaggctgtat    180
cccgagtaaa gcgctgctta aagcgcaga ggtataccgg acagctcgtg aagccgatca   240
attcggagtg gaaacggctg gcgtgtccct caactttgaa aaagtgcagc agcgtaagca   300
agccgttgtt gataagcttg cagcgggtgt aaatcattta atgaaaaag gaaaaattga   360
cgtgtacacc ggatatggac gtatccttgg accgtcaatc ttctctccgc tgccgggaac   420
aatttctgtt gagcggggaa atggcgaaga aaatgacatg ctgatcccga aacaagtgat   480
cattgcaaca ggatcaagac cgagaatgct tccgggtctt gaagtggacg gtaagtctgt   540
actgacttca gatgaggcgc tccaaatgga ggagctgcca cagtcaatca tcattgtcgg   600
cggaggggtt atcggtatcg aatgggcgtc tatgcttcat gattttggcg ttaaggtaac   660
ggttattgaa tacgcggatc gcatattgcc gactgaagat ctagagattt caaaagaat    720
ggaaagtctt cttaagaaaa aaggcatcca gttcataaca ggggcaaaag tgctgcctga   780
cacaatgaca aaaacatcag acgatatcag catacaagcg gaaaagacg gagaaaccgt   840
tacctattct gctgagaaaa tgcttgttc catcggcaga caggcaaata tcgaaggcat   900
cggcctagag aacaccgata ttgttactga aaatggcatg atttcagtca atgaaagctg   960
ccaaacgaag gaatctcata tttatgcaat cggagacgta atcggtggcc tgcagttagc  1020
tcacgttgct tcacatgagg gaattattgc tgttgagcat tttgcaggtc tcaatccgca  1080
tccgcttgat ccgacgcttg tgccgaagtg catttactca agccctgaag ctgccagtgt  1140
cggcttaacc gaagacgaag caaaggcgaa cgggcataat gtcaaaatcg gcaagttccc  1200
atttatggcg attggaaaag cgcttgtata cggtgaaagc gacggttttg tcaaaatcgt  1260
ggctgaccga gatacagatg atattctcgg cgttcatatg attggcccgc atgtcaccga  1320
catgattct gaagcgggtc ttgccaaagt gctggacgca acaccgtggg aggtcggca   1380
aacgattcac ccgcatccaa cgctttctga agcaattgga gaagctgcgc ttgccgcaga  1440
tggcaaagcc attcattttt aaaagcataa aggaggggct tgaatgagta caaaccgaca  1500
tcaagcacta gggctgactg ccaggaaggc gggtttttg acgatgttct tgaaactcaa   1560
```

-continued

```
tgtctttttt tgtagaatca atagaagtgt gtaattgttg atgggacaat aaaaaaggag    1620
ctgaaacaca gtatgggaaa ggtttatgta tttgatcatc ctttaattca gcacaagctg    1680
acatatatac ggaatgaaaa tacaggtacg aaggatttta gagagttagt agatgaagtg    1740
gctacactca tggcatttga aattacccgc gatcttcctc tggaagaagt ggatatcaat    1800
acaccggttc aggctgcgaa atcgaaagtc atctcaggga aaaaactcgg agtggttcct    1860
atcctcagag caggattggg aatggttgac ggcattttaa agctgattcc tgcggcaaaa    1920
gtgggacatg tcggccttta ccgtgatcca gaaaccttaa acccgtgga atactatgtc    1980 aagcttcctt ctgatgtgga agagcgtgaa ttcatcgtgg ttgacccgat gctcgctaca    2040
ggcggttccg cagttgaagc cattcacagc cttaaaaaac gcggtgcgaa aaatatccgt    2100
ttcatgtgtc ttgtagcagc gccggagggt gtggaagaat tgcagaagca tcattcggac    2160
gttgatattt acattgcggc gctagatgaa aaattaaatg aaaaaggata tattgttcca    2220
ggtctcggag atgcgggtga ccgcatgttt ggaacaaaat aaaaaatgaa atccccaaaa    2280
gggggtttca tttttttatc cagtttttg ctattcggtg aatctgtata caattatagg    2340
tgaaaatgtg aacattctgg gatccgataa acccagcgaa ccatttgagg tgataggtaa    2400
gattataccg aggtatgaaa acgagaattg gacctttaca gaattactct atgaagcgcc    2460
atatttaaaa agctaccaag acgaagagga tgaagaggat gaggaggcag attgccttga    2520
atatattgac aatactgata agataatata tcttttatat agaagatatc gccgtatgta    2580
aggatttcag ggggcaaggc ataggcagcg cgcttatcaa tatatctata gaatgggcaa    2640
agcataaaaa cttgcatgga ctaatgcttg aaacccagga caataacctt atagcttgta    2700
aattctatca taattgtggt ttcaaaatcg gctccgtcga tactatgtta tacgccaact    2760
ttcaaaacaa ctttgaaaaa gctgttttct ggtatttaag gttttagaat gcaaggaaca    2820
gtgaattgga gttcgtcttg ttataattag cttcttgggg tatctttaaa tactgtagaa    2880
aagaggaagg aaataataaa tggctaaaat gagaatatca ccggaattga aaaaactgat    2940
cgaaaaatac cgctgcgtaa aagatacgga aggaatgtct cctgctaagg tatataagct    3000
ggtgggagaa aatgaaaacc tatatttaaa aatgacggac agccggtata aagggaccac    3060
ctatgatgtg gaacgggaaa aggacatgat gctatggctg gaaggaaagc tgcctgttcc    3120
aaaggtcctg cactttgaac ggcatgatgg ctggagcaat ctgctcatga gtgaggccga    3180
tggcgtcctt tgctcggaag agtatgaaga tgaacaaagc cctgaaaaga ttatcgagct    3240
gtatgcggag tgcatcaggc tcttttcactc catcgacata tcggattgtc cctatacgaa    3300
tagcttagac agccgcttag ccgaattgga ttacttactg aataacgatc tggccgatgt    3360
ggattgcgaa aactgggaag aagacactcc atttaaagat ccgcgcgagc tgtatgattt    3420
tttaaagacg gaaaagcccg aagaggaact tgtcttttcc cacggcgacc tgggagacag    3480
caacatcttt gtgaaagatg gcaaagtaag tggctttatt gatctgggga aagcggcag    3540 ggcggacaag tggtatgaca ttgccttctg cgtccggtcg atcagggagg atatcgggga    3600
agaacagtat gtcgagctat tttttgactt actggggatc aagcctgatt gggagaaaat    3660
aaaatattat atttttactgg atgaattgtt ttagtaccta ggcctttgag gcagacgtaa    3720
gggaggatac aatcatggca attgaacaaa tgacgatgcc gcagcttgga gaaagcgtaa    3780
cagaggggac gatcagcaaa tggcttgtcg cccccggtga taaagtgaac aaatacgatc    3840
cgatcgcgga agtcatgaca gataaggtaa atgcagaggt tccgtcttct tttactggta    3900
cgataacaga gcttgtggga gaagaaggcc aaaccctgca agtcggagaa atgatttgca    3960
```

```
aaattgaaac agaaggcgcg aatccggctg aacaaaaaca agaacagcca gcagcatcag  4020
aagccgctga gaaccctgtt gcaaaaagtg ctggagcagc cgatcagccc aataaaaagc  4080
gctactcgcc agctgttctc cgtttggccg gagagcacgg cattgacctc gatcaagtga  4140
caggaactgg tgccggcggg cgcatcacac gaaaagatat tcagcgctta attgaaacag  4200
gcggcgtgca agaacagaat cctgaggagc tgaaaacagc agctcctgca ccgaagtctg  4260
catcaaaacc tgagccaaaa gaagagacgt catatcctgc gtctgcagcc ggtgataaag  4320
aaatccctgt cacaggtgta agaaaagcaa ttgcttccaa tatgaagcga agcaaaacag  4380
aaattccgca tgcttggacg atgatggaag tcgacgtcac aaatatggtt gcatatcgca  4440
acagtataaa agattctttt aagaagacag aaggctttaa tttaacgttc ttcgcctttt  4500
ttgtaaaagc ggtcgctcag gcgttaaaag aattcccgca aatgaatagc atgtgggcgg  4560
gggacaaaat tattcagaaa aaggatatca atatttcaat tgcagttgcc acagaggatt  4620
ctttatttgt tccggtgatt aaaaacgctg atgaaaaaac aattaaaggc attgcgaaag  4680
acattaccgg cctagctaaa aaagtaagag acggaaaact cactgcagat gacatgcagg  4740
gaggcacgtt taccgtcaac aacacaggtt cgttcgggtc tgttcagtcg atgggcatta  4800
tcaactaccc tcaggctgcg attcttcaag tagaatccat cgtcaaacgc ccggttgtca  4860
tggacaatgg catgattgct gtcagagaca tggttaatct gtgcctgtca ttagatcaca  4920
gagtgcttga cggtctcgtg tgcggacgat tcctcggacg agtgaaacaa attttagaat  4980
cgattgacga gaagacatct gtttactaaa taagcaaaaa gagcattttt tgaagttttg  5040
tttcaaaaaa tgctctttt ctatgcttta ttattcagcg atccgtattt tcatttcgac  5100
tcgatattct tcttgttttt tcggggagta atgaatcggt atgattaact cgtatacatc  5160
actgacaact gttaattggc ggtccgcgat atatttgata agcttctgta agttgagaaa  5220
ataatgttca ggcgaaaaat tatacgcgat acacgcatac ctcccttag ggatcgttgt  5280 gatttccata tccggcgtaa ttgatgaaat ctgtttattc gtcaatacag gtgtgaaaat  5340
atgacggtaa gtcatttcat caatgctggt gtagggctga aaagagaaag tagcgccgta  5400
gctattgttc gtaaatccat ctgctgactc gataaatttt tttaatttgc tgtaggaggc  5460
gttgagcacg ttttcaggcc cgattccttc tgcctctgtc tgaatgatcc gtatttcttc  5520
ttcatctaaa acaaacacct caccgagcgc gggatattcc atctgccgtt tcatccgctt  5580
tttcaccaat gaaatggttt gctccagggc tgataaaaag tctaatttct ccctgatttg  5640
cctctcctgc tctgtataaa aagcaaacag ttcttccatc tctaagtcct gtgctttttt  5700
catctcttct aaaggtgtgc cgatatattt caatgatttg atcaaatcca gatgaatgag  5760
ctgagaatct gtataatagc ggtagctggt atccgggtcg acgtaggctg gtttaaataa  5820
atcaatttta tcgtaataac ggagcgcttt tatcgacacg tttgccagtt ttgatacttc  5880
cccaattgag taatacgatt ccttcatgcc atcactcctt ctatcatcag tataaagaag  5940
aagcgcattc tttgcagtac acaaagaatg cgcttcttat cacgtgctgg ctttaagatg  6000
tgcaggcgct ttccaagcaa tggtcagtgc aatccctatg gctaaggtga ccgttgcaaa  6060
gtagaaagga tagtttacat ctatatcgaa cagcattccg ccgataatag gcccgaatac  6120
attgccgata cttgtaaaca ttgaattcat accgccggca aaccctgtt catttcccgc  6180 aatctttgac aggtaagtcg ttaccgcagg ccgcatgaga tcaaatccga caaatacggt  6240
gactgtcacc agcagaatcg caacatatga atgtaccgtt gtcagcaaga ataccagact  6300
```

```
cgtcgagaga attaagctgt accgaattaa atgaatttcg ccaaaccatc ttgtgaagcg      6360
gtcgaataag acgacttgcg taatggcgcc aacaatcgct cctcctgtaa tcataatggc      6420
aatgtcgctg gccgtaaatc cgaatttatg atccacgaat aatgcaaata aagat          6475
```

<210> SEQ ID NO 22
<211> LENGTH: 326
<212> TYPE: PRT
<213> ORGANISM: Staphylococcus aureus

<400> SEQUENCE: 22

```
Met Ile Glu Lys Ser Gln Ala Cys His Asp Ser Leu Leu Asp Ser Val
1               5                   10                  15

Gly Gln Thr Pro Met Val Gln Leu His Gln Leu Phe Pro Lys His Glu
            20                  25                  30

Val Phe Ala Lys Leu Glu Tyr Met Asn Pro Gly Gly Ser Met Lys Asp
        35                  40                  45

Arg Pro Ala Lys Tyr Ile Ile Glu His Gly Ile Lys His Gly Leu Ile
    50                  55                  60

Thr Glu Asn Thr His Leu Ile Glu Ser Thr Ser Gly Asn Leu Gly Ile
65                  70                  75                  80

Ala Leu Ala Met Ile Ala Lys Ile Lys Gly Leu Lys Leu Thr Cys Val
                85                  90                  95

Val Asp Pro Lys Ile Ser Pro Thr Asn Leu Lys Ile Ile Lys Ser Tyr
            100                 105                 110

Gly Ala Asn Val Glu Met Val Glu Glu Pro Asp Ala His Gly Gly Tyr
        115                 120                 125

Leu Met Thr Arg Ile Ala Lys Val Gln Glu Leu Leu Ala Thr Ile Asp
    130                 135                 140

Asp Ala Tyr Trp Ile Asn Gln Tyr Ala Asn Glu Leu Asn Trp Gln Ser
145                 150                 155                 160

His Tyr His Gly Ala Gly Thr Glu Ile Val Glu Thr Ile Lys Gln Pro
                165                 170                 175

Ile Asp Tyr Phe Val Ala Pro Val Ser Thr Thr Gly Ser Ile Met Gly
            180                 185                 190

Met Ser Arg Lys Ile Lys Glu Val His Pro Asn Ala Gln Ile Val Ala
        195                 200                 205

Val Asp Ala Lys Gly Ser Val Ile Phe Gly Asp Lys Pro Ile Asn Arg
    210                 215                 220

Glu Leu Pro Gly Ile Gly Ala Ser Arg Val Pro Glu Ile Leu Asn Arg
225                 230                 235                 240

Ser Glu Ile Asn Gln Val Ile His Val Asp Asp Tyr Gln Ser Ala Leu
                245                 250                 255

Gly Cys Arg Lys Leu Ile Asp Tyr Glu Gly Ile Phe Ala Gly Gly Ser
            260                 265                 270

Thr Gly Ser Ile Ile Ala Ala Ile Glu Gln Leu Ile Thr Ser Ile Glu
        275                 280                 285

Glu Gly Ala Thr Ile Val Thr Ile Leu Pro Asp Arg Gly Asp Arg Tyr
    290                 295                 300

Leu Asp Leu Val Tyr Ser Asp Thr Trp Leu Glu Lys Met Lys Ser Arg
305                 310                 315                 320

Gln Gly Val Lys Ser Glu
                325
```

<210> SEQ ID NO 23

<211> LENGTH: 336
<212> TYPE: PRT
<213> ORGANISM: Staphylococcus aureus

<400> SEQUENCE: 23

```
Met Asn Arg Glu Met Leu Tyr Leu Asn Arg Ser Asp Ile Glu Gln Ala
1               5                   10                  15

Gly Gly Asn His Ser Gln Val Tyr Val Asp Ala Leu Thr Glu Ala Leu
            20                  25                  30

Thr Ala His Ala His Asn Asp Phe Val Gln Pro Leu Lys Pro Tyr Leu
        35                  40                  45

Arg Gln Asp Pro Glu Asn Gly His Ile Ala Asp Arg Ile Ile Ala Met
    50                  55                  60

Pro Ser His Ile Gly Gly Glu His Ala Ile Ser Gly Ile Lys Trp Ile
65                  70                  75                  80

Gly Ser Lys His Asp Asn Pro Ser Lys Arg Asn Met Glu Arg Ala Ser
                85                  90                  95

Gly Val Ile Ile Leu Asn Asp Pro Glu Thr Asn Tyr Pro Ile Ala Val
            100                 105                 110

Met Glu Ala Ser Leu Ile Ser Ser Met Arg Thr Ala Ala Val Ser Val
        115                 120                 125

Ile Ala Ala Lys His Leu Ala Lys Lys Gly Phe Lys Asp Leu Thr Ile
    130                 135                 140

Ile Gly Cys Gly Leu Ile Gly Asp Lys Gln Leu Gln Ser Met Leu Glu
145                 150                 155                 160

Gln Phe Asp His Ile Glu Arg Val Phe Val Tyr Asp Gln Phe Ser Glu
                165                 170                 175

Ala Cys Ala Arg Phe Val Asp Arg Trp Gln Gln Arg Pro Glu Ile
            180                 185                 190

Asn Phe Ile Ala Thr Glu Asn Ala Lys Glu Ala Val Ser Asn Gly Glu
        195                 200                 205

Val Val Ile Thr Cys Thr Val Thr Asp Gln Pro Tyr Ile Glu Tyr Asp
    210                 215                 220

Trp Leu Gln Lys Gly Ala Phe Ile Ser Asn Ile Ser Ile Met Asp Val
225                 230                 235                 240

His Lys Glu Val Phe Ile Lys Ala Asp Lys Val Val Asp Asp Trp
                245                 250                 255

Ser Gln Cys Asn Arg Glu Lys Lys Thr Ile Asn Gln Leu Val Leu Glu
            260                 265                 270

Gly Lys Phe Ser Lys Glu Ala Leu His Ala Glu Leu Gly Gln Leu Val
        275                 280                 285

Thr Gly Asp Ile Pro Gly Arg Glu Asp Asp Glu Ile Ile Leu Leu
    290                 295                 300

Asn Pro Met Gly Met Ala Ile Glu Asp Ile Ser Ser Ala Tyr Phe Ile
305                 310                 315                 320

Tyr Gln Gln Ala Gln Gln Asn Ile Gly Thr Thr Leu Asn Leu Tyr
                325                 330                 335
```

<210> SEQ ID NO 24
<211> LENGTH: 360
<212> TYPE: PRT
<213> ORGANISM: Bacillus cereus

<400> SEQUENCE: 24

```
Met Ser Phe Arg Tyr Lys Phe Tyr Leu Lys Tyr Ile Arg Lys Asn Ile
1               5                   10                  15
```

```
Tyr Thr Tyr Leu Ser Leu Ile Ile Phe Leu Asp Phe Asn Gln Glu Arg
            20                  25                  30

Lys Gln Ile Met Leu Lys Lys Leu Glu Ser Leu Glu Arg Val Ile Gly
        35                  40                  45

Asn Thr Pro Met Ile Lys Leu Glu His Glu Lys Ile Asn Leu Tyr Ala
    50                  55                  60

Lys Leu Glu Tyr Tyr Asn Leu Met Asn Ser Val Lys Val Arg Ala Ala
65                  70                  75                  80

Tyr His Ile Leu Lys Ser Ala Ile Asn Arg Gly Glu Val Asn Glu Asn
                85                  90                  95

Ser Thr Ile Ile Glu Ser Ser Ser Gly Asn Phe Ala Val Ala Leu Ala
            100                 105                 110

Thr Leu Cys Arg Tyr Ile Gly Leu Lys Phe Ile Pro Val Ile Asp Pro
        115                 120                 125

Asn Ile Asn Asp Ser Tyr Glu Asn Phe Leu Arg Ala Thr Ser Tyr Gln
    130                 135                 140

Val Ala Asn Val Asp Glu Arg Asp Glu Thr Gly Gly Tyr Leu Leu Thr
145                 150                 155                 160

Arg Leu Asn Lys Val Lys Glu Leu Leu Asn Thr Ile Pro Asn Ala Tyr
                165                 170                 175

Trp Thr Asn Gln Tyr Asn Asn Ala Asp Asn Phe Glu Ala His Tyr Gln
            180                 185                 190

Gly Ile Gly Gly Glu Ile Ser Asn Asp Phe Lys Gln Leu Asp Tyr Ala
        195                 200                 205

Phe Ile Gly Val Ser Thr Gly Gly Thr Ile Ala Gly Val Ser Thr Arg
    210                 215                 220

Leu Lys Glu Lys Phe Pro Asn Ile Lys Ile Ile Ala Val Asp Ser Gln
225                 230                 235                 240

Gly Ser Ile Ile Phe Gly Asp Lys Pro Arg Lys Arg Tyr Ile Pro Gly
                245                 250                 255

Ile Gly Ala Ser Met Ile Pro Gly Met Val Lys Lys Ala Leu Ile Asp
            260                 265                 270

Asp Val Met Ile Val Pro Glu Val His Thr Val Ala Gly Cys Tyr Glu
        275                 280                 285

Leu Phe Asn Lys His Ala Ile Phe Ala Gly Gly Ser Ser Gly Thr Ser
    290                 295                 300

Tyr Tyr Ala Ile Gln Lys Tyr Phe Glu Asn Arg Asp Val Gln Asn Thr
305                 310                 315                 320

Pro Asn Val Val Phe Leu Cys Pro Asp Asn Gly Gln Ala Tyr Thr Ser
                325                 330                 335

Thr Ile Tyr Asn Val Glu Trp Val Glu Trp Leu Asn Thr Gln Lys Ser
            340                 345                 350

Val Glu Asp Gln Leu Val Ser Leu
        355                 360

<210> SEQ ID NO 25
<211> LENGTH: 322
<212> TYPE: PRT
<213> ORGANISM: Bacillus cereus

<400> SEQUENCE: 25

Met Met Tyr Leu Asn Thr Lys His Phe Asn Glu Met Gly Val Asn Trp
1               5                   10                  15

Glu Glu Thr Ile Asn Val Ile Ser Lys Ala Val Lys Ser Leu Asp Ser
```

```
            20                  25                  30
Glu Asp Phe Ser Gln Pro Ile Lys Pro Tyr Leu Arg Phe Asp Asp Pro
                35                  40                  45

Ala Asn Arg Ile Ile Ala Met Pro Ala Tyr Ile Gly Gly Glu Phe Lys
 50                  55                  60

Val Ser Gly Ile Lys Trp Ile Ala Ser Phe Pro Lys Asn Ile Glu Lys
 65                  70                  75                  80

Gly Ile Gln Arg Ala His Ser Val Thr Ile Leu Asn Asp Ala Met Thr
                85                  90                  95

Gly Lys Pro Phe Ala Thr Leu Asn Thr Ala Met Val Ser Val Ile Arg
                100                 105                 110

Thr Ala Ser Val Thr Gly Leu Met Ile Arg Glu Phe Ala Lys Leu Arg
                115                 120                 125

Asp Leu Asn Asn Val Lys Val Gly Ile Gly Phe Gly Pro Ile Gly
                130                 135                 140

Gln Met His Leu Lys Met Val Thr Ala Leu Leu Gly Asp Lys Ile Glu
145                 150                 155                 160

Gly Val Tyr Leu Tyr Asp Ile Asn Gly Ile Lys Asp Glu Leu Ile Pro
                165                 170                 175

Glu Glu Ile Tyr Ser Lys Thr Gln Lys Val Asn Ala Tyr Glu Ala
                180                 185                 190

Tyr Asn Asp Ala Asp Ile Phe Ile Thr Cys Thr Val Ser Ala Glu Gly
                195                 200                 205

Tyr Ile Asp Lys Lys Pro Lys Asp Gly Ala Leu Leu Leu Asn Val Ser
                210                 215                 220

Leu Arg Asp Phe Lys Pro Asp Ile Leu Glu Tyr Thr Lys Ser Leu Val
225                 230                 235                 240

Val Asp Asn Trp Glu Glu Val Cys Arg Glu Lys Thr Asp Val Glu Arg
                245                 250                 255

Met His Leu Glu Arg Gly Leu Gln Lys Glu Asp Thr Val Ser Ile Ala
                260                 265                 270

Asp Val Val Ile Arg Gly Ala Leu Gln Asn Phe Pro Tyr Asp Lys Ala
                275                 280                 285

Ile Leu Phe Asn Pro Met Gly Met Ala Ile Phe Asp Val Ala Ile Ala
                290                 295                 300

Ala Tyr Tyr Tyr Gln Arg Ala Arg Glu Asn Glu Met Gly Val Leu Leu
305                 310                 315                 320

Glu Asp

<210> SEQ ID NO 26
<211> LENGTH: 311
<212> TYPE: PRT
<213> ORGANISM: Bacillus subtilis

<400> SEQUENCE: 26

Met Lys Trp Ser Glu Leu Ser Ile His Thr Thr His Glu Ala Val Glu
 1               5                  10                  15

Pro Ile Ser Asn Ile Leu His Glu Ala Gly Ala Ser Gly Val Val Ile
                20                  25                  30

Glu Asp Pro Leu Asp Leu Ile Lys Glu Arg Glu Asn Val Tyr Gly Glu
                35                  40                  45

Ile Tyr Gln Leu Asp Pro Asn Asp Tyr Pro Asp Glu Gly Val Ile Val
                50                  55                  60

Lys Ala Tyr Leu Pro Val Asn Ser Phe Leu Gly Glu Thr Val Asp Gly
```

Ile Lys Glu Thr Ile Asn Asn Leu Leu Leu Tyr Asn Ile Asp Leu Gly
          65                  70                  75                  80

Arg Asn His Ile Thr Ile Ser Glu Val Asn Glu Glu Glu Trp Ala Thr
                85                  90                  95

Ala Trp Lys Lys Tyr Tyr His Pro Val Lys Ile Ser Glu Lys Phe Thr
            100                 105                 110

Ile Val Pro Thr Trp Glu Glu Tyr Thr Pro Val His Thr Asp Glu Leu
        115                 120                 125

Ile Ile Glu Met Asp Pro Gly Met Ala Phe Gly Thr Gly Thr His Pro
130             135                 140

Thr Thr Val Leu Cys Ile Gln Ala Leu Glu Arg Phe Val Gln Lys Gly
145                 150                 155                 160

Asp Lys Val Ile Asp Val Gly Thr Gly Ser Gly Ile Leu Ser Ile Ala
                165                 170                 175

Ala Ala Met Leu Glu Ala Glu Ser Val His Ala Tyr Asp Leu Asp Pro
            180                 185                 190

Val Ala Val Glu Ser Ala Arg Leu Asn Leu Lys Leu Asn Lys Val Ser
        195                 200                 205

Asp Ile Ala Gln Val Lys Gln Asn Asn Leu Leu Asp Gly Ile Glu Gly
210                 215                 220

Glu His Asp Val Ile Val Ala Asn Ile Leu Ala Glu Val Ile Leu Arg
225                 230                 235                 240

Phe Thr Ser Gln Ala Tyr Ser Leu Leu Lys Glu Gly Gly His Phe Ile
                245                 250                 255

Thr Ser Gly Ile Ile Gly His Lys Lys Gln Glu Val Lys Glu Ala Leu
            260                 265                 270

Glu Gln Ala Gly Phe Thr Ile Val Glu Ile Leu Ser Met Glu Asp Trp
        275                 280                 285

Val Ser Ile Ile Ala Lys Lys
290                 295

<210> SEQ ID NO 27
<211> LENGTH: 293
<212> TYPE: PRT
<213> ORGANISM: Escherichia coli

<400> SEQUENCE: 27

Met Pro Trp Ile Gln Leu Lys Leu Asn Thr Thr Gly Ala Asn Ala Glu
1               5                   10                  15

Asp Leu Ser Asp Ala Leu Met Glu Ala Gly Ala Val Ser Ile Thr Phe
            20                  25                  30

Gln Asp Thr His Asp Thr Pro Val Phe Glu Pro Leu Pro Gly Glu Thr
        35                  40                  45

Arg Leu Trp Gly Asp Thr Asp Val Ile Gly Leu Phe Asp Ala Glu Thr
    50                  55                  60

Asp Met Asn Asp Val Val Ala Ile Leu Glu Asn His Pro Leu Leu Gly
65              70                  75                  80

Ala Gly Phe Ala His Lys Ile Glu Gln Leu Glu Asp Lys Asp Trp Glu
            85                  90                  95

Arg Glu Trp Met Asp Asn Phe His Pro Met Arg Phe Gly Glu Arg Leu
                100                 105                 110

Trp Ile Cys Pro Ser Trp Arg Asp Val Pro Asp Glu Asn Ala Val Asn
            115                 120                 125

Val Met Leu Asp Pro Gly Leu Ala Phe Gly Thr Gly Thr His Pro Thr
130                 135                 140

Thr Ser Leu Cys Leu Gln Trp Leu Asp Ser Leu Asp Leu Thr Gly Lys
145                 150                 155                 160

Thr Val Ile Asp Phe Gly Cys Gly Ser Gly Ile Leu Ala Ile Ala Ala
            165                 170                 175

Leu Lys Leu Gly Ala Ala Lys Ala Ile Gly Ile Asp Ile Asp Pro Gln
            180                 185                 190

Ala Ile Gln Ala Ser Arg Asp Asn Ala Glu Arg Asn Gly Val Ser Asp
        195                 200                 205

Arg Leu Glu Leu Tyr Leu Pro Lys Asp Gln Pro Glu Glu Met Lys Ala
210                 215                 220

Asp Val Val Ala Asn Ile Leu Ala Gly Pro Leu Arg Glu Leu Ala
225                 230                 235                 240

Pro Leu Ile Ser Val Leu Pro Val Ser Gly Leu Leu Gly Leu Ser
            245                 250                 255

Gly Ile Leu Ala Ser Gln Ala Glu Ser Val Cys Glu Ala Tyr Ala Asp
            260                 265                 270

Ser Phe Ala Leu Asp Pro Val Val Glu Lys Glu Glu Trp Cys Arg Ile
    275                 280                 285

Thr Gly Arg Lys Asn
    290

<210> SEQ ID NO 28
<211> LENGTH: 245
<212> TYPE: PRT
<213> ORGANISM: Streptomyces sp.

<400> SEQUENCE: 28

Met Ser Asp Pro Ser Val Tyr Asp Glu Thr Ala Ile Glu Ala Tyr Asp
1               5                   10                  15

Leu Val Ser Ser Met Leu Ser Pro Gly Ala Gly Leu Val Ala Trp Val
            20                  25                  30

Ser Ser His Arg Pro Leu Asp Gly Arg Thr Val Leu Asp Leu Gly Cys
        35                  40                  45

Gly Thr Gly Val Ser Ser Phe Ala Leu Ala Glu Ala Gly Ala Arg Val
    50                  55                  60

Val Ala Val Asp Ala Ser Arg Pro Ser Leu Asp Met Leu Glu Lys Lys
65                  70                  75                  80

Arg Leu Asp Arg Asp Val Glu Ala Val Glu Gly Asp Phe Arg Asp Leu
                85                  90                  95

Thr Phe Asp Ser Thr Phe Asp Val Val Thr Met Ser Arg Asn Thr Phe
            100                 105                 110

Phe Leu Ala Gln Glu Gln Glu Lys Ile Ala Leu Leu Arg Gly Ile
        115                 120                 125

Ala Arg His Leu Lys Pro Gly Gly Ala Ala Phe Leu Asp Cys Thr Asp
130                 135                 140

Pro Ala Glu Phe Gln Arg Ala Gly Asp Ala Arg Ser Val Thr Tyr
145                 150                 155                 160

Pro Leu Gly Arg Asp Arg Met Val Thr Val Thr Gln Thr Ala Asp Arg
            165                 170                 175

Ala Gly Gln Gln Ile Leu Ser Ile Phe Leu Val Gln Gly Ala Thr Thr
        180                 185                 190

Leu Thr Ala Phe His Glu Gln Ala Thr Trp Ala Thr Leu Ala Glu Ile
    195                 200                 205

Arg Leu Met Ala Arg Ile Ala Gly Leu Glu Val Thr Gly Val Asp Gly
    210                 215                 220

Ser Tyr Ala Gly Glu Pro Tyr Thr Ala Arg Ser Arg Glu Met Leu Val
225                 230                 235                 240

Val Leu Glu Arg Gln
            245

<210> SEQ ID NO 29
<211> LENGTH: 245
<212> TYPE: PRT
<213> ORGANISM: Streptomyces griseus

<400> SEQUENCE: 29

Met Ser Glu Pro Thr Val Tyr Asp Ala Ala Ile Asp Ala Tyr Asp
1               5                   10                  15

Leu Ile Ser Ser Met Leu Ser Pro Gly Ala Gly Leu Ala Ala Trp Val
            20                  25                  30

Ser Ser His Arg Pro Leu Ala Gly Arg Thr Val Leu Asp Leu Gly Ala
        35                  40                  45

Gly Thr Gly Val Ser Ser Phe Ala Leu Ala Asp Ala Gly Ala Gln Val
    50                  55                  60

Val Ala Val Asp Ala Ser Arg Pro Ser Leu Asp Leu Leu Glu Ser Arg
65                  70                  75                  80

Arg Gly Glu Arg Lys Val Asp Thr Val Glu Ala Asp Phe Arg Asp Leu
                85                  90                  95

Arg Leu Asp Ser Ala Phe Asp Val Val Thr Met Ser Lys Asn Thr Phe
            100                 105                 110

Phe Leu Ala Gln Ser His Asp Glu Lys Ile Glu Leu Leu Arg Ala Ile
        115                 120                 125

Gly Arg His Leu Lys Pro Gly Gly Ala Val Phe Leu Asp Cys Thr Asp
    130                 135                 140

Pro Val Glu Tyr Leu Arg Ala Asp Gly Ala His Thr Val Thr Tyr
145                 150                 155                 160

Pro Leu Gly Arg Glu Gln Met Val Thr Ile Thr Gln Asn Ala Asp Arg
                165                 170                 175

Ala Thr Gln Ala Ile Met Ser Ile Phe Met Val Gln Ser Ala Ser Thr
            180                 185                 190

Leu Thr Ser Phe His Glu Met Ala Thr Trp Ala Ser Leu Pro Glu Ile
        195                 200                 205

Arg Leu Leu Ala Arg Ala Ala Gly Leu Glu Val Thr Ala Val Asp Gly
    210                 215                 220

Ser Tyr Ala Gly Asp Ala Tyr Thr Ala Arg Ser Arg Glu Met Leu Val
225                 230                 235                 240

Val Leu Glu Ala Lys
            245

<210> SEQ ID NO 30
<211> LENGTH: 317
<212> TYPE: PRT
<213> ORGANISM: Escherichia coli

<400> SEQUENCE: 30

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

```
Ile Val Thr Arg Thr Gly Ile Arg Glu Arg His Ile Ala Ala Pro Asn
                35                  40                  45

Glu Thr Val Ser Thr Met Gly Phe Glu Ala Ala Thr Arg Ala Ile Glu
 50                  55                  60

Met Ala Gly Ile Glu Lys Asp Gln Ile Gly Leu Ile Val Val Ala Thr
 65                  70                  75                  80

Thr Ser Ala Thr His Ala Phe Pro Ser Ala Ala Cys Gln Ile Gln Ser
                 85                  90                  95

Met Leu Gly Ile Lys Gly Cys Pro Ala Phe Asp Val Ala Ala Ala Cys
                100                 105                 110

Ala Gly Phe Thr Tyr Ala Leu Ser Val Ala Asp Gln Tyr Val Lys Ser
                115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
                180                 185                 190

Asn Ala Asp Arg Val Asn Pro Glu Asn Ser Ile His Leu Thr Met Ala
                195                 200                 205

Gly Asn Glu Val Phe Lys Val Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
                260                 265                 270

Gly Asn Thr Ser Ala Ala Ser Val Pro Cys Ala Leu Asp Glu Ala Val
    275                 280                 285

Arg Asp Gly Arg Ile Lys Pro Gly Gln Leu Val Leu Leu Glu Ala Phe
290                 295                 300

Gly Gly Gly Phe Thr Trp Gly Ser Ala Leu Val Arg Phe
305                 310                 315
```

<210> SEQ ID NO 31
<211> LENGTH: 324
<212> TYPE: PRT
<213> ORGANISM: Streptococcus pneumoniae

<400> SEQUENCE: 31

```
Met Ala Phe Ala Lys Ile Ser Gln Val Ala His Tyr Val Pro Glu Gln
 1               5                  10                  15

Val Val Thr Asn His Asp Leu Ala Gln Ile Met Asp Thr Asn Asp Glu
                20                  25                  30

Trp Ile Ser Ser Arg Thr Gly Ile Arg Gln Arg His Ile Ser Arg Thr
                35                  40                  45

Glu Ser Thr Ser Asp Leu Ala Thr Glu Val Ala Lys Lys Leu Met Ala
 50                  55                  60

Lys Ala Gly Ile Thr Gly Glu Glu Leu Asp Phe Ile Ile Leu Ala Thr
 65                  70                  75                  80

Ile Thr Pro Asp Ser Met Met Pro Ser Thr Ala Ala Arg Val Gln Ala
```

Asn Ile Gly Ala Asn Lys Ala Phe Ala Phe Asp Leu Thr Ala Ala Cys
                85                  90                  95

Ser Gly Phe Val Phe Ala Leu Ser Thr Ala Glu Lys Phe Ile Ala Ser
            100                 105                 110

Gly Arg Phe Gln Lys Gly Leu Val Ile Gly Ser Glu Thr Leu Ser Lys
            115                 120                 125

Ala Val Asp Trp Ser Asp Arg Ser Thr Ala Val Leu Phe Gly Asp Gly
130                 135                 140

Ala Gly Gly Val Leu Leu Glu Ala Ser Glu Gln Glu His Phe Leu Ala
145                 150                 155                 160

Glu Ser Leu Asn Ser Asp Gly Ser Arg Ser Glu Cys Leu Thr Tyr Gly
            165                 170                 175

His Ser Gly Leu His Ser Pro Phe Ser Asp Gln Glu Ser Ala Asp Ser
            180                 185                 190

Phe Leu Lys Met Asp Gly Arg Thr Val Phe Asp Phe Ala Ile Arg Asp
            195                 200                 205

Val Ala Lys Ser Ile Lys Gln Thr Ile Asp Glu Ser Pro Ile Glu Val
            210                 215                 220

Thr Asp Leu Asp Tyr Leu Leu Leu His Gln Ala Asn Asp Arg Ile Leu
225                 230                 235                 240

Asp Lys Met Ala Arg Lys Ile Gly Val Asp Arg Ala Lys Leu Pro Ala
            245                 250                 255

Asn Met Met Glu Tyr Gly Asn Thr Ser Ala Ala Ser Ile Pro Ile Leu
            260                 265                 270

Leu Ser Glu Cys Val Glu Gln Gly Leu Ile Pro Leu Asp Gly Ser Gln
            275                 280                 285

Thr Val Leu Leu Ser Gly Phe Gly Gly Gly Leu Thr Trp Gly Thr Leu
            290                 295                 300

Ile Leu Thr Ile
305                 310                 315                 320

<210> SEQ ID NO 32
<211> LENGTH: 634
<212> TYPE: PRT
<213> ORGANISM: Pseudomonas aeruginosa

<400> SEQUENCE: 32

Met Ser Arg Leu Pro Val Ile Val Gly Phe Gly Gly Tyr Asn Ala Ala
1               5                   10                  15

Gly Arg Ser Ser Phe His His Gly Phe Arg Arg Met Val Ile Glu Ser
            20                  25                  30

Met Asp Pro Gln Ala Arg Gln Glu Thr Leu Ala Gly Leu Ala Val Met
            35                  40                  45

Met Lys Leu Val Lys Ala Glu Gly Gly Arg Tyr Leu Ala Glu Asp Gly
        50                  55                  60

Thr Pro Leu Ser Pro Glu Asp Ile Glu Arg Arg Tyr Ala Glu Arg Ile
65                  70                  75                  80

Phe Ala Ser Thr Leu Val Arg Arg Ile Glu Pro Gln Tyr Leu Asp Pro
                85                  90                  95

Asp Ala Val His Trp His Lys Val Leu Glu Leu Ser Pro Ala Glu Gly
            100                 105                 110

Gln Ala Leu Thr Phe Lys Ala Ser Pro Lys Gln Leu Pro Glu Pro Leu
            115                 120                 125

Pro Ala Asn Trp Ser Ile Ala Pro Ala Glu Asp Gly Glu Val Leu Val

```
              130                 135                 140
Ser Ile His Glu Arg Cys Glu Phe Lys Val Asp Ser Tyr Arg Ala Leu
145                 150                 155                 160

Thr Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ser Val Val
                180                 185                 190

Ala Ala Thr Asp Ala Ile Arg Ser Thr Gly Ile Asp Trp Lys Thr Ile
                195                 200                 205

Val Asp Asn Val Gln Pro Asp Glu Ile Ala Val Phe Ser Gly Ser Ile
210                 215                 220

Met Ser Gln Leu Asp Asp Asn Gly Phe Gly Gly Leu Met Gln Ser Arg
225                 230                 235                 240

Leu Lys Gly His Arg Val Ser Ala Lys Gln Leu Pro Leu Gly Phe Asn
                245                 250                 255

Ser Met Pro Thr Asp Phe Ile Asn Ala Tyr Val Leu Gly Ser Val Gly
                260                 265                 270

Met Thr Gly Ser Ile Thr Gly Ala Cys Ala Thr Phe Leu Tyr Asn Leu
                275                 280                 285

Gln Lys Gly Ile Asp Val Ile Thr Ser Gly Gln Ala Arg Val Val Ile
                290                 295                 300

Val Gly Asn Ser Glu Ala Pro Ile Leu Pro Glu Cys Ile Glu Gly Tyr
305                 310                 315                 320

Ser Ala Met Gly Ala Leu Ala Thr Glu Glu Gly Leu Arg Leu Ile Glu
                325                 330                 335

Gly Arg Asp Asp Val Asp Phe Arg Arg Ala Ser Arg Pro Phe Gly Glu
                340                 345                 350

Asn Cys Gly Phe Thr Leu Ala Glu Ser Ser Gln Tyr Val Val Leu Met
                355                 360                 365

Asp Asp Glu Leu Ala Leu Arg Leu Gly Ala Asp Ile His Gly Ala Val
                370                 375                 380

Thr Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
                405                 410                 415

Val Gln Ile Val Gly Leu Asp Thr Val Arg His Ala Ser Phe Val His
                420                 425                 430

Ala His Gly Ser Ser Thr Pro Ala Asn Arg Val Thr Glu Ser Glu Ile
                435                 440                 445

Leu Asp Arg Val Ala Ser Ala Phe Gly Ile Asp Gly Trp Pro Val Thr
450                 455                 460

Ala Val Lys Ala Tyr Val Gly His Ser Leu Thr Ala Ser Ala Asp
465                 470                 475                 480

Gln Leu Ile Ser Ala Leu Gly Thr Phe Lys Tyr Gly Ile Leu Pro Gly
                485                 490                 495

Ile Lys Thr Ile Asp Lys Val Ala Asp Val His Gln Gln Arg Leu
                500                 505                 510

Ser Ile Ser Asn Arg Asp Met Arg Gln Asp Lys Pro Leu Glu Val Cys
                515                 520                 525

Phe Ile Asn Ser Lys Gly Phe Gly Gly Asn Asn Ala Ser Gly Val Val
                530                 535                 540

Leu Ser Pro Arg Ile Ala Glu Lys Met Leu Arg Lys Arg His Gly Gln
545                 550                 555                 560
```

```
Ala Ala Phe Ala Ala Tyr Val Glu Lys Arg Glu Gln Thr Arg Ala Ala
                565                 570                 575

Ala Arg Ala Tyr Asp Gln Arg Ala Leu Gln Gly Asp Leu Glu Ile Ile
            580                 585                 590

Tyr Asn Phe Gly Gln Asp Leu Ile Asp Glu His Ala Ile Glu Val Ser
        595                 600                 605

Ala Glu Gln Val Thr Val Pro Gly Phe Ser Gln Pro Leu Val Tyr Lys
    610                 615                 620

Lys Asp Ala Arg Phe Ser Asp Met Leu Asp
625                 630

<210> SEQ ID NO 33
<211> LENGTH: 423
<212> TYPE: PRT
<213> ORGANISM: Pseudomonas mendocina

<400> SEQUENCE: 33

Met Arg Thr Ala Ile Leu Gly Ala Arg Val Ile Asp Pro Ala Ser Gly
1               5                   10                  15

Leu Asp Gln Val Thr Asp Leu Tyr Ile Asp Gly Thr Lys Leu Val Ala
            20                  25                  30

Phe Gly Gln Ala Pro Ala Gly Phe Thr Ala Asp Lys Thr Leu Asn Ala
        35                  40                  45

Gln Gly Leu Ile Ala Ala Pro Gly Leu Val Asp Leu Ser Val Ala Leu
    50                  55                  60

Arg Glu Pro Gly Tyr Ser Arg Lys Gly Ser Ile Ala Thr Glu Thr Leu
65                  70                  75                  80

Ala Ala Ala Gly Gly Val Thr Ser Leu Cys Cys Pro Pro Leu Thr
                85                  90                  95

Lys Pro Val Leu Asp Thr Pro Ala Val Ala Glu Leu Ile Leu Asp Arg
            100                 105                 110

Ala Arg Glu Ala Gly His Thr Lys Val Phe Pro Ile Gly Ala Leu Ser
        115                 120                 125

Lys Gly Leu Ala Gly Glu Gln Leu Ala Glu Leu Val Ala Leu Arg Asp
    130                 135                 140

Ala Gly Cys Val Ala Phe Gly Asn Gly Leu Asp Asn Phe Arg Ser Ala
145                 150                 155                 160

Arg Thr Leu Arg Arg Ala Leu Glu Tyr Ala Ala Thr Phe Asp Leu Gln
                165                 170                 175

Val Ile Phe His Ser Gln Asp Phe Asp Leu Ala Glu Gly Gly Leu Ala
            180                 185                 190

His Glu Gly Pro Thr Ala Ser Phe Leu Gly Leu Ala Gly Ile Pro Glu
        195                 200                 205

Thr Ala Glu Thr Val Ala Leu Ala Arg Asp Leu Leu Leu Val Glu Gln
    210                 215                 220

Ser Gly Val Arg Ala His Phe Ser Gln Ile Thr Ser Ala Arg Gly Ala
225                 230                 235                 240

Glu Leu Ile Ala Asn Ala Gln Ala Arg Gly Leu Pro Val Thr Ala Asp
                245                 250                 255

Val Ala Leu Tyr Gln Leu Ile Leu Thr Asp Glu Ala Leu Ile Asp Phe
            260                 265                 270

Ser Ser Leu Tyr His Val Gln Pro Pro Leu Arg Ser Arg Ala Asp Arg
        275                 280                 285

Asp Gly Leu Arg Glu Ala Val Lys Ala Gly Val Ile Ser Ala Ile Ala
```

```
                290                 295                 300
Ser His His Gln Pro His Glu Arg Asp Ala Lys Leu Ala Pro Phe Ala
305                 310                 315                 320

Ala Thr Glu Pro Gly Ile Ser Ser Val Gln Leu Gln Leu Pro Leu Ala
                325                 330                 335

Met Ser Leu Val Gln Asp Gly Leu Leu Asp Leu Pro Thr Leu Leu Ala
                340                 345                 350

Arg Leu Ser Ser Gly Pro Ala Ala Ala Leu Arg Leu Pro Ala Gly Thr
                355                 360                 365

Leu Ser Val Gly Gly Ala Ala Asp Ile Val Leu Phe Asp Ala Gln Ala
                370                 375                 380

Ser Thr Val Ala Gly Glu Gln Trp Tyr Ser Lys Gly Ser Asn Cys Pro
385                 390                 395                 400

Phe Ile Gly His Cys Leu Pro Gly Ala Val Arg Tyr Thr Leu Val Asp
                405                 410                 415

Gly His Ile Ser Tyr Gln Ser
                420

<210> SEQ ID NO 34
<211> LENGTH: 635
<212> TYPE: PRT
<213> ORGANISM: Pseudomonas mendocina

<400> SEQUENCE: 34

Met Ser Arg Leu Pro Val Ile Val Gly Phe Gly Gly Tyr Asn Ala Ala
1               5                   10                  15

Gly Arg Ser Ser Phe His His Gly Phe Arg Arg Thr Val Gln Glu Ser
                20                  25                  30

Leu Glu Pro Gln Ala Arg Gln Glu Thr Leu Ala Gly Leu Ala Gln Met
                35                  40                  45

Met Lys Leu Val Arg Val Val Asp Gly Gln Tyr Gln Asp Gln Asp Gly
                50                  55                  60

Gln Pro Leu Ser Leu Ala Asp Ile Glu Ser Arg Tyr Ala Lys Gln Ile
65                  70                  75                  80

Leu Ala Gly Thr Leu Val Arg Arg Ile Glu Lys Gln His Leu Asp Pro
                85                  90                  95

Asp Ala Ala His Trp Gln Lys Ser Ile Gly Val Thr Pro Ala Asp Gly
                100                 105                 110

Thr Ser Leu Ser Phe Leu Thr Gln Arg Lys Gln Leu Pro Glu Pro Leu
                115                 120                 125

Pro Ala Asn Trp Ser Ile Glu Glu Leu Glu Gly Asn Glu Val Arg Val
                130                 135                 140

Thr Leu His Asp Ser Cys Glu Phe Lys Val Asp Ser Tyr Arg Pro Leu
145                 150                 155                 160

Ala Val Lys Ser Ala Gly Gln Leu Pro Thr Gly Phe Glu Pro Ser Glu
                165                 170                 175

Leu Tyr Asn Ala Arg Phe His Pro Arg Gly Leu Ala Met Thr Val Val
                180                 185                 190

Gly Val Thr Asp Ala Leu Arg Ser Val Gly Ile Asp Trp Gln Arg Ile
                195                 200                 205

Val Gln His Val Ala Pro Asp Glu Ile Ala Val Phe Ala Ser Cys Ile
                210                 215                 220

Met Ser Gln Leu Asp Glu Asn Gly Phe Gly Gly Met Met Gln Ser Arg
225                 230                 235                 240
```

-continued

| | | | | | | | | | | | |
|---|---|---|---|---|---|---|---|---|---|---|---|
|Leu|Lys|Gly|Gly|Arg|Val|Thr|Ala|Lys|Gln|Leu|Ala|Leu|Gly|Leu|Asn|
| | | | |245| | | |250| | | |255| | | |

Thr Met Pro Ala Asp Phe Ile Asn Ala Tyr Val Leu Gly Ser Val Gly
          260                 265                 270

Thr Thr Gly Ser Ile Thr Gly Ala Cys Ala Thr Phe Leu Tyr Asn Leu
      275                 280                 285

Gln Lys Gly Ile Glu Gln Ile Ala Ser Gly Lys Ala Arg Val Val Ile
          290                 295                 300

Val Gly Ser Ser Glu Ala Pro Ile Asn Gln Glu Cys Ile Glu Gly Tyr
305                 310                 315                 320

Gly Ala Met Gly Ala Leu Ala Thr Glu Glu Gly Leu Arg Gln Ile Glu
              325                 330                 335

Gly Lys Ser Glu Val Asp Phe Arg Arg Ala Ser Arg Pro Phe Gly Asp
          340                 345                 350

Asn Cys Gly Phe Thr Leu Ala Glu Ala Cys Gln Phe Val Val Leu Met
              355                 360                 365

Asp Asp Glu Leu Ala Leu Glu Leu Gly Ala Asp Ile His Gly Ala Val
370                 375                 380

Pro Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
              405                 410                 415

Val Gln Leu Leu Gly Leu Asp Ala Val Arg Asn Arg Ser Phe Val His
              420                 425                 430

Ala His Gly Ser Ser Thr Pro Ala Asn Arg Val Thr Glu Ser Glu Ile
      435                 440                 445

Leu Asp Arg Val Ala Ala Ala Phe Gly Ile Glu Gln Trp Pro Val Thr
450                 455                 460

Ala Val Lys Ala Phe Val Gly His Ser Leu Ala Thr Ala Ser Gly Asp
465                 470                 475                 480

Gln Val Ile Gly Ala Leu Gly Ala Phe Lys Tyr Gly Ile Val Pro Gly
              485                 490                 495

Ile Lys Thr Ile Asp Ala Val Ala Gly Asp Val His Gln His His Leu
          500                 505                 510

Ser Leu Ser Thr Glu Asp Arg Lys Val Gly Asp Gln Ala Leu Asp Val
      515                 520                 525

Ala Phe Ile Asn Ser Lys Gly Phe Gly Gly Asn Asn Ala Ser Ala Leu
530                 535                 540

Val Leu Ala Pro His Val Thr Glu Arg Met Leu Arg Lys Arg His Gly
545                 550                 555                 560

Gln Ala Ala Phe Asp Ala Tyr Leu Ala Arg Arg Glu Gly Thr Arg Ala
              565                 570                 575

Ala Ala Ala Ala Tyr Asp Gln Gln Ala Leu Gln Gly Lys Leu Asp Ile
              580                 585                 590

Ile Tyr Asn Phe Gly Asn Asp Met Ile Asp Gln Ala Ile Ser Ile
          595                 600                 605

Thr Thr Glu Glu Val Lys Val Pro Gly Phe Asp Gln Pro Leu Val Phe
      610                 615                 620

Arg Lys Asp Ala Arg Tyr Ser Asp Met Leu Asp
625                 630                 635

<210> SEQ ID NO 35
<211> LENGTH: 633
<212> TYPE: PRT

<213> ORGANISM: Pseudomonas fulva

<400> SEQUENCE: 35

```
Met Lys Ser Arg Leu Pro Val Ile Val Gly Phe Gly Tyr Asn Ala
1               5                   10                  15

Ala Gly Arg Ser Ser Phe His His Gly Phe Arg Arg Thr Val Ile Glu
            20                  25                  30

Ser Leu Asp Glu Gln Ala Arg Gln Thr Leu Thr Gly Leu Ala Val
        35                  40                  45

Met Thr Lys Leu Val Arg Val Val Asp Gly Arg Tyr Gln Ser Gln Asp
    50                  55                  60

Gly Glu Ala Leu Ser Pro Ala Asp Ile Glu Arg Arg Tyr Gly Ala Gln
65                  70                  75                  80

Ile Leu Ala Ser Thr Leu Val Arg Arg Ile Glu Lys Gln His Leu Asp
                85                  90                  95

Pro Asp Ala Ala His Trp His Lys Ser Ile Ala Val Gly Gly Glu Ala
                100                 105                 110

Gly Ser Leu Thr Phe Val Ser Ser Arg Lys Gln Leu Pro Glu Pro Leu
            115                 120                 125

Pro Ala Asn Trp Thr Val Glu Glu Leu Gly Gly Asn Asp Val Arg Val
            130                 135                 140

Thr Leu His Asp Ser Cys Glu Phe Lys Val Asp Ser Tyr Arg Ala Leu
145                 150                 155                 160

Pro Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ala Val Val
                180                 185                 190

Gly Val Thr Asp Ala Leu Arg Ala Thr Gly Val Pro Trp Gln Thr Ile
            195                 200                 205

Val Asp His Val Ala Pro Asp Glu Ile Ala Val Phe Ala Gly Ser Ile
210                 215                 220

Met Ser Gln Leu Asp Glu Asn Gly Phe Gly Gly Leu Met Gln Ser Arg
225                 230                 235                 240

Leu Lys Gly His Arg Val Ser Ser Lys Gln Leu Ala Leu Gly Leu Asn
                245                 250                 255

Thr Met Pro Ala Asp Phe Ile Asn Ala Tyr Val Leu Gly Ser Val Gly
                260                 265                 270

Thr Thr Gly Ser Val Thr Gly Ala Cys Ala Thr Phe Leu Tyr Asn Leu
            275                 280                 285

Gln Lys Gly Ile Glu Gln Ile Asn Ala Gly Lys Ala Arg Val Val Ile
            290                 295                 300

Val Gly Asn Ser Glu Ala Pro Ile Asn Ala Glu Cys Ile Glu Gly Tyr
305                 310                 315                 320

Gly Ala Met Gly Ala Leu Ala Thr Glu Asp Gly Leu Arg Leu Ile Glu
                325                 330                 335

Gly Lys Asp Asp Val Asp Phe Arg Arg Ala Ser Arg Pro Phe Gly Glu
                340                 345                 350

Asn Cys Gly Phe Thr Leu Ser Glu Ala Cys Gln Phe Val Val Leu Met
            355                 360                 365

Asp Asp Glu Leu Ala Leu Gln Leu Gly Ala Asp Ile His Gly Ala Ala
            370                 375                 380

Thr Asp Val Phe Ile Asn Ala Asp Gly Phe Lys Lys Ser Ile Ser Ala
385                 390                 395                 400
```

```
Pro Gly Pro Gly Asn Tyr Leu Thr Val Ala Lys Ala Val Ala Ala Ala
                405                 410                 415

Thr Gln Leu Val Gly Ile Asp Ala Val Arg Arg Ser Phe Val His
    420                 425                 430

Ala His Gly Ser Ser Thr Pro Ala Asn Arg Val Thr Glu Ser Glu Leu
        435                 440                 445

Leu Asp Arg Val Ala Ala Phe Ala Ile Asp Ser Trp Pro Val Ala
    450                 455                 460

Ala Val Lys Ala Phe Val Gly His Ser Leu Ala Thr Ala Ser Gly Asp
465                 470                 475                 480

Gln Val Ile Ser Ala Leu Gly Thr Phe Lys Tyr Gly Ile Ile Pro Gly
                485                 490                 495

Ile Lys Thr Ile Asp Glu Val Ala Ala Asp Val His Gln Gln His Leu
                500                 505                 510

Ser Ile Ser Asn Val Asp Arg His Asp Gln Arg Met Asp Val Cys Phe
            515                 520                 525

Ile Asn Ser Lys Gly Phe Gly Gly Asn Ala Ser Ala Val Val Leu
    530                 535                 540

Ala Pro His Val Val Glu Arg Met Leu Arg Lys Arg His Gly Glu Ala
545                 550                 555                 560

Ala Phe Ser Ala Tyr Gln Gln Arg Arg Glu Gln Thr Arg Ala Asn Ala
                565                 570                 575

Gln Ala Tyr Asp Glu Gln Ala Thr Lys Gly Gln Leu Glu Ile Ile Tyr
                580                 585                 590

Asn Phe Gly Asn Asp Leu Ile Asp Asp Thr Glu Ile Ala Ile Asp Asp
                595                 600                 605

Ala Gln Ile Lys Val Pro Gly Phe Ala Gln Pro Leu Leu Tyr Lys Gln
    610                 615                 620

Asp Asp Arg Tyr Ser Asp Met Leu Asp
625                 630

<210> SEQ ID NO 36
<211> LENGTH: 632
<212> TYPE: PRT
<213> ORGANISM: Azotobacter vinelandii

<400> SEQUENCE: 36

Met Ser Arg Leu Pro Val Ile Val Gly Phe Gly Gly Tyr Asn Ser Ala
1               5                   10                  15

Gly Arg Ser Ser Phe His His Gly Phe Arg Arg Thr Val Ile Glu Ser
                20                  25                  30

Leu Thr Pro Gln Ala Arg Gln Glu Thr Leu Ala Gly Leu Ala Val Met
            35                  40                  45

Met Lys Leu Val Ser Val Val Asp Gly Gln Tyr Arg Asp Ser Asp Gly
    50                  55                  60

Ser Thr Leu Thr Pro Ala Glu Ile Glu Arg Arg His Gly Glu Arg Ile
65                  70                  75                  80

Leu Ala Ala Thr Leu Ile Arg Arg Ile Glu Arg Gln Tyr Phe Asp Val
                85                  90                  95

Asp Ala Thr His Trp His Lys Ser Leu Thr Leu Ser Gly Glu Asp Gln
                100                 105                 110

Pro Leu His Phe Thr Thr Ser Ala Lys Gln Leu Pro Glu Pro Leu Pro
            115                 120                 125

Ala Asn Trp Ser Val Glu Pro Leu Glu Glu His Gln Val Arg Val Thr
    130                 135                 140
```

-continued

```
Ile His Gly Ser Cys Glu Phe Lys Val Asp Ser Tyr Arg Glu Met Pro
145                 150                 155                 160

Val Lys Ser Ala Gly Gln Leu Pro Thr Gly Phe Glu Pro Gly Glu Leu
                165                 170                 175

Tyr Asn Ser Arg Phe His Pro Arg Gly Leu Gln Leu Ser Val Val Ala
            180                 185                 190

Ala Thr Asp Ala Leu Arg Ser Thr Gly Ile Asp Trp Gln Thr Ile Leu
        195                 200                 205

Asp His Val Gln Pro Asp Glu Val Ala Val Phe Ser Gly Ser Ile Met
    210                 215                 220

Ser Gln Leu Asp Glu Asn Gly Tyr Gly Gly Leu Leu Gln Ser Arg Leu
225                 230                 235                 240

Lys Gly His Arg Val Ser Ser Lys Gln Leu Pro Leu Gly Phe Asn Ser
                245                 250                 255

Met Pro Thr Asp Phe Ile Asn Ala Tyr Val Leu Gly Ser Val Gly Ser
            260                 265                 270

Thr Gly Ser Ile Thr Gly Ala Cys Ala Thr Phe Leu Tyr Asn Leu Gln
        275                 280                 285

Lys Gly Ile Asp Val Ile Thr Ser Gly Gln Ala Arg Val Val Val Ala
    290                 295                 300

Gly Asn Ala Glu Ala Pro Ile Thr Pro Glu Ile Val Glu Gly Tyr Ala
305                 310                 315                 320

Ala Met Gly Ala Leu Ala Thr Glu Glu Gly Leu Arg His Ile Glu Gly
                325                 330                 335

Arg Asp Gln Val Asp Phe Arg Arg Ala Ser Arg Pro Phe Gly Ala Asn
            340                 345                 350

Cys Gly Phe Thr Leu Ala Glu Ala Ala Gln Tyr Val Val Leu Met Asp
        355                 360                 365

Asp Ser Leu Ala Leu Glu Leu Gly Ala Asp Ile His Gly Ala Val Pro
    370                 375                 380

Asp Val Phe Val Asn Ala Asp Gly Phe Lys Lys Ser Ile Ser Ala Pro
385                 390                 395                 400

Gly Pro Gly Asn Tyr Leu Thr Val Ala Lys Ala Val Ala Ser Ala Met
                405                 410                 415

Gln Leu Val Gly Glu Asp Gly Val Arg Gln Arg Ser Phe Ile His Ala
            420                 425                 430

His Gly Ser Ser Thr Pro Ala Asn Arg Val Thr Glu Ser Glu Leu Leu
        435                 440                 445

Asp Arg Val Ala Gly Ala Phe Gly Ile Ala Asp Trp Pro Val Ala Ala
    450                 455                 460

Val Lys Ala Tyr Val Gly His Ser Leu Ala Thr Ala Ser Gly Asp Gln
465                 470                 475                 480

Leu Ile Ser Ala Leu Gly Thr Phe Lys Tyr Gly Leu Leu Pro Gly Ile
                485                 490                 495

Lys Thr Val Asp Arg Phe Ala Asp Asp Val His Asp Gln His Leu Arg
            500                 505                 510

Leu Ser Met Arg Asp Val Arg Arg Asp Asp Leu Asp Val Cys Phe Ile
        515                 520                 525

Asn Ser Lys Gly Phe Gly Gly Asn Asn Ala Thr Gly Val Leu Leu Ser
    530                 535                 540

Pro Arg Val Thr Glu Lys Met Leu Arg Lys Arg His Gly Glu Ala Ala
545                 550                 555                 560
```

```
Phe Ala Asp Tyr Arg Ser Arg Arg Glu Ala Thr Arg Glu Ala Ala Arg
                565                 570                 575

Arg Tyr Asp Glu Gln Val Leu Gln Gly Arg Phe Asp Ile Leu Tyr Asn
            580                 585                 590

Phe Gly Gln Asp Met Ile Asp Glu His Ala Ile Glu Val Asn Glu Glu
            595                 600                 605

Gly Val Lys Val Pro Gly Phe Lys Gln Ala Ile Arg Phe Arg Lys Asp
            610                 615                 620

Glu Arg Phe Gly Asp Met Leu Asp
625                 630

<210> SEQ ID NO 37
<211> LENGTH: 634
<212> TYPE: PRT
<213> ORGANISM: Pseudomonas aeruginosa

<400> SEQUENCE: 37

Met Ser Arg Leu Pro Val Ile Val Gly Phe Gly Gly Tyr Asn Ala Ala
1               5                   10                  15

Gly Arg Ser Ser Phe His His Gly Phe Arg Arg Met Val Ile Glu Ser
            20                  25                  30

Met Asp Pro Gln Ala Arg Gln Glu Thr Leu Ala Gly Leu Ala Val Met
            35                  40                  45

Met Lys Leu Val Lys Ala Glu Gly Gly Arg Tyr Leu Ala Glu Asp Gly
50                  55                  60

Thr Pro Leu Ser Pro Glu Asp Ile Glu Arg Arg Tyr Ala Glu Arg Ile
65                  70                  75                  80

Phe Ala Ser Thr Leu Val Arg Arg Ile Glu Pro Gln Tyr Leu Asp Pro
                85                  90                  95

Asp Ala Val His Trp His Lys Val Leu Glu Ala Thr Pro Ala Glu Gly
            100                 105                 110

Gln Ala Leu Thr Phe Lys Ala Ser Pro Lys Gln Leu Pro Glu Pro Leu
            115                 120                 125

Pro Gly Asn Trp Ser Val Thr Pro Ala Ala Asp Gly Glu Val Leu Val
        130                 135                 140

Ser Ile His Glu Arg Cys Glu Phe Lys Val Asp Ser Tyr Arg Pro Leu
145                 150                 155                 160

Thr Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ser Val Val
            180                 185                 190

Ala Ala Thr Asp Ala Ile Arg Ser Thr Gly Ile Asp Trp Gln Thr Ile
            195                 200                 205

Val Asp Asn Val Gln Pro Asp Glu Ile Ala Val Phe Ser Gly Ser Ile
        210                 215                 220

Met Ser Gln Leu Asp Asp Asn Gly Phe Gly Leu Met Gln Ser Arg
225                 230                 235                 240

Leu Lys Gly His Arg Val Ser Ala Lys Gln Leu Pro Leu Gly Phe Asn
                245                 250                 255

Ser Met Pro Thr Asp Phe Ile Asn Ala Tyr Val Leu Gly Ser Val Gly
            260                 265                 270

Met Thr Gly Ser Ile Thr Gly Ala Cys Ala Thr Phe Leu Tyr Asn Leu
            275                 280                 285

Gln Lys Gly Ile Asp Val Ile Thr Ser Gly Gln Ala Arg Val Val Ile
        290                 295                 300
```

Val Gly Asn Ser Glu Ala Pro Ile Leu Pro Glu Cys Ile Glu Gly Tyr
305                 310                 315                 320

Ser Ala Met Gly Ala Leu Ala Thr Glu Glu Gly Leu Arg Leu Ile Glu
            325                 330                 335

Gly Arg Asp Glu Val Asp Phe Arg Arg Ala Ser Arg Pro Phe Gly Glu
            340                 345                 350

Asn Cys Gly Phe Thr Leu Ala Glu Ser Ser Gln Tyr Val Val Leu Met
            355                 360                 365

Asp Asp Glu Leu Ala Leu Arg Leu Gly Ala Asp Ile His Gly Ala Val
            370                 375                 380

Thr Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
            405                 410                 415

Val Gln Ile Val Gly Leu Asp Thr Val Arg His Ala Ser Phe Val His
            420                 425                 430

Ala His Gly Ser Ser Thr Pro Ala Asn Arg Val Thr Glu Ser Glu Ile
            435                 440                 445

Leu Asp Arg Val Ala Ser Ala Phe Gly Ile Asp Gly Trp Pro Val Thr
450                 455                 460

Ala Val Lys Ala Tyr Val Gly His Ser Leu Ala Thr Ala Ser Ala Asp
465                 470                 475                 480

Gln Leu Ile Ser Ala Leu Gly Thr Phe Lys Tyr Gly Ile Leu Pro Gly
            485                 490                 495

Ile Lys Thr Ile Asp Lys Val Ala Asp Val His Gln Gln Arg Leu
            500                 505                 510

Ser Ile Ser Asn Arg Asp Val Arg Gln Asp Lys Pro Leu Glu Val Cys
            515                 520                 525

Phe Ile Asn Ser Lys Gly Phe Gly Gly Asn Asn Ala Ser Gly Val Val
530                 535                 540

Leu Ser Pro Arg Ile Ala Glu Lys Met Leu Arg Arg His Gly Glu
545                 550                 555                 560

Ala Ala Phe Ala Ala Tyr Val Glu Lys Arg Glu Gln Thr Arg Gly Ala
            565                 570                 575

Ala Arg Ala Tyr Asp Gln Arg Ala Leu Gln Gly Asp Leu Glu Ile Ile
            580                 585                 590

Tyr Asn Phe Gly Gln Asp Leu Ile Asp Glu Gln Ala Ile Glu Val Ser
            595                 600                 605

Ala Glu Gln Val Thr Val Pro Gly Phe Ser Gln Pro Leu Val Tyr Lys
            610                 615                 620

Lys Asp Ala Arg Phe Ser Asp Met Leu Asp
625                 630

<210> SEQ ID NO 38
<211> LENGTH: 634
<212> TYPE: PRT
<213> ORGANISM: Pseudomonas aeruginosa

<400> SEQUENCE: 38

Met Tyr Arg Leu Pro Val Ile Val Gly Phe Gly Gly Tyr Asn Ala Ala
1               5                   10                  15

Gly Arg Ser Ser Phe His His Gly Phe Arg Arg Met Val Ile Glu Ser
            20                  25                  30

Met Asp Pro Gln Ala Arg Gln Glu Thr Leu Ala Gly Leu Ala Val Met

```
                35                   40                  45
Met Lys Leu Val Lys Ala Glu Gly Gly Arg Tyr Leu Ala Glu Asp Gly
     50                  55                  60

Thr Pro Leu Ser Pro Glu Asp Ile Glu Arg Arg Tyr Ala Glu Arg Ile
 65                  70                  75                  80

Phe Ala Ser Thr Leu Val Arg Arg Ile Glu Pro Gln Tyr Leu Asp Pro
                 85                  90                  95

Asp Ala Val His Trp His Lys Val Leu Glu Leu Ser Pro Ala Glu Gly
            100                 105                 110

Gln Ala Leu Thr Phe Lys Ala Ser Pro Lys Gln Leu Pro Glu Pro Leu
        115                 120                 125

Pro Ala Asn Trp Thr Ile Ala Pro Ala Glu Asp Gly Glu Val Leu Val
    130                 135                 140

Ser Ile His Glu Arg Cys Glu Phe Lys Val Asp Ser Tyr Arg Ala Leu
145                 150                 155                 160

Thr Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ser Val Val
            180                 185                 190

Ala Ala Thr Asp Ala Ile Arg Ser Thr Gly Ile Asp Trp Lys Thr Ile
        195                 200                 205

Val Asp Asn Val Gln Pro Asp Glu Ile Ala Val Phe Ser Gly Ser Ile
    210                 215                 220

Met Ser Gln Leu Asp Asp Asn Gly Phe Gly Gly Leu Met Gln Ser Arg
225                 230                 235                 240

Leu Lys Gly His Arg Val Ser Ala Lys Gln Leu Pro Leu Gly Phe Asn
                245                 250                 255

Ser Met Pro Thr Asp Phe Ile Asn Ala Tyr Val Leu Gly Ser Val Gly
            260                 265                 270

Met Thr Gly Ser Ile Thr Gly Ala Cys Ala Thr Phe Leu Tyr Asn Leu
        275                 280                 285

Gln Lys Gly Ile Asp Val Ile Thr Ser Gly Gln Ala Arg Val Val Ile
    290                 295                 300

Val Gly Asn Ser Glu Ala Pro Ile Leu Pro Glu Cys Ile Glu Gly Tyr
305                 310                 315                 320

Ser Ala Met Gly Ala Leu Ala Thr Glu Glu Gly Leu Arg Leu Ile Glu
                325                 330                 335

Gly Arg Asp Asp Val Asp Phe Arg Arg Ala Ser Arg Pro Phe Gly Glu
            340                 345                 350

Asn Cys Gly Phe Thr Leu Ala Glu Ser Ser Gln Tyr Val Val Leu Met
        355                 360                 365

Asp Asp Glu Leu Ala Leu Arg Leu Gly Ala Asp Ile His Gly Ala Val
    370                 375                 380

Thr Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
                405                 410                 415

Val Gln Ile Val Gly Leu Asp Thr Val Arg His Ala Ser Phe Val His
            420                 425                 430

Ala His Gly Ser Ser Thr Pro Ala Asn Arg Val Thr Glu Ser Glu Ile
        435                 440                 445

Leu Asp Arg Val Ala Ser Ala Phe Gly Ile Asp Gly Trp Pro Val Thr
    450                 455                 460
```

```
Ala Val Lys Ala Tyr Val Gly His Ser Leu Ala Thr Ala Ser Ala Asp
465                 470                 475                 480

Gln Leu Ile Ser Ala Leu Gly Thr Phe Lys Tyr Gly Ile Leu Pro Gly
                485                 490                 495

Ile Lys Thr Ile Asp Lys Val Ala Asp Val His Gln Gln Arg Leu
            500                 505                 510

Ser Ile Ser Asn Arg Asp Met Arg Gln Asp Lys Pro Leu Glu Val Cys
        515                 520                 525

Phe Ile Asn Ser Lys Gly Phe Gly Gly Asn Asn Ala Ser Gly Val Val
530                 535                 540

Leu Ser Pro Arg Ile Ala Glu Lys Met Leu Arg Lys Arg His Gly Gln
545                 550                 555                 560

Ala Ala Phe Ala Ala Tyr Val Glu Lys Arg Glu Gln Thr Arg Ala Ala
                565                 570                 575

Ala Arg Ala Tyr Asp Gln Arg Ala Leu Gln Gly Asp Leu Glu Ile Ile
                580                 585                 590

Tyr Asn Phe Gly Gln Asp Leu Ile Asp Glu His Ala Ile Glu Val Ser
            595                 600                 605

Ala Glu Gln Val Thr Val Pro Gly Phe Ser Gln Pro Leu Val Tyr Lys
610                 615                 620

Lys Asp Ala Arg Phe Ser Asp Met Leu Asp
625                 630

<210> SEQ ID NO 39
<211> LENGTH: 634
<212> TYPE: PRT
<213> ORGANISM: Pseudomonas aeruginosa

<400> SEQUENCE: 39

Met Ser Arg Leu Pro Val Ile Val Gly Phe Gly Gly Tyr Asn Ala Ala
1               5                   10                  15

Gly Arg Ser Ser Phe His His Gly Phe Arg Arg Met Val Ile Glu Ser
            20                  25                  30

Met Asp Pro Gln Ala Arg Gln Glu Thr Leu Ala Gly Leu Ala Val Met
        35                  40                  45

Met Lys Leu Val Lys Ala Glu Gly Gly Arg Tyr Leu Ala Glu Asp Gly
    50                  55                  60

Thr Pro Leu Ser Pro Glu Asp Ile Glu Arg Arg Tyr Ala Glu Arg Ile
65                  70                  75                  80

Phe Ala Ser Thr Leu Val Arg Arg Ile Glu Pro Arg Tyr Leu Asp Pro
                85                  90                  95

Asp Ala Val His Trp His Lys Val Leu Glu Leu Ser Pro Ala Glu Gly
            100                 105                 110

Gln Ala Leu Thr Phe Lys Ala Ser Pro Lys Gln Leu Pro Glu Pro Leu
        115                 120                 125

Pro Ala Asn Trp Ser Ile Ala Pro Ala Glu Asp Gly Glu Val Leu Val
    130                 135                 140

Ser Ile His Glu Arg Cys Glu Phe Lys Val Asp Ser Tyr Arg Ala Leu
145                 150                 155                 160

Thr Val Lys Ser Ala Gly Gln Leu Pro Thr Gly Phe Glu Pro Gly Glu
                165                 170                 175

Leu Tyr Asn Ser Arg Phe His Pro Arg Gly Leu Gln Met Ser Val Val
            180                 185                 190

Ala Ala Thr Asp Ala Ile Arg Ser Thr Gly Ile Asp Trp Lys Thr Ile
```

```
            195                 200                 205
Val Asp Asn Val Gln Pro Asp Glu Ile Ala Val Phe Ser Gly Ser Ile
210                 215                 220

Met Ser Gln Leu Asp Asp Asn Gly Phe Gly Gly Leu Met Gln Ser Arg
225                 230                 235                 240

Leu Lys Gly His Arg Val Ser Ala Lys Gln Leu Pro Leu Gly Phe Asn
                245                 250                 255

Ser Met Pro Thr Asp Phe Ile Asn Ala Tyr Val Leu Gly Ser Val Gly
                260                 265                 270

Met Thr Gly Ser Ile Thr Gly Ala Cys Ala Thr Phe Leu Tyr Asn Leu
                275                 280                 285

Gln Lys Gly Ile Asp Val Ile Thr Ser Gly Gln Ala Arg Val Val Ile
                290                 295                 300

Val Gly Asn Ser Glu Ala Pro Ile Leu Pro Glu Cys Ile Glu Gly Tyr
305                 310                 315                 320

Ser Ala Met Gly Ala Leu Ala Thr Glu Glu Gly Leu Arg Leu Ile Glu
                325                 330                 335

Gly Arg Asp Asp Val Asp Phe Arg Arg Ala Ser Arg Pro Phe Gly Glu
                340                 345                 350

Asn Cys Gly Phe Thr Leu Ala Glu Ser Ser Gln Tyr Val Val Leu Met
                355                 360                 365

Asp Asp Glu Leu Ala Leu Arg Leu Gly Ala Asp Ile His Gly Ala Val
370                 375                 380

Thr Asp Val Phe Ile Asn Ala Asp Gly Phe Lys Lys Ser Ile Ser Ala
385                 390                 395                 400

Pro Gly Pro Gly Asn Tyr Leu Thr Val Ala Lys Ala Val Ala Ser Ala
                405                 410                 415

Val Gln Ile Val Gly Leu Asp Thr Val Arg His Ala Ser Phe Val His
                420                 425                 430

Ala His Gly Ser Ser Thr Pro Ala Asn Arg Val Thr Glu Ser Glu Ile
                435                 440                 445

Leu Asp Arg Val Ala Ser Ala Phe Gly Ile Asp Gly Trp Pro Val Thr
450                 455                 460

Ala Val Lys Ala Tyr Val Gly His Ser Leu Ala Thr Ala Ser Ala Asp
465                 470                 475                 480

Gln Leu Ile Ser Ala Leu Gly Thr Phe Lys Tyr Gly Ile Leu Pro Gly
                485                 490                 495

Ile Lys Thr Ile Asp Lys Val Ala Asp Asp Val His Gln Gln Arg Leu
                500                 505                 510

Ser Ile Ser Asn Arg Asp Met Arg Gln Asp Lys Pro Leu Glu Val Cys
                515                 520                 525

Phe Ile Asn Ser Lys Gly Phe Gly Gly Asn Asn Ala Ser Gly Val Val
                530                 535                 540

Leu Ser Pro Arg Ile Ala Glu Lys Met Leu Arg Lys Arg His Gly Gln
545                 550                 555                 560

Ala Ala Phe Ala Ala Tyr Val Glu Lys Arg Glu Gln Thr Arg Ala Ala
                565                 570                 575

Ala Arg Ala Tyr Asp Gln Arg Ala Leu Arg Gly Asp Leu Glu Ile Ile
                580                 585                 590

Tyr Asn Phe Gly Gln Asp Leu Ile Asp Glu His Ala Ile Glu Val Ser
                595                 600                 605

Ala Glu Gln Val Thr Val Pro Gly Phe Ser Gln Pro Leu Val Tyr Lys
                610                 615                 620
```

Lys Asp Ala Arg Phe Ser Asp Met Leu Asp
625                 630

<210> SEQ ID NO 40
<211> LENGTH: 164
<212> TYPE: DNA
<213> ORGANISM: Bacillus subtilis

<400> SEQUENCE: 40
acgcctcctt tccatatacc atactctatg agtaagatga actgatagtt tagacgaata      60
tattgccatg tgaaaaaaaa taggatagaa ttagtacctg atactaataa ttgatcacaa     120
cctgattgat cttctaaatt taagatataa aggagtcttc ccta                      164

<210> SEQ ID NO 41
<211> LENGTH: 312
<212> TYPE: PRT
<213> ORGANISM: Bacillus subtilis

<400> SEQUENCE: 41

Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Arg Ile Ala Ala Asp Asp
        35                  40                  45

Val Phe Ser Ser His Met Ala Val Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Phe
        195                 200                 205

Ala Val Arg Gln Met Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

```
Gly Asp Val Val Met Val Gly Phe Gly Gly Gly Leu Thr Trp Gly
    290                 295                 300

Ala Ile Ala Ile Arg Trp Gly Arg
305                 310

<210> SEQ ID NO 42
<211> LENGTH: 325
<212> TYPE: PRT
<213> ORGANISM: Bacillus subtilis

<400> SEQUENCE: 42

Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
210                 215                 220

Thr Val Pro Gly Glu Phe Glu Arg Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
290                 295                 300

Val Leu Leu Phe Gly Phe Gly Gly Gly Leu Thr Tyr Thr Gly Leu Leu
305                 310                 315                 320

Ile Lys Trp Gly Met
                325
```

```
<210> SEQ ID NO 43
<211> LENGTH: 484
<212> TYPE: PRT
<213> ORGANISM: Psychrobacter urativorans

<400> SEQUENCE: 43

Met Ile Ala Lys Thr Ala Met Gly Leu Pro Leu Lys Gly Leu Arg Leu
1               5                   10                  15

Ala Ile Lys Ser Ser Asp Ile Leu Ile Gln Thr Ala Gly Thr Gln Ala
            20                  25                  30

Leu Arg Leu Lys Thr Trp Tyr Glu Glu Gly Lys Ala Asn Glu Ala Ala
        35                  40                  45

Ser Glu Gln Pro Thr Ala Thr Ser Asn Val Asn Glu Leu Ser Pro Ala
    50                  55                  60

Asn Asp Asp Thr Ser Ile Asn Thr Lys Thr Ser Ala Ser Thr Ser Asp
65                  70                  75                  80

Asn Asn Lys Thr Leu Ser Thr Glu Lys Pro Ile Asp Ile Arg Glu Leu
                85                  90                  95

Glu Phe Lys Lys Ala Pro Ile Asn Trp Ile Pro Ala Thr Ile Leu Ile
            100                 105                 110

Thr Thr Pro Ile Ala Ala Val Ile Thr Pro Trp Tyr Leu Phe Thr
        115                 120                 125

His Gln Val Ser Ala Pro Val Trp Gly Val Phe Gly Ala Phe Met Val
    130                 135                 140

Trp Thr Gly Ile Ser Ile Thr Ala Gly Tyr His Arg Leu Leu Ala His
145                 150                 155                 160

Arg Ala Tyr Lys Ala His Pro Ile Val Lys Asn Phe Leu Leu Leu Gly
                165                 170                 175

Ser Thr Leu Ala Val Gln Gly Ser Ala Phe Asp Trp Val Ser Gly His
            180                 185                 190

Arg Ser His His Arg His Val Asp Asp Arg Met Asp Asp Pro Tyr Ser
        195                 200                 205

Ala Lys Arg Gly Phe Phe Ser His Ile Gly Trp Met Leu Lys Asn
    210                 215                 220

Tyr Pro Ser Gly Lys Phe Asp Tyr Lys Asn Ile Pro Asp Leu Thr Lys
225                 230                 235                 240

Asp Arg Thr Leu Gln Ile Gln His Lys Tyr Tyr Gly Leu Trp Val Leu
                245                 250                 255

Ala Ala Asn Val Gly Leu Val Ala Ile Gly Trp Leu Ile Gly Asp
            260                 265                 270

Val Trp Gly Thr Leu Val Leu Ala Gly Leu Leu Arg Leu Val Leu Thr
        275                 280                 285

His His Phe Thr Phe Ile Asn Ser Leu Cys His Met Phe Gly Ser
    290                 295                 300

Arg Pro Tyr Thr Asp Thr Asn Thr Ala Arg Asp Asn Phe Phe Leu Ala
305                 310                 315                 320

Leu Phe Thr Trp Gly Glu Gly Tyr His Asn Tyr His His Phe Phe Gln
                325                 330                 335

Tyr Asp Tyr Arg Asn Gly Val Lys Trp Trp Gln Tyr Asp Pro Thr Lys
            340                 345                 350

Trp Leu Ile Ala Gly Leu Ser Lys Val Gly Leu Thr Thr Glu Leu Arg
        355                 360                 365

Thr Ile Asp Asp Thr Thr Ile Lys His Ala Glu Val Gln Met Gln Phe
    370                 375                 380
```

```
Lys Lys Ala Gln Gln Gln Ile Asp Thr Val Asn Ala Gly Gly Leu Asp
385                 390                 395                 400

Ile Pro His Ala Met Lys Thr Phe Gln Asp Arg Ile Lys Phe Glu Phe
            405                 410                 415

Glu Ala Phe Thr Gln Thr Val Glu Glu Trp Gln Ala Leu Lys Ala Lys
            420                 425                 430

Ala Ile Glu Met Lys Lys Thr Glu Phe Ala Asp Arg Leu His Glu Val
            435                 440                 445

Asp Asp Lys Leu Lys His Glu Tyr Ala Asn Ile Glu Gln Lys Ile His
        450                 455                 460

Glu His Asn Asp Asn Leu Lys Val Ala Phe Arg Ser Ile Gly His Asn
465                 470                 475                 480

Ser Lys Ala Ala

<210> SEQ ID NO 44
<211> LENGTH: 445
<212> TYPE: PRT
<213> ORGANISM: Mortierella alpina

<400> SEQUENCE: 44

Met Ala Thr Pro Leu Pro Ser Phe Val Val Pro Ala Thr Gln Thr
1               5                   10                  15

Glu Thr Arg Arg Asp Pro Leu Gln His Glu Glu Leu Pro Pro Leu Phe
            20                  25                  30

Pro Glu Lys Ile Thr Ile Tyr Asn Ile Trp Arg Tyr Leu Asp Tyr Lys
            35                  40                  45

His Val Val Gly Leu Gly Leu Thr Pro Leu Ile Ala Leu Tyr Gly Leu
        50                  55                  60

Leu Thr Thr Glu Ile Gln Thr Lys Thr Leu Ile Trp Ser Ile Ile Tyr
65                  70                  75                  80

Tyr Tyr Ala Thr Gly Leu Gly Ile Thr Ala Gly Tyr His Arg Leu Trp
                85                  90                  95

Ala His Arg Ala Tyr Asn Ala Gly Pro Ala Met Ser Phe Val Leu Ala
            100                 105                 110

Leu Leu Gly Ala Gly Ala Val Glu Gly Ser Ile Lys Trp Trp Ser Arg
            115                 120                 125

Gly His Arg Ala His His Arg Trp Thr Asp Thr Glu Lys Asp Pro Tyr
        130                 135                 140

Ser Ala His Arg Gly Leu Phe Phe Ser His Ile Gly Trp Met Leu Ile
145                 150                 155                 160

Lys Arg Pro Gly Trp Lys Ile Gly His Ala Asp Val Asp Asp Leu Asn
                165                 170                 175

Lys Ser Lys Leu Val Gln Trp Gln His Lys Asn Tyr Leu Pro Leu Val
            180                 185                 190

Leu Ile Met Gly Val Val Phe Pro Thr Leu Val Ala Gly Leu Gly Trp
            195                 200                 205

Gly Asp Trp Arg Gly Gly Tyr Phe Tyr Ala Ala Ile Leu Arg Leu Val
        210                 215                 220

Phe Val His His Ala Thr Phe Cys Val Asn Ser Leu Ala His Trp Leu
225                 230                 235                 240

Gly Asp Gly Pro Phe Asp Asp Arg His Ser Pro Arg Asp His Phe Ile
                245                 250                 255

Thr Ala Phe Val Thr Leu Gly Glu Gly Tyr His Asn Phe His His Gln
            260                 265                 270
```

```
Phe Pro Gln Asp Tyr Arg Asn Ala Ile Arg Phe Tyr Gln Tyr Asp Pro
            275                 280                 285

Thr Lys Trp Val Ile Ala Leu Cys Ala Phe Phe Gly Leu Ala Ser His
        290                 295                 300

Leu Lys Thr Phe Pro Glu Asn Glu Val Arg Lys Gly Gln Leu Gln Met
305                 310                 315                 320

Ile Glu Lys Arg Val Leu Glu Lys Lys Thr Lys Leu Gln Trp Gly Thr
                325                 330                 335

Pro Ile Ala Asp Leu Pro Ile Leu Ser Phe Glu Asp Tyr Gln His Ala
            340                 345                 350

Cys Lys Asn Asp Asn Lys Lys Trp Ile Leu Leu Glu Gly Val Val Tyr
        355                 360                 365

Asp Val Ala Asp Phe Met Ser Glu His Pro Gly Gly Glu Lys Tyr Ile
370                 375                 380

Lys Met Gly Val Gly Lys Asp Met Thr Ala Ala Phe Asn Gly Gly Met
385                 390                 395                 400

Tyr Asp His Ser Asn Ala Ala Arg Asn Leu Leu Ser Leu Met Arg Val
                405                 410                 415

Ala Val Val Glu Tyr Gly Gly Glu Val Glu Ala Gln Lys Lys Asn Pro
            420                 425                 430

Ser Met Pro Ile Tyr Gly Thr Asp His Ala Lys Ala Glu
        435                 440                 445

<210> SEQ ID NO 45
<211> LENGTH: 352
<212> TYPE: PRT
<213> ORGANISM: Bacillus subtilis

<400> SEQUENCE: 45

Met Thr Glu Gln Thr Ile Ala His Lys Gln Lys Gln Leu Thr Lys Gln
1               5                   10                  15

Val Ala Ala Phe Ala Gln Pro Glu Thr Lys Asn Ser Leu Ile Gln Leu
            20                  25                  30

Leu Asn Thr Phe Ile Pro Phe Gly Leu Trp Phe Leu Ala Tyr Leu
        35                  40                  45

Ser Leu Asp Val Ser Tyr Leu Leu Thr Leu Ala Leu Thr Val Ile Ala
    50                  55                  60

Ala Gly Phe Leu Thr Arg Ile Phe Ile Phe His Asp Cys Cys His
65                  70                  75                  80

Gln Ser Phe Phe Lys Gln Lys Arg Tyr Asn His Ile Leu Gly Phe Leu
                85                  90                  95

Thr Gly Val Leu Thr Leu Phe Pro Tyr Leu Gln Trp Gln His Ser His
            100                 105                 110

Ser Ile His His Ala Thr Ser Ser Asn Leu Asp Lys Arg Gly Thr Gly
        115                 120                 125

Asp Ile Trp Met Leu Thr Val Asn Glu Tyr Lys Ala Ala Ser Arg Arg
    130                 135                 140

Thr Lys Leu Ala Tyr Arg Leu Tyr Arg Asn Pro Phe Ile Met Phe Ile
145                 150                 155                 160

Leu Gly Pro Ile Tyr Val Phe Leu Ile Thr Asn Arg Phe Asn Lys Lys
                165                 170                 175

Gly Ala Arg Arg Lys Glu Arg Val Asn Thr Tyr Leu Thr Asn Leu Ala
            180                 185                 190

Ile Val Ala Leu Ala Ala Ala Cys Cys Leu Ile Phe Gly Trp Gln Ser
        195                 200                 205
```

```
Phe Leu Leu Val Gln Gly Pro Ile Phe Leu Ile Ser Gly Ser Ile Gly
        210                 215                 220

Val Trp Leu Phe Tyr Val Gln His Thr Phe Glu Asp Ser Tyr Phe Glu
225                 230                 235                 240

Ala Asp Glu Asn Trp Ser Tyr Val Gln Ala Val Glu Gly Ser Ser
                245                 250                 255

Phe Tyr Lys Leu Pro Lys Leu Leu Gln Trp Leu Thr Gly Asn Ile Gly
        260                 265                 270

Tyr His His Val His His Leu Ser Pro Lys Val Pro Asn Tyr Lys Leu
        275                 280                 285

Glu Val Ala His Glu His His Glu Pro Leu Lys Asn Val Pro Thr Ile
290                 295                 300

Thr Leu Lys Thr Ser Leu Gln Ser Leu Ala Phe Arg Leu Trp Asp Glu
305                 310                 315                 320

Asp Asn Lys Gln Phe Val Ser Phe Arg Ala Ile Lys His Ile Pro Val
                325                 330                 335

Ser Leu Pro Pro Asp Ser Pro Glu Lys Gln Lys Leu Arg Lys Asn Ala
                340                 345                 350

<210> SEQ ID NO 46
<211> LENGTH: 370
<212> TYPE: PRT
<213> ORGANISM: Bacillus subtilis

<400> SEQUENCE: 46

Met Ile Lys Asn His Phe Thr Phe Gln Lys Leu Asn Gly Ile Thr Pro
1               5                   10                  15

Tyr Ile Trp Thr Ile Phe Phe Ile Leu Pro Phe Tyr Phe Ile Trp Lys
                20                  25                  30

Ser Ser Ser Thr Phe Val Ile Ile Val Gly Ile Ile Leu Thr Leu Leu
            35                  40                  45

Phe Phe Ser Val Tyr Arg Phe Ala Phe Val Ser Lys Gly Trp Thr Ile
    50                  55                  60

Tyr Leu Trp Gly Phe Leu Leu Ile Gly Ile Ser Thr Ala Ser Ile Thr
65                  70                  75                  80

Leu Phe Ser Tyr Ile Tyr Phe Ala Phe Phe Ile Ala Tyr Phe Ile Gly
                85                  90                  95

Asn Ile Lys Glu Arg Val Pro Phe His Ile Leu Tyr Tyr Val His Leu
                100                 105                 110

Ile Ser Ala Ala Val Ala Ala Asn Phe Ser Leu Val Leu Lys Lys Glu
            115                 120                 125

Phe Phe Leu Thr Gln Ile Pro Phe Val Val Ile Thr Leu Ile Ser Ala
    130                 135                 140

Ile Leu Leu Pro Phe Ser Ile Lys Ser Arg Lys Glu Arg Glu Arg Leu
145                 150                 155                 160

Glu Glu Lys Leu Glu Asp Ala Asn Glu Arg Ile Ala Glu Leu Val Lys
                165                 170                 175

Leu Glu Glu Arg Gln Arg Ile Ala Arg Asp Leu His Asp Thr Leu Gly
            180                 185                 190

Gln Lys Leu Ser Leu Ile Gly Leu Lys Ser Asp Leu Ala Arg Lys Leu
    195                 200                 205

Ile Tyr Lys Asp Pro Glu Gln Ala Ala Arg Glu Leu Lys Ser Val Gln
210                 215                 220

Gln Thr Ala Arg Thr Ser Leu Asn Glu Val Arg Lys Ile Val Ser Ser
```

```
                225                 230                 235                 240
        Met Lys Gly Ile Arg Leu Lys Asp Glu Leu Ile Asn Ile Lys Gln Ile
                        245                 250                 255

Leu Glu Ala Ala Asp Ile Met Phe Ile Tyr Glu Glu Lys Trp Pro
                    260                 265                 270

Glu Asn Ile Ser Leu Leu Asn Glu Asn Ile Leu Ser Met Cys Leu Lys
                        275                 280                 285

Glu Ala Val Thr Asn Val Val Lys His Ser Gln Ala Lys Thr Cys Arg
                    290                 295                 300

Val Asp Ile Gln Gln Leu Trp Lys Glu Val Val Ile Thr Val Ser Asp
        305                 310                 315                 320

Asp Gly Thr Phe Lys Gly Glu Glu Asn Ser Phe Ser Lys Gly His Gly
                        325                 330                 335

Leu Leu Gly Met Arg Glu Arg Leu Glu Phe Ala Asn Gly Ser Leu His
                        340                 345                 350

Ile Asp Thr Glu Asn Gly Thr Lys Leu Thr Met Ala Ile Pro Asn Asn
                        355                 360                 365

Ser Lys
            370

<210> SEQ ID NO 47
<211> LENGTH: 1064
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Ile Thr Phe Tyr Pro Leu Thr Asp Ala Gln Lys Arg Ile Trp
1               5                   10                  15

Tyr Thr Glu Lys Phe Tyr Pro His Thr Ser Ile Ser Asn Leu Ala Gly
                20                  25                  30

Ile Gly Lys Leu Val Ser Ala Asp Ala Ile Asp Tyr Val Leu Val Glu
            35                  40                  45

Gln Ala Ile Gln Glu Phe Ile Arg Arg Asn Asp Ala Met Arg Leu Arg
        50                  55                  60

Leu Arg Leu Asp Glu Asn Gly Glu Pro Val Gln Tyr Ile Ser Glu Tyr
65                  70                  75                  80

Arg Pro Val Asp Ile Lys His Thr Asp Thr Thr Glu Asp Pro Asn Ala
                85                  90                  95

Ile Glu Phe Ile Ser Gln Trp Ser Arg Glu Glu Thr Lys Lys Pro Leu
            100                 105                 110

Pro Leu Tyr Asp Cys Asp Leu Phe Arg Phe Ser Leu Phe Thr Ile Lys
        115                 120                 125

Glu Asn Glu Val Trp Phe Tyr Ala Asn Val His His Val Ile Ser Asp
    130                 135                 140

Gly Ile Ser Met Asn Ile Leu Gly Asn Ala Ile Met His Ile Tyr Leu
145                 150                 155                 160

Glu Leu Ala Ser Gly Ser Glu Thr Lys Glu Gly Ile Ser His Ser Phe
                165                 170                 175

Ile Asp His Val Leu Ser Glu Gln Glu Tyr Ala Gln Ser Lys Arg Phe
            180                 185                 190

Glu Lys Asp Lys Ala Phe Trp Asn Lys Gln Phe Glu Ser Val Pro Glu
        195                 200                 205
```

```
Leu Val Ser Leu Lys Arg Asn Ala Ser Ala Gly Gly Ser Leu Asp Ala
    210                 215                 220

Glu Arg Phe Ser Lys Asp Val Pro Glu Ala Leu His Gln Gln Ile Leu
225                 230                 235                 240

Ser Phe Cys Glu Ala Asn Lys Val Ser Val Leu Ser Val Phe Gln Ser
                245                 250                 255

Leu Leu Ala Ala Tyr Leu Tyr Arg Val Ser Gly Gln Asn Asp Val Val
                260                 265                 270

Thr Gly Thr Phe Met Gly Asn Arg Thr Asn Ala Lys Glu Lys Gln Met
            275                 280                 285

Leu Gly Met Phe Val Ser Thr Val Pro Leu Arg Thr Asn Ile Asp Gly
    290                 295                 300

Gly Gln Ala Phe Ser Glu Phe Val Lys Asp Arg Met Lys Asp Leu Met
305                 310                 315                 320

Lys Thr Leu Arg His Gln Lys Tyr Pro Tyr Asn Leu Leu Ile Asn Asp
                325                 330                 335

Leu Arg Glu Thr Lys Ser Ser Leu Thr Lys Leu Phe Thr Val Ser Leu
                340                 345                 350

Glu Tyr Gln Val Met Gln Trp Gln Lys Glu Asp Leu Ala Phe Leu
            355                 360                 365

Thr Glu Pro Ile Phe Ser Gly Ser Gly Leu Asn Asp Val Ser Ile His
    370                 375                 380

Val Lys Asp Arg Trp Asp Thr Gly Lys Leu Thr Ile Asp Phe Asp Tyr
385                 390                 395                 400

Arg Thr Asp Leu Phe Ser Arg Glu Glu Ile Asn Met Ile Cys Glu Arg
                405                 410                 415

Met Ile Thr Met Leu Glu Asn Ala Leu Thr His Pro Glu His Thr Ile
            420                 425                 430

Asp Glu Leu Thr Leu Ile Ser Asp Ala Glu Lys Glu Lys Leu Leu Ala
    435                 440                 445

Arg Ala Gly Gly Lys Ser Val Ser Tyr Arg Lys Asp Met Thr Ile Pro
450                 455                 460

Glu Leu Phe Gln Glu Lys Ala Glu Leu Leu Ser Asp His Pro Ala Val
465                 470                 475                 480

Val Phe Glu Asp Arg Thr Leu Ser Tyr Arg Thr Leu His Glu Gln Ser
                485                 490                 495

Ala Arg Ile Ala Asn Val Leu Lys Gln Lys Gly Val Gly Pro Asp Ser
            500                 505                 510

Pro Val Ala Val Leu Ile Glu Arg Ser Glu Arg Met Ile Thr Ala Ile
    515                 520                 525

Met Gly Ile Leu Lys Ala Gly Gly Ala Tyr Val Pro Ile Asp Pro Gly
530                 535                 540

Phe Pro Ala Glu Arg Ile Gln Tyr Ile Leu Glu Asp Cys Gly Ala Asp
545                 550                 555                 560

Phe Ile Leu Thr Glu Ser Lys Val Ala Ala Pro Glu Ala Asp Ala Glu
                565                 570                 575

Leu Ile Asp Leu Asp Gln Ala Ile Glu Glu Gly Ala Glu Glu Ser Leu
            580                 585                 590

Asn Ala Asp Val Asn Ala Arg Asn Leu Ala Tyr Ile Ile Tyr Thr Ser
    595                 600                 605

Gly Thr Thr Gly Arg Pro Lys Gly Val Met Ile Glu His Arg Gln Val
610                 615                 620

His His Leu Val Glu Ser Leu Gln Gln Thr Ile Tyr Gln Ser Gly Ser
```

```
            625                 630                 635                 640
        Gln Thr Leu Arg Met Ala Leu Leu Ala Pro Phe His Phe Asp Ala Ser
                        645                 650                 655
        Val Lys Gln Ile Phe Ala Ser Leu Leu Leu Gly Gln Thr Leu Tyr Ile
                        660                 665                 670
        Val Pro Lys Lys Thr Val Thr Asn Gly Ala Ala Leu Thr Ala Tyr Tyr
                        675                 680                 685
        Arg Lys Asn Ser Ile Glu Ala Thr Asp Gly Thr Pro Ala His Leu Gln
                        690                 695                 700
        Met Leu Ala Ala Ala Gly Asp Phe Glu Gly Leu Lys Leu Lys His Met
        705                 710                 715                 720
        Leu Ile Gly Gly Glu Gly Leu Ser Ser Val Val Ala Asp Lys Leu Leu
                        725                 730                 735
        Lys Leu Phe Lys Glu Ala Gly Thr Ala Pro Arg Leu Thr Asn Val Tyr
                        740                 745                 750
        Gly Pro Thr Glu Thr Cys Val Asp Ala Ser Val His Pro Val Ile Pro
                        755                 760                 765
        Glu Asn Ala Val Gln Ser Ala Tyr Val Pro Ile Gly Lys Ala Leu Gly
                        770                 775                 780
        Asn Asn Arg Leu Tyr Ile Leu Asp Gln Lys Gly Arg Leu Gln Pro Glu
        785                 790                 795                 800
        Gly Val Ala Gly Glu Leu Tyr Ile Ala Gly Asp Gly Val Gly Arg Gly
                        805                 810                 815
        Tyr Leu His Leu Pro Glu Leu Thr Glu Glu Lys Phe Leu Gln Asp Pro
                        820                 825                 830
        Phe Val Pro Gly Asp Arg Met Tyr Arg Thr Gly Asp Val Val Arg Trp
                        835                 840                 845
        Leu Pro Asp Gly Thr Ile Glu Tyr Leu Gly Arg Glu Asp Asp Gln Val
        850                 855                 860
        Lys Val Arg Gly Tyr Arg Ile Glu Leu Gly Glu Ile Glu Ala Val Ile
        865                 870                 875                 880
        Gln Gln Ala Pro Asp Val Ala Lys Ala Val Leu Ala Arg Pro Asp
                        885                 890                 895
        Glu Gln Gly Asn Leu Glu Val Cys Ala Tyr Val Val Gln Lys Pro Gly
                        900                 905                 910
        Ser Glu Phe Ala Pro Ala Gly Leu Arg Glu His Ala Ala Arg Gln Leu
                        915                 920                 925
        Pro Asp Tyr Met Val Pro Ala Tyr Phe Thr Glu Val Thr Glu Ile Pro
                        930                 935                 940
        Leu Thr Pro Ser Gly Lys Val Asp Arg Arg Lys Leu Phe Ala Leu Glu
        945                 950                 955                 960
        Val Lys Ala Val Ser Gly Thr Ala Tyr Thr Ala Pro Arg Asn Glu Thr
                        965                 970                 975
        Glu Lys Ala Ile Ala Ile Trp Gln Asp Val Leu Asn Val Glu Lys
                        980                 985                 990
        Ala Gly Ile Phe Asp Asn Phe Phe Glu Thr Gly Gly His Ser Leu Lys
                        995                 1000                1005
        Ala Met Thr Leu Leu Thr Lys Ile His Lys Glu Thr Gly Ile Glu
                        1010                1015                1020
        Ile Pro Leu Gln Phe Leu Glu His Pro Thr Ile Thr Ala Leu
                        1025                1030                1035
        Ala Glu Glu Ala Asp His Arg Glu Ser Lys Ala Phe Ala Val Ile
                        1040                1045                1050
```

```
Glu Pro Ala Glu Lys Gln Glu His Tyr Pro Leu
    1055                1060

<210> SEQ ID NO 48
<211> LENGTH: 1043
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Met Gln Ser Gln Arg Leu Gly Val Thr Ala Ala Gln Gln Ser
1               5                   10                  15

Val Trp Leu Ala Gly Gln Leu Ala Asp Asp His Arg Leu Tyr His Cys
            20                  25                  30

Ala Ala Tyr Leu Ser Leu Thr Gly Ser Ile Asp Pro Arg Thr Leu Gly
        35                  40                  45

Thr Ala Val Arg Arg Thr Leu Asp Glu Thr Glu Ala Leu Arg Thr Arg
    50                  55                  60

Phe Val Pro Gln Asp Gly Glu Leu Leu Gln Ile Leu Glu Pro Gly Ala
65                  70                  75                  80

Gly Gln Leu Leu Leu Glu Ala Asp Phe Ser Gly Asp Pro Asp Pro Glu
                85                  90                  95

Arg Ala Ala His Asp Trp Met His Ala Ala Leu Ala Ala Pro Val Arg
            100                 105                 110

Leu Asp Arg Ala Gly Thr Ala Thr His Ala Leu Leu Thr Leu Gly Pro
        115                 120                 125

Ser Arg His Leu Leu Tyr Phe Gly Tyr His His Ile Ala Leu Asp Gly
    130                 135                 140

Tyr Gly Ala Leu Leu His Leu Arg Arg Leu Ala His Val Tyr Thr Ala
145                 150                 155                 160

Leu Ser Asn Gly Asp Asp Pro Gly Pro Cys Pro Phe Gly Pro Leu Ala
                165                 170                 175

Gly Val Leu Thr Glu Glu Ala Ala Tyr Arg Asp Ser Asp Asn His Arg
            180                 185                 190

Arg Asp Gly Glu Phe Trp Thr Arg Ser Leu Ala Gly Ala Asp Glu Ala
        195                 200                 205

Pro Gly Leu Ser Glu Arg Glu Ala Gly Ala Leu Ala Val Pro Leu Arg
    210                 215                 220

Arg Thr Val Glu Leu Ser Gly Glu Arg Thr Glu Lys Leu Ala Ala Ser
225                 230                 235                 240

Ala Ala Ala Thr Gly Ala Arg Trp Ser Ser Leu Leu Val Ala Ala Thr
                245                 250                 255

Ala Ala Phe Val Arg Arg His Ala Ala Ala Asp Asp Thr Val Ile Gly
            260                 265                 270

Leu Pro Val Thr Ala Arg Leu Thr Gly Pro Ala Leu Arg Thr Pro Cys
        275                 280                 285

Met Leu Ala Asn Asp Val Pro Leu Arg Leu Asp Ala Arg Leu Asp Ala
    290                 295                 300

Pro Phe Ala Ala Leu Leu Ala Asp Thr Thr Arg Ala Val Gly Thr Leu
305                 310                 315                 320

Ala Arg His Gln Arg Phe Arg Gly Glu Glu Leu His Arg Asn Leu Gly
                325                 330                 335

Gly Val Gly Arg Thr Ala Gly Leu Ala Arg Val Thr Val Asn Val Leu
```

-continued

```
            340                 345                 350
Ala Tyr Val Asp Asn Ile Arg Phe Gly Asp Cys Arg Ala Val Val His
            355                 360                 365
Glu Leu Ser Ser Gly Pro Val Arg Asp Phe His Ile Asn Ser Tyr Gly
    370                 375                 380
Thr Pro Gly Thr Pro Asp Gly Val Gln Leu Val Phe Ser Gly Asn Pro
385                 390                 395                 400
Ala Leu Tyr Thr Ala Thr Asp Leu Ala Asp His Gln Glu Arg Phe Leu
                405                 410                 415
Arg Phe Leu Asp Ala Val Thr Ala Asp Pro Asp Leu Pro Thr Gly Arg
            420                 425                 430
His Arg Leu Leu Ser Pro Gly Thr Arg Ala Arg Leu Leu Asp Asp Ser
        435                 440                 445
Arg Gly Thr Glu Arg Pro Val Pro Arg Ala Thr Leu Pro Glu Leu Phe
    450                 455                 460
Ala Glu Gln Ala Arg Arg Thr Pro Asp Ala Pro Ala Val Gln His Asp
465                 470                 475                 480
Gly Thr Val Leu Thr Tyr Arg Asp Leu His Arg Ser Val Glu Arg Ala
                485                 490                 495
Ala Gly Arg Leu Ala Gly Leu Gly Leu Arg Thr Glu Asp Val Val Ala
            500                 505                 510
Leu Ala Leu Pro Lys Ser Ala Glu Ser Val Ala Ile Leu Leu Gly Ile
        515                 520                 525
Gln Arg Ala Gly Ala Ala Tyr Val Pro Leu Asp Pro Thr His Pro Ala
    530                 535                 540
Glu Arg Leu Ala Arg Val Leu Asp Asp Thr Arg Pro Arg Tyr Leu Val
545                 550                 555                 560
Thr Thr Gly His Ile Asp Gly Leu Ser His Pro Thr Pro Gln Leu Ala
                565                 570                 575
Ala Ala Asp Leu Leu Arg Glu Gly Gly Pro Glu Pro Ala Pro Gly Arg
            580                 585                 590
Pro Ala Pro Gly Asn Ala Ala Tyr Ile Ile Gln Thr Ser Gly Ser Thr
        595                 600                 605
Gly Arg Pro Lys Gly Val Val Val Thr His Glu Gly Leu Ala Thr Leu
    610                 615                 620
Ala Ala Asp Gln Ile Arg Arg Tyr Arg Thr Gly Pro Asp Ala Arg Val
625                 630                 635                 640
Leu Gln Phe Ile Ser Pro Gly Phe Asp Val Phe Val Ser Glu Leu Ser
                645                 650                 655
Met Thr Leu Leu Ser Gly Gly Cys Leu Val Ile Pro Pro Asp Gly Leu
            660                 665                 670
Thr Gly Arg His Leu Ala Asp Phe Leu Ala Ala Glu Ala Val Thr Thr
        675                 680                 685
Thr Ser Leu Thr Pro Gly Ala Leu Ala Thr Met Pro Ala Thr Asp Leu
    690                 695                 700
Pro His Leu Arg Thr Leu Ile Val Gly Gly Glu Val Cys Pro Pro Glu
705                 710                 715                 720
Ile Phe Asp Gln Trp Gly Arg Gly Arg Asp Ile Val Asn Ala Tyr Gly
                725                 730                 735
Pro Thr Glu Thr Thr Val Glu Ala Thr Ala Trp His Arg Asp Gly Ala
            740                 745                 750
Thr His Gly Pro Val Pro Leu Gly Arg Pro Thr Leu Asn Arg Arg Gly
        755                 760                 765
```

```
Tyr Val Leu Asp Pro Ala Leu Glu Pro Val Pro Asp Gly Thr Thr Gly
        770                 775                 780

Glu Leu Tyr Leu Ala Gly Glu Gly Leu Ala Arg Gly Tyr Val Ala Ala
785                 790                 795                 800

Pro Gly Pro Thr Ala Glu Arg Phe Val Ala Asp Pro Phe Gly Pro Pro
                805                 810                 815

Gly Ser Arg Met Tyr Arg Thr Gly Asp Leu Val Arg Arg Ser Gly
                820                 825                 830

Gly Met Leu Glu Phe Val Gly Arg Ala Asp Gly Gln Val Lys Leu Arg
            835                 840                 845

Gly Phe Arg Ile Glu Leu Gly Glu Val Gln Ala Ala Leu Thr Ala Leu
        850                 855                 860

Pro Gly Val Arg Gln Ala Gly Val Leu Ile Arg Glu Asp Arg Pro Gly
865                 870                 875                 880

Asp Pro Arg Leu Val Gly Tyr Ile Val Pro Ala Pro Gly Ala Glu Pro
                885                 890                 895

Asp Ala Gly Glu Leu Arg Ala Ala Leu Ala Arg Thr Leu Pro Pro His
            900                 905                 910

Met Val Pro Trp Ala Leu Val Pro Leu Pro Ala Leu Pro Leu Thr Ser
        915                 920                 925

Asn Gly Lys Leu Asp Arg Ala Ala Leu Pro Val Pro Ala Ala Arg Ala
        930                 935                 940

Gly Gly Ser Gly Gln Arg Pro Val Thr Pro Gln Glu Lys Thr Leu Cys
945                 950                 955                 960

Ala Leu Phe Ala Asp Val Leu Gly Val Thr Glu Val Ala Thr Asp Asp
                965                 970                 975

Val Phe Phe Glu Leu Gly Gly His Ser Leu Asn Gly Thr Arg Leu Leu
            980                 985                 990

Ala Arg Ile Arg Thr Glu Phe Gly Thr Asp Leu Thr Leu Arg Asp Leu
        995                 1000                1005

Phe Ala Phe Pro Thr Val Ala Gly Leu Leu Pro Leu Leu Asp Asp
        1010                1015                1020

Asn Gly Arg Gln His Thr Thr Pro Pro Leu Pro Pro Arg Pro Glu
        1025                1030                1035

Arg Leu Pro Leu Ser
        1040

<210> SEQ ID NO 49
<211> LENGTH: 1090
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ile Asp Arg Arg Pro Glu Arg Leu Pro Leu Ser Phe Ala Gln Arg Arg
1               5                   10                  15

Leu Trp Phe Leu Ser Lys Leu Glu Gly Pro Ser Ala Thr Tyr Asn Ile
            20                  25                  30

Pro Val Ala Val Arg Leu Thr Gly Ala Leu Asp Val Pro Ala Leu Arg
        35                  40                  45

Ala Ala Leu Gly Asp Val Thr Ala Arg His Glu Ser Leu Arg Thr Val
    50                  55                  60

Phe Pro Asp Asp Gly Gly Glu Pro Arg Gln Leu Val Leu Pro His Ala
```

```
            65                  70                  75                  80

Glu Pro Pro Phe Leu Thr His Glu Val Thr Gly Glu Val Ala Glu
                    85                  90                  95

Gln Ala Ala Ser Ala Thr Gly Tyr Ala Phe Asp Ile Thr Ser Asp Thr
                100                 105                 110

Pro Leu Arg Ala Thr Leu Leu Arg Val Ser Pro Glu His Val Leu
            115                 120                 125

Val Val Val Ile His His Ile Ala Gly Asp Gly Trp Ser Met Gly Pro
130                 135                 140

Leu Val Arg Asp Leu Val Thr Ala Tyr Arg Ala Arg Thr Arg Gly Asp
145                 150                 155                 160

Ala Pro Glu Tyr Thr Pro Leu Pro Val Gln Tyr Ala Asp Tyr Ala Leu
                165                 170                 175

Trp Gln His Ala Val Ala Gly Asp Glu Asp Ala Pro Asp Gly Arg Thr
                180                 185                 190

Ala Arg Arg Leu Gly Tyr Trp Arg Glu Met Leu Ala Gly Leu Pro Glu
            195                 200                 205

Glu His Thr Leu Pro Ala Asp Arg Pro Arg Pro Val Arg Ser Ser His
            210                 215                 220

Arg Gly Gly Arg Val Arg Phe Glu Leu Pro Ala Gly Val His Arg Ser
225                 230                 235                 240

Leu Leu Ala Val Ala Arg Asp Arg Arg Ala Thr Leu Phe Met Val Val
                245                 250                 255

Gln Ala Ala Leu Ala Gly Leu Leu Ser Arg Leu Gly Ala Gly Asp Asp
            260                 265                 270

Ile Pro Ile Gly Thr Pro Val Ala Gly Arg Gly Asp Glu Ala Leu Asp
            275                 280                 285

Asp Val Val Gly Phe Phe Val Asn Thr Leu Val Leu Arg Thr Asn Leu
            290                 295                 300

Ala Gly Asp Pro Ser Phe Ala Asp Leu Val Asp Arg Val Arg Thr Ala
305                 310                 315                 320

Asp Leu Asp Ala Phe Ala His Gln Asp Val Pro Phe Glu Arg Leu Val
                325                 330                 335

Glu Ala Leu Ala Pro Arg Arg Ser Leu Ala Arg His Pro Leu Phe Gln
            340                 345                 350

Ile Trp Tyr Thr Leu Thr Asn Ala Asp Gln Asp Ile Thr Gly Gln Ala
            355                 360                 365

Leu Asn Ala Leu Pro Gly Leu Thr Gly Asp Glu Tyr Pro Leu Gly Ala
370                 375                 380

Ser Ala Ala Lys Phe Asp Leu Ser Phe Thr Phe Thr Glu His Arg Thr
385                 390                 395                 400

Pro Asp Gly Asp Ala Ala Gly Leu Ser Val Leu Leu Asp Tyr Ser Ser
                405                 410                 415

Asp Leu Tyr Asp His Gly Thr Ala Ala Ala Leu Gly His Arg Leu Thr
                420                 425                 430

Gly Phe Phe Ala Ala Leu Ala Ala Asp Pro Thr Ala Pro Leu Gly Thr
            435                 440                 445

Val Pro Leu Leu Thr Asp Asp Glu Arg Asp Arg Ile Leu Gly Asp Trp
            450                 455                 460

Gly Ser Gly Thr His Thr Pro Leu Pro Pro Arg Ser Val Ala Glu Gln
465                 470                 475                 480

Ile Val Arg Arg Ala Ala Leu Asp Pro Asp Ala Val Ala Val Ile Thr
                485                 490                 495
```

```
Ala Glu Glu Glu Leu Ser Tyr Arg Glu Leu Glu Arg Leu Ser Gly Glu
            500                 505                 510

Thr Ala Arg Leu Leu Ala Asp Arg Gly Ile Gly Arg Glu Ser Leu Val
        515                 520                 525

Ala Val Ala Leu Pro Arg Thr Ala Gly Leu Val Thr Thr Leu Leu Gly
    530                 535                 540

Val Leu Arg Thr Gly Ala Ala Tyr Leu Pro Leu Asp Thr Gly Tyr Pro
545                 550                 555                 560

Ala Glu Arg Leu Ala His Val Leu Ser Asp Ala Arg Pro Asp Leu Val
                565                 570                 575

Leu Thr His Ala Gly Leu Ala Gly Arg Leu Pro Ala Gly Leu Ala Pro
            580                 585                 590

Thr Val Leu Val Asp Glu Pro Gln Pro Pro Ala Ala Ala Pro Ala
        595                 600                 605

Val Pro Thr Ser Pro Ser Gly Asp His Leu Ala Tyr Val Ile His Thr
    610                 615                 620

Ser Gly Ser Thr Gly Arg Pro Lys Gly Val Ala Ile Ala Glu Ser Ser
625                 630                 635                 640

Leu Arg Ala Phe Leu Ala Asp Ala Val Arg Arg His Asp Leu Thr Pro
                645                 650                 655

His Asp Arg Leu Leu Ala Val Thr Thr Val Gly Phe Asp Ile Ala Gly
            660                 665                 670

Leu Glu Leu Phe Ala Pro Leu Leu Ala Gly Ala Ala Ile Val Leu Ala
        675                 680                 685

Asp Glu Asp Ala Val Arg Asp Pro Ala Ser Ile Thr Ser Leu Cys Ala
690                 695                 700

Arg His His Val Thr Val Val Gln Ala Thr Pro Ser Trp Trp Arg Ala
705                 710                 715                 720

Met Leu Asp Gly Ala Pro Ala Asp Ala Ala Arg Leu Glu His Val
                725                 730                 735

Arg Ile Leu Val Gly Gly Glu Pro Leu Pro Ala Asp Leu Ala Arg Val
            740                 745                 750

Leu Thr Ala Thr Gly Ala Ala Val Thr Asn Val Tyr Gly Pro Thr Glu
        755                 760                 765

Ala Thr Ile Trp Ala Thr Ala Ala Pro Leu Thr Ala Gly Asp Asp Arg
    770                 775                 780

Thr Pro Gly Ile Gly Thr Pro Leu Asp Asn Trp Arg Val His Ile Leu
785                 790                 795                 800

Asp Ala Ala Leu Gly Pro Val Pro Pro Gly Val Pro Gly Glu Ile His
                805                 810                 815

Ile Ala Gly Ser Gly Leu Ala Arg Gly Tyr Leu Arg Arg Pro Asp Leu
            820                 825                 830

Thr Ala Glu Arg Phe Val Ala Asn Pro Phe Ala Pro Gly Glu Arg Met
        835                 840                 845

Tyr Arg Thr Gly Asp Leu Gly Arg Phe Arg Pro Asp Gly Thr Leu Glu
    850                 855                 860

His Leu Gly Arg Val Asp Asp Gln Val Lys Val Arg Gly Phe Arg Ile
865                 870                 875                 880

Glu Leu Gly Asp Val Glu Ala Ala Leu Ala Arg His Pro Asp Val Gly
                885                 890                 895

Arg Ala Ala Ala Ala Val Arg Pro Asp His Arg Gly Gln Gly Arg Leu
            900                 905                 910
```

Val Ala Tyr Val Val Pro Arg Pro Gly Thr Arg Gly Pro Asp Ala Gly
            915                 920                 925

Glu Leu Arg Glu Thr Val Arg Glu Leu Pro Asp Tyr Met Val Pro
        930                 935                 940

Ser Ala Gln Val Thr Leu Thr Thr Leu Pro His Thr Pro Asn Gly Lys
945                 950                 955                 960

Leu Asp Arg Ala Ala Leu Pro Ala Pro Val Phe Gly Thr Pro Ala Gly
                965                 970                 975

Arg Ala Pro Ala Thr Arg Glu Glu Lys Ile Leu Ala Gly Leu Phe Ala
            980                 985                 990

Asp Ile Leu Gly Leu Pro Asp Val Gly Ala Asp Ser Gly Phe Phe Asp
        995                 1000                1005

Leu Gly Gly Asp Ser Val Leu Ser Ile Gln Leu Val Ser Arg Ala
    1010                1015                1020

Arg Arg Glu Gly Leu His Ile Thr Val Arg Asp Val Phe Glu His
    1025                1030                1035

Gly Thr Val Gly Ala Leu Ala Ala Ala Ala Leu Pro Ala Pro Ala
    1040                1045                1050

Asp Asp Ala Asp Asp Thr Val Pro Gly Thr Asp Val Leu Pro Ser
    1055                1060                1065

Ile Ser Asp Asp Glu Phe Glu Glu Phe Glu Leu Glu Leu Gly Leu
    1070                1075                1080

Glu Gly Glu Glu Glu Gln Trp
    1085                1090

<210> SEQ ID NO 50
<211> LENGTH: 1436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Ser Pro Glu Pro Val Ala Glu Val Ser Arg Ala Glu Gln Arg Ile
1               5                   10                  15

Trp Leu Leu Ser Arg Leu Gly Gly His Pro Ala Glu Tyr Ala Ile Pro
            20                  25                  30

Val Ala Leu Arg Leu Ala Gly Pro Leu Asp Val Ala Lys Leu Lys Asn
        35                  40                  45

Ala Val Asp Ala Val Val Arg Arg His Glu Gly Leu Arg His Val Phe
    50                  55                  60

Pro Glu Val Asp Gly Ser Pro Thr Arg Ala Val Leu Asp Pro Gly Ser
65                  70                  75                  80

Ile Thr Val Ala Glu Glu Ala Asn Arg Ser Val Arg Glu Val Leu Ala
                85                  90                  95

Glu Gly Val Ala Ala Leu Asp Pro Ala Thr Gly Pro Leu Ala Arg Phe
            100                 105                 110

Thr Leu Val Asn Gln Gly Pro Gln Asp His Val Leu Ala Ile Val Leu
        115                 120                 125

His His Leu Ile Ala Asp Gly Trp Ser Val Asp Val Leu Leu Arg Asp
    130                 135                 140

Ile Ala Ala His Tyr Thr Gly Ala Pro Thr Ala Thr Pro Gly Arg Tyr
145                 150                 155                 160

Ala Asp Tyr Leu Ala Leu Glu Arg Ala Glu Glu Gln Asp Gly Ala Leu
                165                 170                 175

-continued

Gly Arg Ala Leu Glu His Phe Val Thr Ala Leu Asp Gly Val Pro Asp
            180                 185                 190

Glu Val Ser Phe Pro Pro Asp His Pro Arg Pro Ala Gln Arg Thr Gly
            195                 200                 205

Arg Gly Asp Val Val Arg His Arg Ile Asp Ala Ala Pro Val Thr Ala
        210                 215                 220

Leu Ala Glu Arg Leu Arg Thr Thr Pro Phe Ala Val Leu Leu Ala Ala
225                 230                 235                 240

Val Gly Val Leu Leu His Arg Val Gly Gly His Arg Asp Val Val
            245                 250                 255

Gly Thr Ala Val Ala Arg Arg Pro Asp Ala Gly Leu Asp His Leu Val
            260                 265                 270

Gly Leu Cys Leu Asn Thr Leu Ala Leu Arg Trp Pro Val Gln Pro His
        275                 280                 285

Asp Thr Leu Gly Glu Val Val Arg Ala Val Thr Asp Arg Leu Ala Asp
        290                 295                 300

Gly Leu Gln His Asp Ala Ala Ser Phe Asp Arg Val Val Asp Lys Leu
305                 310                 315                 320

Ala Pro Ala Arg Asp Ser Gly Arg Thr Pro Val Phe Gln Val Met Ala
                325                 330                 335

Leu Tyr Glu Glu Pro Tyr Glu Thr Ala Leu Ala Leu Pro Asp Val Thr
            340                 345                 350

Thr Thr Asp Val Thr Val His Cys Gly Ser Ala Gln Ala Asp Ala Ala
        355                 360                 365

Phe Gly Phe Val Pro Arg Glu Gly Gly Ile Asp Leu Thr Leu Gln Phe
    370                 375                 380

Ser Thr Asp Val Phe Thr Arg Ala Thr Ala Ser Arg Trp Ala Arg Arg
385                 390                 395                 400

Leu Ala Thr Leu Leu Ala Gly Ala Arg Ala Asp Thr Arg Val Ala Asp
                405                 410                 415

Leu Pro Leu Leu Pro Glu Asp Glu Ser Gln Asp Leu Glu Arg Trp Ser
            420                 425                 430

Gly Thr Thr Gly Glu Ala Pro Thr Thr Leu His Ala Leu Ala His
            435                 440                 445

Glu Ile Ala Gln Arg His Pro Asp Arg Pro Ala Ile His Phe Gly Gln
    450                 455                 460

Asn Ser Leu Thr Tyr Gly Glu Phe Asp Ala Arg Ser Ala Gln Leu Ala
465                 470                 475                 480

His Glu Leu Arg Ala Arg Gly Val Arg Ala Glu Thr Pro Val Val Val
                485                 490                 495

Cys Leu Glu Arg Ser Pro Glu Ala Leu Ile Ala Val Tyr Gly Val Leu
            500                 505                 510

Lys Ala Gly Gly Ala Tyr Val Pro Val Glu Thr Ser Asn Pro Asp Leu
            515                 520                 525

Arg Ile Ala Glu Leu Ile Ala Asp Ser Gly Ala Ala Leu Val Leu Thr
    530                 535                 540

Gln Arg Arg Leu Ala Asp Arg Leu Ala Ala Leu Gly Ala Glu Val Val
545                 550                 555                 560

Val Val Asp Glu Pro Leu Pro Arg His Pro Thr Thr Asp Pro Glu Pro
                565                 570                 575

Leu Thr Gly Pro Asp His Leu Ala Tyr Val Ile Tyr Thr Ser Gly Ser
            580                 585                 590

Thr Gly Arg Pro Lys Gly Val Met Val Gln His Gly Ser Val Leu Asn
            595                 600                 605

Phe Leu Asp Ala Leu Asp Arg Arg Phe Asp Leu Thr Pro Asp Arg
610                 615                 620

Leu Leu His Lys Ser Pro Leu Ala Phe Asp Val Ser Val Arg Glu Val
625                 630                 635                 640

Phe Trp Ala Leu Thr Arg Gly Ala Ser Val Val Ala Glu Pro Gly
                645                 650                 655

Arg His Ala Asp Pro Gly His Leu Val Asp Leu Val Glu Glu Arg
                660                 665                 670

Val Thr Val Ala His Phe Val Pro Ser Ser Leu Ala Val Phe Leu Glu
            675                 680                 685

Gly Leu Pro Gly Pro Gly Arg Cys Pro Thr Leu Arg His Val Leu Thr
690                 695                 700

Ser Gly Glu Thr Leu Pro Val Thr Thr Ala Arg Ala Ala Arg Asp Leu
705                 710                 715                 720

Leu Gly Ala Arg Leu Arg Asn Met Tyr Gly Pro Thr Glu Thr Thr Val
                725                 730                 735

Glu Met Thr Asp His Asp Val Val Asp Asp Thr Val Asp Arg Leu Pro
                740                 745                 750

Ile Gly His Pro Phe Glu Gly Ala Val Val Arg Val Leu Asp Ala Asp
            755                 760                 765

Leu Arg Pro Val Pro Pro Gly Ser Thr Gly Glu Leu Cys Val Gly Gly
770                 775                 780

Leu Pro Val Ala Arg Gly Tyr Leu Gly Arg Pro Ala Leu Thr Ala Glu
785                 790                 795                 800

Arg Phe Val Pro Asp Pro Leu Gly Pro Ala Gly Ala Arg Leu Tyr Arg
                805                 810                 815

Thr Gly Asp Leu Ala Arg Leu Leu Pro Asp Gly Gln Leu Asp Phe Leu
                820                 825                 830

Gly Arg Asn Asp Phe Gln Val Lys Val Arg Gly His Arg Ile Glu Pro
            835                 840                 845

Gly Glu Val Glu Ala Val Leu Gly Ala Leu Pro Gly Val His Gly Ala
850                 855                 860

Leu Val Thr Ala His Asp Asp Arg Leu Ile Gly Tyr Ala Val Thr Asp
865                 870                 875                 880

Arg Asp Gly Glu Glu Leu Arg Thr Ala Leu Ala Glu Arg Leu Pro Glu
                885                 890                 895

His Leu Val Pro Ser Val Val Leu Thr Leu Asp Arg Phe Pro Leu Thr
                900                 905                 910

Gly Asn Gly Lys Leu Asp Arg Ala Ala Leu Pro Thr Pro Thr Gly Arg
            915                 920                 925

His Thr Gly Asp Ser Arg Pro Leu Thr Ala Thr Glu Ala Ala Leu Ala
930                 935                 940

Ala Ile Trp Arg Asp Leu Leu Asp Val Pro Glu Val Arg Ala Asp Asp
945                 950                 955                 960

His Phe Phe Ala Leu Gly Gly His Ser Leu Leu Ala Ala Arg Val Ala
                965                 970                 975

Ala Arg Ala Gly Ala Ala Leu Gly Val Ala Leu Pro Leu Pro Thr Val
            980                 985                 990

Leu Arg Phe Pro Arg Leu Ala Asp Leu Ala Thr Ala Val Asp Gly Thr
            995                 1000                1005

Arg Ala Asp Arg Glu Pro Val Arg Pro Arg Pro Asp Arg Arg Arg

```
                    1010                1015                1020

Arg Ala Pro Leu Ser Ser Ala Gln Arg Arg Leu Trp Ile Glu Glu
        1025                1030                1035

Asn Leu Arg Pro Gly Thr Ala Thr Tyr Thr Val Ala Glu Ala Phe
        1040                1045                1050

Arg Leu Arg Gly Glu Leu Asp Glu Glu Ala Phe Ala Ala Ala Val
        1055                1060                1065

Asp Asp Val Leu Arg Arg His Asp Ala Leu Arg Ala His Val Glu
        1070                1075                1080

Ser Val Glu Asp Gly Glu Pro Glu Leu Val Val Ala Pro Glu Pro
        1085                1090                1095

Arg Thr Ala Leu Arg Val Gly Asp Leu Pro Ala Asp Arg Val Arg
        1100                1105                1110

Asp Ala Leu Ala Ala Glu Ser Ala Arg Val Phe Asp Pro Ala Gly
        1115                1120                1125

Pro Leu Val Ala Thr Ser Leu His Arg Leu Ala Pro Asp Glu Trp
        1130                1135                1140

Leu Phe Gln Phe Thr Ala His His Leu Val Val Asp Gly Trp Ser
        1145                1150                1155

Leu Asp Val Leu Trp Arg Asp Leu Ala Ala Cys Tyr His Asp Arg
        1160                1165                1170

Arg Ala Gly Arg Ala Pro Arg Pro Arg Asp Gly Leu Thr Phe Thr
        1175                1180                1185

Asp Tyr Thr Trp Trp Glu Arg Asp Val Arg Ser Arg Asp Leu Glu
        1190                1195                1200

Pro His Leu Ala Phe Trp Arg Gly Glu Leu Ala Gly Leu Arg Pro
        1205                1210                1215

Gln Pro Pro Ala Asp Ala His Gly Pro Gly Ala Val Leu Asp Phe
        1220                1225                1230

Ala Leu Gly Ala Ala Leu Ser Asp Glu Leu Arg Ala Thr Ala Ala
        1235                1240                1245

Gly Leu Gly Val Ser Pro Phe Val Leu Gly Leu Thr Ala Phe Ala
        1250                1255                1260

Leu Ala Leu Gly Glu Asp Ser Pro Gly Ala Ile Gly Val Glu Val
        1265                1270                1275

Ala Asn Arg Ala Ser Ala Glu Thr Ala Asp Leu Val Gly Leu Phe
        1280                1285                1290

Val Asn His Val Pro Val Arg Val Ala Pro Arg Gly Thr Gly Arg
        1295                1300                1305

Ala Ala Val Ala Ala Val Asp Glu Ala Arg Arg Arg Val Leu Pro
        1310                1315                1320

His Glu His Val Pro Phe Asp Leu Val Val Asp Leu Leu Gly Pro
        1325                1330                1335

Gly Arg Ala Pro Thr Ser Val Ala Phe Ser His Leu Asp Val Arg
        1340                1345                1350

Gly His Ser Pro Arg Leu Asp Gly Val Thr Ala Thr Arg Leu Thr
        1355                1360                1365

Pro Pro His Asn Gly Thr Ala Lys Phe Asp Leu Leu Glu Val
        1370                1375                1380

Leu Asp Thr Glu His Gly Leu Thr Gly Ala Phe Glu Tyr Arg Pro
        1385                1390                1395

Glu Arg Phe Thr Ala Ala Arg Val Ala Gln Val Arg Asn His Trp
        1400                1405                1410
```

```
Glu Ala Ala Leu Leu Thr Leu Leu Ala Asp Pro Asp Leu Pro Val
    1415                1420                1425

Asp Ala Arg Arg Pro Asp Phe Ala
    1430                1435

<210> SEQ ID NO 51
<211> LENGTH: 3971
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Tyr Thr Ser Gln Phe Gln Thr Leu Val Asp Val Ile Arg Asn Arg
1               5                   10                  15

Ser Asn Ile Ser Asp Arg Gly Ile Arg Phe Ile Glu Ser Asp Lys Ile
            20                  25                  30

Glu Thr Phe Val Ser Tyr Arg Gln Leu Phe Asp Glu Ala Gln Gly Phe
        35                  40                  45

Leu Gly Tyr Leu Gln His Ile Gly Ile Gln Pro Lys Gln Glu Ile Val
    50                  55                  60

Phe Gln Ile Gln Glu Asn Lys Ser Phe Val Val Ala Phe Trp Ala Cys
65                  70                  75                  80

Leu Leu Gly Gly Met Ile Pro Val Pro Val Ser Ile Gly Glu Asp Asn
                85                  90                  95

Asp His Lys Leu Lys Val Trp Arg Ile Trp Asn Ile Leu Asn Asn Pro
            100                 105                 110

Phe Leu Leu Ala Ser Glu Thr Val Leu Asp Lys Met Lys Lys Phe Ala
        115                 120                 125

Ala Asp His Asp Leu Gln Asp Phe His His Gln Leu Ile Glu Lys Ser
    130                 135                 140

Asp Ile Ile Gln Asp Arg Ile Tyr Asp His Pro Ala Ser Gln Tyr Glu
145                 150                 155                 160

Pro Glu Ala Asp Glu Leu Ala Phe Ile Gln Phe Ser Ser Gly Ser Thr
                165                 170                 175

Gly Asp Pro Lys Gly Val Met Leu Thr His His Asn Leu Ile His Asn
            180                 185                 190

Thr Cys Ala Ile Arg Asn Ala Leu Ala Ile Asp Leu Lys Asp Thr Leu
        195                 200                 205

Leu Ser Trp Met Pro Leu Thr His Asp Met Gly Leu Ile Ala Cys His
    210                 215                 220

Leu Val Pro Ala Leu Ala Gly Ile Asn Gln Asn Leu Met Pro Thr Glu
225                 230                 235                 240

Leu Phe Ile Arg Arg Pro Ile Leu Trp Met Lys Lys Ala His Glu His
                245                 250                 255

Lys Ala Ser Ile Leu Ser Ser Pro Asn Phe Gly Tyr Asn Tyr Phe Leu
            260                 265                 270

Lys Phe Leu Lys Asp Asn Lys Ser Tyr Asp Trp Asp Leu Ser His Ile
        275                 280                 285

Arg Val Ile Ala Asn Gly Ala Glu Pro Ile Leu Pro Glu Leu Cys Asp
    290                 295                 300

Glu Phe Leu Thr Arg Cys Ala Ala Phe Asn Met Lys Arg Ser Ala Ile
305                 310                 315                 320

Leu Asn Val Tyr Gly Leu Ala Glu Ala Ser Val Gly Ala Thr Phe Ser
```

Asn Ile Gly Glu Arg Phe Val Pro Val Tyr Leu His Arg Asp His Leu
               325                 330                 335
                    340                 345                 350

Asn Leu Gly Glu Arg Ala Val Glu Val Ser Lys Glu Asp Gln Asn Cys
                    355                 360                 365

Ala Ser Phe Val Glu Val Gly Lys Pro Ile Asp Tyr Cys Gln Ile Arg
            370                 375                 380

Ile Cys Asn Glu Ala Asn Glu Gly Leu Glu Asp Gly Phe Ile Gly His
385                 390                 395                 400

Ile Gln Ile Lys Gly Glu Asn Val Thr Gln Gly Tyr Tyr Asn Asn Pro
                405                 410                 415

Glu Ser Thr Asn Arg Ala Leu Thr Pro Asp Gly Trp Val Lys Thr Gly
                420                 425                 430

Asp Leu Gly Phe Ile Arg Lys Gly Asn Leu Val Val Thr Gly Arg Glu
                435                 440                 445

Lys Asp Ile Ile Phe Val Asn Gly Lys Asn Val Tyr Pro His Asp Ile
450                 455                 460

Glu Arg Val Ala Ile Glu Leu Glu Asp Ile Asp Leu Gly Arg Val Ala
465                 470                 475                 480

Ala Cys Gly Val Tyr Asp Gln Glu Thr Arg Ser Arg Glu Ile Val Leu
                    485                 490                 495

Phe Ala Val Tyr Lys Lys Ser Ala Asp Arg Phe Ala Pro Leu Val Lys
                500                 505                 510

Asp Ile Lys Lys His Leu Tyr Gln Arg Gly Gly Trp Ser Ile Lys Glu
                515                 520                 525

Ile Leu Pro Ile Arg Lys Leu Pro Lys Thr Thr Ser Gly Lys Val Lys
            530                 535                 540

Arg Tyr Glu Leu Ala Glu Gln Tyr Glu Ser Gly Lys Phe Ala Leu Glu
545                 550                 555                 560

Ser Thr Lys Ile Lys Glu Phe Leu Glu Gly His Ser Thr Glu Pro Val
                    565                 570                 575

Gln Thr Pro Ile His Glu Ile Glu Thr Ala Leu Leu Ser Ile Phe Ser
                580                 585                 590

Glu Val Met Asp Gly Lys Lys Ile His Leu Asn Asp His Tyr Phe Asp
            595                 600                 605

Met Gly Ala Thr Ser Leu Gln Leu Ser Gln Ile Ala Glu Arg Ile Glu
            610                 615                 620

Gln Lys Phe Gly Cys Glu Leu Thr Val Ala Asp Leu Phe Thr Tyr Pro
625                 630                 635                 640

Ser Ile Ala Asp Leu Ala Ala Phe Leu Val Glu Asn His Ser Glu Ile
                    645                 650                 655

Lys Gln Thr Asp Thr Ala Lys Pro Ser Arg Ser Ser Lys Asp Ile
                660                 665                 670

Ala Ile Ile Gly Met Ser Leu Asn Val Pro Gly Ala Ser Asn Lys Ser
                675                 680                 685

Asp Phe Trp His Leu Leu Glu Asn Gly Glu His Gly Ile Arg Glu Tyr
            690                 695                 700

Pro Ala Pro Arg Val Lys Asp Ala Ile Asp Tyr Leu Arg Ser Ile Lys
705                 710                 715                 720

Ser Glu Arg Asn Glu Lys Gln Phe Val Arg Gly Gly Tyr Leu Asp Glu
                    725                 730                 735

Ile Asp Arg Phe Asp Tyr Ser Phe Phe Gly Leu Ala Pro Lys Thr Ala
                740                 745                 750

-continued

Lys Phe Met Asp Pro Asn Gln Arg Leu Phe Leu Gln Ser Ala Trp His
    755                 760                 765
Ala Ile Glu Asp Ala Gly Tyr Ala Gly Asp Thr Ile Ser Gly Ser Gln
    770                 775                 780
Leu Gly Val Tyr Val Gly Tyr Ser Lys Val Gly Tyr Asp Tyr Glu Arg
785                 790                 795                 800
Leu Leu Ser Ala Asn Tyr Pro Glu Glu Leu His His Tyr Ile Val Gly
                805                 810                 815
Asn Leu Pro Ser Val Leu Ala Ser Arg Ile Ala Tyr Phe Leu Asn Leu
            820                 825                 830
Lys Gly Pro Ala Val Thr Val Asp Thr Ala Cys Ser Ser Leu Val
        835                 840                 845
Ala Val His Met Ala Cys Lys Ala Leu Leu Thr Gly Asp Cys Glu Met
    850                 855                 860
Ala Leu Ala Gly Gly Ile Arg Thr Ser Leu Leu Pro Met Arg Ile Gly
865                 870                 875                 880
Leu Asp Met Glu Ser Ser Asp Gly Leu Thr Lys Thr Phe Ser Lys Asp
                885                 890                 895
Ser Asp Gly Thr Gly Ser Gly Glu Gly Val Ala Ala Val Leu Leu Lys
            900                 905                 910
Pro Leu Gln Ala Ala Ile Arg Asp Gly Asp His Ile Tyr Gly Val Ile
        915                 920                 925
Lys Gly Ser Ala Ile Asn Gln Asp Gly Thr Thr Val Gly Ile Thr Ala
    930                 935                 940
Pro Ser Pro Ala Ala Gln Thr Glu Val Ile Glu Met Ala Trp Lys Asp
945                 950                 955                 960
Ala Gly Ile Ala Pro Glu Thr Leu Ser Phe Ile Glu Ala His Gly Thr
                965                 970                 975
Gly Thr Lys Leu Gly Asp Pro Val Glu Phe Asn Gly Leu Cys Lys Ala
            980                 985                 990
Phe Glu Lys Val Thr Glu Lys Lys Gln Phe Cys Ala Ile Gly Ser Val
        995                 1000                1005
Lys Ala Asn Ile Gly His Leu Phe Glu Ala Ala Gly Ile Val Gly
    1010                1015                1020
Leu Ile Lys Ser Ala Leu Met Leu Asn His Lys Lys Ile Pro Pro
    1025                1030                1035
Leu Ala His Phe Asn Lys Pro Asn Pro Leu Ile Pro Phe His Ser
    1040                1045                1050
Ser Pro Phe Tyr Val Asn Gln Glu Val Met Asp Phe Thr Pro Glu
    1055                1060                1065
Asp Arg Pro Leu Arg Gly Gly Ile Ser Ser Phe Gly Phe Ser Gly
    1070                1075                1080
Thr Asn Ala His Val Val Leu Glu Glu Tyr Thr Pro Glu Ser Glu
    1085                1090                1095
Tyr Ala Pro Glu Asp Gly Asn Asp Pro His Leu Phe Val Leu Ser
    1100                1105                1110
Ala His Thr Glu Ala Ser Leu Tyr Glu Leu Thr His Gln Tyr Arg
    1115                1120                1125
Gln Tyr Ile Ser Asp Asp Ser Gln Ser Ser Leu Arg Ser Ile Cys
    1130                1135                1140
Tyr Thr Ala Ser Thr Gly Arg Ala His Leu Asp Tyr Cys Leu Ala
    1145                1150                1155

```
Met Ile Val Ser Ser Asn Gln Glu Leu Ile Asp Lys Leu Thr Ser
1160                1165                1170

Leu Ile Gln Gly Glu Arg Asn Leu Pro Gln Val His Phe Gly Tyr
1175                1180                1185

Lys Asn Ile Lys Glu Met Gln Pro Ala Glu Lys Asp Asn Leu Ser
1190                1195                1200

Lys Gln Ile Ser Asp Leu Met Gln His Arg Pro Cys Thr Lys Asp
1205                1210                1215

Glu Arg Ile Thr Trp Leu Asn Arg Ile Ala Glu Leu Tyr Val Gln
1220                1225                1230

Arg Ala Val Ile Asp Trp Arg Ala Val Tyr Ser Asn Glu Val Val
1235                1240                1245

Gln Lys Thr Pro Leu Pro Leu Tyr Pro Phe Glu Arg Asn Arg Cys
1250                1255                1260

Trp Val Glu Ala Val Tyr Glu Ser Ala Lys Glu Arg Lys Glu Lys
1265                1270                1275

Gly Glu Val Ala Leu Asp Ile Asn His Thr Lys Thr His Ile Glu
1280                1285                1290

Ser Phe Leu Lys Thr Val Ile Ser Asn Ala Ser Gly Ile Arg Ala
1295                1300                1305

Asp Glu Ile Asp Ser Asn Ala His Phe Ile Gly Phe Gly Leu Asp
1310                1315                1320

Ser Ile Met Leu Thr Gln Val Lys Lys Ala Ile Ala Asp Glu Phe
1325                1330                1335

Asn Val Asp Ile Pro Met Glu Arg Phe Phe Asp Thr Met Asn Asn
1340                1345                1350

Ile Glu Ser Val Val Asp Tyr Leu Ala Glu Asn Val Pro Ser Ala
1355                1360                1365

Ala Ser Thr Pro Pro Gln Glu Ser Val Thr Ala Gln Glu Glu Leu
1370                1375                1380

Val Ile Ser Gly Ala Gln Pro Glu Leu Glu His Gln Glu His Met
1385                1390                1395

Leu Asp Lys Ile Ile Ala Ser Gln Asn Gln Leu Ile Gln Gln Thr
1400                1405                1410

Leu Gln Ala Gln Leu Asp Ser Phe Asn Leu Leu Arg Asn Asn Ser
1415                1420                1425

His Phe Val Ser Lys Glu Ser Glu Ile Ser Gln Asp Lys Thr Ser
1430                1435                1440

Leu Ser Pro Lys Ser Val Thr Ala Lys Lys Asn Ser Ala Gln Glu
1445                1450                1455

Ala Lys Pro Tyr Ile Pro Phe Gln Arg Gln Thr Leu Asn Glu Gln
1460                1465                1470

Val Asn Tyr Thr Pro Gln Gln Arg Gln Tyr Leu Glu Ser Phe Ile
1475                1480                1485

Glu Lys Tyr Val Asp Lys Thr Lys Gly Ser Lys Gln Tyr Thr Asp
1490                1495                1500

Glu Thr Arg Phe Ala His Ala Asn Asn Arg Asn Leu Ser Ser Phe
1505                1510                1515

Arg Ser Tyr Trp Lys Glu Met Val Tyr Pro Ile Ile Ala Glu Arg
1520                1525                1530

Ser Asp Gly Ser Arg Met Trp Asp Ile Asp Gly Asn Glu Tyr Ile
1535                1540                1545

Asp Ile Thr Met Gly Phe Gly Val Asn Leu Phe Gly His His Pro
```

-continued

```
                1550                1555                1560

Ser Phe Ile Thr Gln Thr Val Val Asp Ser Thr His Ser Ala Leu
    1565                1570                1575

Pro Pro Leu Gly Pro Met Ser Asn Val Ala Gly Glu Val Ala Asp
1580                1585                1590

Arg Ile Arg Ala Cys Thr Gly Val Glu Arg Val Ala Phe Tyr Asn
    1595                1600                1605

Ser Gly Thr Glu Ala Val Met Val Ala Leu Arg Leu Ala Arg Ala
    1610                1615                1620

Ala Thr Gly Arg Thr Lys Val Val Phe Ala Gly Ser Tyr His
    1625                1630                1635

Gly Thr Phe Asp Gly Val Leu Gly Val Ala Asn Thr Lys Gly Gly
    1640                1645                1650

Ala Glu Pro Ala Asn Pro Leu Ala Pro Gly Ile Pro Gln Ser Phe
    1655                1660                1665

Met Asn Asp Leu Ile Ile Leu His Tyr Asn His Pro Asp Ser Leu
    1670                1675                1680

Asp Val Ile Arg Asn Leu Gly Asn Glu Leu Ala Ala Val Leu Val
    1685                1690                1695

Glu Pro Val Gln Ser Arg Arg Pro Asp Leu Gln Pro Glu Ser Phe
    1700                1705                1710

Leu Lys Glu Leu Arg Ala Ile Thr Gln Gln Ser Gly Thr Ala Leu
    1715                1720                1725

Ile Met Asp Glu Ile Ile Thr Gly Phe Arg Ile Gly Leu Gly Gly
    1730                1735                1740

Ala Gln Glu Trp Phe Asp Ile Gln Ala Asp Leu Val Thr Tyr Gly
    1745                1750                1755

Lys Ile Ile Gly Gly Gly Pro Leu Gly Ile Val Ala Gly Lys
    1760                1765                1770

Ala Glu Phe Met Asn Thr Ile Asp Gly Gly Thr Trp Gln Tyr Gly
    1775                1780                1785

Asp Asp Ser Tyr Pro Thr Asp Glu Ala Lys Arg Thr Phe Val Ala
    1790                1795                1800

Gly Thr Phe Asn Thr His Pro Leu Thr Met Arg Met Ser Leu Ala
    1805                1810                1815

Val Leu Arg Tyr Leu Gln Ala Glu Gly Glu Thr Leu Tyr Glu Arg
    1820                1825                1830

Leu Asn Gln Lys Thr Thr Tyr Leu Val Asp Gln Leu Asn Ser Tyr
    1835                1840                1845

Phe Glu Gln Ser Gln Val Pro Ile Arg Met Val Gln Phe Gly Ser
    1850                1855                1860

Leu Phe Arg Phe Val Ser Ser Val Asp Asn Asp Leu Phe Phe Tyr
    1865                1870                1875

His Leu Asn Tyr Lys Gly Val Tyr Val Trp Glu Gly Arg Asn Cys
    1880                1885                1890

Phe Leu Ser Thr Ala His Thr Ser Asp Asp Ile Ala Tyr Ile Ile
    1895                1900                1905

Gln Ala Val Gln Glu Thr Val Lys Asp Leu Arg Arg Gly Gly Phe
    1910                1915                1920

Ile Pro Glu Gly Pro Asp Ser Pro Asn Asp Gly Gly His Lys Glu
    1925                1930                1935

Pro Glu Thr Tyr Glu Leu Ser Pro Glu Gln Lys Gln Leu Ala Val
    1940                1945                1950
```

-continued

Val Ser Gln Tyr Gly Asn Asp Ala Ser Ala Ala Leu Asn Gln Ser
    1955                1960            1965

Ile Met Leu Lys Val Lys Gly Ala Val Gln His Thr Leu Leu Lys
    1970            1975            1980

Gln Ala Val Arg Asn Ile Val Lys Arg His Asp Ala Leu Arg Thr
    1985            1990            1995

Val Ile His Val Asp Asp Glu Val Gln Gln Val Gln Ala Arg Ile
    2000            2005            2010

Asn Val Glu Ile Pro Ile Ile Asp Phe Thr Gly Tyr Pro Asn Glu
    2015            2020            2025

Gln Arg Glu Ser Glu Val Gln Lys Trp Leu Thr Glu Asp Ala Lys
    2030            2035            2040

Arg Pro Phe His Phe His Glu Gln Lys Pro Leu Phe Arg Val His
    2045            2050            2055

Val Leu Thr Ser Lys Gln Asp Glu His Leu Ile Val Leu Thr Phe
    2060            2065            2070

His His Ile Ile Ala Asp Gly Trp Ser Ile Ala Val Phe Val Gln
    2075            2080            2085

Glu Leu Glu Ser Thr Tyr Ala Ala Ile Val Gln Gly Ser Pro Leu
    2090            2095            2100

Pro Ser His Glu Val Val Ser Phe Arg Gln Tyr Leu Asp Trp Gln
    2105            2110            2115

Gln Ala Gln Ile Glu Asn Gly His Tyr Glu Glu Gly Ile Arg Tyr
    2120            2125            2130

Trp Arg Gln Tyr Leu Ser Glu Pro Ile Pro Gln Ala Ile Leu Thr
    2135            2140            2145

Ser Met Ser Ser Ser Arg Tyr Pro His Gly Tyr Glu Gly Asp Arg
    2150            2155            2160

Tyr Thr Val Thr Leu Asp Arg Pro Leu Ser Lys Ala Ile Lys Ser
    2165            2170            2175

Leu Ser Ile Arg Met Lys Asn Ser Val Phe Ala Thr Ile Leu Gly
    2180            2185            2190

Ala Phe His Leu Phe Leu Gln Gln Leu Thr Lys Gln Ala Gly Leu
    2195            2200            2205

Val Ile Gly Ile Pro Thr Ala Gly Gln Leu His Met Lys Gln Pro
    2210            2215            2220

Met Leu Val Gly Asn Cys Val Asn Met Val Pro Val Lys Asn Thr
    2225            2230            2235

Ala Ser Ser Glu Ser Thr Leu Ala Asp Tyr Leu Gly His Met Lys
    2240            2245            2250

Glu Asn Met Asp Gln Val Met Arg His Gln Asp Val Pro Met Thr
    2255            2260            2265

Leu Val Ala Ser Gln Leu Pro His Asp Gln Met Pro Asp Met Arg
    2270            2275            2280

Ile Ile Phe Asn Leu Asp Arg Pro Phe Arg Lys Leu His Phe Gly
    2285            2290            2295

Gln Met Glu Ala Glu Leu Ile Ala Tyr Pro Ile Lys Cys Ile Ser
    2300            2305            2310

Tyr Asp Leu Phe Leu Asn Val Thr Glu Phe Asp Gln Glu Tyr Val
    2315            2320            2325

Leu Asp Phe Asp Phe Asn Thr Ser Val Ile Ser Ser Glu Ile Met
    2330            2335            2340

-continued

```
Asn Lys Trp Gly Thr Gly Phe Val Asn Leu Leu Lys Lys Met Val
    2345                2350                2355
Glu Gly Asp Ser Ala Ser Leu Asp Ser Leu Lys Met Phe Ser Lys
    2360                2365                2370
Glu Asp Gln His Asp Leu Leu Glu Leu Tyr Ala Asp His Gln Leu
    2375                2380                2385
Arg Ile Ser Ser Thr Leu Asp His Lys Gly Val Arg Ala Val Tyr
    2390                2395                2400
Glu Glu Pro Glu Asn Glu Thr Glu Leu Gln Ile Ala Gln Ile Trp
    2405                2410                2415
Ala Glu Leu Leu Gly Leu Glu Lys Val Gly Arg Ser Asp His Phe
    2420                2425                2430
Leu Ser Leu Gly Gly Asn Ser Leu Lys Ala Thr Leu Met Leu Ser
    2435                2440                2445
Lys Ile Gln Gln Thr Phe Asn Gln Lys Val Ser Ile Gly Gln Phe
    2450                2455                2460
Phe Ser His Gln Thr Val Lys Glu Leu Ala Asn Phe Ile Arg Gly
    2465                2470                2475
Glu Lys Asn Val Lys Tyr Pro Pro Met Lys Pro Val Glu Gln Lys
    2480                2485                2490
Ala Phe Tyr Arg Thr Ser Pro Ala Gln Gln Arg Val Tyr Phe Leu
    2495                2500                2505
His Gln Met Glu Pro Asn Gln Val Ser Gln Asn Met Phe Gly Gln
    2510                2515                2520
Ile Ser Ile Ile Gly Lys Tyr Asp Glu Lys Ala Leu Ile Ala Ser
    2525                2530                2535
Leu Gln Gln Val Met Gln Arg His Glu Ala Phe Arg Thr Ser Phe
    2540                2545                2550
His Ile Ile Asp Gly Glu Ile Val Gln Ile Ala Gly Glu Leu
    2555                2560                2565
Asp Phe Asn Val Arg Val His Ser Met Asp Arg Glu Glu Phe Glu
    2570                2575                2580
Ala Tyr Ala Asp Gly Tyr Val Lys Pro Phe Arg Leu Glu Gln Ala
    2585                2590                2595
Pro Leu Val Arg Ala Glu Leu Ile Lys Val Asp Asn Glu Gln Ala
    2600                2605                2610
Glu Leu Leu Ile Asp Met His His Ile Ile Ser Asp Gly Tyr Ser
    2615                2620                2625
Met Ser Ile Leu Thr Asn Glu Leu Phe Ala Leu Tyr His Gly Asn
    2630                2635                2640
Pro Leu Pro Glu Ile Pro Phe Glu Tyr Lys Asp Phe Ala Glu Trp
    2645                2650                2655
Gln Asn Gln Leu Leu Ile Gly Glu Val Met Glu Gln Gln Glu Glu
    2660                2665                2670
Tyr Trp Leu Glu Gln Phe Lys Gln Glu Val Pro Ile Leu Gln Leu
    2675                2680                2685
Pro Ala Asp Gly Ser Arg Ala Met Glu Trp Ser Ser Glu Gly Gln
    2690                2695                2700
Arg Val Thr Cys Ser Leu Gln Ser Ser Leu Ile Arg Ser Leu Gln
    2705                2710                2715
Glu Met Ala Gln Gln Lys Gly Thr Thr Leu Tyr Met Val Leu Leu
    2720                2725                2730
Ala Ala Tyr Asn Val Leu Leu His Lys Tyr Thr Gly Gln Glu Asp
```

-continued

```
            2735                2740                2745
Ile Val Val Gly Thr Pro Val Ser Gly Arg Asn Gln Pro Asn Ile
            2750                2755                2760
Glu Ser Met Ile Gly Ile Phe Ile Gln Thr Met Gly Ile Arg Thr
            2765                2770                2775
Lys Pro Gln Ala Asn Lys Arg Phe Thr Asp Tyr Leu Asp Glu Val
            2780                2785                2790
Lys Arg Gln Thr Leu Asp Ala Phe Glu Asn Gln Asp Tyr Pro Phe
            2795                2800                2805
Asp Trp Leu Val Glu Lys Val Asn Val Gln Arg Glu Thr Thr Gly
            2810                2815                2820
Lys Ser Leu Phe Asn Thr Met Phe Val Tyr Gln Asn Ile Glu Phe
            2825                2830                2835
Gln Glu Ile His Gln Asp Gly Cys Thr Phe Arg Val Lys Glu Arg
            2840                2845                2850
Asn Pro Gly Val Ser Leu Tyr Asp Leu Met Leu Thr Ile Glu Asp
            2855                2860                2865
Ala Glu Lys Gln Leu Asp Ile His Phe Asp Phe Asn Pro Asn Gln
            2870                2875                2880
Phe Glu Gln Glu Thr Ile Glu Gln Ile Ile Arg His Tyr Thr Ser
            2885                2890                2895
Leu Leu Asp Ser Leu Val Lys Glu Pro Glu Lys Ser Leu Ser Ser
            2900                2905                2910
Val Pro Met Leu Ser Asp Ile Glu Arg His Gln Leu Leu Met Gly
            2915                2920                2925
Cys Asn Asp Thr Glu Thr Pro Phe Pro His Asn Asp Thr Val Cys
            2930                2935                2940
Gln Trp Phe Glu Thr Gln Ala Glu Gln Arg Pro Asp Asp Glu Ala
            2945                2950                2955
Val Ile Phe Gly Asn Glu Arg Cys Thr Tyr Gly Gln Leu Asn Glu
            2960                2965                2970
Arg Val Asn Gln Leu Ala Arg Thr Leu Arg Thr Lys Gly Val Gln
            2975                2980                2985
Ala Asp Gln Phe Val Ala Ile Ile Cys Pro His Arg Ile Glu Leu
            2990                2995                3000
Ile Val Gly Ile Leu Ala Val Leu Lys Ala Gly Gly Ala Tyr Val
            3005                3010                3015
Pro Ile Asp Pro Glu Tyr Pro Glu Asp Arg Ile Gln Tyr Met Leu
            3020                3025                3030
Lys Asp Ser Glu Ala Lys Ile Val Leu Ala Gln Leu Asp Leu His
            3035                3040                3045
Lys His Leu Thr Phe Asp Ala Asp Val Val Leu Leu Asp Glu Glu
            3050                3055                3060
Ser Ser Tyr His Glu Asp Arg Ser Asn Leu Glu Pro Thr Cys Gly
            3065                3070                3075
Ala Asn Asp Leu Ala Tyr Met Ile Tyr Thr Ser Gly Ser Thr Gly
            3080                3085                3090
Asn Pro Lys Gly Val Leu Ile Glu His Arg Gly Leu Ala Asn Tyr
            3095                3100                3105
Ile Glu Trp Ala Lys Glu Val Tyr Val Asn Asp Glu Lys Thr Asn
            3110                3115                3120
Phe Pro Leu Tyr Ser Ser Ile Ser Phe Asp Leu Thr Val Thr Ser
            3125                3130                3135
```

-continued

```
Ile Phe Thr Pro Leu Val Thr Gly Asn Thr Ile Ile Val Phe Asp
    3140                3145                3150

Gly Glu Asp Lys Ser Ala Val Leu Ser Thr Ile Met Gln Asp Pro
    3155                3160                3165

Arg Ile Asp Ile Ile Lys Leu Thr Pro Ala His Leu His Val Leu
    3170                3175                3180

Lys Glu Met Lys Ile Ala Asp Gly Thr Thr Ile Arg Lys Met Ile
    3185                3190                3195

Val Gly Gly Glu Asn Leu Ser Thr Arg Leu Ala Gln Ser Val Ser
    3200                3205                3210

Glu Gln Phe Lys Gly Gln Leu Asp Ile Phe Asn Glu Tyr Gly Pro
    3215                3220                3225

Thr Glu Ala Val Val Gly Cys Met Ile Tyr Arg Tyr Asp Thr Lys
    3230                3235                3240

Arg Asp Arg Arg Glu Phe Val Pro Ile Gly Ser Pro Ala Ala Asn
    3245                3250                3255

Thr Ser Ile Tyr Val Leu Asp Ala Ser Met Asn Leu Val Pro Val
    3260                3265                3270

Gly Val Pro Gly Glu Met Tyr Ile Gly Gly Ala Gly Val Ala Arg
    3275                3280                3285

Gly Tyr Trp Asn Arg Pro Asp Leu Thr Ala Glu Lys Phe Val His
    3290                3295                3300

Asn Pro Phe Ala Pro Gly Thr Ile Met Tyr Lys Thr Gly Asp Leu
    3305                3310                3315

Ala Lys Arg Leu Arg Asp Gly Asn Leu Ile Tyr Leu Gly Arg Ile
    3320                3325                3330

Asp Glu Gln Val Lys Ile Arg Gly His Arg Ile Glu Leu Gly Glu
    3335                3340                3345

Val Glu Ala Ala Met His Lys Val Glu Ala Val Gln Lys Ala Val
    3350                3355                3360

Val Leu Ala Arg Glu Glu Glu Asp Gly Leu Gln Gln Leu Cys Ala
    3365                3370                3375

Tyr Tyr Val Ser Asn Lys Pro Ile Thr Ile Ala Glu Ile Arg Glu
    3380                3385                3390

Gln Leu Ser Leu Glu Leu Pro Asp Tyr Met Val Pro Ser His Tyr
    3395                3400                3405

Ile Gln Leu Glu Gln Leu Pro Leu Thr Ser Asn Gly Lys Ile Asn
    3410                3415                3420

Arg Lys Ala Leu Pro Ala Pro Glu Val Ser Leu Glu Gln Ile Ala
    3425                3430                3435

Glu Tyr Val Pro Pro Gly Asn Glu Val Glu Ser Lys Leu Ala Val
    3440                3445                3450

Leu Trp Gln Glu Met Leu Gly Ile His Arg Val Gly Ile Lys His
    3455                3460                3465

Asn Phe Phe Asp Leu Gly Gly Asn Ser Ile Arg Ala Thr Ala Leu
    3470                3475                3480

Ala Ala Arg Ile His Lys Glu Leu Asp Val Asn Leu Ser Val Lys
    3485                3490                3495

Asp Ile Phe Lys Phe Pro Thr Ile Glu Gln Leu Ala Asn Met Ala
    3500                3505                3510

Leu Arg Met Glu Lys Ile Arg Tyr Val Ser Ile Pro Ser Ala Gln
    3515                3520                3525
```

```
Lys Ile Ser Tyr Tyr Pro Val Ser Ser Ala Gln Lys Arg Met Tyr
    3530                3535                3540

Leu Leu Ser His Thr Glu Gly Gly Glu Leu Thr Tyr Asn Met Thr
    3545                3550                3555

Gly Ala Met Ser Val Glu Gly Ala Ile Asp Leu Glu Arg Leu Thr
    3560                3565                3570

Ala Ala Phe Gln Lys Leu Ile Glu Arg His Glu Val Leu Arg Thr
    3575                3580                3585

Ser Phe Glu Leu Tyr Glu Gly Glu Pro Ala Gln Arg Ile His Pro
    3590                3595                3600

Ser Ile Glu Phe Thr Ile Glu Gln Ile Gln Ala Arg Glu Glu Glu
    3605                3610                3615

Val Glu Asp His Val Leu Asp Phe Ile Lys Ser Phe Asp Leu Ala
    3620                3625                3630

Lys Pro Pro Leu Met Arg Val Gly Leu Ile Glu Leu Thr Pro Glu
    3635                3640                3645

Lys His Val Leu Leu Val Asp Met His His Ile Ile Ser Asp Gly
    3650                3655                3660

Val Ser Met Asn Ile Leu Met Lys Asp Leu Asn Gln Phe Tyr Lys
    3665                3670                3675

Gly Ile Glu Pro Asp Pro Leu Pro Ile Gln Tyr Lys Asp Tyr Ala
    3680                3685                3690

Val Trp Gln Gln Thr Glu Ala Gln Arg Gln Asn Ile Lys Lys Gln
    3695                3700                3705

Glu Ala Tyr Trp Leu Asn Arg Phe His Asp Glu Ile Pro Val Leu
    3710                3715                3720

Asp Met Pro Thr Asp Tyr Glu Arg Pro Ala Ile Arg Asp Tyr Glu
    3725                3730                3735

Gly Glu Ser Phe Glu Phe Leu Ile Pro Ile Glu Leu Lys Gln Arg
    3740                3745                3750

Leu Ser Gln Met Glu Glu Ala Thr Gly Thr Thr Leu Tyr Met Ile
    3755                3760                3765

Leu Met Ala Ala Tyr Thr Ile Leu Leu Ser Lys Tyr Ser Gly Gln
    3770                3775                3780

Glu Asp Ile Val Val Gly Thr Pro Val Ser Gly Arg Ser His Met
    3785                3790                3795

Asp Val Glu Ser Val Val Gly Met Phe Val Asn Thr Leu Val Ile
    3800                3805                3810

Arg Asn His Pro Ala Gly Arg Lys Ile Phe Glu Asp Tyr Leu Asn
    3815                3820                3825

Glu Val Lys Glu Asn Met Leu Asn Ala Tyr Gln Asn Gln Asp Tyr
    3830                3835                3840

Pro Leu Glu Glu Leu Ile Gln His Val His Leu Leu Lys Asp Ser
    3845                3850                3855

Ser Arg Asn Pro Leu Phe Asp Thr Met Phe Val Leu Gln Asn Leu
    3860                3865                3870

Asp Gln Val Glu Leu Asn Leu Asp Ser Leu Arg Phe Thr Pro Tyr
    3875                3880                3885

Lys Leu His His Thr Val Ala Lys Phe Asp Leu Thr Leu Ser Ile
    3890                3895                3900

Gln Thr Asp Gln Asp Lys His His Gly Leu Phe Glu Tyr Ser Lys
    3905                3910                3915

Lys Leu Phe Lys Lys Ser Arg Ile Glu Ala Leu Ser Lys Asp Tyr
```

```
                    3920                3925                 3930

Leu His  Ile Leu Ser Val Ile  Ser Gln Gln Pro Ser  Ile Gln Ile
         3935                3940                3945

Glu His  Ile Glu Leu Ser Gly  Ser Thr Ala Glu Asp  Asp Asn Leu
         3950                3955                3960

Ile His  Ser Ile Glu Leu Asn  Phe
         3965                3970

<210> SEQ ID NO 52
<211> LENGTH: 6854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
tcgcgcgttt cggtgatgac ggtgaaaacc tctgacacat gcagctcccg gagacggtca    60
cagcttgtct gtaagcggat gccgggagca acaagcccg tcaggcgcg tcagcgggtg     120 ttggcgggtg tcggggctgg cttaactatg cggcatcaga gcagattgta ctgagagtgc   180
accatatatc gacaaaaatg tcatgaaaga tcgttgtaa gacgctcttc gcaagggtgt    240 cttttttgc cttttttcg gttttgcgc ggtacacata gtcatgtaaa gattgtaaat      300
tgcattcagc aataaaaaaa gattgaacgc agcagtttgg tttaaaaatt tttattttc    360 tgtaaataat gtttagtgga aatgattgcg gcatcccgca aaaatattg ctgtaaataa    420 actggaatct tcggcatcc cgcatgaaac ttttcaccca ttttccggtg ataaaaacat    480
tttttccatt taaactgaac ggtagaaaga taaaaaatat tgaaaacaat gaataaatag   540
ccaaaattgg tttcttatta gggtggggtc ttgcggtctt tatccgctta tgttaaacgc   600
cgcaatgctg actgacggca gcctgcttta atagcggcca tctgtttttt gattggaagc   660 actgctttt aagtgtagta ctttgggcta tttcggctgt tagttcataa gaattaaaag   720
ctgatatgga taagaaagag aaaatgcgtt gcacatgttc actgcttata aagattaggg   780
gaggtatgac aatatggaaa taacttttta ccctttaacg gatgcacaaa acgaatttg    840 gtacacagaa aaattttatc ctcacacgag catttcaaat cttgcgggga ttggtaagct   900
ggtttcagct gatgcgattg attatgtgct tgttgagcag gcgattcaag agtttattcg   960
cagaaatgac gccatgcgcc ttcggttgcg gctagatgaa aacggggagc ctgttcaata  1020
tattagcgag tatcggcctg ttgatataaa acatactgac actactgaag atccgaatgc  1080
gatagagttt atttcacaat ggagccggga ggaaacgaag aaacctttgc cgctatacga  1140
ttgtgatttg ttccgttttt ccttgttcac cataaaggaa aatgaagtgt ggttttacgc  1200
aaatgttcat cacgtgattt ctgatggtat gtccatgaat attgtcggga atgcgatcat  1260 gcacattat ttagaattag ccagcggctc agagacaaaa gaaggaatct cgcattcatt  1320
tatcgatcat gttttatctg aacaggaata tgctcaatcg aagcggtttg aaaaggacaa  1380
ggcgttttgg aacaaacaat ttgaatcggt gcctgaactt gtttccttga acggaatgc   1440 atccgcaggg ggaagtttag atgctgagag gttctctaaa gatgtgcctg aagcgcttca  1500
tcagcagatt ctgtcgtttt gtgaggcgaa taaagtcagt gttctttcgg tatttcaatc  1560
gctgctcgcc gcctatttgt acagggtcag cggccagaat gatgttgtga cgggaacatt  1620
tatgggcaac cggcaaaatg cgaaagagaa gcagatgctt ggcatgtttg tttctacggt  1680
tccgcttcgg acaaacattg acggcgggca ggcgttttca gaatttgtca aagaccggat  1740
```

| | |
|---|---|
| gaaggatctg atgaagacac ttcgccacca aaagtatccg tataatctcc taatcaacga | 1800 |
| tttgcgtgaa acaaagagct ctctgaccaa gctgttcacg gtttctcttg aatatcaagt | 1860 |
| gatgcagtgg cagaaagaag aggatcttgc cttttgact gagccgattt tcagcggcag | 1920 |
| cggattaaat gatgtctcaa ttcatgtaaa ggatcgatgg gatactggga aactcaccat | 1980 |
| agattttgat taccgcactg atttattttc acgtgaagaa atcaacatga tttgtgagcg | 2040 |
| catgattacc atgctggaga acgcgttaac gcatccagaa catacaattg atgaattaac | 2100 |
| actgatttct gatgcggaga aacgcgattt gttttgcgg gtgaacgata cagccaaggc | 2160 |
| gtatccgaac aagctgatca tgtcgatgct ggaggattgg gcggcggcta ccctgacaa | 2220 |
| aacagcgcta gtcttccgcg aacaacgcgt gacgtatcgc gagctgaacg agcgggtcaa | 2280 |
| ccagttggca cacactttgc gcgaaaaagg ggtgcaacct gacgatctcg tgatgctgat | 2340 |
| ggcagagcgg tcggtcgaga tgatggtggc gattttcgct gtgttgaaag cgggcggagc | 2400 |
| gtacttgccc atcgacccgc acagtccggc ggagcgaatc gcctacattt tcgcagacag | 2460 |
| cggagccaag ctggtgctgg cacagtcgcc gtttgtggaa aaggcaagca tggcggaagt | 2520 |
| ggtccttgat ctgaacagtg cgagcagcta tgcggcggat acgagcaacc cgccactggt | 2580 |
| caaccagcca ggcgatctgg tgtatgtcat gtacacttcc ggctcaacgg gaaaaccaaa | 2640 |
| aggcgtgatg atcgagcacg gagcgctgct caatgtgctt cacgaatgc aggacgagta | 2700 |
| cccgcttttg caggacgatg ccttcttgct caagacaacc tacatattcg atatttcagt | 2760 |
| cgcggaaatt ttcgggtggg ttccgggtcg tggcaaactg gtgattttgg aaccggaggc | 2820 |
| ggaaaagaac ccgaaggcta tttggcaggc ggtagtcgga gcgggaatta cccacatcaa | 2880 |
| cttcgtgccc tccatgctga tcccgtttgt cgagtatttg gaagggcgaa cagaagcaaa | 2940 |
| tcgcttgcgg tacatcttgg cttgcggcga agcgatgccg gatgaactcg tgccaaaagt | 3000 |
| gtacgaagta ttgccagagg tgaagctgga aaacatctac ggcccgacag aagcgacgat | 3060 |
| ttacgcttcc cgttactcgc tcgcgaaagg ctcgcaggaa agtcctgttc caatcggaaa | 3120 |
| gccgctgccc aactatcgca tgtatatcat caatcggcat ggacaactgc aaccaatcgg | 3180 |
| cgtaccagga gagctatgca tcgcaggagc aagtctggcg agagggtatt tgaacaatcc | 3240 |
| agcgctgaca gaagaaaaat tcactcctca tccgctggag aaaggcgagc ggatttatcg | 3300 |
| cacgggtgat ctcgcccgtt atcgcgagga tggcaacatc gaatacctcg gacggatgga | 3360 |
| ccatcaggtg aaaattgcg gataccggat cgaactggac gaaatccgca gcaagctgat | 3420 |
| tcaggaggaa acgattcagg acgcggtggt cgtagcccga acgatcaaa acggccaagc | 3480 |
| gtacttgtgc gcctacctgc tgtccgaaca ggagtggaca gtcggtcaac tgcgcgagtt | 3540 |
| gcttcgccgt gaactgcctg aatacatgat tccggcccat ttcgttttgc tgaaacagtt | 3600 |
| cccgctcaca gccaatggca agctcgatcg caaggctttg ccagaaccgg acggcagtgt | 3660 |
| gaaagcggaa gcggaatatg cagcgccgcg cacggaactg gaagcgactt tggcgcacat | 3720 |
| ttggggcgaa gtgctcggaa tcgaacggat cgggattcgc gacgatttct ttgcgctcgg | 3780 |
| agggcattcc ttgaaggcca tgaccgccgt cccgcatcaa caagagctcg ggattgatct | 3840 |
| tccagtgaag cttttgtttg aagcgccgac gatcgccggc atttcagcgt atttgaaaaa | 3900 |
| cgggggctct gatggcttgc aggatgtaac gataatgaat caggatcagg agcagatcat | 3960 |
| tttcgcattt ccgccggttc tgggctatgg cctatgtac caaaatctgt ccagccgctt | 4020 |
| gccgtcatac aagctatgcg cctttgattt tattgaggag gaagaccggc ttgaccgcta | 4080 |

```
tgcggatttg atccagaagc tgcagccgga agggccttta acattgtttg gatattcagc    4140
gggatgcagc ctggcgtttg aagctgcgaa aaagcttgag gaacaaggcc gtattgttca    4200
gcggatcatc atggtggatt cctataaaaa acaaggtgtc agtgatctgg acggacgcac    4260
ggttgaaagt gatgtcgaag cgttgatgaa tgtcaatcgg gacaatgaag cgctcaacag    4320
cgaagccgtc aaacacggcc tcaagcaaaa aacacatgcc ttttactcat actacgtcaa    4380
cctgatcagc acaggccagg tgaaagcaga tattgatctg ttgacttccg gcgctgattt    4440
tgacatgccg gaatggcttg catcatggga agaagctaca acaggtgttt accgtgtgaa    4500
aagaggcttc ggaacacacg cagaaatgct gcagggcgaa acgctagata ggaatgcgga    4560
gattttgctc gaatttctta atacacaaac cgtaacggtt tcataaaggc atgcaagctt    4620
ggcgtaatca tggtcatagc tgtttcctgt gtgaaattgt tatccgctca caattccaca    4680
caacatacga gccggaagca taaagtgtaa agcctggggt gcctaatgag tgagctaact    4740
cacattaatt gcgttgcgct cactgcccgc tttccagtcg ggaaacctgt cgtgccagct    4800
gcattaatga atcggccaac gcgcggggag aggcggtttg cgtattgggc gctcttccgc    4860
ttcctcgctc actgactcgc tgcgctcggt cgttcggctg cggcgagcgg tatcagctca    4920
ctcaaaggcg gtaatacggt tatccacaga atcaggggat aacgcaggaa agaacatgtg    4980
agcaaaaggc cagcaaaagg ccaggaaccg taaaaaggcc gcgttgctgg cgttttttcca   5040 taggctccgc cccctgacg agcatcacaa aaatcgacgc tcaagtcaga ggtggcgaaa     5100
cccgacagga ctataaagat accaggcgtt tccccctgga agctccctcg tgcgctctcc    5160
tgttccgacc ctgccgctta ccggatacct gtccgccttt ctcccttcgg gaagcgtggc    5220
gctttctcat agctcacgct gtaggtatct cagttcggtg taggtcgttc gctccaagct    5280
gggctgtgtg cacgaacccc ccgttcagcc cgaccgctgc gccttatccg gtaactatcg    5340
tcttgagtcc aacccggtaa gacacgactt atcgccactg gcagcagcca ctggtaacag    5400
gattagcaga gcgaggtatg taggcggtgc tacagagttc ttgaagtggt ggcctaacta    5460
cggctacact agaagaacag tatttggtat ctgcgctctg ctgaagccag ttaccttcgg    5520
aaaaagagtt ggtagctctt gatccggcaa acaaaccacc gctggtagcg gtggtttttt    5580
tgtttgcaag cagcagatta cgcgcagaaa aaaaggatct caagaagatc ctttgatctt    5640
ttctacgggg tctgacgctc agtggaacga aaactcacgt taagggattt tggtcatgag    5700
attatcaaaa aggatcttca cctagatcct tttaaattaa aaatgaagtt ttaaatcaat    5760
ctaaagtata tatgagtaaa cttggtctga cagttaccaa tgcttaatca gtgaggcacc    5820
tatctcagcg atctgtctat ttcgttcatc catagttgcc tgactccccg tcgtgtagat    5880
aactacgata cgggagggct taccatctgg ccccagtgct gcaatgatac cgcgagaccc    5940
acgctcaccg gctccagatt tatcagcaat aaaccagcca gccggaaggg ccgagcgcag    6000
aagtggtcct gcaactttat ccgcctccat ccagtctatt aattgttgcc gggaagctag    6060
agtaagtagt tcgccagtta atagtttgcg caacgttgtt gccattgcta caggcatcgt    6120
ggtgtcacgc tcgtcgtttg gtatggcttc attcagctcc ggttcccaac gatcaaggcg    6180
agttacatga tcccccatgt tgtgcaaaaa agcggttagc tccttcggtc ctccgatcgt    6240
tgtcagaagt aagttggccg cagtgttatc actcatggtt atggcagcac tgcataattc    6300
tcttactgtc atgccatccg taagatgctt ttctgtgact ggtgagtact caaccaagtc    6360
attctgagaa tagtgtatgc ggcgaccgag ttgctcttgc ccggcgtcaa tacgggataa    6420
taccgcgcca catagcagaa ctttaaaagt gctcatcatt ggaaaacgtt cttcggggcg    6480
```

-continued

```
aaaactctca aggatcttac cgctgttgag atccagttcg atgtaaccca ctcgtgcacc    6540
caactgatct tcagcatctt ttactttcac cagcgtttct gggtgagcaa aaacaggaag    6600
gcaaaatgcc gcaaaaaagg gaataagggc gacacggaaa tgttgaatac tcatactctt    6660 ccttttcaa tattattgaa gcatttatca gggttattgt ctcatgagcg atacatatt     6720 tgaatgtatt tagaaaaata aacaaatagg ggttccgcgc acatttcccc gaaaagtgcc    6780
acctgacgtc taagaaacca ttattatcat gacattaacc tataaaaata ggcgtatcac    6840
gaggcccttt cgtc                                                     6854
```

<210> SEQ ID NO 53
<211> LENGTH: 597
<212> TYPE: PRT
<213> ORGANISM: Streptomyces roseosporus

<400> SEQUENCE: 53

```
Met Ser Glu Ser Arg Cys Ala Gly Gln Gly Leu Val Gly Ala Leu Arg
1               5                   10                  15

Thr Trp Ala Arg Thr Arg Ala Arg Glu Thr Ala Val Val Leu Val Arg
                20                  25                  30

Asp Thr Gly Thr Thr Asp Asp Thr Ala Ser Val Asp Tyr Gly Gln Leu
            35                  40                  45

Asp Glu Trp Ala Arg Ser Ile Ala Val Thr Leu Arg Gln Gln Leu Ala
        50                  55                  60

Pro Gly Gly Arg Ala Leu Leu Leu Pro Ser Gly Pro Glu Phe Thr
65                  70                  75                  80

Ala Ala Tyr Leu Gly Cys Leu Tyr Ala Gly Leu Ala Ala Val Pro Ala
                85                  90                  95

Pro Leu Pro Gly Gly Arg His Phe Glu Arg Arg Val Ala Ala Ile
                100                 105                 110

Ala Ala Asp Ser Gly Ala Gly Val Val Leu Thr Val Ala Gly Glu Thr
            115                 120                 125

Ala Ser Val His Asp Trp Leu Thr Glu Thr Thr Ala Pro Ala Thr Arg
        130                 135                 140

Val Val Ala Val Asp Asp Arg Ala Ala Leu Gly Asp Pro Ala Gln Trp
145                 150                 155                 160

Asp Asp Pro Gly Val Ala Pro Asp Val Ala Leu Ile Gln Tyr Thr
                165                 170                 175

Ser Gly Ser Thr Gly Asn Pro Lys Gly Val Val Val Thr His Ala Asn
            180                 185                 190

Leu Leu Ala Asn Ala Arg Asn Leu Ala Glu Ala Cys Glu Leu Thr Ala
        195                 200                 205

Ala Thr Pro Met Gly Gly Trp Leu Pro Met Tyr His Asp Met Gly Leu
    210                 215                 220

Leu Gly Thr Leu Thr Pro Ala Leu Tyr Leu Gly Thr Thr Cys Val Leu
225                 230                 235                 240

Met Ser Ser Thr Ala Phe Ile Lys Arg Pro His Leu Trp Leu Arg Thr
                245                 250                 255

Ile Asp Arg Phe Gly Leu Val Ser Ser Ala Pro Phe Ala Tyr
            260                 265                 270

Asp Met Cys Leu Lys Arg Val Thr Asp Glu Gln Ile Ala Gly Leu Asp
        275                 280                 285

Leu Ser Arg Trp Arg Trp Ala Gly Asn Gly Ala Glu Pro Ile Arg Ala
    290                 295                 300
```

```
Ala Thr Val Arg Ala Phe Gly Glu Arg Phe Ala Arg Tyr Gly Leu Arg
305                 310                 315                 320

Pro Glu Ala Leu Thr Ala Gly Tyr Gly Leu Ala Glu Ala Thr Leu Phe
            325                 330                 335

Val Ser Arg Ser Gln Gly Leu His Thr Ala Arg Val Ala Thr Ala Ala
        340                 345                 350

Leu Glu Arg His Glu Phe Arg Leu Ala Val Pro Gly Glu Ala Ala Arg
    355                 360                 365

Glu Ile Val Ser Cys Gly Pro Val Gly His Phe Arg Ala Arg Ile Val
370                 375                 380

Glu Pro Gly Gly His Arg Val Leu Pro Pro Gly Gln Val Gly Glu Leu
385                 390                 395                 400

Val Leu Gln Gly Ala Ala Val Cys Ala Gly Tyr Trp Gln Ala Lys Glu
            405                 410                 415

Glu Thr Glu Gln Thr Phe Gly Leu Thr Leu Asp Gly Glu Asp Gly His
        420                 425                 430

Trp Leu Arg Thr Gly Asp Leu Ala Ala Leu His Glu Gly Asn Leu His
    435                 440                 445

Ile Thr Gly Arg Cys Lys Glu Ala Leu Val Ile Arg Gly Arg Asn Leu
450                 455                 460

Tyr Pro Gln Asp Ile Glu His Glu Leu Arg Leu Gln His Pro Glu Leu
465                 470                 475                 480

Glu Ser Val Gly Ala Ala Phe Thr Val Pro Ala Ala Pro Gly Thr Pro
            485                 490                 495

Gly Leu Met Val Val His Glu Val Arg Thr Pro Val Pro Ala Asp Asp
        500                 505                 510

His Pro Ala Leu Val Ser Ala Leu Arg Gly Thr Ile Asn Arg Glu Phe
    515                 520                 525

Gly Leu Asp Ala Gln Gly Ile Ala Leu Val Ser Arg Gly Thr Val Leu
530                 535                 540

Arg Thr Thr Ser Gly Lys Val Arg Arg Gly Ala Met Arg Asp Leu Cys
545                 550                 555                 560

Leu Arg Gly Glu Leu Asn Ile Val His Ala Asp Lys Gly Trp His Ala
            565                 570                 575

Ile Ala Gly Thr Ala Gly Glu Asp Ile Ala Pro Thr Asp His Ala Pro
        580                 585                 590

His Pro His Pro Ala
    595

<210> SEQ ID NO 54
<211> LENGTH: 89
<212> TYPE: PRT
<213> ORGANISM: Streptomyces roseosporus

<400> SEQUENCE: 54

Met Asn Pro Pro Glu Ala Val Ser Thr Pro Ser Glu Val Thr Ala Trp
1               5                   10                  15

Ile Thr Gly Gln Ile Ala Glu Phe Val Asn Glu Thr Pro Asp Arg Ile
            20                  25                  30

Ala Gly Asp Ala Pro Leu Thr Asp His Gly Leu Asp Ser Val Ser Gly
        35                  40                  45

Val Ala Leu Cys Ala Gln Val Glu Asp Arg Tyr Gly Ile Glu Val Asp
    50                  55                  60

Pro Glu Leu Leu Trp Ser Val Pro Thr Leu Asn Glu Phe Val Gln Ala
```

```
                65                  70                  75                  80
Leu Met Pro Gln Leu Ala Asp Arg Thr
                85

<210> SEQ ID NO 55
<211> LENGTH: 400
<212> TYPE: PRT
<213> ORGANISM: Bacillus subtilis

<400> SEQUENCE: 55

Met Asn Asn Leu Ala Phe Leu Phe Pro Gly Gln Gly Ser Gln Phe Val
1               5                   10                  15

Gly Met Gly Lys Ser Phe Trp Asn Asp Phe Val Leu Ala Lys Arg Leu
            20                  25                  30

Phe Glu Glu Ala Ser Asp Ala Ile Ser Met Asp Val Lys Lys Leu Cys
        35                  40                  45

Phe Asp Gly Asp Met Thr Glu Leu Thr Arg Thr Met Asn Ala Gln Pro
    50                  55                  60

Ala Ile Leu Thr Val Ser Val Ile Ala Tyr Gln Val Tyr Met Gln Glu
65                  70                  75                  80

Ile Gly Ile Lys Pro His Phe Leu Ala Gly His Ser Leu Gly Glu Tyr
                85                  90                  95

Ser Ala Leu Val Cys Ala Gly Val Leu Ser Phe Gln Glu Ala Val Lys
            100                 105                 110

Leu Ile Arg Gln Arg Gly Ile Leu Met Gln Asn Ala Asp Pro Glu Gln
        115                 120                 125

Leu Gly Thr Met Ala Ala Ile Thr Gln Val Tyr Ile Gln Pro Leu Gln
    130                 135                 140

Asp Leu Cys Thr Glu Ile Ser Thr Glu Asp Phe Pro Val Gly Val Ala
145                 150                 155                 160

Cys Met Asn Ser Asp Gln Gln His Val Ile Ser Gly His Arg Gln Ala
                165                 170                 175

Val Glu Phe Val Ile Lys Lys Ala Glu Arg Met Gly Ala Asn His Thr
            180                 185                 190

Tyr Leu Asn Val Ser Ala Pro Phe His Ser Ser Met Met Arg Ser Ala
        195                 200                 205

Ser Glu Gln Phe Gln Thr Ala Leu Asn Gln Tyr Ser Phe Arg Asp Ala
    210                 215                 220

Glu Trp Pro Ile Ile Ser Asn Val Thr Ala Ile Pro Tyr Asn Asn Gly
225                 230                 235                 240

His Ser Val Arg Glu His Leu Gln Thr His Met Thr Met Pro Val Arg
                245                 250                 255

Trp Ala Glu Ser Met His Tyr Leu Leu Leu His Gly Val Thr Glu Val
            260                 265                 270

Ile Glu Met Gly Pro Lys Asn Val Leu Val Gly Leu Leu Lys Lys Ile
        275                 280                 285

Thr Asn His Ile Ala Ala Tyr Pro Leu Gly Gln Thr Ser Asp Leu His
    290                 295                 300

Leu Leu Ser Asp Ser Ala Glu Arg Asn Glu Asn Ile Val Asn Leu Arg
305                 310                 315                 320

Lys Lys Gln Leu Asn Lys Met Met Ile Gln Ser Ile Ile Ala Arg Asn
                325                 330                 335

Tyr Asn Lys Asp Ala Lys Thr Tyr Ser Asn Leu Thr Thr Pro Leu Phe
            340                 345                 350
```

```
Pro Gln Ile Gln Leu Leu Lys Glu Arg Val Glu Arg Lys Glu Val Glu
        355                 360                 365

Leu Ser Ala Glu Glu Leu Glu His Ser Ile His Leu Cys Gln Leu Ile
    370                 375                 380

Cys Glu Ala Lys Gln Leu Pro Thr Trp Glu Gln Leu Arg Ile Leu Lys
385                 390                 395                 400
```